(12) United States Patent
Carter et al.

(10) Patent No.: US 7,378,409 B2
(45) Date of Patent: May 27, 2008

(54) SUBSTITUTED CYCLOALKYLAMINE DERIVATIVES AS MODULATORS OF CHEMOKINE RECEPTOR ACTIVITY

(75) Inventors: Percy H. Carter, Princeton, NJ (US); Robert J. Cherney, Newtown, PA (US); Douglas G. Batt, Wilmington, DE (US); Gregory D. Brown, Lansdale, PA (US); John V. Duncia, Newtown, PA (US); Daniel S. Gardner, Furlong, PA (US); Michael G. Yang, Narberth, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 554 days.

(21) Appl. No.: 10/923,538

(22) Filed: Aug. 19, 2004

(65) Prior Publication Data

US 2005/0054626 A1    Mar. 10, 2005

Related U.S. Application Data

(60) Provisional application No. 60/496,974, filed on Aug. 21, 2003.

(51) Int. Cl.
| | |
|---|---|
| A61K 31/166 | (2006.01) |
| C07D 265/30 | (2006.01) |
| C07D 487/04 | (2006.01) |
| C07D 239/74 | (2006.01) |
| C07D 239/26 | (2006.01) |
| C07D 213/76 | (2006.01) |
| C07D 231/12 | (2006.01) |
| C07D 207/333 | (2006.01) |
| C07D 205/04 | (2006.01) |
| C07D 307/46 | (2006.01) |

(52) U.S. Cl. .............. 514/210.18; 514/237.5; 514/262.1; 514/266.1; 514/354; 514/406; 514/423; 514/741; 544/168; 544/256; 544/283; 544/334; 546/314; 548/374.1; 548/537; 548/953; 549/487; 564/152

(58) Field of Classification Search ......... 514/210.18, 514/237.5, 262.1, 266.1, 354, 406, 423, 71; 544/168, 256, 283, 334; 546/314; 548/374.1, 548/537, 953; 549/487; 564/152
See application file for complete search history.

(56) References Cited

U.S. PATENT DOCUMENTS

| | | | |
|---|---|---|---|
| 3,226,419 | A | 12/1965 | Zangg et al. |
| 5,972,946 | A | 10/1999 | Murata et al. |
| 6,362,177 | B1 | 3/2002 | Shiota et al. |
| 6,410,566 | B1 | 6/2002 | Shiota et al. |
| 6,451,842 | B1 | 9/2002 | Shiota et al. |
| 6,624,184 | B1 | 9/2003 | Gu et al. |
| 6,706,712 | B2 | 3/2004 | Cherney |
| 2003/0060459 | A1 | 3/2003 | Carter et al. |
| 2003/0216434 | A1 | 11/2003 | Cherney |
| 2003/0229119 | A1 | 12/2003 | Kym et al. |
| 2004/0186143 | A1 | 9/2004 | Carter et al. |
| 2004/0235835 | A1 | 11/2004 | Carter |
| 2004/0235836 | A1 | 11/2004 | Cherney |

FOREIGN PATENT DOCUMENTS

| | | |
|---|---|---|
| GB | 2373186 | 9/2002 |
| JP | 2003183286 | 7/2003 |
| WO | WO 9633170 | 10/1996 |
| WO | WO 9805336 | 2/1998 |
| WO | WO 9845262 | 10/1998 |
| WO | WO 9925686 | 5/1999 |
| WO | WO 9926615 | 6/1999 |
| WO | WO 99/52895 | 10/1999 |
| WO | WO 0000464 | 1/2000 |
| WO | WO 00/26197 | 5/2000 |
| WO | WO 0069432 | 11/2000 |
| WO | WO 0069815 | 11/2000 |
| WO | WO 0076970 | 12/2000 |
| WO | WO 0076971 | 12/2000 |

(Continued)

OTHER PUBLICATIONS

Ritter et al., "Amino Acid-Derived Chiral Acyl Nitroso Compounds: Diastereoselectivity in Intermolecular Hetero Diels-Alder Reactions", Journal of Organic Chemistry, vol. 59 (16), pp. 4602-4611, 1994.

(Continued)

Primary Examiner—Kamal A. Saeed
Assistant Examiner—Joseph R. Kosack
(74) Attorney, Agent, or Firm—Terence J. Bogie; Laurelee L. Duncan; Mary K. VanAtten

(57) ABSTRACT

The present application describes modulators of MCP-1 of formula (I):

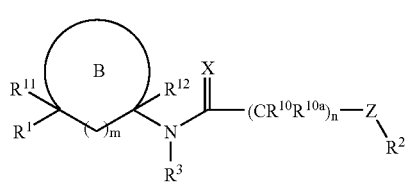

or pharmaceutically acceptable salt forms thereof, useful for the prevention of asthma, multiple sclerosis, artherosclerosis, and rheumatoid arthritis.

9 Claims, No Drawings

FOREIGN PATENT DOCUMENTS

| | | |
|---|---|---|
| WO | WO 0077027 | 12/2000 |
| WO | WO 0110439 | 2/2001 |
| WO | WO 0114333 | 3/2001 |
| WO | WO 0142208 | 6/2001 |
| WO | WO 0144226 | 6/2001 |
| WO | WO 0147875 | 7/2001 |
| WO | WO 0192204 | 12/2001 |
| WO | WO 0250019 | 6/2002 |
| WO | WO 02060859 | 8/2002 |
| WO | WO 02/089783 A | 11/2002 |
| WO | WO 03000657 | 1/2003 |
| WO | WO 03000680 | 1/2003 |
| WO | WO 03016302 | 2/2003 |
| WO | WO 03/022799 A | 3/2003 |
| WO | WO 03028641 | 4/2003 |
| WO | WO 03068233 | 8/2003 |
| WO | WO 03068235 | 8/2003 |
| WO | WO 03070244 | 8/2003 |
| WO | WO 03070244 A1 * | 8/2003 |
| WO | WO 03075853 | 9/2003 |
| WO | WO 2004/050024 | 6/2004 |
| WO | WO 2004/058715 | 7/2004 |
| WO | WO 2004/071449 | 8/2004 |
| WO | WO 2004/087669 A | 10/2004 |
| WO | WO 2004/098512 | 11/2004 |
| WO | WO 2004/098516 | 11/2004 |
| WO | WO 2004/098516 A | 11/2004 |

OTHER PUBLICATIONS

Berkhout et al., "CCR2: Characterization of the Antagonist Binding Site from a Combined Receptor Modeling/Mutagenesis Approach", Journal of Medicinal Chemistry, vol. 46(19), pp. 4070-4086, 2003.

U.S. Appl. No. 10/922,406, filed Aug. 19, 2004, Carter et al.

U.S. Appl. No. 10/923,619, filed Aug. 19, 2004, Carter et al.

U.S. Appl. No. 10/922,726, filed Aug. 19, 2004, Carter et al.

U.S. Appl. No. 10/776,828, filed Feb. 11, 2004, Cherney et al.

Grabowski, et al., Tetrahedron Letters, Elsevier, Amsterdam, NL, vol. 38, No. 31, pp. 5485-5488 (1997).

Tanaka et al., European Journal of Organic Chemistry, vol. 16, pp. 3043-3046 (Aug. 2003).

* cited by examiner

SUBSTITUTED CYCLOALKYLAMINE DERIVATIVES AS MODULATORS OF CHEMOKINE RECEPTOR ACTIVITY

CROSS-REFERENCE TO RELATED APPLICATIONS

This application claims the priority benefit of U.S. application Ser. No. 60/496,974 filed on Aug. 21, 2003, which is expressly incorporated fully herein by reference.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, asthma, rheumatoid arthritis, atherosclerosis, and multiple sclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Luster, New Eng. J. Med. 1998, 338, 436-445 and Rollins, Blood 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, Trends Pharm. Sci. 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns(reviewed in Zlotnik and Oshie Immunity 2000, 12, 121): CCR-1 (or "CKR-1" or "CC—CKR-1") [MIP-1α, MCP-3, MCP-4, RANTES] (Ben-Barruch, et al., Cell 1993, 72, 415-425, and Luster, New Eng. J. Med. 1998, 338, 436-445); CCR-2A and CCR-2B (or "CKR-2A"/"CKR-2B" or "CC—CKR-2A"/ "CC-CKR-2B") [MCP-1, MCP-2, MCP-3, MCP-4, MCP-5] (Charo, et al., Proc. Natl. Acad. Sci. USA 1994, 91, 2752-2756, and Luster, New Eng. J. Med. 1998, 338, 436-445); CCR-3 (or "CKR-3" or "CC—CKR-3") [eotaxin-1, eotaxin-2, RANTES, MCP-3, MCP-4] (Combadiere, et al., J. Biol. Chem. 1995, 270, 16491-16494, and Luster, New Eng. J. Med. 1998, 338, 436-445); CCR-4 (or "CKR-4" or "CC—CKR-4") [TARC, MDC] (Power, et al., J. Biol. Chem. 1995, 270, 19495-19500, and Luster, New Eng. J. Med. 1998, 338, 436-445); CCR-5 (or "CKR-5" OR "CC—CKR-5") [MIP-1α, RANTES, MIP-1β] (Sanson, et al., Biochemistry 1996, 35, 3362-3367); CCR-6 (or "CKR-6" or "CC—CKR-6") [LARC] (Baba, et al., J. Biol. Chem. 1997, 272, 14893-14898); CCR-7 (or "CKR-7" or "CC—CKR-7") [ELC] (Yoshie et al., J. Leukoc. Biol. 1997, 62, 634-644); CCR-8 (or "CKR-8" or "CC—CKR-8") [I-309] (Napolitano et al., J. Immunol., 1996, 157; 2759-2763); CCR-10 (or "CKR-10" or "CC—CKR-10") [MCP-1, MCP-3] (Bonini; et al., DNA and Cell Biol. 1997, 16, 1249-1256); and CCR-11 [MCP-1, MCP-2, and MCP-4] (Schweickert, et al., J. Biol. Chem. 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, Curr. Opin. Biotech. 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: P. H. Carter, Current Opinion in Chemical Biology 2002, 6, 510; Trivedi, et al, Ann. Reports Med. Chem. 2000, 35, 191; Saunders and Tarby, Drug Disc. Today 1999, 4, 80; Premack and Schall, Nature Medicine 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, cellular degranulation, and the promotion of leukocyte migration. Demonstration of the importance of the MCP-1/ CCR-2 interaction has been provided by experiments with genetically modified mice. MCP-1−/− mice had normal numbers of leukocytes and macrophages, but were unable to recruit monocytes into sites of inflammation after several different types of immune challenge (Bao Lu, et al., J. Exp. Med. 1998, 187, 601). Likewise, CCR-2−/− mice were unable to recruit monocytes or produce interferon-γ when challenged with various exogenous agents; moreover, the leukocytes of CCR-2 null mice did not migrate in response to MCP-1 (Landin Boring, et al., J. Clin. Invest. 1997, 100, 2552), thereby demonstrating the specificity of the MCP-1/ CCR-2 interaction. Two other groups have independently reported equivalent results with different strains of CCR-2−/− mice (William A. Kuziel, et al., Proc. Natl. Acad. Sci. USA 1997, 94, 12053, and Takao Kurihara, et al., J. Exp. Med. 1997, 186, 1757). The viability and generally normal health of the MCP-1−/− and CCR-2−/− animals is noteworthy, in that disruption of the MCP-1/CCR-2 interaction does not induce physiological crisis. Taken together, these data lead one to the conclusion that molecules that block the actions of MCP-1 would be useful in treating a number of inflammatory and autoimmune disorders. This hypothesis has now been validated in a number of different animal disease models, as described below.

It is known that MCP-1 is upregulated in patients with rheumatoid arthritis (Alisa Koch, et al., *J. Clin. Invest.* 1992, 90, 772-779). Moreover, several studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, inflammatory disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1(9-76), was shown both to prevent disease onset and to reduce disease symptoms (depending on the time of administration) in the MRL-1pr mouse model of arthritis (Jiang-Hong Gong, et al., *J. Exp. Med.* 1997, 186, 131).

It is known that MCP-1 is upregulated in atherosclerotic lesions, and it has been shown that circulating levels of MCP-1 are reduced through treatment with therapeutic agents, plays a role in disease progression (Abdolreza Rezaie-Majd, et al, *Arterioscler. Thromb. Vasc. Biol.* 2002, 22, 1194-1199). Four key studies have demonstrated the potential therapeutic value of antagonism of the MCP-1/CCR2 interaction in treating atherosclerosis. For example, when MCP-1-/- mice are mated with LDL receptor-deficient mice, an 83% reduction in aortic lipid deposition was observed (Long Gu, et al., *Mol. Cell* 1998, 2, 275). Similarly, when MCP-1 was genetically ablated from mice which already overexpressed human apolipoprotein B, the resulting mice were protected from atherosclerotic lesion formation relative to the MCP-1+/+ apoB control mice (Jennifa Gosling, et al., *J. Clin. Invest.* 1999, 103, 773). Likewise, when CCR-2-/- mice are crossed with apolipoprotein E-/- mice, a significant decrease in the incidence of atherosclerotic lesions was observed (Landin Boring, et al, *Nature* 1998, 394, 894). Finally, when apolipoprotein E-/- mice are administered a gene encoding a peptide antagonist of CCR2, then lesion size is decreased and plaque stability is increased (W. Ni, et al. *Circulation* 2001, 103, 2096-2101).

It is known that MCP-1 is upregulated in human multiple sclerosis, and it has been shown that effective therapy with interferon b-1b reduces MCP-1 expression in peripheral blood mononuclear cells, suggesting that MCP-1 plays a role in disease progression (Carla Iarlori, et al., *J. Neuroimmunol.* 2002, 123, 170-179). Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple scelerosis. Administration of antibodies for MCP-1 to animals with EAE significantly diminished disease relapse (K. J. Kennedy, et al., *J. Neuroimmunol.* 1998, 92, 98). Furthermore, two recent reports have now shown that CCR-2-/- mice are resistant to EAE (Brian T. Fife, et al., *J. Exp. Med.* 2000, 192, 899; Leonid Izikson, et al., *J. Exp. Med.* 2000, 192, 1075).

It is known that MCP-1 is upregulated in patients who develop bronchiolitis obliterans syndrome after lung transplantation (Martine Reynaud-Gaubert, et al., *J. of Heart and Lung Transplant.*, 2002, 21, 721-730; John Belperio, et al., *J. Clin. Invest.* 2001, 108, 547-556). In a murine model of bronchiolitis obliterans syndrome, administration of an antibody to MCP-1 led to-attenuation of airway obliteration; likewise, CCR2-/- mice were resistant to airway obliteration in this same model (John Belperio, et al., *J. Clin. Invest.* 2001, 108, 547-556). These data suggest that antagonism of MCP-1/CCR2 may be beneficial in treating rejection of organs following transplantation.

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., J. Immunol. 1997, 158, 4398). Consistent with this, MCP-1 -/- mice displayed a reduced response to challenge with Schistosoma mansoni egg (Bao Lu, et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., *J. Exp. Med.* 1997, 185, 1371). In addition, MCP-1-/- mice with induced nephrotoxic serum nephritis showed significantly less tubular damage than their MCP-1+/+ counterparts (Gregory H. Tesch, et al., *J. Clin. Invest.* 1999, 103, 73).

One study has demonstrated the potential therapeutic value of antagonism-of the MCP-1/CCR2 interaction in treating systemic lupus erythematosus. Crossing of MCP-1-/- mice with MRL-FAS$^{1Pr}$ mice—the latter of which have a fatal autoimmune disease that is analogous to human systemic lupus erythematosus—results mice that have less disease and longer survival than the wildtype MRL-FAS$^{1Pr}$ mice (Gregory H. Tesch, et al., *J. Exp. Med.* 1999, 190, 1813).

One study has demonstrated the potential therapeutic value of antagonism of the MCP-1/CCR2 interaction in treating colitis. CCR-2-/- mice were protected from the effects of dextran sodium sulfate-induced colitis (Pietro G. Andres, et al., *J. Immunol.* 2000, 164, 6303).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially aleviated (Michael L. Jones, et al., *J. Immunol.* 1992, 149, 2147).

One study has demonstrated the potential therapeutic value of antagonism of the MCP-1/CCR2 interaction in treating cancer. When immunodeficient mice bearing human breast carcinoma cells were treated with an anti-MCP-1 antibody, inhibition of lung micrometastases and increases in survival were observed (Rosalba Salcedo, et al., *Blood* 2000, 96, 34-40).

One study has demonstrated the potential therapeutic value of antagonism of the MCP-1/CCR2 interaction in treating restinosis. Mice deficient in CCR2 showed reductions in the intimal area and in the intima/media ratio (relative to wildtype littermates) after injury of the femoral artery (Merce Roque, et al. *Arterioscler. Thromb. Vasc. Biol.* 2002, 22, 554-559).

Other studies have provided evidence that MCP-1 is overexpressed in various disease states not mentioned above. These reports provide correlative evidence that MCP-1 antagonists could be useful therapeutics for such diseases. Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804). Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). Another study has demonstrated the overexpression of MCP-1 in rodent cardiac allografts, suggesting a role for MCP-1 in the pathogenesis of transplant arteriosclerosis (Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127). Finally, a recent report has shown that MCP-1 is overexpressed in the brains and cerebrospinal fluid of patients with HIV-1-associated dementia (Alfredo Garzino-Demo, WO 99/46991).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR-2 is also the receptor for the chemokines MCP-2, MCP-3, MCP-4, and MCP-5 (Luster, *New Eng. J. Med.* 1998, 338, 436-445). Since it is presumed that the new compounds of formula (I) described herein antagonize MCP-1 by binding to the CCR-2 receptor, it may be that these compounds of formula (I) are also effective antagonists of the actions of MCP-2, MCP-3, MCP-4, and MCP-5 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis, multiple sclerosis, and atherosclerosis, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

These and other features of the invention, which will become apparent during the following detailed description, have been achieved by the inventors' discovery that compounds of formula (I):

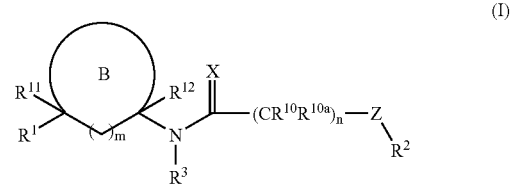

(I)

or stereoisomers or pharmaceutically acceptable salts thereof, wherein B, X, Z, m, n, $R^1$, $R^2$, $R^3$, $R^{10}$, $R^{10a}$, $R^{11}$, and $R^{12}$, are defined below, are effective modulators of MCP-1 and chemokine activity.

DETAILED DESCRIPTION OF EMBODIMENTS OF THE PRESENT INVENTION

Thus, in a first embodiment, the present invention provides novel compounds of formula (I):

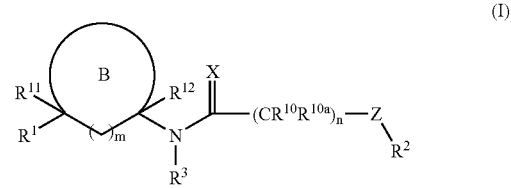

(I)

or a stereoisomer or a pharmaceutically acceptable salt thereof, wherein:

ring B is a cycloalkyl group of 3 to 8 carbon atoms wherein the cycloalkyl group is saturated or partially unsaturated; and being substituted with 1-2 $R^5$ and further substituted with 0-1 $R^{5'}$; or a heterocycle of 3 to 7 atoms wherein the heterocycle is saturated or partially unsaturated, the heterocycle containing a heteroatom selected from —O—, —S—, —S(=O)—, —S(=O)$_2$—, and —N($R^4$)—, the heterocycle optionally containing a —C(O)— and being substituted with 0-2 $R^5$ and further substituted with 0-1 $R^{5'}$;

X is selected from O or S;

Z is selected from a bond, —C(O)—, —C(O)$NR^8$—, —$NR^8$—, —$NR^8$—$CR^{14}R^{14}$—, —$NR^8C(O)$—, —$NR^8C(O)NH$—, —$NR^8C(S)NH$—, —$NR^8SO_2$—, and —$NR^8SO_2NH$—, —$OC(O)NR^8$—, —$NR^8C(O)O$—, —$(CR^{25}R^{25})_u$—, —$CR^{24}$=$CR^{24}$—, —$CR^{25}R^{25}C(O)$—, —C(O)CR$^{25}$R$^{25}$—, —CR$^{25}$R$^{25}$C(=N—OR$^{26}$)—, —O—CR$^{24}$R$^{24}$—, —CR$^{24}$R$^{24}$—O—, —O—, —NR$^{8}$—CR$^{24}$R$^{24}$—, —CHR$^{24}$—NR$^{15}$—, —S(O)$_p$—, —S(O)$_p$—CR$^{24}$R$^{24}$—, and —S(O)$_p$—NR$^{8}$—;

R$^1$ is selected from H, R$^6$, C$_{1-10}$ alkyl substituted with 0-3 R$^6$, C$_{2-6}$ alkenyl substituted with 0-3 R$^6$, C$_{2-6}$ alkynyl substituted with 0-3 R$^6$, C$_{6-10}$ aryl group substituted with 0-5 R$^6$, and a 5-10 membered heterocyclic system containing 1-4 heteroatoms selected from N, O, and S, substituted with 0-3 R$^6$;

with the proviso that if R$^1$ is H, then ring B is a cycloalkyl group of 3 to 8 carbon atoms wherein the cycloalkyl group is saturated or partially unsaturated and is substituted with at least one R$^5$ wherein R$^5$ is (CRR)$_r$NR$^{5a}$R$^{5a}$ and R$^{5a}$ is selected from H, methyl substituted with 0-1 R$^{5g}$, C$_{2-6}$ alkyl substituted with 0-2 R$^{5e}$, and a (CH$_2$)$_r$—C$_{3-10}$ carbocyclic residue substituted with 0-5 R$^{5e}$;

R$^2$ is selected from a C$_{6-10}$ aryl group substituted with 0-5 R$^7$ and a 5-10 membered heteroaryl system containing 1-4 heteroatoms selected from N, O, and S, substituted with 0-3 R$^7$;

R$^3$ is selected from H, methyl, and ethyl;

R$^4$ is selected from H, C$_{1-6}$ alkyl, C$_{3-8}$ alkenyl, C$_{3-8}$ alkynyl, (CRR)$_r$OH, (CRR)$_r$SH, (CRR)$_t$OR$^{4d}$, (CHR)$_r$SR$^{4d}$, (CRR)$_t$ NR$^{4a}$R$^{4a}$, (CRR)$_q$C(O)OH, (CRR)$_q$C(O)R$^{4b}$, (CRR)$_q$C(O)NR$^{4a}$R$^{4a}$, (CRR)$_r$OC(O)NR$^{4a}$R$^{4d}$, (CRR)$_t$ NR$^{4a}$C(O)OR$^{4d}$, (CRR)$_t$NR$^{4a}$C(O)R$^{4b}$, (CRR)$_q$C(O)OR$^{4d}$, (CRR)$_r$OC(O)R$^{4b}$, (CRR)$_q$S(O)$_p$R$^{4b}$, (CRR)$_q$S(O)$_2$NR$^{4a}$R$^{4a}$, (CRR)$_t$NR$^{4a}$S(O)$_2$R$^{4b}$, C$_{1-6}$ haloalkyl, a (CRR)$_r$— phenyl substituted with 0-3 R$^{4e}$, and a (CRR)$_r$-4-10 membered heterocyclic system containing 1-4 heteroatoms selected from N, O, and S, substituted with 0-2 R$^{4e}$;

R$^{4a}$, at each occurrence, is independently selected from H, methyl substituted with 0-1 R$^{4c}$, C$_{2-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, a (CH$_2$)$_r$—C$_{3-10}$ carbocyclic residue substituted with 0-4 R$^{4e}$, and a (CHR)$_r$-4-10 membered heterocyclic system containing 1-4 heteroatoms selected from N, O, and S, substituted with 0-2 R$^{4e}$;

R$^{4b}$, at each occurrence, is selected from H, C$_{1-6}$ alkyl substituted with 0-3 R$^{4e}$, C$_{1-6}$ haloalkyl, C$_{3-8}$ alkenyl substituted with 0-3 R$^{4e}$, C$_{3-8}$ alkynyl substituted with 0-3 R$^{4e}$, a (CH$_2$)$_r$—C$_{3-6}$ carbocyclic residue substituted with 0-2 R$^{4e}$, and a (CHR)$_r$-4-10 membered heterocyclic system containing 1-4 heteroatoms selected from N, O, and S, substituted with 0-2 R$^{4e}$;

R$^{4c}$ is independently selected from —C(O)R$^{4b}$, —C(O)OR$^{4d}$, —C(O)NR$^{4f}$R$^{4f}$, and (CH$_2$)$_r$phenyl;

R$^{4d}$, at each occurrence, is selected from methyl, CF$_3$, C$_{2-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, and a C$_{3-10}$ carbocyclic residue substituted with 0-3 R$^{4e}$;

R$^{4e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, —C(O)R$^{4i}$, —C(O)OR$^{4j}$, —C(O)NR$^{4h}$R$^{4h}$, —OC(O)NR$^{4h}$R$^{4h}$, —NR$^{4h}$C(O)NR$^{4h}$R$^{4h}$, —NR$^{4h}$C(O)OR$^{4j}$, C(O)OH, (CH$_2$)$_r$C(O)NHSO$_2$—R$^{4k}$, NHSO$_2$R$^{4k}$, (CH$_2$)$_r$tetrazolyl, and (CH$_2$)$_r$phenyl;

R$^{4f}$, at each occurrence, is selected from H, C$_{1-6}$ alkyl, C$_{3-6}$ cycloalkyl, and phenyl;

R$^{4h}$, at each occurrence, is independently selected from H, C$_{1-6}$ alkyl, C$_{3-8}$ alkenyl, C$_{3-8}$ alkynyl, and a (CH$_2$)$_r$—C$_{3-10}$ carbocyclic;

R$^{4i}$, at each occurrence, is selected from H, C$_{1-6}$ alkyl, C$_{3-8}$ alkenyl, C$_{3-8}$ alkynyl, and a (CH$_2$)$_r$—C$_{3-6}$ carbocyclic residue;

R$^{4j}$, at each occurrence, is selected from CF$_3$, C$_{1-6}$ alkyl, C$_{3-8}$ alkenyl, C$_{3-8}$ alkynyl, and a C$_{3-10}$ carbocyclic residue;

R$^{4k}$, at each occurrence, is selected from C$_{1-5}$ alkyl, C$_{1-5}$ haloalkyl, and C$_{3-6}$ cycloalkyl, and phenyl;

R$^5$, at each occurrence, is independently selected from F, (CRR)$_r$OR$^{5d}$, (CRR)$_r$SR$^{5d}$, (CRR)$_r$NR$^{5a}$R$^{5a}$, (CRR)$_r$S(O)$_p$R$^{5b}$, and a (CRR)$_r$-4-10 membered heterocyclic system containing 1-4 heteroatoms selected from N, O, and S, substituted with 0-2 R$^{5c}$;

R$^{5'}$, at each occurrence, is independently selected from H, =O, C$_{1-6}$ alkyl, C$_{2-8}$ alkenyl, C$_{2-8}$ alkynyl, F, Cl, Br, I, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$N(O)R$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$NR$^{5a}$C(S)R$^{5b}$, (CRR)$_r$OC(O)NR$^{5a}$R$^{5a}$, (CRR)$_r$NR$^{5a}$C(O)OR$^{5d}$, (CRR)$_r$NR$^{5a}$C(O)NR$^{5a}$R$^{5a}$, (CRR)$_r$NR$^{5a}$C(O)H, (CRR)$_r$C(O)OR$^{5d}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, (CRR)$_r$NR$^{5a}$S(O)$_2$NR$^{5a}$R$^{5a}$, (CRR)$_r$NHC(=NR$^{5f}$)NR$^{5f}$R$^{5f}$, C$_{1-6}$ haloalkyl, a (CRR)$_r$—C$_{3-0}$ carbocyclic residue substituted with 0-3 R$^{5c}$, and a (CRR)$_r$-4-10 membered heterocyclic system containing 1-4 heteroatoms selected from N, O, and S, substituted with 0-2 R$^{5c}$;

R$^{5a}$, at each occurrence, is independently selected from H, methyl substituted with 0-1 R$^{5g}$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-10}$ carbocyclic residue substituted with 0-5 R$^{5e}$, C$_{2-6}$ haloalkyl, and a (CH$_2$)$_r$-5-10 membered heterocyclic system containing 1-4 heteroatoms selected from N, O, and S, substituted with 0-3 R$^{5e}$;

wherein when R$^{5'}$ is (CRR)$_r$N(O)R$^{5a}$R$^{5a}$, neither R$^{5a}$ are H;

R$^{5b}$, at each occurrence, is selected from C$_{1-6}$ alkyl substituted with 0-3 R$^{5e}$, C$_{1-6}$ haloalkyl, C$_{3-8}$ alkenyl substituted with 0-2 R$^{5e}$, C$_{3-8}$ alkynyl substituted with 0-2 R$^{5e}$, a (CH$_2$)$_r$—C$_{3-6}$ carbocyclic residue substituted with 0-2 R$^{5e}$, and a (CH$_2$)$_r$-5-6 membered heterocyclic system containing 1-4 heteroatoms selected from N, O, and S, substituted with 0-3 R$^{5e}$;

R$^{5c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{5f}$R$^{5f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{5b}$, (CH$_2$)$_r$C(O)NR$^{5f}$R$^{5f}$, (CH$_2$)$_r$OC(O)NR$^{5f}$R$^{5f}$, (CH$_2$)$_r$NR$^{5f}$C(O)R$^{5b}$, (CH$_2$)$_r$C(O)OC$_{1-4}$ alkyl, (CH$_2$)$_r$NR$^5$C(O)OC$_{1-4}$ alkyl, (CH$_2$)$_r$OC(O)R$^{5b}$, (CH$_2$)$_r$C(=NR$^{5f}$)NR$^{5f}$R$^{5f}$, (CH$_2$)$_r$S(O)$_p$R$^{5b}$, (CH$_2$)$_r$NHC(=NR$^{5f}$)NR$^{5f}$R$^{5f}$, (CH$_2$)$_r$S(O)$_2$NR$^{5f}$R$^{5f}$, (CH$_2$)$_r$NR$^{5f}$S(O)$_2$R$^{5b}$, and (CH$_2$)$_r$phenyl substituted with 0-3 R$^{5e}$;

R$^{5d}$, at each occurrence, is selected from methyl, CF$_3$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, and a C$_{3-10}$ carbocyclic residue substituted with 0-3 R$^{5e}$;

R$^{5e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{5f}$R$^{5f}$, (CH$_2$)$_r$C(O)NHR$^{5h}$, (CH$_2$)$_r$OC(O)NHR$^{5h}$, (CH$_2$)$_r$OH, (CH$_2$)$_r$C(O)OH, (CH$_2$)$_r$C(O)OR$^{5h}$, (CH$_2$)$_r$C(O)NHSO$_2$—R$^5$h, NHSO$_2$R$^{5h}$, a (CH$_2$)$_r$-5-6 membered heterocyclic system containing 1-4 heteroatoms selected from N, O, and S, and (CH$_2$)$_r$phenyl;

R$^{5f}$, at each occurrence, is selected from H, C$_{1-6}$ alkyl, and C$_{3-6}$ cycloalkyl;

$R_{5g}$ is independently selected from —CN, —C(O)$R^{5b}$, —C(O)O$R^{5d}$, —C(O)NR$^{5f}$R$^{5f}$, —C(O)OH, (CH$_2$)$_r$C(O)NHSO$_2$—R$^{5h}$, and (CH$_2$)$_r$phenyl;

$R^{5h}$, at each occurrence, is selected from C$_{1-5}$ alkyl, C$_{1-5}$ haloalkyl, and C$_{3-6}$ cycloalkyl, and phenyl;

R, at each occurrence, is selected from H, C$_{1-6}$ alkyl substituted with R$^{5e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{5e}$;

$R^6$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{6a}$R$^{6a'}$, (CR'R')$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$SC(O) (CR'R')$_r$R$^{6b}$, (CR' R')$_r$C(O)OH, (CR'R')$_r$C(O)(CR'R')$_r$R$^{6b}$, (CR'R')$_r$C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$OC(O)(CR'R')$_r$R$^{6b}$, (CR'R')$_r$OC(O)NR$^{6a}$(CR'R')$_r$R$^{6d}$, (CR'R')$_r$NR$^{6a}$C(O)NR$^{6a}$R$^{6d'}$, (CR'R')$_r$NR$^{6a}$C(S)NR$^{6a}$(CR'R')$_r$R$^{6d}$, (CR'R')$_r$NR$^{6f}$C(O)O(CR'R')$_r$R$^{6b}$, (CR'R')$_r$C(=NR$^{6f}$)NR$^{6a}$R$^{6a}$, (CR'R')$_r$NHC(=NR$^{6f}$)NR$^{6f}$R$^{6f}$, (CR'R')$_r$S(O)$_p$R$^{6b'}$, (CR'R')$_r$S(O)$_2$NR$^{6a}$R$^{6a}$, (CR'R')$_r$NR$^{6f}$S(O)$_p$NR$^{6a}$R$^{6a'}$, (CR'R')$_r$NR$^{6f}$S(O)$_2$(CR'R')$_r$R$^{6b}$, C$_{1-6}$ haloalkyl, C$_{2-8}$ alkenyl substituted with 0-3 R', C$_{2-8}$ alkynyl substituted with 0-3 R', (CR'R')$_r$phenyl substituted with 0-3 R$^{6e}$, and a (CH$_2$)$_r$-5-6 membered heterocyclic system containing 1-2 heteroatoms selected from N, O, and S, substituted with 0-2 R$^{6e}$;

alternatively, two R$^6$ on adjacent atoms on R$^1$ may join to form a cyclic acetal;

$R^{6a}$, at each occurrence, is selected from H, methyl substituted with 0-1 R$^{6g}$, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$—C$_{3-10}$ carbocyclic residue substituted with 0-5 R$^{6e}$, and a (CH$_2$)$_r$-5-10 membered heterocyclic system containing 1-4 heteroatoms selected from N, O, and S, substituted with 0-2 R$^{6e}$;

alternatively, two R$^{6a}$, together with the N to which they are attached, join to form a 3-8 membered heterocycle containing 0-1 additional heteroatoms selected from N, O, and S;

$R^{6a'}$, at each occurrence, is selected from H, C$_{1-6}$ alkyl, and C$_{3-6}$ cycloalkyl;

$R^{6b}$, at each occurrence, is selected from H, C$_{1-6}$ alkyl substituted with 0-3 R$^{6e}$, C$_{1-6}$ haloalkyl, C$_{3-8}$ alkenyl substituted with 0-2 R$^{6e}$, C$_{3-8}$ alkynyl substituted with 0-2 R$^{6e}$, a (CH$_2$)$_r$C$_{3-6}$ carbocyclic residue substituted with 0-3 R$^{6e}$, and a (CH$_2$)$_r$-5-6 membered heterocyclic system containing 1-4 heteroatoms selected from N, O, and S, substituted with 0-2 R$^{6e}$;

$R^{6b'}$, at each occurrence, is selected from H, C$_{1-6}$ alkyl, and C$_{3-6}$ cycloalkyl;

$R^{6d}$, at each occurrence, is selected from C$_{3-8}$ alkenyl substituted with 0-2 R$^{6e}$, C$_{3-8}$ alkynyl substituted with 0-2 R$^{6e}$, methyl, CF$_3$, C$_{2-6}$ alkyl substituted with 0-3 R$^{6e}$, C$_{2-4}$ haloalkyl, a (CH$_2$)$_r$—C$_{3-10}$ carbocyclic residue substituted with 0-3 R$^{6e}$, and a (CH$_2$)$_r$-5-6 membered heterocyclic system containing 1-4 heteroatoms selected from N, O, and S, substituted with 0-3 R$^{6e}$;

$R^{6d'}$, at each occurrence, is selected from H, CF$_3$ and C$_{1-6}$ alkyl and C$_{3-6}$ cycloalkyl;

$R^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, C(O)NHR$^{6h}$, C(O)NHR$^{6h}$, (CH$_2$)$_r$OH, C(O)OH, C(O)OC$_{1-5}$ alkyl, (CH$_2$)$_r$C(O)NHSO$_2$—R$^{6h}$, NHSO$_2$R$^{6h}$, (CH$_2$)$_r$tetrazolyl,and (CH$_2$)$_r$phenyl and a (CH$_2$)$_r$-5-6 membered heterocyclic system containing 1-4 heteroatoms selected from N, O, and S;

$R^{6f}$, at each occurrence, is selected from H, C$_{1-5}$ alkyl, and C$_{3-6}$ cycloalkyl, and phenyl;

$R^{6g}$ is independently selected from —C(O)R$^{6b}$, —C(O)OR$^{6d}$, —C(O)NR$^{6f}$R$^{6f}$, (CH$_2$)$_r$OH, C(O)OH, (CH$_2$)$_r$C(O)NHSO$_2$—R$^{6h}$, NHSO$_2$R$^{6h}$, (CH$_2$)$_r$tetrazolyl,and (CH$_2$)$_r$phenyl;

$R^{6h}$, at each occurrence, is selected from C$_{1-5}$ alkyl, C$_{1-5}$ haloalkyl, and C$_{3-6}$ cycloalkyl, and phenyl, and phenyl further substituted with 1-2 of C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, or (CH$_2$)$_r$NR$^{6f}$R$^{6f}$;

$R^7$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CR'R')$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O) (CR'R')$_r$R$^{7b}$, (CR'R')$_r$C(O)NR$^{7a}$R$^{7a}$, (CR'R')$_r$NR$^{7f}$C(O) (CR'R')$_r$R$^{7b}$, (CR'R')$_r$C(O)O(CR'R')$_r$R$^{7d}$, (CR'R')$_r$OC(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7d}$, (CR'R')$_r$C(=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, (CR'R')$_r$C(O)NHSO$_2$R$^{7b}$, C$_{1-6}$ haloalkyl, C$_{2-8}$ alkenyl substituted with 0-3 R', C$_{2-8}$ alkynyl substituted with 0-3 R', and (CR'R')$_r$phenyl substituted with 0-3 R$^{7e}$, and a (CH$_2$)$_r$-5-6 membered heterocyclic system containing 1-4 heteroatoms selected from N, O, and S, substituted with 0-3 R$^{7e}$;

alternatively, two R$^7$ on adjacent atoms on R$^2$ may join to form a cyclic acetal;

$R^{7a}$, at each occurrence, is independently selected from H, methyl substituted with 0-1 R$^{7g}$, C$_{2-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$—C$_{3-10}$ carbocyclic residue substituted with 0-5 R$^{7e}$, and a (CH$_2$)$_r$-5-10 membered heterocyclic system containing 1-4 heteroatoms selected from N, O, and S, substituted with 0-2 R$^{7e}$;

$R^{7b}$, at each occurrence, is selected from C$_{1-6}$ alkyl substituted with 0-3 R$^{7e}$, C$_{1-6}$ haloalkyl, C$_{3-8}$ alkenyl substituted with 0-2 R$^{7e}$, C$_{3-8}$ alkynyl substituted with 0-2 R$^{7e}$, a (CH$_2$)$_r$C$_{3-6}$ carbocyclic residue substituted with 0-3 R$^{7e}$, and a (CH$_2$)$_r$-5-6 membered heterocyclic system containing 1-4 heteroatoms selected from N, O, and S, substituted with 0-2 R$^{7e}$;

$R^{7d}$, at each occurrence, is selected from C$_{3-8}$ alkenyl substituted with 0-2 R$^{7e}$, C$_{3-8}$ alkynyl substituted with 0-2 R$^{7e}$, methyl, CF$_3$, C$_{2-4}$ haloalkyl, C$_{2-6}$ alkyl substituted with 0-3 R$^{7e}$, a (CH$_2$)$_r$—C$_{3-10}$ carbocyclic residue substituted with 0-3 R$^{7e}$, and a (CH$_2$)$_r$-5-6 membered heterocyclic system containing 1-4 heteroatoms selected from N, O, and S, substituted with 0-3 R$^{7e}$;

$R^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, OH, SH, C(O)OH, C(O)NHR$^{7h}$, C(O)OC$_{1-5}$ alkyl, (CH$_2$)$_r$SC$_{1-5}$ alkyl, (CH$_2$)$_r$NR$^{7f}$R$^{7f}$, (CH$_2$)$_r$C(O)NHSO$_2$—R$^{7h}$, NHSO$_2$R$^{7h}$, and (CH$_2$)$_r$phenyl, (CH$_2$)$_r$tetrazolyl;

$R^{7f}$, at each occurrence, is selected from H, C$_{1-5}$ alkyl, and C$_{3-6}$ cycloalkyl, and phenyl;

$R^{7g}$ is independently selected from —C(O)R$^{7b}$, —C(O)OR$^{7d}$, —C(O)NR$^{7f}$R$^{7f}$, and (CH$_2$)$_r$phenyl;

$R^{7h}$, at each occurrence, is selected from $C_{1-5}$ alkyl, $C_{1-5}$ haloalkyl, and $C_{3-6}$ cycloalkyl, and phenyl;

R', at each occurrence, is independently, selected from H, $C_{1-6}$ alkyl substituted with $R^{6e}$, $C_{2-8}$ alkenyl, $C_{2-8}$ alkynyl, $(CH_2)_r C_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^{10}$ and $R^{10a}$ are independently selected from H, and $C_{1-4}$alkyl substituted with 0-1 $R^{10b}$, alternatively, $R^{10}$ and $R^{10a}$ can join to form a $C_{3-6}$ cycloalkyl;

$R^{10b}$, at each occurrence, is independently selected from —OH, —SH, $NR^{10c}R^{10c}$, —$C(O)NR^{10c}R^{10c}$, and —NHC$(O)R^{10c}$;

$R^{10c}$ is selected from H, $C_{1-4}$ alkyl and $C_{3-6}$ cycloalkyl;

$R^{11}$ is selected from H, $C_{1-4}$ alkyl, $(CHR)_q OH$, $(CHR)_q SH$, $(CHR)_q OR^{11d}$, $(CHR)_q S(O)_p R^{11d}$, $(CHR)_r C(O)R^{11b}$, $(CHR)_r NR^{11a}R^{11a}$, $(CHR)_r C(O)NR^{11a}R^{11a}$, $(CHR)_r C(O)$ $NR^{11a}OR^{11d}$, $(CHR)_q NR^{11a}C(O)R^{11b}$, $(CHR)_q NR^{11a}C(O)OR^{11d}$, $(CHR)_q OC(O)NR^{11a}R^{11a}$, $(CHR)_r C(O)OR^{11d}$, a $(CHR)_r$—$C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_r C_{3-6}$ cycloalkyl, a $(CH_2)_r$—$C_{3-6}$-cycloalkyl substituted with 0-5 $R^{11e}$, and a $(CH_2)_r$-5-6 membered nonaromatic heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ cycloalkyl substituted with 0-2 $R^{11e}$, and a $(CH_2)_r$-5-6 membered nonaromatic heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ cycloalkyl substituted with 0-3 $R^{11e}$, and a $(CH_2)_r$-5-6 membered nonaromatic heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, —O—$C_{1-6}$ alkyl, SH, $(CH_2)_r SC_{1-5}$ alkyl, $(CH_2)_r NR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, and a $(CHR)_r$—$C_{3-6}$ carbocyclic residue substituted with 0-5 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, —O—$C_{1-6}$ alkyl, SH, $(CH_2)_r SC_{1-5}$ alkyl, $(CH_2)_r NR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{15}$ is independently selected from H, $C_{1-4}$ alkyl, and $C_{3-4}$ cycloalkyl;

$R^{24}$, at each occurrence, is independently selected from H and $C_{1-4}$alkyl;

alternatively, two $R^{24}$s, along with the carbon atom to which they are attached, join to form a $C_{3-6}$ carbocyclic ring;

$R^{25}$, at each occurrence, is independently selected from H, $C_{1-4}$alkyl, OH, $NH_2$, —O—$C_{1-4}$ alkyl, $NR^{25a}R^{25a}$, $C(O)$ $NR^{25a}R^{25a}$, $NR^{25a}C(O)R^{25b}$, $NR^{25a}C(O)OR^{25d}$, $OC(O)$ $NR^{25a}R^{25a}$, and $(CHR)_r C(O)OR^{25d}$;

alternatively, two $R^{25}$s, along with the carbon atom or atoms to which they are attached, join to form a $C_{3-6}$ carbocyclic ring;

$R^{25a}$, at each occurrence, is independently seleced from H, and $C_{1-4}$ alkyl, $R^{25b}$, at each occurrence, is independently selected from H, $C_{1-4}$ alkyl, $C_{3-6}$ alkenyl, and $C_{3-6}$ alkynyl;

$R^{25d}$, at each occurrence, is independently selected from $C_{1-4}$ alkyl, $C_{3-6}$ alkenyl, and $C_{3-6}$ alkynyl;

$R^{26}$ is selected from $C_{1-4}$ alkyl;

n is selected from 1 and 2;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4; and t, at each occurrence, is independently selected from 2, 3, and 4, and u is selected from 1, 2 and 3;

with the proviso that the compound is not

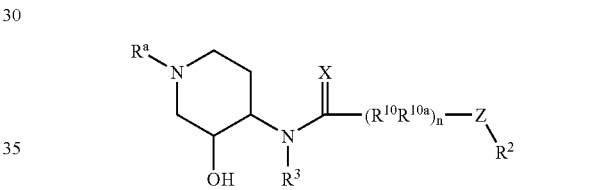

wherein $R^a$ is $C_{1-6}$ alkyl or $(CRR)_t NR^{4a}C(O)OR^{4d}$.

In another embodiment, the present invention provides novel compounds of formula (I):

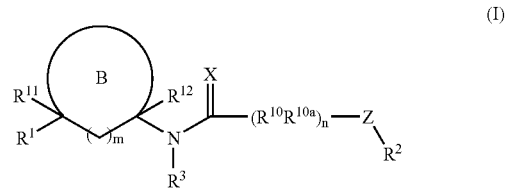

(I)

or a stereoisomer or a pharmaceutically acceptable salt thereof, wherein:

ring B is a cycloalkyl group of 3 to 8 carbon atoms wherein the cycloalkyl group is saturated or partially unsaturated; or a heterocycle of 3 to 7 atoms wherein the heterocycle is saturated or partially unsaturated, the heterocycle containing a heteroatom selected from —O—, —S—, —S(=O)—, —S(=O)$_2$—, and —N($R^4$)—, the heterocycle optionally containing a —C(O)—; ring B being substituted with 1-2 $R^5$;

X is selected from O or S;

Z is selected from a bond, —C(O)—, —C(O)$NR^8$—, —$NR^8$—, —$NR^8$—$CR^{14}R^{14}$—, —$NR^8C(O)$—, —$NR^8C$ (O)NH—, —$NR^8C(S)NH$—, —$NR^8SO_2$—, and —$NR^8SO_2NH$—, —$OC(O)NR^8$—, —$NR^8C(O)O$—, —$(CR^{25}R^{25})_r$—, —$CR^{24}$=$CR^{24}$—, —$CR^{25}R^{25}C(O)$—, —$C(O)CR^{25}R^{25}$—, —$CR^{25}R^{25}C(=N-OR^{26})$—, —$O$—$CR^{24}R^{24}$—, —$CR^{24}R^{24}$—$O$—, —$O$—, —$NR^{8}$—$CR^{24}R^{24}$—, —$CHR^{24}$—$NR^{15}$—, —$S(O)_p$—, —$S(O)_p$—$CR^{24}R^{24}$—, and —$S(O)_p$—$NR^{8}$—;

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, and a 5-10 membered heteroaryl system containing 1-4 heteroatoms selected from N, O, and S, substituted with 0-3 $R^6$;

with the proviso that $R^1$ is not —$CH_2S(O)_p$—$R^{1a}$, —$CH_2S(O)_2$—$R^{1a}$, —$NHC(O)$—$R^{1a}$, —$NHC(O)NH$—$R^{1a}$, —$NHCH_2$—$R^{1a}$, —$SO_2NH$—$R^{1a}$, —$NHSO_2NH$—$R^{1a}$, when $R^{1a}$ is equal to aryl or heteraryl; (with the proviso that the compounds of the present invention are not those as defined in U.S. patent application Ser. No. 10/027,644, filed Dec. 20, 2001, U.S. patent application Ser. No. 10/383,391, filed Mar. 7, 2003, U.S. Provisional Patent Application 60/446,850, filed Feb. 2, 2002, and U.S. Provisional Patent Application 60/467,003, filed May 1, 2003;

$R^2$ is selected from a $C_{6-10}$ aryl group substituted with 0-5 $R^7$ and a 5-10 membered heteroaryl system containing 1-4 heteroatoms selected from N, O, and S, substituted with 0-3 $R^7$;

$R^3$ is selected from H, methyl, and ethyl;

$R^4$ is selected from H, $C_{1-6}$ alkyl, $C_{3-8}$ alkenyl, $C_{3-8}$ alkynyl, $(CRR)_tOH$, $(CRR)_tSH$, $(CRR)_tOR^{4d}$, $(CHR)_tSR^{4d}$, $(CRR)_t NR^{4a}R^{4a}$, $(CRR)_qC(O)OH$, $(CRR)_rC(O)R^{4b}$, $(CRR)_rC(O)NR^{4a}R^{4a}$, $(CRR)_rOC(O)NR^{4a}R^{4a}$, $(CRR)_t NR^{4a}C(O)OR^{4d}$, $(CRR)_rNR^{4a}C(O)R^{4b}$, $(CRR)_rC(O)OR^{4d}$, $(CRR)_t OC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$, $C_{1-6}$ haloalkyl, a $(CRR)_r$—$C_{3-10}$ carbocyclic residue substituted with 0-3 $R^{4e}$, and a $(CHR)_r$-4-10 membered heterocyclic system containing 1-4 heteroatoms selected from N, O, and S, substituted with 0-2 $R^{4e}$;

$R^{4a}$, at each occurrence, is independently selected from H, methyl substituted with 0-1 $R^{4c}$, $C_{2-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, a $(CH_2)_r$—$C_{3-10}$ carbocyclic residue substituted with 0-4 $R^{4e}$, and a $(CHR)_r$-4-10 membered heterocyclic system containing 1-4 heteroatoms selected from N, O, and S, substituted with 0-2 $R^{4e}$;

$R^{4b}$, at each occurrence, is selected from H, $C_{1-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, a $(CH_2)_r$—$C_{3-6}$ carbocyclic residue substituted with 0-2 $R^{4e}$, and a $(CHR)_r$ -4-10 membered heterocyclic system containing 1-4 heteroatoms selected from N, O, and S, substituted with 0-2 $R^{4e}$;

$R^{4c}$ is independently selected from —$C(O)R^{4b}$, —$C(O)OR^{4d}$, —$C(O)NR^{4f}R^{4f}$, and $(CH_2)_r$phenyl;

$R^{4d}$, at each occurrence, is selected from methyl, $CF_3$, $C_{2-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, and a $C_{3-10}$ carbocyclic residue substituted with 0-3 $R^{4e}$;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, —$C(O)R^{4i}$, —$C(O)OR^{4j}$, —$C(O)NR^{4h}R^{4h}$, —$OC(O)NR^{4h}R^{4h}$, —$NR^{4h}C(O)NR^{4h}R^{4h}$, —$NR^{4h}C(O)OR^{4j}$, and $(CH_2)_r$phenyl;

$R^{4f}$, at each occurrence, is selected from H, $C_{1-6}$ alkyl, $C_{3-6}$ cycloalkyl, and phenyl;

$R^{4h}$, at each occurrence, is independently selected from H, $C_{1-6}$ alkyl, $C_{3-8}$ alkenyl, $C_{3-8}$ alkynyl, and a $(CH_2)_r$—$C_{3-10}$ carbocyclic;

$R^{4i}$, at each occurrence, is selected from H, $C_{1-6}$ alkyl, $C_{3-8}$ alkenyl, $C_{3-8}$ alkynyl, and a $(CH_2)_r$—$C_{3-6}$ carbocyclic residue;

$R^{4j}$, at each occurrence, is selected from $CF_3$, $C_{1-6}$ alkyl, $C_{3-8}$ alkenyl, $C_{3-8}$ alkynyl, and a $C_{3-10}$ carbocyclic residue;

$R^5$, at each occurrence, is independently selected from H, =O, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rN(O)R^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_r NR^{5a}C(S)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5d}$, $(CRR)_rOC(O)R^{5b}$, $(CRR)_rS(O)_p R^{5b}$, $(CRR)_rS(O)_2NR^{5a}R^{5a}$, $(CRR)_rNR^{5a}S(O)_2R^{5b}$, $(CRR)_rNR^{5a}S(O)_2NR^{5a}R^{5a}$, $(CRR)_rNHC(=NR^{5f})NR^{5f}R^{5f}$, $C_{1-6}$ haloalkyl, a $(CRR)_r$—$C_{3-10}$ carbocyclic residue substituted with 0-3 $R^{5c}$, and a $(CRR)_r$-4-10 membered heterocyclic system containing 1-4 heteroatoms selected from N, O, and S, substituted with 0-2 $R^{5c}$;

$R^{5a}$, at each occurrence, is independently selected from H, methyl substituted with 0-1 $R^{5g}$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-10}$ carbocyclic residue substituted with 0-5 $R^{5e}$, $C_{2-6}$ haloalkyl, and a $(CH_2)_r$-5-10 membered heterocyclic system containing 1-4 heteroatoms selected from N, O, and S, substituted with 0-3 $R^{5e}$;

wherein when $R^5$ is $(CRR)_rN(O)R^{5a}R^{5a}$, neither $R^{5a}$ are H;

$R^{5b}$, at each occurrence, is selected from $C_{1-6}$ alkyl substituted with 0-3 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-6}$ carbocyclic residue substituted with 0-2 $R^{5e}$, and a $(CH_2)_r$-5-6 membered heterocyclic system containing 1-4 heteroatoms selected from N, O, and S, substituted with 0-3 $R^{5e}$;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)rOC(O)NR^{5f}R^{5f}$, $(CH_2)_rNR^{5f}C(O)R^{5b}$, $(CH_2)_rC(O)OC_{1-4}$ alkyl, $(CH_2)_rNR_5C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from —$C(O)R^{5b}$, —$C(O)OR^{5d}$, —$C(O)NR^{5f}R^{5f}$, and $(CH_2)_r$phenyl;

R, at each occurrence, is selected from H, $C_{1-6}$ alkyl substituted with $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{6a}R^{6a}$, $(CR'R')_rOH$, $(CR'R')_rO(CR'R')_rR^{6d}$, $(CR'R')_rSH$, $(CR'R')_rC(O)H$, $(CR'R')_rS$ (CR'R')$_r$R$^{6d}$, (CR'R')$_r$SC(O)(CR'R')$_r$R$^{6b}$, (CR'R')$_r$C(O) OH, (CR'R')$_r$C(O)(CRR')$_r$R$^{6b}$, (CR'R')$_r$NR$^{6a}$R$^{6a}$, (CR'R')$_r$ C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$OC(O)(CR'R')$_r$R$^{6b}$, (CR'R')$_r$OC(O)NR$^{6a}$(CR'R')$_r$R$^{6d}$, (CR'R')$_r$NR$^{6a}$C(O) NR$^{6a}$(CR'R')$_r$R$^{6d}$, (CR'R')$_r$NR$^{6a}$C(S)NR$^{6a}$(CR'R')$_r$R$^{6d}$, (CR'R')$_r$NR$^{6f}$C(O)O(CR'R')$_r$R$^{6b}$, (CR'R')$_r$C(=NR$^{6f}$) NR$^{6a}$R$^{6a}$, (CR'R')$_r$NHC(=NR$^{6f}$)NR$^{6f}$R$^{6f}$, (CR'R')$_r$S(O)$_p$ (CR'R')$_r$R$^{6b}$, (CR'R')$_r$S(O)$_2$NR$^{6a}$R$^{6a}$, (CR'R')$_r$NR$^{6f}$S(O)$_2$ NR$^{6a}$R$^{6a}$, (CR'R')$_r$NR$^{6f}$S(O)$_2$(CR'R')$_r$R$^{6b}$, C$_{1-6}$ haloalkyl, C$_{2-8}$ alkenyl substituted with 0-3 R', C$_{2-8}$ alkynyl substituted with 0-3 R', (CR'R')$_r$phenyl substituted with 0-3 R$^{6e}$, and a (CH$_2$)$_r$-5-$^6$ membered heterocyclic system containing 1-2 heteroatoms selected from N, O, and S, substituted with 0-2 R$^{6e}$;

alternatively, two R$^6$ on adjacent atoms on R$^1$ may join to form a cyclic acetal;

R$^{6a}$, at each occurrence, is selected from H, methyl substituted with 0-1 R$^{6g}$, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$—C$_{3-10}$ carbocyclic residue substituted with 0-5 R$^{6e}$, and a (CH$_2$)$_r$-5-10 membered heterocyclic system containing 1-4 heteroatoms selected from N, O, and S, substituted with 0-2 R$^{6e}$;

alternatively, two R$^{6a}$, together with the N to which they are attached, join to form a 3-8 membered heterocycle containing 0-1 additional heteroatoms selected from N, O, and S;

R$^{6b}$, at each occurrence, is selected from H, C$_{1-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$C$_{3-6}$ carbocyclic residue substituted with 0-3 R$^{6e}$, and a (CH$_2$)$_r$-5-6 membered heterocyclic system containing 1-4 heteroatoms selected from N, O, and S, substituted with 0-2 R$^{6e}$;

R$^{6d}$, at each occurrence, is selected from C$_{3-8}$ alkenyl substituted with 0-2 R$^{6e}$, C$_{3-8}$ alkynyl substituted with 0-2 R$^{6e}$, methyl, CF$_3$, C$_{2-6}$ alkyl substituted with 0-3 R$^{6e}$, C$_{2-4}$ haloalkyl, a (CH$_2$)$_r$—C$_{3-10}$ carbocyclic residue substituted with 0-3 R$^{6e}$, and a (CH$_2$)$_r$-5-6 membered heterocyclic system containing 1-4 heteroatoms selected from N, O, and S, substituted with 0-3 R$^{6e}$;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, C$_{1-5}$ alkyl, and C$_{3-6}$ cycloalkyl, and phenyl;

R$^{6g}$ is independently selected from —C(O)R$^{6b}$, —C(O) OR$^{6d}$, —C(O)NR$^{6f}$R$^{6f}$, and (CH$_2$)$_r$phenyl;

R$^7$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O (CR'R')$_r$R$^{7d}$, (CR'R')$_r$SH, (CR'R')$_r$C(O)H, (CR'R')$_r$S (CR'R')$_r$R$^{7d}$, (CR'R')$_r$C(O)OH, (CR'R')$_r$C(O)(CR'R')$_r$R$^{7b}$, (CR'R')$_r$C(O)NR$^{7a}$R$^{7a}$, (CR'R')$_r$NR$^{7f}$C(O) (CR'R')$_r$R$^{7b}$, (CR'R')$_r$C(O)O(CR'R)$_r$R$^{7d}$, (CR'R')$_r$OC(O)(CR'R')$_r$R$^{7b}$, (CR'R')$_r$OC(O)NR$^{7a}$(CR'R')$_r$R$^{7a}$, (CR'R')$_r$NR$^{7a}$C(O) NR$^{7a}$(CR'R')$_r$R$^{7a}$, (CR'R')$_r$NR$^{7f}$C(O)O(CR'R')$_r$R$^{7d}$, (CR'R')$_r$C(=NR$^{7f}$)NR$^{7a}$R$^{7a}$, (CR'R')$_r$NHC(=NR$^{7f}$) NR$^{7f}$R$^{7f}$, (CR'R')$_r$S(O)$_p$(CR'R')$_r$R$^{7b}$, (CR'R')$_r$S(O)$_2$ NR$^{7a}$R$^{7a}$, (CR'R')$_r$NR$^{7a}$S(O)$_2$NR$^{7a}$R$^{7a}$, (CR'R')$_r$NR$^{7f}$S (O)$_2$(CR'R')$_r$R$^{7b}$, C$_{1-6}$ haloalkyl, C$_{2-8}$ alkenyl substituted with 0-3 R', C$_{2-8}$ alkynyl substituted with 0-3 R', and (CR'R')$_r$phenyl substituted with 0-3 R$^{7e}$;

alternatively, two R$^7$ on adjacent atoms on R$^2$ may join to form a cyclic acetal;

R$^{7a}$, at each occurrence, is independently selected from H, methyl substituted with 0-1 R$^{7g}$, C$_{2-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$—C$_{3-10}$ carbocyclic residue substituted with 0-5 R$^{7e}$, and a (CH$_2$)$_r$-5-10 membered heterocyclic system containing 1-4 heteroatoms selected from N, O, and S, substituted with 0-2 R$^{7e}$;

R$^{7b}$, at each occurrence, is selected from C$_{1-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$C$_3$-6 carbocyclic residue substituted with 0-3 R$^{7e}$, and a (CH$_2$)$_r$-5-6 membered heterocyclic system containing 1-4 heteroatoms selected from N, O, and S, substituted with 0-2 R$^{7e}$;

R$^{7d}$, at each occurrence, is selected from C$_{3-8}$ alkenyl substituted with 0-2 R$^{7e}$, C$_{3-8}$ alkynyl substituted with 0-2 R$^{7e}$, methyl, CF$_3$, C$_{2-4}$ haloalkyl, C$_{2-6}$ alkyl substituted with 0-3 R$^{7e}$, a (CH$_2$)$_r$—C$_{3-10}$ carbocyclic residue substituted with 0-3 R$^{7e}$, and a (CH$_2$)$_r$-5-6 membered heterocyclic system containing 1-4 heteroatoms selected from N, O, and S, substituted with 0-3 R$^{7e}$;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, C(O) OC$_{1-5}$ alkyl, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, C$_{1-5}$ alkyl, and C$_{3-6}$ cycloalkyl, and phenyl;

R$^{7g}$ is independently selected from —C(O)R$^{7b}$, —C(O) OR$^{7d}$, —C(O)NR$^{7f}$R$^{7f}$, and (CH$_2$)$_r$phenyl;

R', at each occurrence, is independently selected from H, C$_{1-6}$ alkyl substituted with R$^{6e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{6e}$;

R$^8$ is selected from H, C$_{1-4}$ alkyl, and C$_{3-4}$ cycloalkyl;

R$^{10}$ and R$^{10a}$ are independently selected from H, and C$_{1-4}$alkyl substituted with 0-1 R$^{10b}$, alternatively, R$^{10}$ and R$^{10a}$ can join to form a C$_{3-6}$ cycloalkyl;

R$^{10b}$, at each occurrence, is independently selected from —OH, —SH, NR$^{10c}$R$^{10c}$, —C(O)NR$^{10c}$R$^{10c}$, and —NHC (O) R$^{10c}$;

R$^{10c}$ is selected from H, C$_{1-4}$ alkyl and C$_{3-6}$ cycloalkyl;

R$^{11}$ is selected from H, C$_{1-4}$ alkyl, (CHR)$_q$OH, (CHR)$_q$SH, (CHR)$_q$OR$^{11d}$, (CHR)$_q$S(O)$_p$R$^{11d}$, (CHR)$_r$C(O)R$^{11b}$, (CHR)$_r$NR$^{11a}$R$^{11a}$, (CHR)$_r$C(O)NR$^{11a}$R$^{11a}$, (CHR)$_r$C(O) NR$^{11a}$OR$^{11d}$, (CHR)$_q$NR$^{11a}$C(O)R$^{11b}$, (CHR)$_q$NR$^{11a}$C (O)OR$^{11d}$, (CHR)$_q$OC(O)NR$^{11a}$R$^{11a}$, (CHR)$_r$C(O)OR$^{11d}$, a (CHR)$_r$—C$_{3-6}$ carbocyclic residue substituted with 0-5 R$^{11e}$, and a (CHR)$_r$-5-10 membered heterocyclic system containing 1-4 heteroatoms selected from N, O, and S, substituted with 0-3 R$^{11e}$;

R$^{11a}$, at each occurrence, is independently selected from H, C$_{1-4}$ alkyl, C$_{3-4}$ alkenyl, C$_{3-4}$ alkynyl, (CH$_2$)$_r$C$_{3-6}$ cycloalkyl, a (CH$_2$)$_r$—C$_{3-6}$ carbocyclic residue substituted with 0-5 R$^{11e}$, and a (CH$_2$)$_r$-5-$^6$ membered heterocyclic system containing 1-4 heteroatoms selected from N, O, and S, substituted with 0-3 R$^{11e}$;

R$^{11b}$, at each occurrence, is independently selected from C$_{1-4}$ alkyl, C$_{2-4}$ alkenyl, C$_{2-4}$ alkynyl, a (CH$_2$)$_r$—C$_{3-6}$ carbocyclic residue substituted with 0-2 R$^{11e}$, and a (CH$_2$)$_r$—5-6 membered heterocyclic system containing 1-4 heteroatoms selected from N, O, and S, substituted with 0-3 R$^{11e}$;

R$^{11d}$, at each occurrence, is independently selected from H, methyl, —CF$_3$, C$_{2-4}$ alkyl, C$_{3-6}$ alkenyl, C$_{3-6}$ alkynyl, a $C_{3-6}$ carbocyclic residue substituted with 0-3 $R^{11e}$, and a $(CH_2)_r$-5-6 membered heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, $(CHR)_qOH$, $(CHR)_qSH$, $(CHR)_qOR^{12d}$, $(CHR)_qS(O)_pR^{12d}$, $(CHR)_rC(O)R^{12b}$, $(CHR)_rNR^{12a}R^{12a}$, $(CHR)_rC(O)NR^{12a}R^{12a}$, $(CHR)_rC(O)NR^{12a}OR^{12d}$, $(CHR)_qNR^{12a}C(O) R_{12b}$, $(CHR)_qNR^{12a}C(O)OR^{12d}$, $(CHR)_qOC(O)NR^{12a}R^{12a}$, $(CHR)_rC(O)OR^{12d}$, a $(CHR)_r$—$C_{3-6}$ carbocyclic residue substituted with 0-5 $R^{12e}$, and a $(CHR)_r$-5-10 membered heterocyclic system containing 1-4 heteroatoms selected from N, O, and S, substituted with 0-3 $R^{12e}$;

$R^{12a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0-5 $R^{12e}$, and a $(CH_2)_r$-5-6 membered heterocyclic system containing 1-4 heteroatoms selected from N, O, and S, substituted with 0-3 $R^{12e}$;

$R^{12b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0-2 $R^{12e}$, and a $(CH_2)_r$-5-6 membered heterocyclic system containing 1-4 heteroatoms selected from N, O, and S, substituted with 0-3 $R^{12e}$;

$R^{12d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0-3 $R^{12e}$, and a $(CH_2)_r$-5-6 membered heterocyclic system containing 1-4 heteroatoms selected from N, O, and S, substituted with 0-3 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{24}$, at each occurrence, is independently selected from H and $C_{1-4}$alkyl;

alternatively, two $R^{24}$s, along with the carbon atom to which they are attached, join to form a $C_{3-6}$ carbocyclic ring;

$R^{25}$, at each occurrence, is independently selected from H, $C_{1-4}$alkyl, OH, $NH_2$, —O—$C_{1-4}$ alkyl, $NR^{25a}R^{25a}$, $C(O)NR^{25a}R^{25a}$, $NR^{25a}C(O)R^{25b}$, $NR^{25a}C(O)OR^{25d}$, $OC(O)NR^{25a}R^{25a}$, and $(CHR)_rC(O)OR^{25d}$;

alternatively, two $R^{25}$s, along with the carbon atom or atoms to which they are attached, join to form a $C_{3-6}$ carbocyclic ring;

$R^{25a}$, at each occurrence, is independently seleced from H, and $C_{1-4}$ alkyl, $R^{25b}$, at each occurrence, is independently selected from H, $C_{1-4}$ alkyl, $C_{3-6}$ alkenyl, and $C_{3-6}$ alkynyl;

$R^{25d}$, at each occurrence, is independently selected from $C_{1-4}$ alkyl, $C_{3-6}$ alkenyl, and $C_{3-6}$ alkynyl;

$R^{26}$ is selected from $C_{1-4}$ alkyl;

n is selected from 1 and 2;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4; and t, at each occurrence, is independently selected from 2, 3, and 4, and u is selected from 1, 2 and 3.

Thus, in a another embodiment, the present invention provides novel compounds of formula (I):

m is 0.

In another embodiment, the present invention provides novel compound of formula (I), wherein:

ring B is selected from

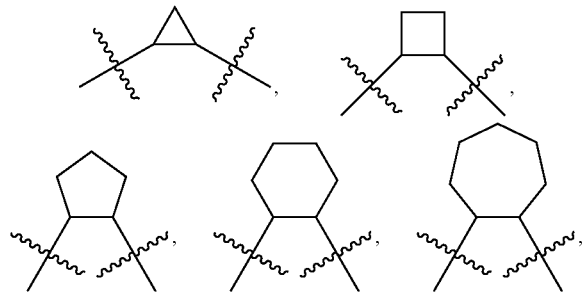

and being substituted with 1-2 $R^5$ and further substituted with 0-1 $R^{5'}$;

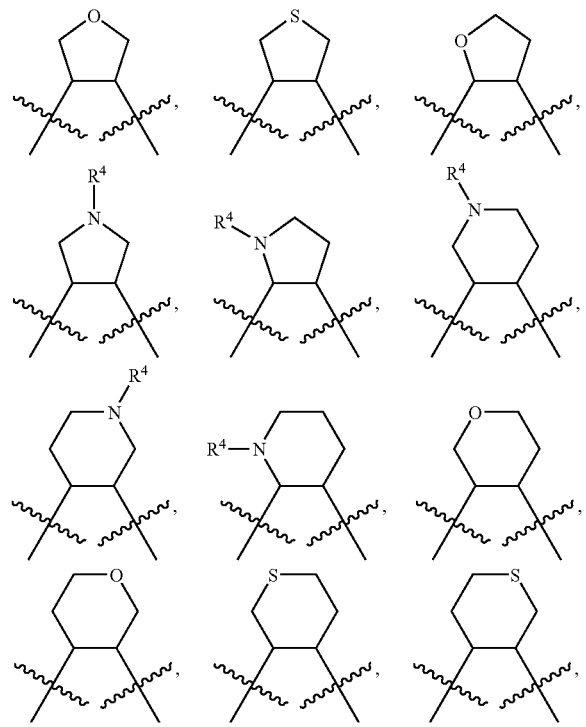

-continued

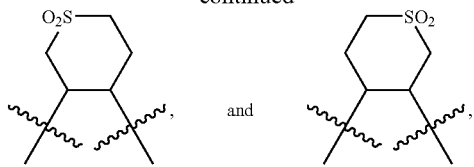

and being substituted with 0-2 $R^5$ and further substituted with 0-1 $R^{5'}$; and
$R^{11}$ and $R^{12}$ are H.

In another embodiment, the present invention provides novel compounds of formula (I), wherein:
ring B is selected from

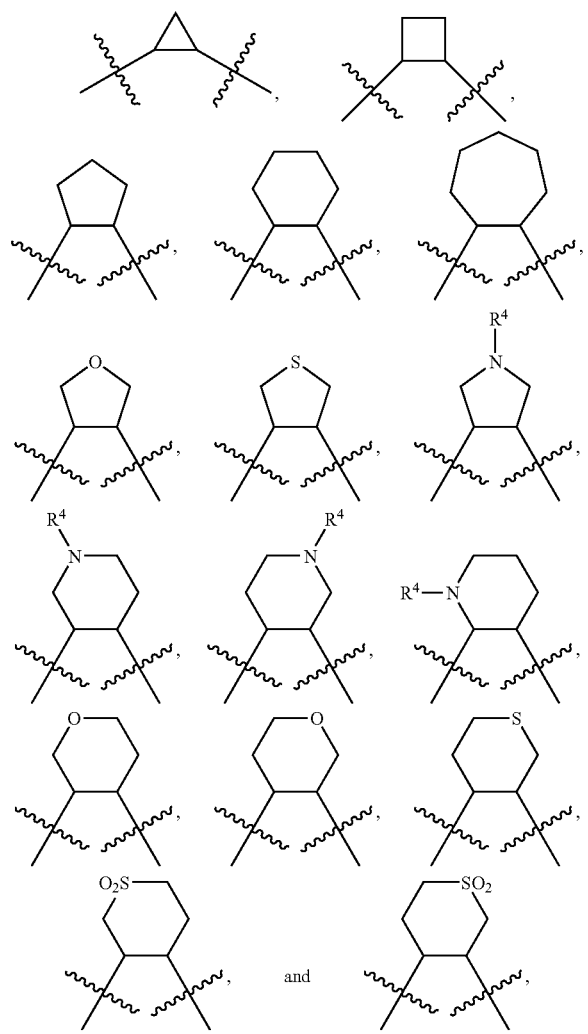

ring B being optionally substituted with 0-1 $R^5$; and
$R^{11}$ and $R^{12}$ are H.

In another embodiment, the present invention provides novel compounds of formula (I), wherein:
$R^5$, at each occurrence, is independently selected from F, $(CRR)_rOR^{5d}$, $(CRR)_rSR^{5d}$, $(CRR)_rNR^{5a}R^{5a}$, and a $(CRR)_r$ -4-10 membered heterocyclic system containing 1-4 heteroatoms selected from N, O, and S, substituted with 0-2 $R^{5c}$, wherein the heterocyclic system is selected form pyrrolidinyl, piperidinyl, imidazolyl, and tetrazolyl;

$R^{5a}$, at each occurrence, is independently selected from H, methyl, $C_{1-6}$ alkyl substituted with 0-2 $R^{5e}$ wherein the alkyl is selected from ethyl, propyl, i-propyl, butyl, i-butyl, s-butyl, t-butyl, 2-methyl-butyl, pentyl, hexyl, $C_3$ alkenyl substituted with 0-1 $R^{5e}$, wherein the alkenyl is selected from allyl, $C_3$ alkynyl substituted with 0-1 $R^{5e}$ wherein the alkynyl is selected from propynyl, and a $(CH_2)_r$—$C_{3-4}$ carbocyclic residue substituted with 0-5 $R^{5e}$, wherein the carbocyclic residue is selected from cyclopropyl, cyclobutyl, cyclopentyl, and cyclohexyl;

$R^{5b}$, at each occurrence, is selected from $C_{1-6}$ alkyl substituted with 0-2 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0-2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0-2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$.

In another embodiment, the present invention provides novel compounds of formula (I), wherein:

$R^5$, at each occurrence, is independently selected from H, $C_{1-6}$ alkyl, $C_{2-8}$ alkenyl, $C_{2-8}$ alkynyl, $(CRR)_rOH$, $(CRR)_r$ SH, $(CRR)_rOR^{5d}$, $(CRR)_rSR^{5d}$, $(CRR)_rNR^{5a}R^{5a}$, $(CRR)_r$ C(O)OH, $(CRR)_rC(O)R^{5b}$, $(CRR)_rC(O)NR^{5a}R^{5a}$, $(CRR)_r$ $NR^{5a}C(O)R^{5b}$, $(CRR)_rNR^{5a}C(O)OR^{5d}$, $(CRR)_rOC(O)$ $NR^{5a}R^{5a}$, $(CHR)_rNR^{5a}C(O)NR^{5a}R^{5a}$, $CRR(CRR)_r$ $NR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S$ $(O)_2R^{5b}$, and $C_{1-6}$ haloalkyl;

$R^{5a}$, at each occurrence, is independently selected from H, methyl, $C_{1-6}$ alkyl substituted with 0-2 $R^{5e}$ wherein the alkyl is selected from ethyl, propyl, i-propyl, butyl, i-butyl, pentyl, hexyl, $C_3$ alkenyl substituted with 0-1 $R^{5e}$, wherein the alkenyl is selected from allyl, $C_3$ alkynyl substituted with 0-1 $R^{5e}$ wherein the alkynyl is selected from propynyl, and a $(CH_2)_r$—$C_{3-4}$ carbocyclic residue substituted with 0-5 $R^{5e}$, wherein the carbocyclic residue is selected from cyclopropyl, and cyclobutyl;

$R^{5b}$, at each occurrence, is selected from $C_{1-6}$ alkyl substituted with 0-2 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0-2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0-2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$.

In another embodiment, the present invention provides novel compounds of formula (I), wherein:

$R^4$ is selected from H, $C_{1-6}$ alkyl, $C_{3-8}$ alkenyl, $C_{3-8}$ alkynyl, $(CRR)_qOH$, $(CRR)_rSH$, $(CRR)_rOR^{4d}$, $(CRR)_rSR^{4d}$, $(CRR)_rNR^{4a}R^{4a}$, $(CRR)_qC(O)OH$, $(CRR)_qC(O)R^{4b}$, $(CRR)_qC(O)NR^{4a}R^{4a}$, $(CRR)_rNR^{4a}C(O)R^{4b}$, $(CRR)_rOC$ $(O)NR^{4a}R^{4a}$, $(CRR)_rNR^{4a}C(O)OR^{4d}$, $(CRR)_rNR^{4a}C(O)$ $R^{4b}$, $(CRR)_qC(O)OR^{4b}$, $(CRR)_rOC(O)R^{4b}$, $(CRR)_qS(O)_p$ $R^{4b}$, $(CRR)_qS(O)_2NR^{4a}R^{4a}$, $(CRR)_rNR^{4a}S(O)_2R^{4b}$;

R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$;

$R^5$, at each occurrence, is independently selected from $(CH_2)_rOR^{5d}$, $(CH_2)_rNR^{5a}R^{5a}$, and a $(CH_2)_r$-4-10 membered heterocyclic system containing 1-4 heteroatoms selected from N, O, and S, substituted with 0-2 $R^{5c}$, wherein the heterocyclic system is selected form pyrrolidinyl, piperidinyl, imidazolyl, and tetrazolyl;

$R^{5a}$, at each occurrence, is independently selected from H, $C_{1-6}$ alkyl substituted with 0-2 $R^{5e}$ wherein the alkyl methyl, ethyl, propyl, i-propyl, butyl, i-butyl, pentyl, hexyl, cyclopropyl, cyclobutyl, and cyclohexyl; and r, at each occurrence, is selected from 0, 1, and 2.

In another embodiment, the present invention provides novel compounds of formula (I), wherein:

$R^4$ is selected from H, $C_{1-6}$ alkyl, $C_{3-8}$ alkenyl, $C_{3-8}$ alkynyl, $(CRR)_qOH$, $(CRR)_rSH$, $(CRR)_rOR^{4d}$, $(CRR)_rSR^{4d}$, $(CRR)_rNR^{4a}R^{4a}$, $(CRR)_qC(O)OH$, $(CRR)_rC(O)R^{4b}$, $(CRR)_rC(O)NR^{4a}R^{4a}$, $(CRR)_tNR^{4a}C(O)R^{4b}$, $(CRR)_rOC(O)NR^{4a}R^{4a}$, $(CRR)_tNR^{4a}C(O)OR^{4d}$, $(CRR)_rNR^{4a}C(O)R^{4b}$, $(CRR)_rC(O)OR^{4b}$, $(CRR)_rOC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$;

R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$;

$R^5$, at each occurrence, is independently selected from H, methyl, ethyl, propyl, i-propyl, butyl, i-butyl, allyl, propynyl, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O) R^{5b}$, $(CH_2)_rOC(O)NR^{5a}R^{5a}$, $(CH_2)_rNR^{5a}C(O)OR^{5d}$, $(CH_2)_rNR^{5a}C(O) R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl;

$R^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

In another embodiment, the present invention provides novel compounds of formula (I), wherein:

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, wherein the aryl group is selected from phenyl and napthyl, and a 5-10 membered heterocyclic system containing 1-4 heteroatoms selected from N, O, and S, substituted with 0-3 $R^6$, wherein the heterocyclic system is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, oxadiazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isonicotinyl, isoquinolinyl isothiazolyl, isoxazolinyl, isoxazolyl, oxazolyl, phthalazinyl, picolinyl, pyrazinyl, pyrazolyl, pyridazinyl, pyridyl, pyridinyl, pyrimidinyl, pyrrolyl, pyrrolotriazinyl, quinazolinyl, quinolinyl, thiazolyl, thienyl, tetrazolyl, and triazinyl;

$R^4$ is selected from H, methyl, ethyl, propyl, i-propyl, butyl, i-butyl, allyl, propynyl, $(CRR)_tOH$, $(CRR)_rSH$, $(CRR)_tOR^{4d}$, $(CRR)_rSR^{4d}$, $(CRR)_rNR^{4a}R^{4a}$, $(CRR)_qC(O)OH$, $(CRR)_rC(O)R^{4b}$, $(CRR)_qC(O)NR^{4a}R^{4a}$, $(CRR)_tNR^{4a}C(O)R^{4b}$, $(CRR)_rOC(O)NR^{4a}R^{4a}$, $(CRR)_rNR^{4a}C(O)OR^{4d}$, $(CRR)_tNR^{4a}C(O)R^{4b}$, $(CRR)_qC(O)OR^{4b}$, $(CRR)_tOC(O)R^{4b}$, $(CRR)_qS(O)_pR^{4b}$, $(CRR)_qS(O)_2NR^{4a}R^{4a}$, $(CRR)_rNR^{4a}S(O)_2R^{4b}$;

$R^{4a}$, at each occurrence, is independently selected from H, methyl substituted with 0-1 $R^{4c}$, $C_{2-6}$ alkyl substituted with 0-3 $R^{4e}$ wherein $C_{2-6}$ is selected from ethyl, propyl, i-propyl, butyl, i-butyl, t-butyl, pentyl and hexyl, and a $(CH_2)_r$—$C_{3-6}$ carbocyclic residue substituted with 0-4 $R^{4e}$ wherein the carbocyclic residue is selected from cyclopropyl, cyclohexyl, and phenyl;

$R^{4b}$ is selected from H, methyl, ethyl, propyl, i-propyl, butyl, i-butyl, t-butyl, pentyl, and cyclopropyl;

$R^{4d}$ is selected from methyl, ethyl, propyl, i-propyl, butyl, i-butyl, t-butyl, pentyl, and cyclopropyl; and $R^8$ is selected from H, methyl, ethyl, propyl, i-propyl, and cyclopropyl.

In another embodiment, the present invention provides novel compounds of formula (I), wherein:

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, wherein the aryl group is selected from phenyl and napthyl, and a 5-10 membered heteroaryl system containing 1-4 heteroatoms selected from N, O, and S, substituted with 0-3 $R^6$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^4$ is selected from H, methyl, ethyl, propyl, i-propyl, butyl, i-butyl, allyl, propynyl, $(CRR)_qOH$, $(CRR)_rSH$, $(CRR)_tOR^{4d}$, $(CRR)_rSR^{4d}$, $(CRR)_rNR^{4a}R^{4a}$, $(CRR)_qC(O)OH$, $(CRR)_rC(O)R^{4b}$, $(CRR)_rC(O)NR^{4a}R^{4a}$, $(CRR)_tNR^{4a}C(O)R^{4b}$, $(CRR)_rOC(O)NR^{4a}R^{4a}$, $(CRR)_rNR^{4a}C(O)OR^{4d}$, $(CRR)_tNR^{4a}C(O)R^{4b}$, $(CRR)_rC(O)OR^{4b}$, $(CRR)_tOC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$;

$R^{4a}$, at each occurrence, is independently selected from H, methyl substituted with 0-1 $R^{4c}$, $C_{2-6}$ alkyl substituted with 0-3 $R^{4e}$ wherein $C_{2-6}$ is selected from ethyl, propyl, i-propyl, butyl, i-butyl, t-butyl, pentyl and hexyl, and a $(CH_2)_r$—$C_{3-6}$ carbocyclic residue substituted with 0-4 $R^{4e}$ wherein the carbocyclic residue is selected from cyclopropyl, cyclohexyl, and phenyl;

$R^{4b}$ is selected from H, methyl, ethyl, propyl, i-propyl, butyl, i-butyl, t-butyl, pentyl, and cyclopropyl;

$R^{4d}$ is selected from methyl, ethyl, propyl, i-propyl, butyl, i-butyl, t-butyl, pentyl, and cyclopropyl; and $R^8$ is selected from H, methyl, ethyl, propyl, i-propyl, and cyclopropyl.

In another embodiment, the present invention provides novel compounds of formula (I), wherein:

$R^6$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{6a}R^{6a'}$, $(CRR)_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rC(O)OH$, $(CR'R')_rC(O)(CR'R')_rR^{6b}$, $(CR'R')_rC(O)NR^{6a}R^{6a}$, $(CR'R')_rNR^{6f}C(O)(CR'R')_rR^{6b'}$, $(CR'R')_rC(O)O(CR'R')_rR^{6d}$, $(CR'R')_rNR^{6a}C(O)NR^{6a'}R^{6a'}$, $(CR'R')_rNR^{6a}C(S)NR^{6a}R^{6a}$, $(CR'R')_rOC(O)(CR'R')_rR^{6b}$, $(CR'R')_rOC(O)NR^{6a}(CR'R')_rR^{6d}$, $(CR'R')_rS(O)_p'R^{6b'}$, $(CR'R')_rS(O)_2NR^{6a}R^{6a}$, $(CR'R')_rNR^{6f}S(O)_2(CR'R')_rR^{6b}$, $(CR'R')_rNR^{6f}S(O)_2NR^{6a'}R^{6a'}$, $C_{1-6}$ haloalkyl, and $(CR'R')_r$phenyl substituted with 0-3 $R^{6e}$, and a $(CH_2)_r$-5-6 membered heterocyclic system containing 1-2 heteroatoms selected from N, O, and S, substituted with 0-2 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{7a}R^{7a}$, $(CR'R')_rOH$, $(CR'R')_rO(CH)_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O) (CR'R')_rR^{7b}$, $(CR'R')_rC(O)NR^{7a}R^{7a}$, $(CR'R')_rNR^{7f}C(O) (CR'R')_rR^{7b}$, $(CR'R')_rC(O)O(CR'R')_rR^{7d}$, $(CR'R')_rOC(O) (CR'R')_rR^{7b}$, $(CR'R')_rNR^{7a}C(O)NR^{7a}R^{7a}$, $(CR'R')_rNR^{7a}C(O)O(CR'R')_rR^{7d}$, $(CR'R')_rS(O)_p(CR'R')_rR^{7b}$, $(CR'R')_rS(O)_2NR^{7a}R^{7a}$, $(CR'R')_rNR^{7f}S(O)_2(CR'R')_rR^{7b}$, $C_{1-6}$ haloalkyl, adamantyl, and $(CR'R')_r$phenyl substituted with 0-3 $R^{7e}$, and pyridyl substituted with 0-3 $R^{7e}$;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, piperidinyl, morpholinyl, piperizenyl substituted with 0-1 $R^{7e}$, and azetidinyl;

$R^{7d}$, at each occurrence, is selected from methyl, $CF_3$, $CF_2CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, $(CH_2)_rOH$, OH, SH, $C(O)OH$, $C(O)NHR^{7h}$, $C(O)OC_{1-5}$ alkyl, $(CH_2)_rSC_{1-5}$ alkyl, $(CH_2)_rNR^{7f}R^{7f}$, $(CH_2)_rC(O)NHSO_2$—$R^{7h}$, $NHSO_2R^{7h}$, and $(CH_2)_r$phenyl, $(CH_2)_r$tetrazolyl;

$R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

In another embodiment, the present invention provides novel compounds of formula (I), wherein:

$R^6$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{6a}R^{6a}$, $(CRR)_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rC(O)OH$, $(CR'R')_rC(O) (CR'R')_rR^{6b}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rNR^{6a}C(O)NR^{6a}R^{6a}$, $(CR'R')_rNR^{6a}C(S)NR^{6a}R^{6a}$, $(CR'R')_rOC(O)(CR'R')_rR^{6b}$, $(CR'R')_rS(O)_p(CR'R')_rR^{6b}$, $(CR'R')_rS(O)_2NR^{6a}R^{6a}$, $(CR'R')_rNR^{6f}S(O)_2(CR'R')_rR^{6b}$, $(CR'R')_rNR^{6f}S(O)_2NR^{6a}R^{6a}$, $C_{1-6}$ haloalkyl, and $(CR'R')_r$phenyl substituted with 0-3 $R^{6e}$, and a $(CH_2)_r$-5-6 membered heterocyclic system containing 1-2 heteroatoms selected from N, O, and S, substituted with 0-2 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$; $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{7a}R^{7a}$, $(CR'R')_rOH$, $(CR'R')_rO(CH)_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O) (CR'R')_rR^{7b}$, $(CR'R')_rC(O)NR^{7a}R^{7a}$, $(CR'R')_rNR^{7f}C(O) (CR'R')_rR^{7b}$, $(CR'R')_rC(O)O(CR'R')_rR^{7d}$, $(CR'R')_rOC(O) (CR'R')_rR^{7b}$, $(CR'R')_rNR^{7a}C(O)NR^{7a}R^{7a}$, $(CR'R')_rNR^{7a}C(O)O(CR'R')_rR^{7d}$, $(CR'R')_rS(O)_p(CR'R')_rR^{7b}$, $(CR'R')_rS(O)_2NR^{7a}R^{7a}$, $(CR'R')_rNR^{7f}S(O)_2(CR'R')_rR^{7b}$, $C_{1-6}$ haloalkyl, and $(CR'R')_r$phenyl substituted with 0-3 $R^{7e}$;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, CH$_2$-cyclohexyl, CF$_3$, pyrrolidinyl, morpholinyl, piperizenyl substituted with 0-1 R$^{7e}$, and azetidinyl;

R$^{7d}$, at each occurrence, is selected from methyl, CF$_3$, CF$_2$CF$_3$, CHF$_2$, CH$_2$F, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, C(O)OC$_{1-5}$ alkyl, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

In another embodiment, the present invention provides novel-compounds of formula (I), wherein:

R$^6$, at each occurrence, is selected from C$_{1-8}$ alkyl, C$_{2-8}$ alkenyl, C$_{2-8}$ alkynyl, (CHR')$_r$C$_{3-6}$ cycloalkyl, Cl, Br, I, F, NO$_2$, CN, (CHR')$_r$NR$^{6a}$R$^{6a'}$, (CHR')$_r$OH, (CHR')$_r$OR$^{6d}$, (CHR')$_r$SH, (CHR')$_r$C(O)H, (CHR')$_r$SR$^{6d}$, (CHR')$_r$C(O)OH, (CHR')$_r$C(O)R$^{6b}$, (CHR')$_r$C(O)NR$^{6a}$R$^{6a}$, (CHR')$_r$NR$^{6f}$C(O)R$^{6b'}$, (CHR')$_r$C(O)OR$^{6d}$, (CHR')$_r$OC(O)NR$^{6a}$R$^{6d}$, (CHR')$_r$NR$^{6a}$C(O)NR$^{6a}$R$^{6a}$, (CHR')$_r$NR$^{6a}$C(S)NR$^{6a}$R$^{6a}$, (CHR')$_r$OC(O) R$^{6b}$, (CHR')$_r$S(O)$_p$R$^{6b'}$, (CHR')$_r$S(O)$_2$NR$^{6a}$R$^{6a}$, (CHR')$_r$NR$^{6f}$S(O)$_2$R$^{6b}$, (CHR')$_r$NR$^{6f}$S-(Q)$_2$' NR$^{6a}$R$^{6a'}$, C$_{1-6}$ haloalkyl, and (CHR')$_r$phenyl substituted with 0-3 R$^{6e}$.

In another embodiment, the present invention provides novel compounds of formula (I), wherein:

R$^6$, at each occurrence, is selected from C$_{1-8}$ alkyl, C$_{2-8}$ alkenyl, C$_{2-8}$ alkynyl, (CHR')$_r$C$_{3-6}$ cycloalkyl, Cl, Br, I, F, NO$_2$, CN, (CHR')$_r$NR$^{6a}$R$^{6a}$, (CHR')$_r$OH, (CHR')$_r$OR$^{6d}$, (CHR')$_r$SH, (CHR')$_r$C(O)H, (CHR')$_r$SR$^{6d}$, (CHR')$_r$C(O)OH, (CHR')$_r$C(O)R$^{6b}$, (CHR')$_r$C(O)NR$^{6a}$R$^{6a}$, (CHR')$_r$NR$^{6f}$C(O)R$^{6b}$, (CHR')$_r$C(O)OR$^{6d}$, (CHR')$_r$NR$^{6a}$C(O)NR$^{6a}$R$^{6a}$, (CHR')$_r$NR$^{6a}$C(S)NR$^{6a}$R$^{6a}$, (CHR')$_r$OC(O)R$^{6b}$, (CHR')$_r$S(O)$_p$R$^{6b}$, (CHR')$_r$S(O)$_2$NR$^{6a}$R$^{6a}$, (CHR')$_r$NR$^{6f}$S(O)$_2$R$^{6b}$, (CHR')$_r$NR$^{6f}$S(O)2 NR$^{6a}$R$^{6a}$, C$_{1-6}$ haloalkyl, and (CHR')$_r$phenyl substituted with 0-3 R$^{6e}$;

R$^7$ is selected from methyl, ethyl, propyl, i-propyl, butyl, i-butyl, s-butyl, pentyl, hexyl, Cl, Br, I, F, CN, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, CF$_2$CF$_3$, CHF$_2$, CH$_2$F, OCF$_3$, C(O)R$^{7b}$, C(O)OR$^{7d}$, NR$^{7f}$C(O)NR$^{7a}$R$^{7a}$, NHS(O)$_2$R$^{7b}$,

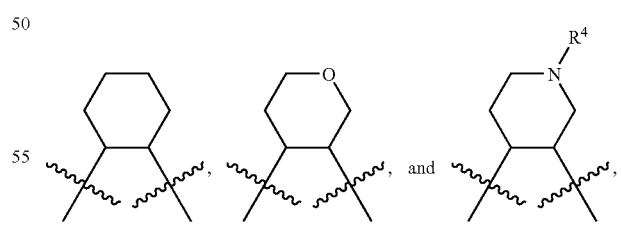

In another embodiment, the present invention provides novel compounds of formula (I), wherein:

ring B is selected from

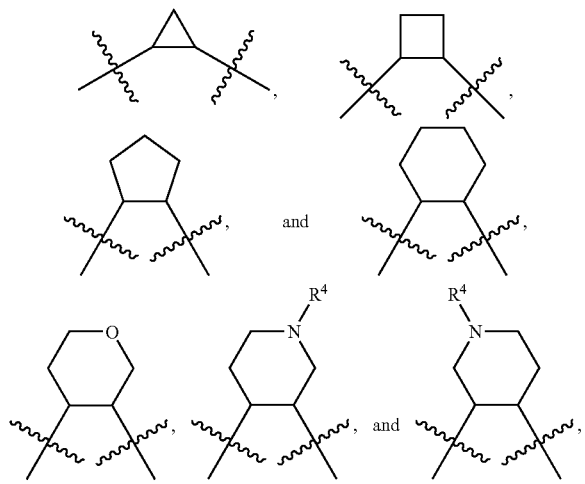

ring B being optionally substituted with 0-1 R$^5$;

R$^1$ is selected from H, C$_{1-6}$ alkyl substituted with 0-3 R$^6$ wherein the alkyl is selected from methyl, ethyl, propyl, i-propyl, butyl, pentyl and hexyl, C$_{2-6}$ alkenyl substituted with 0-3 R$^6$, C$_{2-6}$ alkynyl substituted with 0-3 R$^6$;

R$^2$ is phenyl substituted with 0-2 R$^7$;

R$^4$ is selected from H, methyl, ethyl, propyl, i-propyl, butyl, i-butyl, t-butyl, pentyl, hexyl, and (CH$_2$)$_r$C(O)R$^{4b}$;

R$^6$ is selected from methyl, ethyl, propyl, i-propyl, butyl, F, Cl, Br, I, NO$_2$, CN, (CH$_2$)$_r$O(CH$_2$)$_r$R$^{6d}$, C(O) R$^{6d}$, SR$^{6d}$, NR$^{6a}$R$^{6a}$, C(O)NR$^{6a}$R$^{6a}$, NC(O) R$^{6b}$, OC(O)R$^{6b}$, S(O)$_p$R$^{6b}$, (CHR')$_r$S(O)$_2$NR$^{6a}$R$^{6a}$, and CF$_3$;

R$^{6a}$ is H, methyl, ethyl, propyl, i-propyl, butyl, and phenyl;

alternatively, two R$^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

R$^{6b}$ is H, methyl, ethyl, propyl, i-propyl or butyl;

R$^{6d}$ is methyl, phenyl, CF$_3$, and (CH$_2$)-phenyl; and r is 0 or 1.

In another embodiment, the present invention provides novel compounds of formula (I), wherein:

ring B is selected from ring B being substituted with 0-1 R$^5$;

R$^4$ is selected from H, methyl, ethyl, propyl, i-propyl, butyl, i-butyl, t-butyl, pentyl, hexyl, allyl and (CH$_2$)$_r$C(O)R$^{4b}$;

R$^5$ is selected from H, OH, OCH$_3$, and NR$^{5a}$R$^{5a}$;

R$^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, —C(O)CF$_3$, C(=N)NH$_2$, benzyl, and —C(O)O-t-butyl;

$R^7$ is selected from methyl, ethyl, propyl, i-propyl, butyl, i-butyl, s-butyl, pentyl, hexyl, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $OCF_2CF_3$, $OCHF_2$, and $OCH_2F$, $C(O)OR^{7d}$, $C(O)R^{7b}$, $NR^{7a}C(O)NR^{7a}R^{7a}$, $NHS(O)_2R^{7b}$,

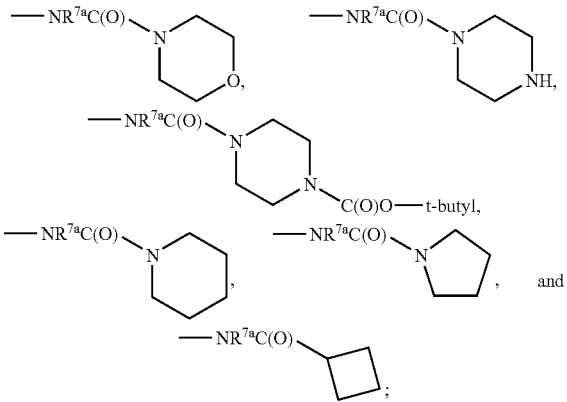

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;
$R^{7b}$ is selected from cyclohexyl and $CF_3$; and.
$R^{7d}$ is selected from methyl, ethyl, propyl, i-propyl, butyl, i-butyl, and t-butyl.

In another embodiment, the present invention provides novel compounds of formula (I), wherein:
ring B is selected from

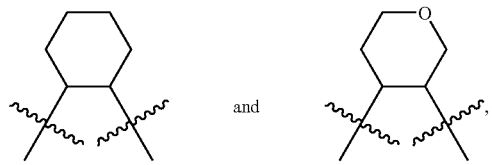

ring B being substituted with 0-1 $R^5$;
$R^5$ is selected from H, OH, $OCH_3$, and $NR^{5a}R^{5a}$;
$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, —$C(O)CF_3$, $C(=N)NH_2$, benzyl, and —$C(O)O$-t-butyl;
$R^7$ is selected from Cl, Br, CN, $NR^{7a}R^{7a}$, $CF_3$, $CF_2CF_3$, $CHF_2$, $CH_2F$, $OCF_3$ $OCF_2CF_3$, $OCHF_2$, and $OCH_2F$; and
$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl.

In another embodiment, the present invention provides novel compounds of formula (I), wherein:
B is

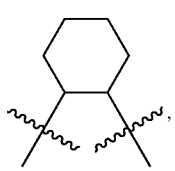

ring B being substituted with 1 $R^5$.

In another embodiment, the present invention provides novel compounds of formula (I), wherein:
$R^5$ is selected from $NR^{5a}R^{5a}$;
$R^{5a}$ is selected from H, methyl, ethyl, propyl, i-propyl, butyl, s-butyl, i-butyl, t-butyl, pentyl, hexyl, propargyl, allyl, cyclopropylmethyl, cyclopropyl, and phenyl.

In another embodiment, the present invention provides novel compounds of formula (I), wherein:
Z is selected from a bond and —$C(O)NR^8$—, —$NR^8$—, —$NR^8C(O)$—.

In another embodiment, the present invention provides novel compounds of formula (I), wherein:
$R^7$ is selected from Cl, Br, $NR^{7a}R^{7a}$, $NR^{7a}C(O)OR^{7d}$, NHC(O)$NHR^{7a}$, $OCF_3$, $NO_2$, and $CF_3$;
$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;
$R^{7d}$ is selected from methyl, ethyl, propyl, i-propyl, butyl., i-butyl, and t-butyl.

[17] In another embodiment, the present invention provides novel compounds of formula (I), wherein:
Z is selected from a bond and —NH—; and
$R^2$ is a 5-10 membered heteroaryl system containing 1-4 heteroatoms selected from N, O, and S, substituted with 0-3 $R^7$ wherein the heteroaryl is selected from quinazolinyl, triazinyl, pyrimidinyl, picolinyl, isonicotinyl, furanyl, indolyl, pyridinyl, pyrazolyl, pyrazinyl, thiazolyl, thiophenyl, and isoxazolyl.

In another embodiment, the present invention provides novel compounds of formula (Ia) or (Ic), wherein:
Z is a bond; and
$R^2$ is a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, the present invention provides novel compounds of formula (I), wherein:
$R^5$, at each occurrence, is independently selected from H, $C_{1-6}$ alkyl, $N_3$, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(O)OR^{5d}$, $(CRR)_rOC(O)NR^{5a}R^{5a}$, $(CHR)_rNR^{5a}C(O)NR^{5a}R^{5a}$, CRR $(CRR)_r$. $NR^{5a}C(O)H$, $(CRR)_rC(O)OR^{5b}$, $(CRR)_rOC(O)R^{5b}$, $(CRR)_sS(O)_pR^{5b}$, $(CRR)_sS(O)_2NR^{5a}R^{5a}$, $(CRR)_rNR^{5a}S(O)_2R^{5b}$, $(CRR)_rNR^{5a}C(=N)NR^{5a}R^{5a}$, and $C_{1-6}$ haloalkyl, and a $(CH_2)_r$-5-10 membered heterocyclic system containing 1-4 heteroatoms selected from N, O, and S, substituted with 0-2 $R^{5c}$, wherein the heterocyclic system is selected from piperidinyl;
$R^{5a}$, at each occurrence, is independently selected from H, methyl, $C_{2-6}$ alkyl substituted with 0-2 $R^{5e}$ wherein the alkyl is selected from ethyl, propyl, i-propyl, butyl, i-butyl, pentyl, hexyl, $C_3$ alkenyl substituted with 0-1 $R^{5e}$, wherein the alkenyl is selected from allyl, $C_3$ alkynyl substituted with 0-1 $R^{5e}$ wherein the alkynyl is selected from propynyl, and a $(CH_2)_r$—$C_{3-4}$ carbocyclic residue substituted with 0-5 $R^{5e}$, wherein the carbocyclic residue is selected from cyclopropyl, cyclobutyl, cyclopentyl, cyclohexyl, and phenyl;
$R^{5b}$, at each occurrence, is selected from $C_{1-6}$ alkyl substituted with 0-3 $R^{5e}$, wherein the alkyl is selected from methyl, ethyl, propyl, i-propyl, butyl, i-butyl, pentyl, and hexyl, a (CH$_2$)$_r$—C$_{3-4}$ carbocyclic residue substituted with 0-2 R$^{5e}$, wherein the carbocyclic residue is selected from cyclopropyl, and cyclobutyl; and R$^{5d}$, at each occurrence, is selected from methyl, CF$_3$, C$_{2-6}$ alkyl substituted with 0-2 R$^{5e}$, wherein the alkyl is selected from methyl, ethyl, propyl, i-propyl, butyl, i-butyl, pentyl, and hexyl, C$_{3-8}$ alkenyl, C$_{3-8}$ alkynyl, and a C$_{3-10}$ carbocyclic residue substituted with 0-3 R$^{5e}$.

In another embodiment, the present invention provides novel compounds of formula (I), wherein R$^4$ is selected from H, C$_{1-6}$ alkyl, C$_{3-8}$ alkenyl, C$_{3-8}$ alkynyl, (CRR)$_t$OH, (CRR)$_t$SH, (CRR)$_t$OR$^{4d}$, (CRR)$_t$SR$^{4d}$, (CRR)$_t$ NR$^{4a}$R$^{4a}$, (CRR)$_q$C(O)OH, (CRR)$_t$C(O)R$^{4b}$, (CRR)$_t$C(O)NR$^{4a}$R$^{4a}$, (CRR)$_t$NR$^{4a}$C(O)R$^{4b}$, (CRR)$_t$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_t$C(O)OR$^{4b}$, (CRR)$_t$OC(O)R$^{4b}$, (CRR)$_t$S(O)$_p$R$^{4b}$, (CRR)$_t$S(O)$_2$NR$^{4a}$R$^{4a}$, (CRR)$_t$NR$^{4a}$S(O)$_2$R$^{4b}$;

R, at each occurrence, is independently selected from H, C$_{1-6}$ alkyl substituted with 0-3 R$^{5e}$, wherein the C$_{1-6}$ alkyl is selected from methyl, ethyl, propyl, allyl, propynyl, (CH$_2$)$_r$C$_{3-6}$ cycloalkyl, and (CH$_2$)$_r$phenyl substituted with R$^{6e}$;

R$^5$, at each occurrence, is independently selected from H, methyl, ethyl, propyl, i-propyl, butyl, i-butyl, allyl, propynyl, N$_3$, (CH$_2$)$_r$OH, (CH$_2$)$_r$OR$^{5d}$, (CH$_2$)$_r$NR$^{5a}$R$^{5a}$, (CH$_2$)$_r$C(O)OH, (CH$_2$)$_r$C(O)R$^{5b}$, (CH$_2$)$_r$C(O)NR$^{5a}$R$^{5a}$, (CH$_2$)$_r$NR$^{5a}$C(O) R$^{5b}$, (CH$_2$)$_r$OC(O)NR$^{5a}$R$^{5a}$, (CH$_2$)$_r$NR$^{5a}$C(O)OR$^{5d}$, (CH$_2$)$_r$NR$^{5a}$C(O) R$^{5b}$, (CH$_2$)$_r$C(O)OR$^{5b}$, (CH$_2$)$_r$OC(O) R$^{5b}$, (CH$_2$)$_r$NR$^{5a}$S(O)$_2$R$^{5b}$, (CH$_2$)$_r$NR$^{5a}$C(=N)NR$^{5a}$R$^{5a}$, and C$_{1-6}$ haloalkyl, and a (CH$_2$)$_r$-5-10 membered heterocyclic system containing 1-4 heteroatoms selected from N, O, and S, substituted with 0-2 R$^{5c}$, wherein the heterocyclic system is selected from piperidinyl;

R$^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

In another embodiment, the present invention provides novel compounds of formula (I), wherein R$^6$, at each occurrence, is selected from C$_{1-8}$ alkyl, C$_{2-8}$ alkenyl, C$_{2-8}$ alkynyl, (CHR')$_r$C$_{3-6}$ cycloalkyl, Cl, Br, I, F, NO$_2$, CN, (CHR')$_r$NR$^{6a}$R$^{6a}$, (CHR')$_r$OH, (CHR')$_r$OR$^{6d}$, (CHR')$_r$SH, (CHR')$_r$C(O)H, (CHR')$_r$SR$^{6d}$, (CHR')$_r$C(O)OH, (CHR')$_r$C(O)R$^{6b}$, (CHR')$_r$C(O)NR$^{6a}$R$^{6a}$, (CHR')$_r$NR$^{6f}$C(O)R$^{6b}$, (CHR')$_r$C(O)OR$^{6d}$, (CHR')$_r$NR$^{6a}$C(O)NR$^{6a}$R$^{6a}$, (CHR')$_r$NR$^{6a}$C(S)NR$^{6a}$R$^{6a}$, (CHR')$_r$OC(O)R$^{6b}$, (CHR')$_r$S(O)$_p$R$^{6b}$, (CHR')$_r$S(O)$_2$NR$^{6a}$R$^{6a}$, (CHR')$_r$NR$^{6f}$S(O)$_2$R$^{6b}$, (CHR')$_r$NR$^{6f}$S(O)$_2$NR$^{6a}$R$^{6a}$, C$_{1-6}$ haloalkyl, and (CHR')$_r$phenyl substituted with 0-3 R$^{6e}$;

R$^{6a}$, at each occurrence, is independently selected from H, methyl, ethyl, propyl, i-propyl, butyl, i-butyl, t-butyl, pentyl, hexyl, cyclopropyl and phenyl;

R$^{6b}$, at each occurrence, is selected from methyl, ethyl, propyl, i-propyl, butyl, i-butyl, t-butyl, pentyl, hexyl, —(CH$_2$)$_r$-cyclopropyl, and —(CH$_2$)$_r$-phenyl;

R$^{6d}$, at each occurrence, is selected from methyl, CF$_3$, ethyl, propyl, i-propyl, butyl, i-butyl, t-butyl, pentyl, hexyl, -(CH$_2$)$_r$-cyclopropyl, and —(CH$_2$)$_r$-phenyl;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, methyl, ethyl, propyl, i-propyl, butyl, i-butyl, t-butyl, pentyl, hexyl, cyclopropyl, and phenyl;

R$^7$ is selected from methyl, ethyl, propyl, i-propyl, butyl, i-butyl, s-butyl, t-butyl, pentyl, hexyl, (CRR)$_r$C$_{3-6}$ cycloalkyl, Cl, Br, I, F, NO$_2$, CN, (CHR')$_r$NR$^{7a}$R$^{7a}$, (CHR')$_r$OH, (CHR')$_r$O(CH)$_r$R$^{7d}$, (CHR')$_r$SH, (CHR')$_r$C(O)H, (CHR')$_r$SR$^{7d}$, (CHR')$_r$C(O)OH, (CHR')$_r$C(O)R$^{7b}$, (CHR')$_r$C(O)NR$^{7a}$R$^{7a}$, (CHR')$_r$NR$^{7f}$C(O)R$^{7b}$, (CHR')$_r$C(O)O(CRR)$_r$R$^{7d}$, (CHR')$_r$OC(O) R$^{7b}$, (CHR')$_r$NR$^{7a}$C(O)NR$^{7a}$R$^{7a}$, (CHR')$_r$NR$^{7a}$C(O)OR$^{7d}$, (CHR')$_r$S(O)$_p$(CRR)$_r$R$^{7b}$, (CHR')$_r$S(O)$_2$NR$^{7a}$R$^{7a}$, (CHR')$_r$NR$^{7f}$S(O)$_2$(CRR)$_r$R$^{7b}$, C$_{1-6}$ haloalkyl, and (CHR')$_r$phenyl substituted with 0-3 R$^{7e}$;

R$^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, CH$_2$cyclopropyl, phenyl, and benzyl;

R$^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, piperizenyl substituted with 0-1 R$^{7e}$, and azetidinyl;

R$^{7d}$, at each occurrence, is selected from methyl, CF$_3$, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, C(O)OC$_{1-5}$ alkyl, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

In another embodiment, the present invention provides novel-compounds of formula (I), wherein ring B is selected from

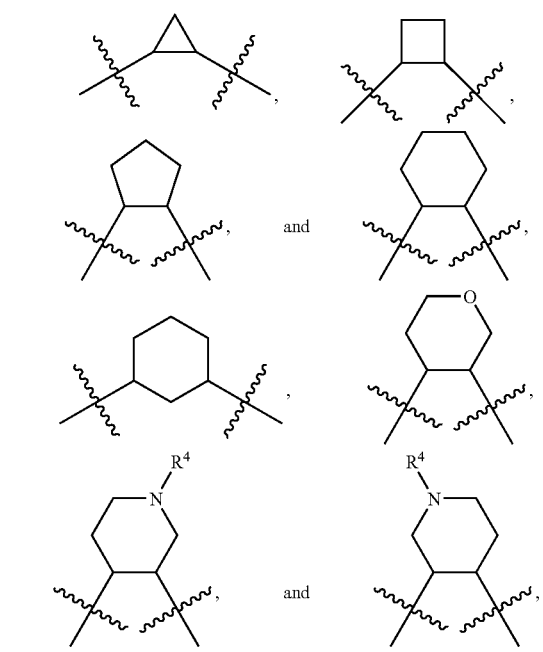

ring B being optionally substituted with 0-1 R$^5$;

$R^4$ is selected from H, methyl, ethyl, propyl, i-propyl, butyl, i-butyl, t-butyl, pentyl, hexyl, allyl, OH, C(O)OR$^{4d}$, and (CH$_2$)$_r$C(O) R$^{4b}$;

$R^6$ is selected from methyl, ethyl, propyl, i-propyl, butyl, vinyl, F, Cl, Br, I, NO$_2$, CN, O(CH$_2$)$_r$R$^{6d}$, C(O)H, (CH$_2$)OH, —CHOH—CH$_2$OH SR$^{6d}$, C(O)R$^{6b}$, NR$^{6a}$R$^{6a}$, NC(O)R$^{6b}$, OC(O)R$^{6b}$, S(O)$_p$R$^{6b}$, (CHR')$_r$S(O)$_2$NR$^{6a}$R$^{6a}$, CF$_3$;

$R^{6a}$ is H, methyl, or ethyl;

$R^{6b}$ is H, or methyl;

$R^{6d}$ is methyl, phenyl, CF$_3$, and (CH$_2$)-phenyl; and r is 0 or 1.

In another embodiment, the present invention provides novel compounds of formula (I), wherein
ring B is selected from

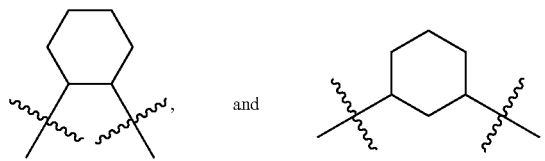

ring B being substituted with 0-1 R$^5$.

In another embodiment, the present invention provides novel compounds of formula (I), wherein is of formula (Ia) or (Ib)

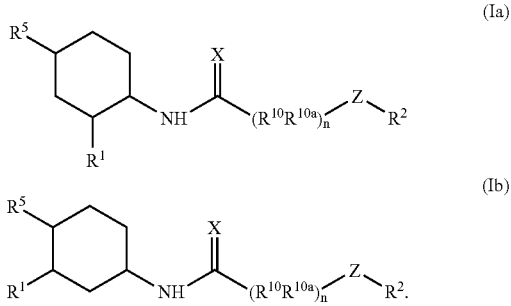

In another embodiment, the present invention provides novel compounds of formula (I), wherein
ring B is selected from

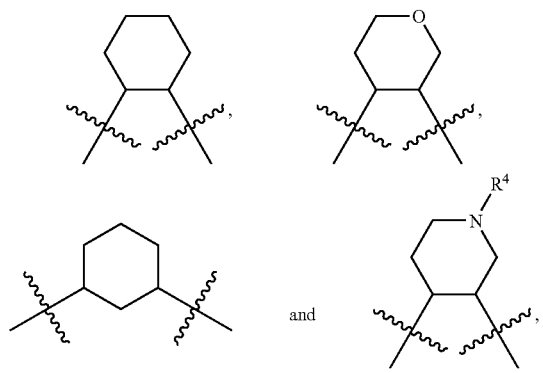

ring B being substituted with 0-1 R$^5$;

$R^4$ is selected from H, methyl, ethyl, propyl, i-propyl, butyl, i-butyl, t-butyl, pentyl, hexyl, allyl and (CH$_2$)$_r$C(O)R$^{4b}$;

$R^5$ is selected from H, OH, OCH$_3$, N$_3$, NHC(=NH)NH$_2$, NR$^{5a}$R$^{5a}$, and piperidinyl;

$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, —C(O)CF$_3$, C(=N)NH$_2$, benzyl, and —C(O)O-t-butyl;

$R^7$ is selected from methyl, ethyl, propyl, i-propyl, butyl, i-butyl, s-butyl, pentyl, hexyl, Cl, Br, I, F, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, OCF$_3$, C(O)OR$^{7d}$, C(O)R$^{7b}$, NR$^{7f}$C(O)NR$^{7a}$R$^{7a}$, NHS(O)$_2$ R$^{7b}$,

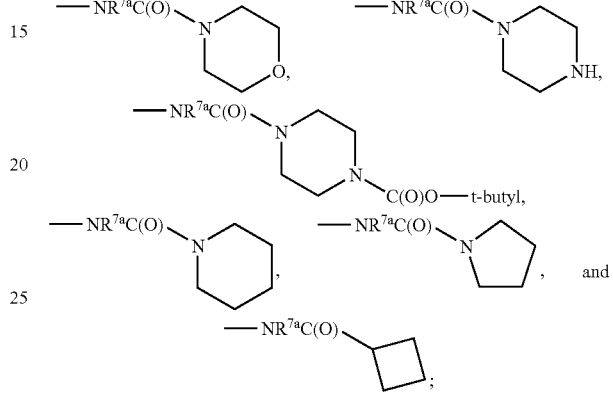

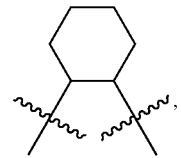

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from methyl, ethyl, propyl, i-propyl, butyl, cyclohexyl and CF$_3$;

$R^{7d}$ is selected from methyl, ethyl, propyl, i-propyl, butyl, i-butyl, and t-butyl; and $R^{14}$ is selected from H and methyl.

In another embodiment, the present invention provides novel compounds of formula (I), wherein
B is

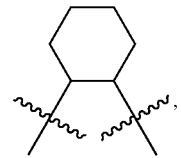

ring B being substituted with 1 R$^5$.

In another embodiment, the present invention provides novel compounds of formula (I), wherein
$R^5$ is selected from NR$^{5a}$R$^{5a}$;

$R^{5a}$ is selected from H, methyl, ethyl, propyl, i-propyl, butyl, s-butyl, i-butyl, t-butyl, pentyl, hexyl, propargyl, allyl, cyclopropylmethyl, cyclopropyl, and phenyl.

In another embodiment, the present invention provides novel compounds of formula (I), wherein the compound is selected from the compounds of table 1.

In another embodiment, the present invention is directed to a pharmaceutical composition, comprising a pharmaceutically acceptable carrier and a therapeutically effective amount of a compound of Formula (I).

In another embodiment, the present invention is directed to a method for modulation of chemokine or chemokine receptor activity comprising administering to a patient in need thereof a therapeutically effective amount of a compound of Formula (I).

In another embodiment, the present invention is directed to a method for modulation of CCR-2 receptor activity comprising administering to a patient in need thereof a therapeutically effective amount of a compound of Formula (I).

In another embodiment, the present invention is directed to a method for modulation of MCP-1, MCP-2, MCP-3 and MCP-4, and MCP-5 activity that is mediated by the CCR2 receptor comprising administering to a patient in need thereof a therapeutically effective amount of a compound of Formula (I).

In another embodiment, the present invention is directed to a method for modulation of MCP-1 activity comprising administering to a patient in need thereof a therapeutically effective amount of a compound of Formula (I).

In another embodiment, the present invention is directed to a method for inhibiting $CCR^2$ and $CCR^5$ activity comprising administering to a patient in need thereof a therapeutically effective amount of a compound of Formula (I).

In another embodiment, the present invention is directed to a method for treating disorders, comprising administering to a patient in need thereof a therapeutically effective amount of a compound of Formula (I), said disorders being selected from osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer.

In another embodiment, the present invention is directed to a method for treating disorders, of Formula (I), wherein said disorders being selected from psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer.

In another embodiment, the present invention is directed to a method for treating disorders, of Formula (I), wherein said disorders being selected from alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer.

In another embodiment, the present invention is directed to a method for treating disorders, of Formula (I), wherein said disorders being selected from asthma, multiple sclerosis, artherosclerosis, and rheumatoid arthritis.

In another embodiment, the present invention is directed to a method for treating disorders, of Formula (I), wherein said disorders being selected from restinosis, organ transplantation, and cancer.

In another embodiment, the present invention is directed to a method for treating rheumatoid arthritis, comprising administering to a patient in need thereof a therapeutically effective amount of a compound of Formula (I).

In another embodiment, the present invention is directed to a method for treating multiple sclerosis, comprising administering to a patient in need thereof a therapeutically effective amount of a compound of Formula (I).

In another embodiment, the present invention is directed to a method for treating atherosclerosis, comprising administering to a patient in need thereof a therapeutically effective amount of a compound of Formula (I).

In another embodiment, the present invention is directed to a method for treating asthma, comprising administering to a patient in need thereof a therapeutically effective amount of a compound of Formula (I).

In another embodiment, the present invention is directed to a method for treating restinosis, comprising administering to a patient in need thereof a therapeutically effective amount of a compound of Formula (I).

In another embodiment, the present invention is directed to a method for treating organ transplantation, comprising administering to a patient in need thereof a therapeutically effective amount of a compound of Formula (I).

In another embodiment, the present invention is directed to a method for treating cancer, comprising administering to a patient in need thereof a therapeutically effective amount of a compound of Formula (I).

In another embodiment, the present invention is directed to a method for treating inflammatory diseases, comprising administering to a patient in need thereof a therapeutically effective amount of a compound of Formula (I).

In another embodiment, the present invention is directed to a method for treating inflammatory diseases which are at least partially mediated by CCR-2, comprising administering to a patient in need thereof a therapeutically effective amount of a compound of Formula (I).

In another embodiment, the present invention is directed to a method for modulation of $CCR^2$ activity comprising administering to a patient in need thereof a therapeutically effective amount of a compound of Formula (I).

In another embodiment, the present invention is directed the use of a compound of Formula (I) in the preparation of a medicament for the treatment of osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus-erythematosus, nephrotoxic serum nephritis, glomerularnephritis, asthma, multiple sclerosis, artherosclerosis, and rheumatoid arthritis.

In another embodiment, the present invention is directed to a compound of formula (I) for use in therapy.

In another embodiment of the present invention, ring B is selected from

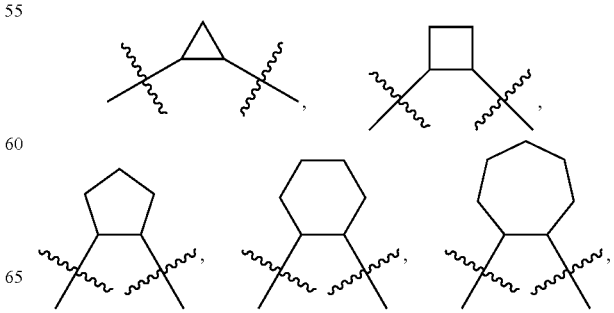

-continued

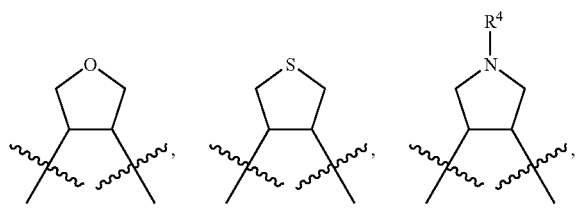

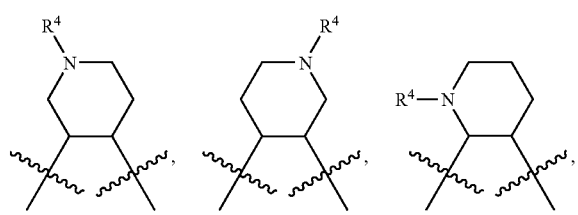

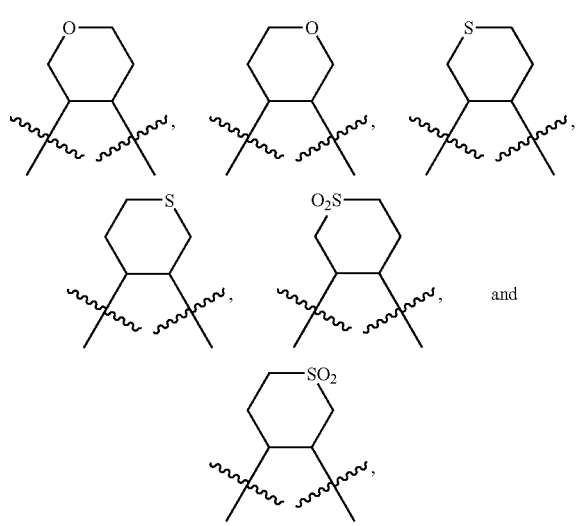

ring B being optionally substituted with 0-1 R⁵.
In another embodiment, ring B is selected from

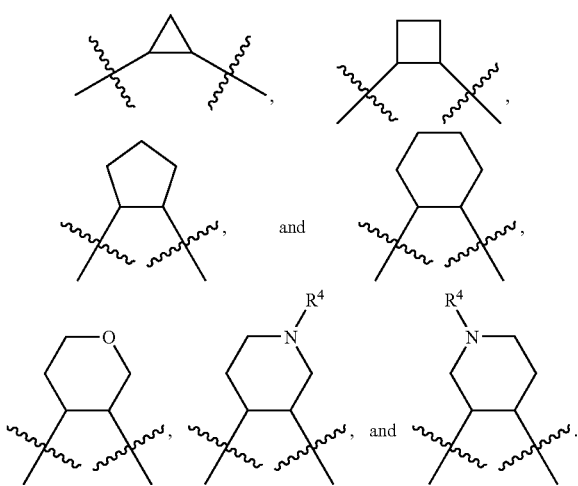

In another embodiment, ring B is selected from

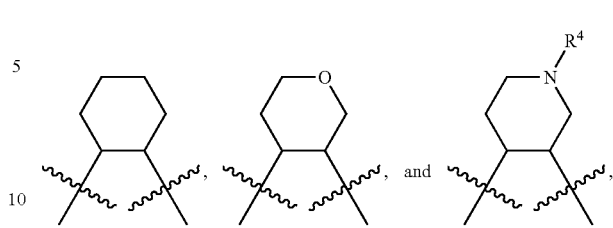

ring B being substituted with 0-1 R⁵;
In another embodiment, ring B is

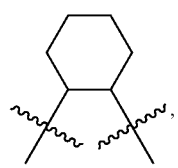

ring B being substituted with 0-1 R⁵.
In another embodiment, ring B is

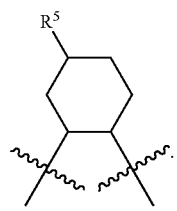

In another embodiment, Z is selected from a bond, —NR⁸C(O)—, —NR⁸—, —NR⁸C(O)NH—, and —C(O)NR⁸—.
In another embodiment, Z is selected from a bond, —NR⁸C(O)—, —NR⁸—, —C(O)NH—, and —NHC(O)NH—.
In another embodiment, Z is selected from a bond, —NR⁸C(O)—, —NR⁸—, and —C(O)NH—.
In another embodiment, Z is selected from —C(O)NH—.
In another embodiment, Z is selected from a bond, and —NHC(O)—;
In another embodiment, Z is a bond; and R² is a 5-10 membered heteroaryl system containing 1-4 heteroatoms selected from N, O, and S, substituted with 0-3 R⁷ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, Z is —NH—; and R² is a 5-10 membered heteroaryl system containing 1-4 heteroatoms selected from N, O, and S, substituted with 0-3 R⁷ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^4$ is selected from H, methyl, ethyl, propyl, i-propyl, butyl, i-butyl, allyl, propynyl, $(CRR)_q$ OH, $(CRR)_r$SH, $(CRR)_r$OR$^{4d}$, $(CRR)_r$SR$^{4d}$, $(CRR)_r$NR$^{4a}$R$^{4a}$, $(CRR)_q$C(O)OH, $(CRR)_r$C(O)R$^{4b}$, $(CRR)_r$C(O)NR$^{4a}$R$^{4a}$, $(CRR)_r$NR$^{4a}$C(O)R$^{4b}$, $(CRR)_r$OC(O)NR$^{4a}$R$^{4a}$, $(CRR)_r$NR$^{4a}$C(O)OR$^{4d}$, $(CRR)_r$NR$^{4a}$C(O)R$^{4b}$, $(CRR)_r$C(O)OR$^{4b}$, $(CRR)_r$OC(O)R$^{4b}$, $(CRR)_r$S(O)$_p$R$^{4b}$, $(CRR)_r$S(O)$_2$NR$^{4a}$R$^{4a}$, $(CRR)_r$NR$^{4a}$S(O)$_2$R$^{4b}$.

$R^{4b}$ is selected from H, methyl, ethyl, propyl, i-propyl, butyl, i-butyl, t-butyl, pentyl, and cyclopropyl; and $R^{4d}$ is selected from methyl, ethyl, propyl, i-propyl, butyl, i-butyl, t-butyl, pentyl, and cyclopropyl.

In another embodiment, $R^4$ is selected from H, methyl, ethyl, propyl, i-propyl, butyl, i-butyl, allyl, propynyl, $(CH_2)_r$C(O)R$^{4b}$.

In another embodiment, $R^5$, at each occurrence, is independently selected from H, methyl, ethyl, propyl, i-propyl, butyl, i-butyl, allyl, propynyl, $(CH_2)_r$OH, $(CH_2)_r$OR$^{5d}$, $(CH_2)_r$NR$^{5a}$R$^{5a}$, $(CH_2)_r$C(O)OH, $(CH_2)_r$C(O)R$^{5b}$, $(CH_2)_r$C(O)NR$^{5a}$R$^{5a}$, $(CH_2)_r$NR$^{5a}$C(O) R$^{5b}$, $(CH_2)_r$OC(O)NR$^{5a}$R$^{5a}$, $(CH_2)_r$NR$^{5a}$C(O)OR$^{5d}$, $(CH_2)_r$NR$^{5a}$C(O) R$^{5b}$, $(CH_2)_r$C(O)OR$^{5b}$, $(CH_2)_r$OC(O) R$^{5b}$, $(CH_2)_r$NR$^{5a}$S(O)$_2$R$^{5b}$, and $C_{1-6}$ haloalkyl; and $R^{5a}$, at each occurrence, is independently selected from H, methyl, ethyl, propyl, i-propyl, butyl, i-butyl, pentyl, hexyl, cyclopropyl, and cyclobutyl.

In another embodiment, $R^5$, at each occurrence, is independently selected from H, OH, OR$^{5d}$, $(CH_2)_r$NR$^{5a}$R$^{5a}$, $(CH_2)_r$NR$^{5a}$C(O)R$^{5b}$, and $(CH_2)_r$NR$^{5a}$C(O)OR$^{5d}$.

In another embodiment, $R^5$ is NR$^{5a}$R$^{5a}$.

In another embodiment, $R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, wherein the aryl group is selected from phenyl and napthyl, and a 5-10 membered heteroaryl system containing 1-4 heteroatoms selected from N, O, and S, substituted with 0-3 $R^6$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^1$ is selected from H, $R^6$, $C_{1-6}$ alkyl substituted with 0-3 $R^6$ wherein the alkyl is selected from methyl, ethyl, propyl, i-propyl, butyl, pentyl and hexyl, $C_{2-6}$ alkenyl substituted with 0-3 $R^6$, $C_{2-6}$ alkynyl substituted with 0-3 $R^6$.

In another embodiment, $R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, and a 5-10 membered heteroaryl system containing 1-4 heteroatoms selected from N, O, and S, substituted with 0-3 $R^6$;

with the proviso that $R^1$ is not —CH$_2$S(O)$_2$—R$^{1a}$, —CH$_2$S(O)$_2$—R$^{1a}$, —NHC(O)—R$^{1a}$, —NHC(O)NH—R$^{1a}$, —NHCH$_2$—R$^{1a}$, —SO$_2$NH—R$^{1a}$, —NHSO$_2$NH—R$^{1a}$, when $R^{1a}$ is equal to aryl or heteraryl; (with the proviso that the compounds of the present invention are not those as defined in U.S. patent application Ser. No. 10/027,644, filed Dec. 20, 2001, U.S. patent application Ser. No. 10/383,391, filed Mar. 7, 2003, U.S. Provisional Patent Application 60/446,850, filed Feb. 12, 2002, and U.S. Provisional Patent Application 60/467,003, filed May 1, 2003; and $R^5$ is NR$^{5a}$R$^{5a}$.

In another embodiment $R^{5a}$ is selected from H, methyl, ethyl, propyl, i-propyl, butyl, i-butyl, t-butyl, pentyl, hexyl.

In another embodiment, $R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^2$ is selected from phenyl substituted with 0-2 $R^7$.

In another embodiment, $R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, Z is a bond and $R^2$ is selected from a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, $R^6$, at each occurrence, is selected from $C_{1-8}$ alkyl, $C_{2-8}$ alkenyl, $C_{2-8}$ alkynyl, (CR'R')$_r$C$_{3-6}$ cycloalkyl, Cl, Br, I, F, NO$_2$, CN, (CR'R')$_r$NR$^{6a}$R$^{6a}$, (CRR)$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$C(O)OH, (CR'R')$_r$C(O) (CR'R')$_r$R$^{6b}$, (CR'R')$_r$C(O)NR$^{6a}$R$^{6a}$, (CR'R')$_r$NR$^{6f}$C(O) (CR'R')$_r$R$^{6b}$, (CR'R')$_r$C(O)O(CR'R')$_r$R$^{6d}$, (CR'R')$_r$NR$^{6a}$C(O)NR$^{6a}$R$^{6a}$, (CR'R')$_r$NR$^{6a}$C(S)NR$^{6a}$R$^{6a}$, (CR'R')$_r$OC(O) (CR'R')$_r$R$^{6b}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$(CR'R')$_r$R$^{6b}$, (CR'R')$_r$NR$^{6f}$S(O)$_2$ NR$^{6a}$R$^{6a}$, $C_{1-6}$ haloalkyl, and (CR'R')$_r$ phenyl substituted with 0-3 $R^{6e}$, and a (CH$_2$)$_r$-5-6 membered heterocyclic system containing 1-2 heteroatoms selected from N, O, and S, substituted with 0-2 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, CF$_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{6f}R^{6f}$, and $(CH_2)_r$phenyl;

$R^{6f}$, at each occurrence, is selected from H, methyl, ethyl, propyl, i-propyl, butyl, i-butyl, t-butyl, pentyl, hexyl, cyclopropyl, and phenyl.

In another embodiment, $R^6$, at each occurrence, is selected from $C_{1-8}$ alkyl, $C_{2-8}$ alkenyl, $C_{2-8}$ alkynyl, $(CHR')_rC_{3-6}$ cycloalkyl, Cl, Br, I, F, $NO_2$, CN, $(CHR')_rNR^{6a}R^{6a}$, $(CHR')_rOH$, $(CHR')_rOR^{6d}$, $(CHR')_rSH$, $(CHR')_rC(O)H$, $(CHR')_rSR^{6d}$, $(CHR')_rC(O)OH$, $(CHR')_rC(O)R^{6b}$, $(CHR')_rC(O)NR^{6a}R^{6a}$, $(CHR')_rNR^{6f}C(O)R^{6b}$, $(CHR')_rC(O)OR^{6d}$, $(CHR')_rNR^{6a}C(O)NR^{6a}R^{6a}$, $(CHR')_rNR^{6a}C(S)NR^{6a}R^{6a}$, $(CHR')_rOC(O)R^{6b}$, $(CHR')_rS(O)_pR^{6b}$, $(CHR')_rS(O)_2NR^{6a}R^{6a}$, $(CHR')_rNR^{6f}S(O)_2R^{6b}$, $(CHR')_rNR^{6f}S(O)_2NR^{6a}R^{6a}$, $C_{1-6}$ haloalkyl, and $(CHR')_r$phenyl substituted with 0-3 $R^{6e}$.

In another embodiment, $R^6$ is selected from methyl, ethyl, propyl, i-propyl, butyl, F, Cl, Br, I, $NO_2$, CN, $(CH_2)_rO$ $(CH_2)_rR^{6d}$, $C(O)R^{6d}$, $SR^{6d}$, $NR^{6a}R^{6a}$, $C(O)NR^{6a}R^{6a}$, $NC(O)R^{6b}$, $OC(O)R^{6b}$, $S(O)_pR^{6b}$, $(CHR')_rS(O)_2NR^{6a}R^{6a}$, and $CF_3$;

$R^{6a}$ is H, methyl, ethyl, propyl, i-propyl, butyl, and phenyl; alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$ is H, methyl, ethyl, propyl, i-propyl or butyl;

$R^{6d}$ is methyl, phenyl, $CF_3$, and $(CH_2)$-phenyl.

In another embodiment, $R^7$ is selected from methyl, ethyl, propyl, i-propyl, butyl, i-butyl, s-butyl, t-butyl, pentyl, hexyl, $(CH_2)_rC_{3-6}$cycloalkyl, Cl, Br, I, F, $NO_2$, CN, $(CH_2)_r NR^{7a}R^{7a}$, $(CH_2)_rOH$, $(CH_2)_rO(CH_2)_rR^{7d}$, $(CH_2)_r SH$, $(CH_2)_rC(O)H$, $(CH_2)_rS(CH_2)_rR^{7d}$, $(CH_2)_rC(O)OH$, $(CH_2)_rC(O)(CH_2)_rR^{7b}$, $(CH_2)_rC(O)NR^{7a}R^{7a}$, $(CH_2)_r NR^{7f}C(O)(CH_2)_rR^{7b}$, $(CH_2)_rC(O)O(CH_2)_rR^{7d}$, $(CH_2)_r OC(O)(CH_2)_rR^{7b}$, $(CH_2)_rNR^{7a}C(O)NR^{7a}R^{7a}$, $(CH_2)_r NR^{7a}C\ O)O(CH_2)_rR^{7d}$, $(CH_2)_rS(O)_p(CH_2)_rR^{7b}$, $(CH_2)_rS(O)_2NR^{7a}R^{7a}$, $(CH_2)_rNR^{7f}S(O)_2(CH_2)_rR^{7b}$, $C_{1-6}$ haloalkyl, and $(CH_2)_r$phenyl substituted with 0-3 $R^{7e}$;

$R^{7a}$, at each occurrence, is selected from H, methyl, ethyl, propyl, i-propyl, butyl, i-butyl, t-butyl, pentyl, hexyl, and cyclopropyl;

$R^{7b}$, at each occurrence, is selected from methyl, ethyl, propyl, i-propyl, butyl, i-butyl, t-butyl, pentyl, hexyl, and cyclopropyl;

$R^{7d}$, at each occurrence, is selected from methyl, $CF_3$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{7f}R^{7f}$, and $(CH_2)_r$phenyl; and $R^{7f}$, at each occurrence, is selected from H, methyl, ethyl, propyl, i-propyl, butyl, i-butyl, t-butyl, pentyl, hexyl, cyclopropyl, and phenyl.

In another embodiment, $R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)R^{7b}$, $NR^{7f}C(O)NHR^{7a}$, and $NHS(O)_2R^{7b}$.

In another embodiment, $R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)OR^{7d}$, $C(O)R^{7b}$, $NR^{7f}C(O)NR^{7a}R^{7a}$, $NHS(O)_2R^{7b}$,

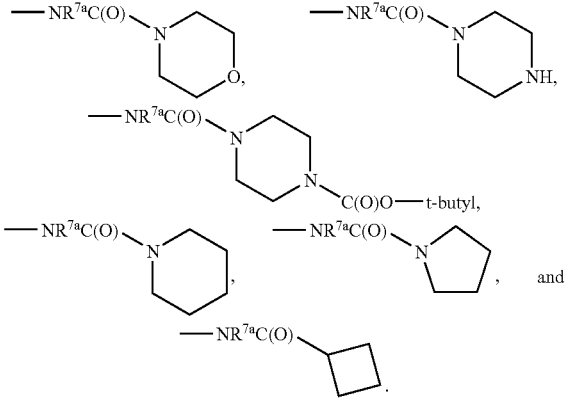

In another embodiment, $R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from cyclohexyl and $CF_3$; and $R^{7d}$ is selected from methyl, ethyl, propyl, i-propyl, butyl, i-butyl, and t-butyl.

In another embodiment, $R^8$ is H.

In another embodiment, $R^{11}$ and $R^{12}$ are H.

In another embodiment, ring B is substituted with at least one $R^5$ which is —$NR^{5a}R^{5a}$.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C═N double bonds, and the like can also be present in the compounds described herein, and all such stable isomers are contemplated in the present invention; Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602-2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced.

When any variable (e.g., $R^{10}$) occurs more than one time in any constituent or formula for a compound, its definition at each occurrence is independent of its definition at every other occurrence. Thus, for example, if a group is shown to be substituted with 0-2 $R^{10}$, then said group may optionally be substituted with up to two $R^{10}$ groups and $R^{10}$ at each occurrence is selected independently from the definition of $R^{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

As used herein, the term "cyclic acetal" or or the phrase when two variables "join to form a cyclic acetal" is intended to mean the substituent —O—CH$_2$—O—.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Chemokine antagonists can be derived from compounds of formula 1.1, as shown in Schemes 1 and 2. Thus, compounds of formula 1.3 can be derived from compounds of formula 1.1 through coupling to acids of formula 1.2. Likewise, compounds of formula 1.5 are available through initial alkylation of 1.1 to 1.4 and subsequent coupling with acids of formula 1.2.

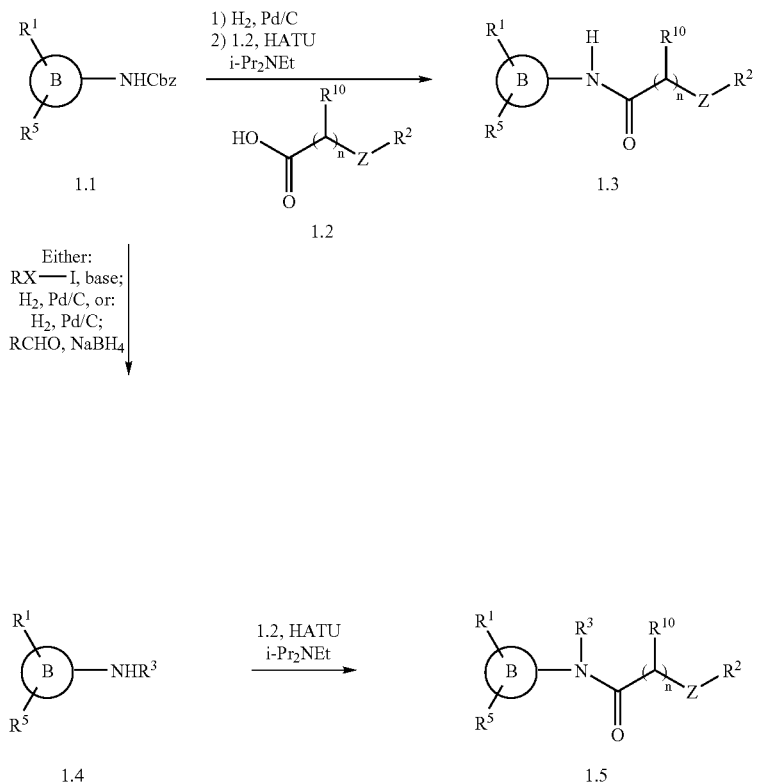

Scheme 1

Other compounds of formula 1.3 can be synthesized using alternative methods, as shown in Scheme 2 (see 2.4, 2.5, and 2.6, all of which are variants of formula 1.3). Thus, coupling of the amine derivative of 1.1 with protected amino acid 2.1 affords amide 2.2. This can be deprotected to form amine 2.3, which is easily derivatized through reaction of an isocyanate to give urea 2.4. Alternatively, amine 2.3 can be arylated (see D. Zim & S. L. Buchwald, *Organic Letters* 2003, 5, 2413 and T. Wang, D. R. Magnia, & L. G. Hamann, ibid, 897, and references cited therein) to give compound 2.5. Alternatively, amine 2.3 can be arylated with iminoyl chlorides to give 2.6. It is obvious that an $R^3$ group could be incorporated into compounds of formulas 2.4, 2.5, and 2.6 simply by starting with compound 1.4. Likewise, it is obvious that an $R^8$ group could be incorporated into compounds of formulas 2.4, 2.5, and 2.6 simply by starting with an appropriately N-alkylated, N-protected amino acid.

achieved through chemistry well known to one skilled in the art. Thus, the remainder of this discussion focuses on the synthesis of compounds of formulas 1.2 and 1.1.

A variety of compounds of formula 1.2 are commercially available, or are derived readily from commercially available materials. Other derivatives of formula 1.2 may be synthesized as shown in Scheme 3 (see 3.3, 3.6, and 3.8, all of which fit compounds of formula 1.2). Thus, compounds of formula 3.1 are readily converted into a wide variety of compounds of formula 3.3 (see also P. H. Carter, R. J. Cherney, WO-PCT 0250019, 2002, which is hereby incorporated by reference). A series of manolamide variants of formula 1.2 (see 3.6) are synthesized from commercially available malonic acid mono-esters 3.4, which can be coupled to commercially available amines to provide the malonamides 3.5; deprotection (hydrolysis with LiOH or KOH; or hydrogenolysis with Pd/C and $H_2$) affords the

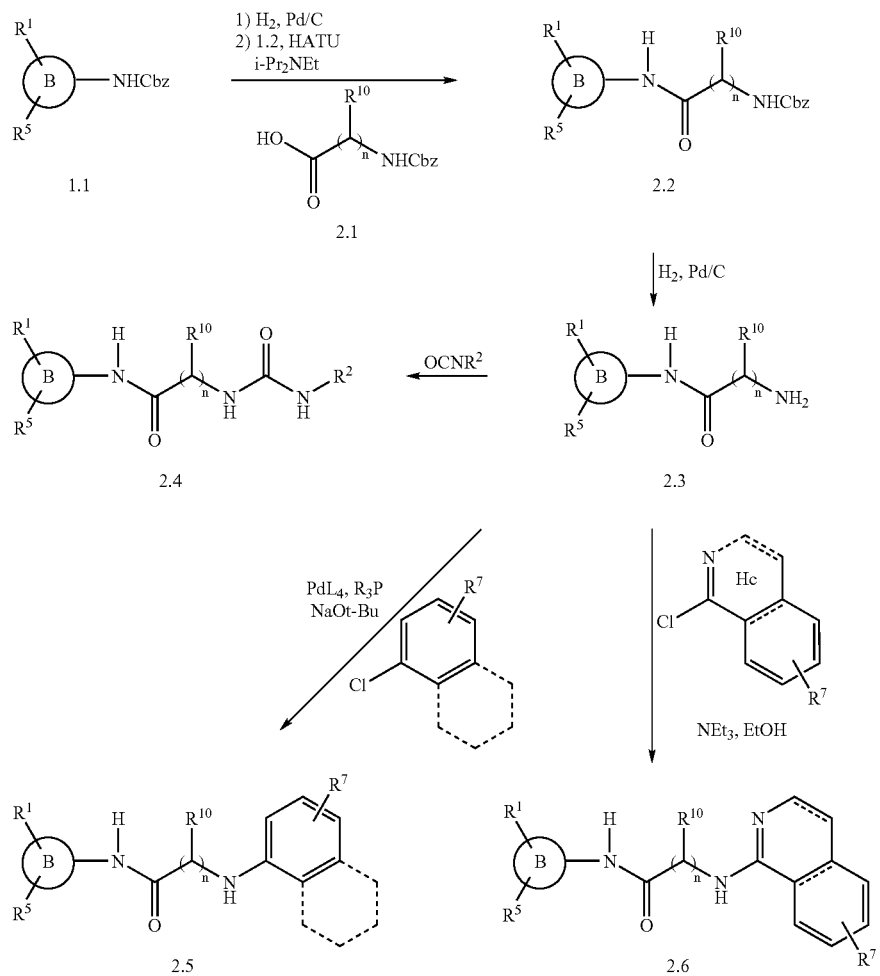

Based on the chemistry described in Schemes 1 and 2, the synthesis of the compounds of this invention can be simplified to the synthesis of compounds of formula 1.1, together with the synthesis of compounds of formula 1.2. The synthesis of the reagents shown in Scheme 2 (i.e. reagents other than 1.2 that can derivatize 1.1) is generally not necessary (given commercial availability) or is readily carboxylates 3.6. A series of heterocyclic variants of 1.2 (see 3.8) are also synthesized from malonic acid mono-esters 3.4. Coupling to mixed anilines 3.9 affords the amides 3.7. These amides (where X=OH, SH, $NH_2$, $NHR^{5a}$) can be cyclized (K. Takeuchi et al. *Bioorg. Med. Chem. Lett.* 2000, 2347; G. Nawwar et al. *Collect. Czech. Chem. Commun.* 1995, 2200; T. Hisano et al. *Chem. Pharm. Bull.* 1982, 2996) and then deprotected (hydrolysis with LiOH or KOH; or hydrogenolysis with Pd/C and $H_2$) to give compounds of formula 3.8. Compounds of formula 3.8 can also be made directly through the condensation of acids 3.4 and bifunctionalized anilines 3.9 (G. Trapani et al. *Eur. J. Med. Chem.* 1992, 39; P. Baudet et al. *Helv. Chim. Acta.* 1970, 1683; D. McKinnon et al. *Can J. Chem.* 1988, 2339; K. Nivalkar et al. *Synth. Commun.* 1996, 3535), followed by appropriate ester deprotection.

protecting groups where necessary) to give compounds of formula 4.3, which may be transformed through reductive amination and protection (see note above) to give compounds of formula 4.4 (a variant of 1.1). If $R^1$ is a carbon-connected linker, a convenient method for compound synthesis is shown in the enantioselective transformation of 4.2 (El=$CO_2R$) to 4.6 via enamine 4.5 (C. Cimarelli, et al, *J. Org. Chem.* 1996, 61, 5557 and Y. Hayashi, et al., *J. Am. Chem. Soc.* 1996, 118, 5502). Elaboration to 4.4 (a derivative of formula 1.1) may proceed directly from 4.6 or via initial epimerization to 4.7.

Scheme 3

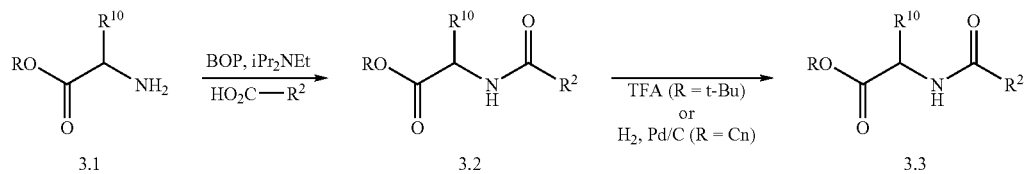

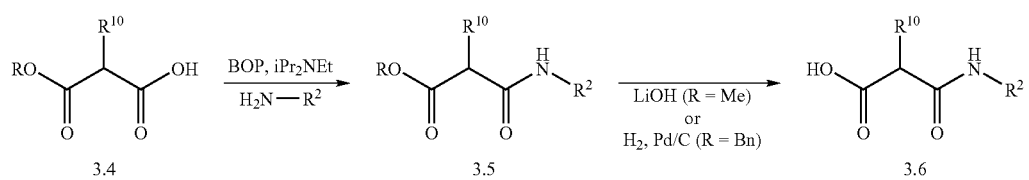

Compounds of formula 1.1 may sometimes be derived in a trivial fashion from manipulation of commercially available cyclic amines (nota bene: although amines of formula 1.1 are shown with Cbz protection, they may synthesized with alternative protecting groups or in unprotected form; only minor adjustments to the chemistry of Schemes 1 and 2 would need be made in this instance). In other instances, they are readily derived from commercially available ketones of general formula 4.1, as shown in Scheme 4. These ketones may be alpha-functionalized (as well documented in the synthetic literature; enantioselective variants of this alkylation are available) to give compounds of formula 4.2. In some instances (El=halide, hydroxyl or azide), these compounds may be elaborated further (through nucleophilic or electrophilic displacement chemistry, making recourse to Scheme 4

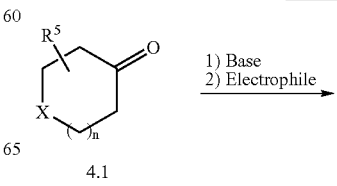

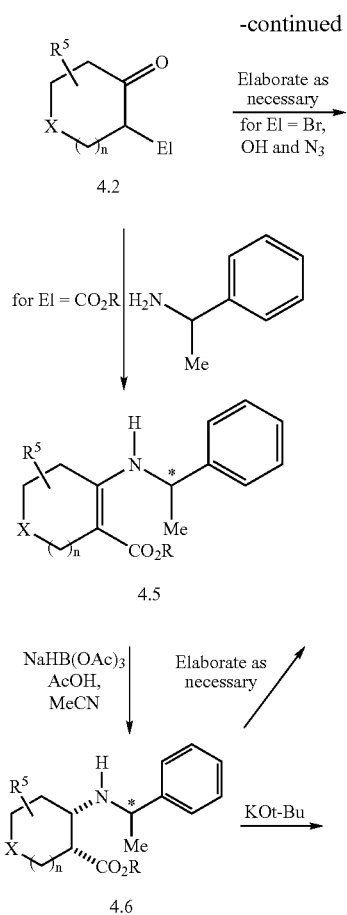

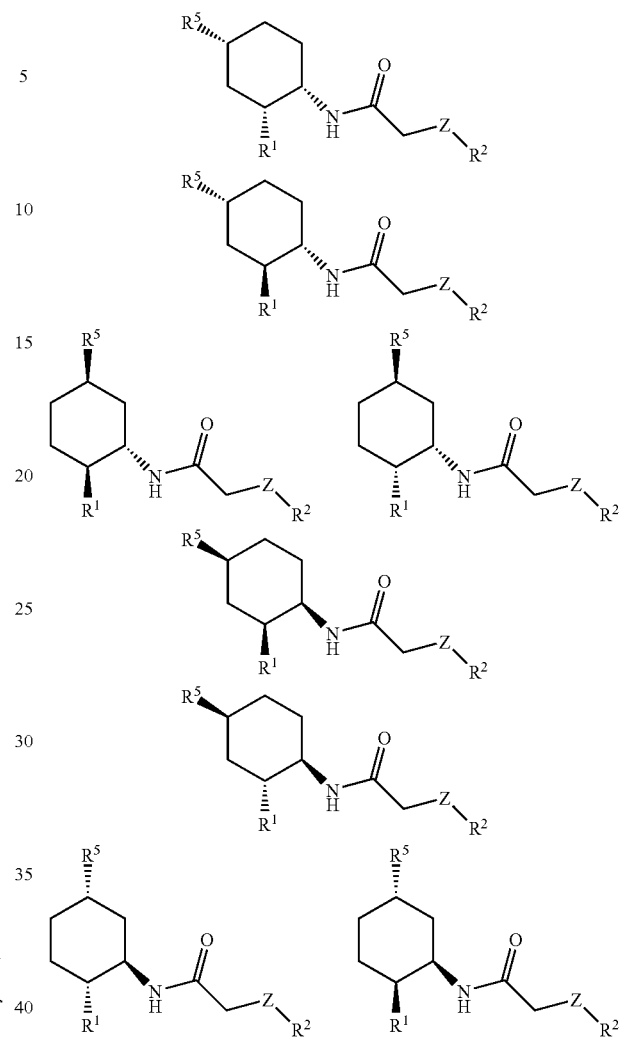

Other methods for the synthesis of 1,2-diaminocarbo- and heterocycles (see R. Cherney WO-PCT 02/060859, which is hereby incorporated by reference) and the synthesis of 2-aminocycloalkanecarboxylic acids do exist (reviewed in Ference Fulop, *Chem. Rev.* 2001, 101, 2181; see also J. Duan, et al. WO-01/70673 and Soo S. Ko, et al. WO-02/02525). In particular, 2-aminocycloalkanecarboxylic acids (and their heterocyclic varients) are versatile precursors of compounds of formula 1.1, because the carboxylic acid can be derivatized to a wide variety of $R^1$ groups through addition reactions, amide formation, Wittig extension, reduction and alcohol derivitization, reduction and then reductive amination, Curtius rearrangement, and so forth. In instances where the cycloalkyl group contains a pendant olefin, the carboxylic acid can also serve to relay stereochemical information and allow for further functionalization of the ring, so as to provide for the stereoselective installation of $R^5$. This chemistry has been generally described in the literature (Ference Fulop, *Chem. Rev.* 2001, 101, 2181); specific examples of this strategy are described in the Examples section (vide infra). When these methods are considered along those highlighted in Scheme 4, it is apparent that a large number of compounds of formula 1.1 can be synthesized.

One diastereomer of a compound of Formula I may display superior activity compared with the others. Thus, while not limiting the invention, the following stereochemistries are examples of stereochemistires that are considered to be a part of the present invention.

Additional stereoisomers are envisioned based on the schematic shown below. The examples illustrated here are limited to ring B being a cyclohexyl ring. Additional ring systems are possible and therefore additional stereoisomers are envisioned. The compounds of the present invention may also exist in additional stereoisomers which are not shown herein.

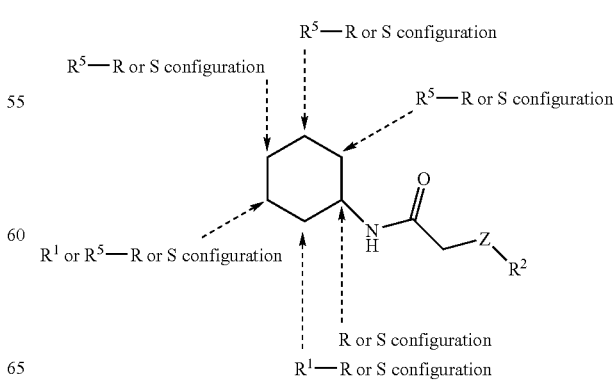

When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of Formula I may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Copending patent applications, all filed on Aug. 19, 2004, disclose additional chemokine receptor antagonists. These applications are hereby incorporated by reference in their entirety: "N-ALKYLATED DIAMINOPROPANE DERIVATIVES AS MODULATORS OF CHEMOKINE RECEPTOR ACTIVITY", U.S. application Ser. No. 10/922,406; "LACTAMS OF ALYKLATED ACYCLIC DIAMINE DERIVATIVES AS MODULATORS OF CHEMOKINE RECEPTOR ACTIVITY", U.S. application Ser. No. 10/922,726; and "CYCLIC DERIVATIVES AS MODULATORS OF CHEMOKINE RECEPTOR ACTIVITY", U.S. application Ser. No. 10/923,619, Other features of the invention will become apparent in the course of the following descriptions of exemplary embodiments that are given for illustration of the invention and are not intended to be limiting thereof.

EXAMPLES

Unless otherwise indicated, it may be assumed that reactions are run under inert atmosphere ($N_2$ or Ar gas). Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1H$" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art. "RP-HPLC" refers to reverse-phase high performance liquid chromatography. Chromatographic methods are not typically specified, given that many different methods will perform equally well; gradient elution using acid-doped MeOH/water or acid-doped acetonitrile/water were typically utilized. Products were often obtained as acid salts after RP-HPLC; if desired, their parent free base can be derived through dissolution in aqueous base and extraction with organic solvents, as will be obvious to one skilled in the art. Chemical names were derived using ChemDraw Ultra, version 8.0.8 (May 2004). When this program failed to provide a name for the exact structure in question, an appropriate name was assigned using the same methodology utilized by the program.

Preparation of Non-Standard Reagents and Synthetic Intermediates Utilized in the Examples Preparation A1: Synthesis of Benzyloxycarbonylamino-7-oxo-6-aza-bicyclo[3.2.1]octane-6-carboxylic acid tert-butyl ester Preparation A1, Step 1: (1S, 2R)-cis-2-Methoxycarbonyl-cyclohex-4-ene-1-carboxylic acid (66.0 g, see Bolm et al. *J. Org. Chem.* 2000, 65, 6984-6991) was dissolved in dry acetone (815 mL) prior to the addition of triethylamine (43.4 g). This solution was cooled to 0° C. and ethyl chloroformate (46.7 g) was added. The resulting solution was stirred 1 h before $NaN_3$ (35.0 g) was added. The cooling bath was removed, and the reaction was warmed to rt overnight. All solid material was removed by filtration, and the solution was partially concentrated. Water was slowly added and the organic layer was separated. The aqueous layer was extracted with ether. The combined organic layers were washed with water and brine before they were dried, filtered, and concentrated. The resulting oil (66.1 g) was dissolved in benzene (800 mL) and was warmed to a gentle reflux. After 4 h, the solution was cooled back to rt. Benzyl alcohol (37.5 g) and p-TsOH (1.5 g) were added, and the solution was warmed back to a gentle reflux overnight. After cooling to rt, the reaction was washed with $NaHCO_3$ and brine, dried, filtered, and concentrated to give (1R,6S)-6-benzyloxycarbonylamino-cyclohex-3-enecarboxylic acid methyl ester (97.7 g). MS found: $(M+H)^+=290.2$.

Preparation A1, Step 2: A sample of (1R,6S)-6-benzyloxycarbonylamino-cyclohex-3-enecarboxylic acid methyl ester (91.4 g) was dissolved in MeOH (500 mL) prior to the dropwise addition of NaOH (25.3 g) in water (95 mL). After 3 h, the solution was partially concentrated and an $Et_2O$/water mixture was added. The aqueous layer was separated and was acidified (pH ~2) with concentrated HCl. The resulting mixture was extracted with EtOAc. The combined organic layers were washed with water and brine before they were dried, filtered, and concentrated to give (1R,6S)-6-benzyloxycarbonylamino-cyclohex-3-enecarboxylic acid (72.7 g). MS found: $(M+H)+=276.2$.

Preparation A1, Step 3: A sample of (1R,6S)-6-benzyloxycarbonylamino-cyclohex-3-enecarboxylic acid (72 g) was dissolved in $CH_2Cl_2$ (750 mL) prior to the addition of CDI (50.9 g). After 2.5 h water was added, and the solution was extracted with $CH_2Cl_2$. The combined organic layers were dried, filtered, and concentrated. The resulting material was dissolved in $CH_2Cl_2$ and ammonia gas was bubbled through the solution for 1.5 h. After stirring overnight, the majority of the solvent was removed and $Et_2O$ was added. The product precipitated as a white solid and was collected to give (1R,6S)-6-carbamoyl-cyclohex-3-enyl)-carbamic acid benzyl ester (61.5 g). MS found: $(M+H)^+=275.3$.

Preparation A1, Step 4: A sample of (1R,6S)-(6-carbamoyl-cyclohex-3-enyl)-carbamic acid benzyl ester (30.7 g) was dissolved in THF (1100 mL) and NMP (220 mL). At −78° C., 2.3M n-BuLi (96.3 mL) was added dropwise. After 2 h, a solution of $Boc_2O$ (24.4 g) in THF (40 mL) was added dropwise. This solution was stirred 1.2 h before it was quenched with a saturated $NH_4Cl$ solution. Water and $Et_2O$ were added. The organic layer was filtered then washed with water, brine, dried, filtered, and concentrated. Flash chromatography of the resulting residue gave (1R,6S)-(6-tert-butoxycarbonylaminocarbonyl-cyclohex-3-enyl)-carbamic acid benzyl ester (29.2 g). MS found: $(M+Na)^+=397.4$.

Preparation A1, Step 5: A sample of (1R,6S)-(6-tert-butoxycarbonyl-aminocarbonyl-cyclohex-3-enyl)-carbamic acid benzyl ester (29.0 g) was dissolved in THF (1290 mL). This was cooled in an ice/brine bath prior to the addition of n-BuLi (1.5 mL, 2.4M). After 30 min, iodine (59.0 g) was added in a single portion. The bath was removed, and the reaction was warmed to rt overnight. The resulting solution was quenched with saturated thiosulfate solution. Water and EtOAc were added. The organic layer was washed with water, brine, dried, filtered, and concentrated. The resulting slurry was diluted with $Et_2O$ and (1R,2S,4S,5R)-2-benzyloxycarbonylamino-4-iodo-7-oxo-6-aza-bicyclo[3.2.1]octane-6-carboxylic acid tert-butyl ester (22.8 g) was collected by vacuum filtration. MS found: $(M-C_5H_8O_2+H)^+=401.1$.

Preparation A1, Step 6: A sample of (1R,2S,4S,5R)-2-benzyloxycarbonylamino-4-iodo-7-oxo-6-aza-bicyclo[3.2.1]octane-6-carboxylic acid tert-butyl ester (43.3 g) was dissolved in benzene (580 mL) prior to the addition of Bu₃SnH (27.8 g) and AIBN (0.7 g). The resulting mixture was warmed to a gentle reflux for 3 h. After cooling, the solvent was removed and hexane was added. The resulting white solid was collected by vacuum filtration to give the title compound, (1R,2S,5R)-2-Benzyloxycarbonylamino-7-oxo-6-aza-bicyclo[3.2.1]octane-6-carboxylic acid tert-butyl ester (29.5 g). MS found: $(M+Na)^+=397.4$.

Preparation A2: Synthesis of 7-Oxo-6-oxa-bicyclo[3.2.1]oct-2-yl)-carbamic acid benzyl ester The title compound was prepared using the method of Suga (H. Suga et al., *J. Am. Chem. Soc.* 1994, 116, 11197-98) from the known 1S,2R-cis-2-methoxycarbonyl-cyclohex-4-ene-1-carboxylic acid (see: Bolm et al., *J. Org. Chem.* 2000, 65, 6984-6991).

Preparation A3: Synthesis of (1R,2S,5R)-tert-butyl 2-((S)-3-(benzyloxycarbonylamino)-2-oxopyrrolidin-1-yl)-7-oxo-6-aza-bicyclo[3.2.1]octane-6-carboxylate Preparation A3, Step 1: (1R,2S,5R)-Tert-butyl 2-benzyloxycarbonylamino-7-oxo-6-aza-bicyclo[3.2.1]octane-6-carboxylate (4.0 g) in MeOH (30 mL) was charged with 10% Pd/C, Degussa (600 mg). The reaction flask was evacuated and then back-filled with hydrogen; this was repeated three more times. The reaction was stirred under 1 atm of H₂ for 3 h and then filtered and concentrated to provide (1R,2S,5R)-tert-butyl 2-amino-7-oxo-6-aza-bicyclo[3.2.1]octane-6-carboxylate (2.5 g). MS (ES+)=241.1 $(M+H)^+$.

Preparation A3, Step 2: A solution of (1R,2S,5R)-tert-butyl 2-amino-7-oxo-6-aza-bicyclo[3.2.1]octane-6-carboxylate (2.5 g) was dissolved in DMF (34 mL) and cooled to 0° C. prior to the addition of N-Cbz methionine (5.3 g), 4-methyl morpholine (3.7 g), and BOP (8.3 g). The reaction was stirred for 12 h at RT and then partitioned between EtOAc and 1N HCl solution. The organic phases were combined, washed with saturated NaHCO₃ and brine, dried (MgSO₄), filtered, and concentrated in vacuo. The residue was purified by flash chromatography to afford (1R,2S,5R)-tert-butyl 2-((S)-2-(benzyloxycarbonylamino)-4-(methylthio)butanamido)-7-oxo-6-aza-bicyclo[3.2.1]octane-6-carboxylate (5.1 g). MS found: $(M+H)^+=506.2$.

Preparation A3, Step 3: (1R,2S,5R)-Tert-butyl 2-((S)-2-(benzyloxycarbonylamino)-4-(methylthio)butanamido)-7-oxo-6-aza-bicyclo[3.2.1]octane-6-carboxylate (5.1 g) was dissolved in iodomethane (40 mL). The resulting solution was stirred at rt for 12 h before being concentrated in vacuo. The residue was dissolved in methylene chloride, and the resulting solution was concentrated; this was repeated to afford the salt. This material was dissolved in DMF (30 mL) and the solution was charged with Cs₂CO₃ (6.6 g). After 12 h, the reaction was partitioned between EtOAc and brine. The organic phase was dried (MgSO₄), filtered, and concentrated. The resulting residue was purified by flash chromatography to afford (1R,2S,5R)-tert-butyl 2-((S)-3-(benzyloxycarbonylamino)-2-oxopyrrolidin-1-yl)-7-oxo-6-aza-bicyclo[3.2.1]octane-6-carboxylate (2.0 g). MS found: $(M+H)^+=458.6$.

Preparation A4: Synthesis of ((7S,8S)-7-Hydroxymethyl-1,4-dioxa-spiro[4.5]dec-8-yl)-carbamic acid benzyl ester Preparation A4, Step 1: Into a 2-L 3-neck flask was added NaH 60% dispersion (60 g, 1.56 mol) and washed with 700 ml of hexane (2×), suspended in 1 L of THF and treated with diethyl carbonate (150 g, 1.25 mol). The suspension was heated to reflux and treated drop wise with a solution of ketone (1,4-Dioxa-spiro[4.5]decan-8-one) (80.0 g, 0.51 mol) in THF (300 ml). After the addition was complete the suspension was heated to reflux for an additional 4 hours. The mixture was cooled in an ice bath to 0° C. and then poured, while vigorously stirring, into a mixture of ice (1.5 L), water (100 ml) and acetic acid (150 ml). The resulting mixture is extracted into hexane (3 L total) and the extract washed with water and brine. The hexane extract is dried over Na₂SO₄, filtered and concentrated to give the ester as a pale yellow oil. This was used without further purification. ¹H NMR (300 MHz, CDCl₃) δ (TMS): 12.25 (s, 1 H), 4.20 (q, J=7 Hz, 2 H), 4.06-3.96 (m, 4 H), 2.53-2.48 (m, 4 H), 1.84 (t, J=6.6 Hz, 2 H), 1.29 (t, J=7 Hz, 3 H).

Preparation A4, Step 2: A solution of crude ester (Step 1) in benzene (500 ml) was treated with (S)-1-Phenyl-ethylamine (61.8 g, 0.51 mol) and Yb catalyst (0.8 g) and heated to reflux for 2-3 hours with the removal of water with a Dean-Stark trap. The resulting solution is concentrated on a rotary evaporator to give a brown solid. This is titurated with 300 ml of 20% isopropyl alcohol in hexane to 150 grams of ene-amine as a tan solid. ¹H NMR (500 MHz, CDCl₃) δ(TMS): 9.41 (d, J=7.4 Hz, 1 H), 7.35-7.20 (m, 5 H), 4.63-4.61 (m, 1 H), 4.14 (q, J=7 Hz, 2 H), 3.99-3.88 (m, 4 H), 2.57-2.49 (m, 3 H), 2.24-2.18 (m, 1 H), 1.72-1.62 (m, 2 H), 1.48 (d, J=7.4 Hz, 3 H), 1.28 (t, J=7 Hz, 3 H).

Preparation A4, Step 3: A solution of ene-amine (Step 2)(150 g, 0.45 mol) in 300 ml acetonitrile and 150 ml of acetic acid is cooled in an ice bath and treated with NaBH(OAc)₃ (170 g, 0.8 mol) powder and stirred 30 min-removed ice bath and stirred overnight at room temperature. The solution is concentrated on a rotary evaporator and the residue dissolved in CH₂Cl₂ and concentrated on a rotary evaporator a couple of times to removed as much acetic acid as possible. The residue is dissolved in 2 L of CH₂Cl₂ and divided in 2 equal parts. While cooling in an ice bath and by adding ice into the solution, each part of the solution was neutralized by the slow addition of 30% NaOH while vigorously stirring. The resulting mixture was separated and the organic phase washed with water and brine, dried over Na₂SO₄, filtered and concentrated on a rotary evaporator to give 137 g of the cis ester amine as a thick dark oil. The crude product was chromatographed on 2 Kg silica gel (15% Ethyl Acetate/Hexane) to give 113 g of (7R,8S)-8-(S-1-Phenyl-ethylamino)-1,4-dioxa-spiro[4.5]decane-7-carboxylic acid ethyl ester as a slightly yellow oil. ¹H NMR (400 MHz, CDCl₃) δ(TMS): 7.34-7.19 (m, 5 H), 4.18 (m, 2 H), 3.95-3.88 (m, 4 H), 3.73 (q, J=7 Hz, 1 H), 3.14 (m, 1 H), 2.81 (m, 1 H), 2.08 (m, 1 H), 1.80-1.38 (m, 6 H), 1.32-1.25 (m, 6 H). MS: $(M+H)^+=334$.

Preparation A4, Step 4: A solution of (7R,8S)-8-(S-1-Phenyl-ethylamino)-1,4-dioxa-spiro[4.5]decane-7-carboxylic acid ethyl ester (55 g, 0.165 mol) in ether (300 ml) is cooled to 0° C. in an ice bath and treated slowly with LAH (12.5 g, 0.32 mol). After the addition is complete the mixture is stirred for an additional 45 mins and then quenched by drop-wise addition of 12 ml of water followed by 50 ml of 1 N NaOH (caution: vigorous foaming). The resultant suspension is stirred in the ice bath for 1-2 hours to give a granular white suspension which is filtered on a buchner funnel. The solid is washed with ether and the combine ether filtrates are concentrated to give 48 g of the alcohol as a colorless syrup. This is used without further purification. A solution of this alcohol (42 g, 0.14 mol) in 500 ml of MeOH was treated with 13 g of 20% Pd(OH)$_2$/C and hydrogenated overnight at 55 psi. The mixture was filtered through Celite and concentrated on a rotary evaporator to give ((7S,8S)-8-Amino-1,4-dioxa-spiro[4.5]dec-7-yl)-methanol as a syrup. This was used without further purification. $^1$H NMR (300 MHz, CDCl$_3$) δ (TMS): 3.99-3.92 (bm, 4 H), 3.84 (dd, J=3 Hz, J=12 Hz, 1 H), 3.67 (dd, J=5 Hz, J=12 Hz, 1 H), 3.27 (m, 1 H), 2.51 (bs, 3 H), 1.67-1.55 (m, 7 H).

Preparation A4, Step 5: ((7S,8S)-7-Hydroxymethyl-1,4-dioxa-spiro[4.5]dec-8-yl)-carbamic acid benzyl ester [Intermediate 5]: A solution of crude ((7S,8S)-8-Amino-1,4-dioxa-spiro[4.5]dec-7-yl)-methanol (27 g, 0.14 mol) in 200 mL of CH$_2$Cl$_2$ was treated with an aqueous solution of K$_2$CO$_3$ (20 g, 0.14 mol) and cooled in a ice bath. The mixture is stirred vigorously while benzyl chloroformate (25.6 g, 0.15 mol) is added slowly. After the addition is complete the mixture is stirred an additional 30 min. The organic layer is separated and washed with water, brine and concentrated to give 45 g of ((7S,8S)-7-Hydroxymethyl-1,4-dioxa-spiro[4.5]dec-8-yl)-carbamic acid benzyl ester. $^1$H NMR (300 MHz, CDCl$_3$) δ(TMS): 7.40-7.33 (m, 5 H), 5.11 (s, 2 H), 5.07 (d, J=8 Hz, 1 H), 4.11-4.09 (m, 1 H), 3.95-3.91 (m, 4 H), 3.39-3.31 (m, 2 H), 2.23 (m, 1 H), 1.92-1.85 (m, 2 H), 1.69 (m, 1H), 1.50-1.43 (m, 2 H), 1.24 (t, J=13 Hz, 1 H).

Preparation A5: Synthesis of (1R,2S)-ethyl 5-oxo-2-((S)-1-phenylethylamino)cyclohexanecarboxylate A solution of (7R,8S)-8-(S-1-Phenyl-ethylamino)-1,4-dioxa-spiro[4.5]decane-7-carboxylic acid ethyl ester (55 g, 0.165 mol; See preparation A4, Step 3) in acetone (100 ml) is treated with 1 N HCl (100 ml) and heated to reflux for 2 hrs. The mixture is concentrated on a rotary evaporator and the residue neutralized with 1 N NaOH and extracted into CH$_2$Cl$_2$. The organic extracts were washed with water, brine, and the solvent remove under vacuum to give 10 g of the (1R,2S)-ethyl 5-oxo-2-((S)-1-phenylethylamino) cyclohexanecarboxylate as a colorless oil. This is used without further purification. MS: (M+H)$^+$=290.3.

Preparation A6: Synthesis of (1R,2S,5R)-2-(benzyloxycarbonyl)-5-(tert-butoxycarbonyl)cyclohexanecarboxylic acid To a solution of (1R,2S,5R)-tert-butyl 2-(benzyloxycarbonyl)-7-oxo-6-aza-bicyclo[3.2.1]octane-6-carboxylate (3.00 g, 0.008 mol) in THF (30 ml) was added LiOH (0.32 g, 0.03 mol) in water (7 ml). The reaction mixture was stirred at RT for 20 h and quenched with saturated ammonium chloride solution (20 ml) and extracted with ethyl acetate (2×100 ml). The extract was washed with brine (50 ml), dried (Na$_2$SO$_4$) and concentrated to 3 g (96%) of (1R,2S,5R)-2-(benzyloxycarbonyl)-5-(tert-butoxycarbonyl) cyclohexanecarboxylic acid as an off-white solid. $^1$H NMR (400 MHz, DMSO-d$_6$) δ 1.30 to 1.99 (m, 6H), 1.40 (s, 9H), 2.50 (m, 1H), 3.2 (bs, 1H), 4.10 (bs, 1H), 5.0 (s, 2H), 6.50 (bs, 1H), 7.00 (bs, 1H), 7.35 (m, 5H); MS found: (M+H)$^+$=415.

Preparation A7: Synthesis of tert-butyl (1R,3R,4S)-4-benzyloxycarbonylamino-3-(hydroxymethyl)cyclohexylcarbamate A solution of (1R,2S,5R)-tert-butyl 2-(benzyloxycarbonylamino)-7-oxo-6-aza-bicyclo[3.2.1]octane-6-carboxylate (2.0 g, 5.34 mmol) in tetrahydrofuran (40 mL) was treated with water (8 mL) and then with NaBH$_4$ (1.01 g, 26.7 mmol). The mixture was stirred at rt for 5 h, then was treated with aqueous NaOH (1.0 M, 100 mL) and stirred for 60 min. The mixture was extracted four times with ethyl acetate. The combined extracts were washed with saturated aqueous NaCl, dried over Na$_2$SO$_4$, and concentrated under vacuum. The residue was recrystallized from ethyl acetate-hexane to provide tert-butyl (1R,3R,4S)-4-benzyloxycarbonylamino-3-(hydroxymethyl)cyclohexylcarbamate as a white solid (1.438 g). MS found: (M+H)$^+$=379.3.

Preparation A8: Synthesis of (1R,2S,5R)-tert-butyl 2-(benzyloxycarbonylamino)-7-hydroxy-6-aza-bicyclo[3.2.1]octane-6-carboxylate A solution of (1R,2S,5R)-tert-butyl 2-(benzyloxycarbonylamino)-7-oxo-6-aza-bicyclo[3.2.1]octane-6-carboxylate (2.62 g, 7.0 mmol) in dichloromethane (50 mL) was stirred on an ice bath and treated dropwise with diisobutylaluminum hydride (1.0 M in tetrahydrofuran, 21 mL, 21 mmol) over ca. 10 min. The solution was stirred on ice for 4 h 5 min, then was treated dropwise over 10 min with methanol (1.75 mL). The mixture was stirred on ice for 10 min, then was treated with water (2.75 mL) over ca. 1 min. The mixture was stirred at rt for 35 min, then was filtered and the gelatinous solid was triturated 3× with dichloromethane and filtered. The combined filtrates were combined and concentrated under vacuum to provide (1R,2S,5R)-tert-butyl 2-(benzyloxycarbonylamino)-7-hydroxy-6-aza-bicyclo [3.2.1]octane-6-carboxylate as a sticky semicrystalline solid (2.41 g). MS found: (M+H—H$_2$O)$^+$=359.3.

Preparation B1: Synthesis of 2-(3-ethylureido)-5-(trifluoromethyl)benzoic acid

Preparation B1, Step 1: N-Boc 2-amino-5-(trifluoromethyl)benzoic acid (S. Takagishi, et al., Synlett 1992, 360; 5.1 g, 17 mmol) was dissolved in DMF (42 mL) and the solution was charged with allyl bromide (3.8 mL, 44 mmol) and potassium carbonate (3.4 g, 25 mmol). The slurry was stirred for 14 h at RT, diluted with EtOAc, and washed successively with brine, water, and brine. The organic phase was dried (Na$_2$SO$_4$), filtered, and concentrated in vacuo to provide the allyl ester as a white solid. This material was dissolved in methylene chloride (30 mL) and TFA (15 mL) and stirred at RT for 2 h before being concentrated in vacuo. The residue was dissolved in methylene chloride and the solution was concentrated in vacuo; this procedure was repeated twice to provide the presumed TFA salt of allyl 2-amino-5-(trifluoromethyl)benzoate. MS found: (free M+H)$^+$=246.29.

Preparation B1, Step 2: The allyl 2-amino-5-(trifluoromethyl)benzoate from step 1 (ca. 15.7 mmol) was dissolved in THF (60 mL) and phosgene (24.9 mL, 47 mmol) was added at 0° C. dropwise. The reaction was stirred for 15 minutes at 0° C. Triethylamine (13.1 mL, 94 mmol) was slowly added and stirring was continued for 2 hours. The reaction was concentrated in vacuo to afford a yellow solid. A portion (2.4 g, ca. 7.7 mmol) of the yellow solid was dissolved in THF (40 mL) and the solution was charged with ethylamine (20 mL of a 2.0 M solution in THF). The reaction was stirred for 14 h at RT and then diluted with EtOAc. The organic phase was washed successively with 1N HCl (2×) and brine (1×) before being dried (Na$_2$SO$_4$), filtered, and concentrated in vacuo to give allyl 2-(3-ethylureido)-5-(trifluoromethyl) benzoate as a white solid (1.8 g). MS found: (M+Na)$^+$=339.29.

Preparation B1, Step 3: The allyl 2-(3-ethylureido)-5-(trifluoromethyl)benzoate (1.8 g, ca. 5.7 mmol) was dissolved in acetonitrile (50 mL) The solution was charged with pyrrolidine (1.0 mL, 12 mmol) and Ph(PPh$_3$)$_4$ (140 mg, 0.17 mmol) and then stirred for 2 h at RT before being concentrated in vacuo. The residue was diluted with EtOAc and this was washed successively with 1N HCl (2×) and brine (1×) before being dried (Na$_2$SO$_4$), filtered, and concentrated in vacuo. The residue was triturated with methylene chloride to afford pure 2-(3-ethylureido)-5-(trifluoromethyl)benzoic acid (0.89 g). $^1$H-NMR (300 MHz, d$_4$-MeOH): δ 8.59 (d, 1 H, J=9.6 Hz), 8.26 (d, 1 H, J=1.5 Hz), 7.72 (dd, 1 H, J=9.2, 1.8 Hz), 3.23 (q, 2 H, J=7.3 Hz), 1.17 (t, 3 H, J=7.2 Hz).

Preparation B2: Synthesis of 2-(isopropylureido)-5-(trifluoromethyl)benzoic acid The complete three-step procedure described in Preparation B1 was followed, substituting isopropylamine for ethylamine in Step 2 to provide the title compound. MS found: (M–H)–=289.

Preparation B3: Synthesis of 2-(azetidine-1-carboxamido)-5-(trifluoromethyl)benzoic acid The complete three-step procedure described in Preparation B1 was followed, substituting azetidine for ethylamine in Step 2 to provide the title compound. MS found: (M–H)–=287.

Preparation B4: Synthesis of 2-(cyclopropylureido)-5-(trifluoromethyl)benzoic acid The complete three-step procedure described in Preparation B1 was followed, substituting cyclopropylamine for ethylamine in Step 2 to provide the title compound. $^1$H NMR (300 MHz, CD$_3$OD) δ 8.56 (d, J=9.8 Hz, 1H), 8.32 (s, 1H), 7.59 (d, J=9.8 Hz, 1H), 2.62-2.61 (m, 1H), 0.83 (s, 2H), 0.58 (s, 2H); $^{19}$F NMR (282 MHz, CD$_3$OD) δ –61.7.

Preparation B5: Synthesis of 2-(methylsulfonamido)-5-(trifluoromethyl)benzoic acid Preparation B5, Step 1: To a solution of 4-(trifluoromethyl)benzenamine (10.0 g, 0.0617 mol) in dry methanol (200 ml) was added iodine monochloride (10.49 g, 0.148 mol) in dry MDC (40 ml) at RT slowly. Reaction mixture was stirred at RT over night. The reaction mixture was concentrated, water was added and extracted with ethyl acetate (2×100 ml). The organic layer was washed with water, brine (2×50 ml), dried over Na$_2$SO$_4$ and concentrated. The crude product was purified by column chromatography using 6% ethyl acetate in pet-ether to get 2-iodo-4-(trifluoromethyl)benzenamine (12.5 g, 70%) as pale yellow liquid. $^1$H NMR (400 MHz, CDCl$_3$) δ 4.42 (bs, 2H), 6.75 (d, 1H), 7.38 (d, 1H), 7.87 (s, 1H).

Preparation B5, Step 2: A mixture of 2-iodo-4-(trifluoromethyl)benzenamine (11.0 g, 0.0382 mol), pyridine (40 ml), methanesulfonylchloride (5.3 g, 0.046 mol) and DMAP (0.46 g, 0.0038 mol) in a 100 ml RB flask was heated slowly to 105° C. and maintained the same temperature for over night. The reaction mixture was concentrated to remove the pyridine. The crude product obtained was purified by column chromatography using 10% ethyl acetate in pet ether as eluent to get N-(2-iodo-4-(trifluoromethyl)phenyl)methanesulfonamide (4.5 g, 32%) as white solid. $^1$H NMR (400 MHz, CDCl$_3$) δ 3.08 (s, 3H), 6.88 (bs, 1H), 7.65 (d, 1H), 7.75 (d, 1H), 8.07 (s, 1H).

Preparation B5, Step 3: To a mixture of N-(2-iodo-4-(trifluoromethyl)phenyl)methanesulfonamide (3.5 g, 9.589 mmol) dry methanol (30 ml) DMF (30 ml) was added palladium(II)acetate (0.07 g,0.35 mmol), 1,1-bis(diphenylphosphene)ferrocene (0.32 g, 0.577 mmol) and TEA (1.96 g, 19.4 mmol) at RT. To that reaction mixture was purged with carbon monoxide for 30 min at RT. Reaction mixture was slowly heated to 60° C. and maintained at the same temperature for over night under carbon monoxide atm. Water was added and the reaction mixture was extracted with ethyl acetate (3×50 ml). The organic layer was washed with brine, dried (Na$_2$SO$_4$) and concentrated. The crude product was purified by column chromatography 15% ethyl acetate in pet ether as eluent to get methyl 2-(methylsulfonamido)-5-(trifluoromethyl)benzoate (2.0 g, 70%) as white solid. $^1$H NMR (400 MHz, CDCl$_3$) δ 3.14 (s, 3H), 3.99 (s, 3H), 7.78 (d, 1H), 7.87 (d, 1H), 8.34 (s, 1H), 10.75 (bs, 1H).

Preparation B5, Step 4: To a mixture of methyl 2-(methylsulfonamido)-5-(trifluoromethyl)benzoate (1.0 g, 3.367 mmol) in THF (20 ml) and water (20 ml) was added lithium hydroxide (0.4242 g, 10.10 mmol) and stirred at RT for 6 h. The reaction mixture was acidified with 1.5 N HCl and extracted with ethyl acetate (3×50 ml). The organic layer was washed with water, brine, dried (Na$_2$SO$_4$) and concentrated. The solid was filtered and dried under vaccum to get 2-(methylsulfonamido)-5-(trifluoromethyl)benzoic acid (0.7 g, 73%) as white solid. $^1$H NMR (400 MHz, CDCl$_3$) δ 3.31 (s, 3H), 7.78 (d, 1H), 7.97 (d, 1H), 8.24 (s, 1H), 11.13 (bs, 1H); $^{13}$C NMR (100 MHz, CDCl$_3$) δ 40.74, 116.5, 118.3, 122.8 (m), 128.8, 131.6, 144.3, 169.1. MS found: (M–H)–=282.

Preparation B6: Synthesis of 5-(trifluoromethyl)-2-(trifluoromethylsulfonamido)benzoic acid Preparation B6, Step 1: To a solution of 4-trifluoromethylaniline (5 g, 0.031 mol) in 50 ml of dry benzene was added triethylamine (6.26 g, 8.63 ml, 0.06 mol) at 0° C. Pivaloyl chloride (4.5 g, 0.04 mol) was added slowly and stirred at RT over night. The RM was quenched with water and extracted with ethyl acetate. The organic layer was washed with water, brine and concentrated. To the solid was triturated with pet-ether and filtered to give N-(4-(trifluoromethyl)phenyl)-pivalamide (6.7 g) as white solid.

Preparation B6, Step 2: To a solution of N-(4-(trifluoromethyl)phenyl)pivalamide (1 g, 4.08 mmol) in 20 ml of dry THF under nitrogen was added n-butyllithium (0.65 g, 4.1 ml) at 0° C. The reaction mixture was maintained at 0° C. for 3 h and added onto dry ice and stirred at RT over night. The reaction mixture was concentrated and the solid product obtained was dissolved in 25 ml of dry methanol and purged HCl gas for 30 min at 0° C. The mixture was stirred at RT for 2 h and heated at 55° C. over night. The reaction mixture was concentrated, basified with sodium bicarbonate solution and extracted with ethyl acetate. The organic layer was washed with water, brine and concentrated. The crude product was purified by flash chromatography to give methyl 2-amino-5-(trifluoromethyl)benzoate (0.55 g) as white solid.

Preparation B6, Step 3: To a solution of methyl 2-amino-5-(trifluoromethyl)benzoate (0.25 g, 1.141 mmol) and triethylamine (0.115 g, 0.16 ml, 1.14 mmol) in 3 ml of dry dichloromethane was added trifluoromethane sulfonic anhydride (0.64 g, 2.28 mmol) at –78° C. The mixture was maintained below –40° C. for 3 h and stirred at RT for over night. Water was added and extracted with dichloromethane. The organic layer was dried and concentrated. The product was purified by flash chromatography to give 0.3 g (75%) of methyl 5-(trifluoromethyl)-2-(trifluoromethylsulfonamido) benzoate as white solid. MS found: $(M+H)^+=352$.

Preparation B6, Step 4: To a solution of methyl 5-(trifluoromethyl)-2-(trifluoromethylsulfonamido)benzoate (2.7 g, 7.7 mmol) in 55 ml of THF was added lithium hydroxide (0.97 g, 23.1 mmol) in 55 ml of water and stirred at RT over night. The reaction mixture was acidified with 1.5N HCl and extracted with ethyl acetate. The organic layer was washed with water, brine and concentrated to give 5-(trifluoromethyl)-2-(trifluoromethylsulfonamido)benzoic acid (2 g) as white solid. $^1$H NMR (DMSO-$d_6$, 400 MHz) δ 7.77 (m, 2H), 8.18 (s, 1H). MS found: $(M-H)^-=336$.

Preparation B7: Synthesis of 5-isopropyl-2-(trifluoromethylsulfonamido)benzoic acid The complete four-step procedure described in Preparation B6 was followed, substituting 4-isopropylaniline for 4-trifluoromethylaniline in Step 1 to provide the title compound. $^1$H NMR (DMSO-$d_6$, 400 MHz) δ 1.19 (d, 6H), 2.92 (m, 1H), 7.37 (d, 1H), 7.47 (d, 1H), 7.77 (s, 1H). MS found: $(M-H)^-=310$.

Preparation C1: Synthesis of 2-tert-butylpyrimidine-4-carboxylic acid

Preparation C1, Step 1: A 22% solution of sodium ethoxide in ethanol (53 mL, 165 mmol) was added dropwise to a magnetically stirred suspension of tert-butylcarbamidine hydrochloride (20.0 g, 146 mmol) in ethanol (100 mL). When the addition was complete, the yellow suspension was warmed to 50° C., the heating mantle was removed, and a solution of mucobromic acid (15.7 g, 61 mmol) in ethanol (50 mL) was added dropwise at a rate which did not allow the temperature to exceed 55° C. When this addition was complete, a 22% solution of sodium ethoxide in ethanol (32 mL, 98 mmol) was added dropwise, then the mixture was allowed to cool to room temperature. The suspension was filtered, the solids were rinsed with ethanol (2×20 mL), and the combined filtrates were concentrated in-vacuo. The residue thus obtained was stirred in 2 N aqueous HCl (30 mL). The resulting solids were collected by filtration, rinsed with ice-cold water (2×20 mL), and air dried to yield 12.1 g of 5-Bromo-2-tert-butyl-pyrimidine-4-carboxylic acid as a beige powder. MS (ES+)=259, 261 $(M+H)^+$.

Preparation C1, Step 2: A mixture of 5-Bromo-2-tert-butyl-pyrimidine-4-carboxylic acid (1.65 g, 6.37 mmol) and aqueous sodium hydroxide (1.0 N, 19.1 mL, 19.1 mmol) in methanol (100 ml) was treated with a catalytic amount of 10% palladium on carbon. The mixture was degassed under vacuum/nitrogen, then hydrogenated at 50 psi for 2 hours. The catalyst was removed by filtration, the methanol was removed under vacuum, and the aqueous was acidified by the addition of 1.0 N aqueous hydrochloric acid (40 mL). The resulting suspension was extracted with ethyl acetate (4×50 mL), the combined organic phases were washed with brine, dried over sodium sulfate, and concentrated in-vacuo to yield 1.06 g of 2-tert-butylpyrimidine-4-carboxylic acid as a white powder. MS (ES+)=181 (M+H+).

Preparation C2: Synthesis of 3-tert-Butyl-benzoic acid

Preparation C2, Step 1: A mixture of the commercially available methyl 3-bromo-5-tert-butylbenzoate (700 mg, 2.58 mMol), aqueous NaOH (1 N, 7.75 mL, 7.75 mMol), and Pearlman's catalyst (100 mg) in methanol (20 mL) was hydrogenated at 50 psi for 22 hours. The catalyst was removed by filtration and rinsed with a small amount of methanol. The filtrate was concentrated in-vacuo to remove methanol, and the aqueous mixture was acidified with 1 N HCl (10 mL), then extracted with ethyl acetate (3×20 mL). The combined organic phases were dried over sodium sulfate, then concentrated in-vacuo. Analysis of the resulting material by LC/MS showed that the ester had hydrolyzed to the carboxylic acid, but that the bromide was still present. The material was dissolved in methanol (20 mL), and hydrogenated overnight at 50 psi in the presence of 1 N aqueous NaOH (5.2 mL, 5.2 mMol) and 10% palladium on activated carbon (50 mg). Analysis of the crude reaction mixture by LC/MS showed that the bromine was still present, so Pearlman's catalyst (200 mg) was added, and hydrogenation at 50 psi was continued for 23 hours. MS showed that the reaction was now complete, so the reaction was worked up as described previously in this example to yield 376 mg (81% yield) of white powder as product. MS (AP−)=177 (M−H)

Preparation C3: Synthesis of 6-tert-butylpicolinic acid HCl salt

Preparation C3, Step 1: 2-tert-butylpyridine (2.00 g, 14.8 mmol, 1 eq.) was dissolved in HOAc (10 mL) and 30% hydrogen peroxide (1.68 mL, 14.8 mmol, 1 eq.) at room temperature then the reaction was refluxed for 20 hours. The reaction was stripped to obtain an amber oil which was dissolved in methylene chloride (10 mL) then dried over sodium sulfate and stripped to obtain 2-tert-butylpyridine-N-oxide (1.60 g) as an amber oil. Yield=71.5%. LCMS detects $(M+H)^+=152.09$.

Preparation C3, Step 2: 2-tert-butylpyridine-N-oxide (1.60 g, 10.6 mmol, 1 eq) was dissolved in methylene chloride (25 mL) at room temperature under nitrogen then trimethylsilyl cyanide (1.79 mL, 13.4 mmol, 1.27 eq.) was added followed by the dropwise addition of dimethylcarbamyl chloride (1.24 mL, 13.4 mmol, 1.27 eq.) over 3 minutes. Stirred for 20 hours. Worked up by adding 10% potassium carbonate (aqueous) (25 mL). Foaming occurred. Stirred 10 minutes then extracted 3 times with methylene chloride (25 mL). The organic layers were combined, dried over sodium sulfate then stripped to give an amber oil. Purified over silica gel in 3:1 hexanes/ethyl acetate. Obtained 6-tert-butylpicolinonitrile (1.08 g) as an amber oil. Yield=59%. LCMS detects $(M+H)^+=161.14$.

Preparation C3, Step 3: 6-tert-butylpicolinonitrile (1.05 g) was dissolved in 6N HCl (aqueous) at room temperature then refluxed for 20 hours. Worked up by stripping 3 times from acetonitrile. Obtained solids. The solids were refluxed in 10 mL of acetonitrile. Solids which didn't dissolve were filtered off. The filtrate was stripped to give 6-tert-butylpicolinic acid HCl salt (680 mg) as a colorless oil. Yield=48%. LCMS detects $(M+H)^+=180.16$.

Preparation C4: Synthesis of 6-(trifluoromethyl)picolinic acid

Preparation C4, Step 1: 2-bromo-6-(trifluoromethyl)-pyridine (100 mg, 0.44 mmol, 1 eq.) was dissolved in diethyl ether at room temperature under nitrogen then cooled to −70° C. Added 1.6M n-Butyllithium in hexanes (0.28 mL, 0.44 mmol, 1 eq.) dropwise via an addition funnel. Stirred at −40° C. for 15 minutes then cooled to −70° C. and bubbled in CO$_2$ gas for 10 minutes. Allowed to warm to room temperature. Added water then rinsed 3 times with diethyl ether. The aqueous pH was adjusted to=3 with conc. HCl. Extracted the acidic aqueous layer 3 times with ethyl acetate. The ethyl acetate layers were combined, dried over sodium sulfate and stripped to give 6-(trifluoromethyl)picolinic acid (30 mg) as a white solid. Yield=35%. LCMS detects (M+H)$^+$ =192.06.

Preparation C5: Synthesis of 3-(adamant-1-yl)-pyrrole-5-carboxylic acid

Preparation C5, Step 1: Ethyl pyrrole-2-carboxylate (2.09 g, 15 mmol, 1 eq), was added to a mixture of gallium(III) chloride (2.90 g, 16.5 mmol, 1.1 eq) in carbon disulfide (40 mL) and the contents heated at 40° C. for 30 min. Afterwards, 1-chloroadamantane (2.82 g, 16.5 mmol, 1.1 eq), was added thereto and the contents heated for another 40 minutes. The reaction was poured onto a mixture of ice and 1.0 N HCl, and extracted with chloroform. The extracts were washed with saturated sodium bicarbonate, dried (MgSO$_4$) and the solvent stripped to yield a crude solid. Recrystallization from EtOAc yielded 2 crops of ethyl 3-(adamanty-1-yl)-pyrrole-5-carboxylate. 1$^{st}$ crop wt.=0.67 grams. 2$^{nd}$ crop wt.=1.10 grams. MS found: (M+H)+=274.44 and 274.45, respectively.

Preparation C5, Step 2: Ethyl 3-(adamanty-1-yl)-pyrrole-5-carboxylate (0.29 g, 1.1 mmol, 1 eq), 1.000 N NaOH (2.20 mL, 2.2 mmol, 2 eq) and MeOH (15 mL) were mixed and stirred overnight. After only partial reaction, more 1.000 N NaOH (21 mL) together with more MeOH to dissolve were added and the contents refluxed for 4 hours. The contents were acidified to pH=1 with 1.0 N HCl. The MeOH was stripped off to yield solids and aqueous. The mixture was extracted with EtOAc, the EtOAc layers were combined, washed with brine, dried (MgSO4) and stripped to yield 250 mg of 3-(adamant-1-yl)-pyrrole-5-carboxylic acid as a white powder. MS found: (M+H)+=246.44

Preparation C6: Synthesis of 3-(Adamant-1-yl)-1-methylpyrrole-5-carboxylic acid Preparation C6, Step 1. Ethyl 3-(adamant-1-yl)-pyrrole-5-carboxylate (0.20 g, 0.7 mmol, 1 eq) was dissolved in THF (20 mL). Potassium bis(trimethylsilyl)amide (0.5 M in Tol, 1.62 mL, 0.81 mmol, 1.1 eq) was added thereto followed by iodomethane (.0.102 mL, 1.6 mmol, 2.2 eq). The next day, the same amounts of potassium bis(trimethylsilyl)amide and iodomethane were again added to drive the reaction to completion. In 4 h, the reaction was finished. Ethyl acetate was added (100 mL) and the organic layer was washed with water (2×), brine, dried (MgSO$_4$) and stripped to yield 600 mg of ethyl 3-(adamant-1-yl)-1-methylpyrrole-5-carboxylate, which was used as is in the next step. MS found: (M+H)+=288.16.

Preparation C6, Step 2: Saponification of ethyl 3-(adamant-1-yl)-1-methylpyrrole-5-carboxylate (entire contents from Step 1) by the procedure in Preparation C5, step 2 yielded 160 mg of 3-(adamant-1-yl)-1-methylpyrrole-5-carboxylic acid. MS found: (M−H)+=258.10.

Preparation C7: Synthesis of 6-tert-Butyl-4-chloro-pyrrolo[2,1-f][1,2,4]triazine Preparation C7, Step 1: Ethyl pyrrole-2-carboxylate (7.24 g, 52 mmol, 1 eq), 2-chloro-2-methylpropane (6.18 mL, 57 mmol, 1.1 eq), gallium trichloride (10.0 g, 57 mMol, 1.1 eq), and carbon disulfide (200 mL) were mixed and refluxed for 45 min. The reaction was poured onto a mixture of ice and 1.0 N HCl. The aqueous mixture was extracted with chloroform, the chloroform layer was washed with saturated sodium bicarbonate, dried over magnesium sulfate, and stripped to yield 9.78 g of a golden oil, which eventually crystallized. Flash chromatography over silica gel in 9:1 hexane/ethyl acetate yielded 3.62 g of ethyl 4-tert-butyl-1H-pyrrole-2-carboxylate. MS found: (M−H)+=196.28.

Preparation C7, Step 2: Preparation of monochloramine by the method of John Hynes, Jr., et al., *J. Org. Chem.*, 2004, 69, 1368: NH$_4$Cl (3 g, 56 mmol, was mixed in ether (110 mL) and cooled to −5° C. Concentrated NH$_4$OH (4.7 mL) was then added followed by dropwise addition of bleach (Chlorox, 72 mL) over 15 minutes. The mixture was stirred for 15 minutes, the layers separated and the organic layer washed with brine. The organic layer was dried over powdered CaCl$_2$ in the freezer for 1 h and used for the subsequent step immediately. Ethyl 4-tert-butyl-1H-pyrrole-2-carboxylate (1.67 g, 8.6 mmol, 1 eq) was dissolved in DMF. Sodium hydride (60% suspension in oil) (0.41 g, 10 mmol, 1.2 eq) was then added thereto cautiously and stirred for 45 minutes at RT under nitrogen. Monochloramine was then added (0.15M in ether, 68.4 mL, 10 mmol, 1.2 eq). The next morning, the reaction is quenched with saturated aqueous Na$_2$S$_2$O$_3$, diluted with water and extracted into ether. The ether layer is dried, filtered and stripped to yield 3.19 g of ethyl 3-tert-butyl-1-aminopyrrole-5-carboxylate as a yellow oil which eventually crystallized as long needles. MS found: (M+H)+=211.34.

Preparation C7, Step 3: Ethyl 3-tert-butyl-1-aminopyrrole-5-carboxylate (1.00 g, 4.76 mmol, 1 eq), formamidine acetate (1.46 g, 14.3 mmol, 3 eq.) and 2-ethoxyethanol (10 mL) were mixed and refluxed for 3 hours. The solvent was stripped and then restripped from chloroform (3×) to yield a solid. This solid was stirred in 5 mL MeOH, filtered, and the collected solids rinsed with Et$_2$O and dried to yield 233 mg of 6-tert-butyl-pyrrolo[2,1-f][1,2,4]triazin-4-ol as a white solid. LCMS found: (M+H)+=191.

Preparation C7, Step 4: 6-tert-Butyl-pyrrolo[2,1-f][1,2,4]triazin-4-ol (0.43 mg, 2.26 mmol, 1 eq.) and POCl$_3$ (4.21 mL, 45.2 mmol, 20 eq.) were mixed and refluxed for 4 hours. The mixture was stripped then restripped 3× from methylene chloride and then dissolved in methylene chloride and rinsed 3× with sat'd NaHCO$_3$, 1× with brine. The organic layers were collected, dried and stripped in vacuo to yield 490 mg of 6-tert-butyl-4-chloro-pyrrolo[2,1-f][1,2,4]triazine as an amber oil. LCMS detects (M+H)+=210.

Preparation C8: Synthesis of 3-(tert-Butyl)-pyrrole-5-carboxylic acid

Preparation C8, Step 1: Ethyl 4-tert-butyl-1H-pyrrole-2-carboxylate (from C7, Step 1) (38 mg, 1.95 mmol, 1 eq), 1.000 N NaOH (39 mL, 39 mmol, 20 eq) and MeOH (50 mL) were mixed and refluxed for 1 hour. The mixture was acidified with 1.0 N HCl, (1.0 N), the MeOH stripped, and the remaining aqueous extracted with ethyl acetate (2×). The organic layers were combined, dried (MgSO4), and stripped to yield 290 mg of an off-white solid. NMR (CDCl3+2 drops DMSO-D6) δ 6.50 (s, 1H); 6.46 (s, 1H); 0.95 (s, 9H).

Preparation C9: Synthesis of 3-(tert-Butyl)-1-methylpyrrole-5-carboxylic Acid Preparation C9, Step 1: Ethyl 4-tert-butyl-1H-pyrrole-2-carboxylate was first methylated by the method of C6, Step 1 and then saponified by the method of C8, Step 1 (reflux lasting 4 hours) yielding 3-(tert-butyl)-1-methylpyrrole-5-carboxylic acid. MS found: $(M+H)^+=182.10$.

Preparation C10: Synthesis of lithium 2-tert-butyl-1-oxo-pyrimidine-4-carboxylate The titled compound was prepared from 2-tert-butylpyrimidine-4-carboxylic acid utilizing the procedures used to synthesize lithium 2-phenylisonicotinate, N-oxide (Preparation H1). The synthesis yielded a 3:1 mixture of desired product, lithium 2-tert-butyl-l-oxo-pyrimidine-4-carboxylate, and the des-oxo derivative, lithium 2-tert-butylpyrimidine-4-carboxylate. This mixture was used as is. MS found: $(M+H)^+=197.24$.

Preparation C11: Synthesis of 3-tert-butyl-4-methoxybenzoic acid

Preparation C11, Step 1: 3-tert-butyl-4-hydroxybenzoic acid (1.00 g, 5.15 mmol, 1 eq), dimethyl sulfate (1.07 mL, 11.3 mmol, 2.2 eq) and potassium carbonate (2.85 g, 20.6 mmol, 4 eq) were refluxed in methyl ethyl ketone (20 mL) for 3 hours. Worked up by adding $H_2O$ (20 mL) then stripped off the methyl ethyl ketone. The aqueous was extracted 3 times with diethyl ether (25 mL). The organic layers were combined, dried (sodium sulfate) and stripped to give methyl 3-tert-butyl-4-methoxybenzoate (1.12 g) of an amber oil Yield=97%. LCMS detects $(M+H)^+=223.23$.

Preparation C11, Step 2: Methyl 3-tert-butyl-4-methoxybenzoate (1.12 g, 5.03 mmol, 1 eq) was dissolved in 1N NaOH in methanol (50.38 mL, 50.3 mmol, 10 eq) at room temperature then refluxed for 4 hours. Worked up stripping off the methanol. Added $H_2O$ (10 mL) then adjusted the pH to 3 with 6N HCl. Solids precipitated. Extracted the suspension 3 times with methylene chloride (20 mL). The organic layers were combined, dried (sodium sulfate) and stripped to give 3-tert-butyl-4-methoxybenzoic acid (0.98 g) as a white solid. Yield=93%. LCMS detects $(M+H)^+=208.25$.

Preparation C12: Synthesis of lithium 3-bromo-5-tert-butylbenzoate

Preparation C12, Step 1: A solution of the commercially available methyl 3-bromo-5-tert-butylbenzoate (87 mg, 0.32 mmol) in THF (2 mL) was treated with 0.5 N aqueous lithium hydroxide (0.71 mL, 0.35 mmol), and the mixture was stirred at room temperature for six hours. The THF was stripped in-vacuo, and the aqueous was freeze dried to yield 112 mg of light brown solids. This material was used as-is in the next step.

Preparation C13: Synthesis of 5-Adamantan-1-yl-2H-pyrazole-3-carboxylic acid

Preparation C13, Step 1: Diethyl oxalate (3.81 mL, 28 mmol, 1 eq.) was dissolved in THF (25 mL) at RT under nitrogen then taken to near-reflux. Sodium hydride (1.18 g, 29 mmol, 1.05 eq.) was added in 5 portions carefully. A solution of 1-adamantyl methyl ketone (5.00 g, 28 mmol, 1 eq.), in THF (10 mL) was added dropwise via an addition funnel. After the addition was complete, the mixture was refluxed for 1 hour. Cooled to RT and very carefully quenched with saturated $NH_4Cl$ (50 mL) then extracted 3 times with methylene chloride. The organic layers were combined, dried and stripped in vacuo to give 7.80 g of 4-adamantan-1-yl-2,4-dioxo-butyric acid ethyl ester as an amber oil. MS found: $(M+H)^+=279$.

Preparation C13, Step 2: 4-Adamantan-1-yl-2,4-dioxo-butyric acid ethyl ester 7.80 g, 28 mmol, 1 eq.), hydrazine hydrate (1.36 mL, 28 mmol, 1 eq.) and ethanol (20 mL) were refluxed until reaction was complete by LCMS. Stripped off the ethanol, and extracted (3×) with ethyl acetate (50 mL). The organic layers were combined, dried and stripped to give 7.00 g of 5-adamantan-1-yl-2H-pyrazole-3-carboxylic acid ethyl ester as a yellow solid. MS found: $(M+H)^+=275$.

Preparation C13, Step 3: 5-Adamantan-1-yl-2H-pyrazole-3-carboxylic acid ethyl ester (1.00 g, 3.64 mmol, 1 eq.) was dissolved in THF (20 mL) at RT then 1.000 N NaOH (7.29 mL, 7.29 mmol, 2 eq.) was added. Stirred overnight. Stripped off the THF in vacuo then adjusted the pH=3 with 1 N HCl. Extracted 3 times with ethyl acetate (25 mL). The organic layers were combined, dried and stripped to give 830 mg of 5-adamantan-1-yl-2H-pyrazole-3-carboxylic acid as an off-white solid. MS found: $(M+H)^+=247$.

Preparation C14: Synthesis of 5-Adamantan-1-yl-2-methyl-2H-pyrazole-3-carboxylic acid and 5-Adamantan-1-yl-1-methyl-1H-pyrazole-3-carboxylic acid Preparation C14, Step 1: 5-Adamantan-1-yl-2H-pyrazole-3-carboxylic acid ethyl ester (2.00 g, 7.29 mmol, 1 eq.) was dissolved in DMF (25 mL) at RT under of nitrogen then sodium hydride (0.31 g; 7.65 mmol, 1.05 eq.) was added carefully. After 10 minutes, added iodomethane (0.55 mL, 8.75 mmol, 1.2 eq.) in DMF (2 mL). Stirred overnight. Quenched with saturated NH4Cl (25 mL) then extracted 3 times with ethyl acetate (25 mL). The organic layers were combined, dried and stripped then purified over silica gel in 9:1 to 3:1 hexanes/ethyl acetate. Obtained 2 product isomers. Isomer A, wt=1.40 g of solid product. Isomer B, wt=0.38 g of solid product. (Isomer A), MS (ES+)=289 (M+H)+. (Isomer B), MS (ES+)=289 (M+H)+.

Preparation C14, Step 2: Followed the procedure of Preparation C13, Step 3, starting from 5-adamantan-1-yl-2-methyl-2H-pyrazole-3-carboxylic acid ethyl ester and 5-adamantan-1-yl-1-methyl-1H-pyrazole-3-carboxylic acid ethyl ester to afford the titled compounds. For both, MS found: $(M+H)^+=261$.

Preparation D1: Synthesis of 4,6-dichloroquinazoline

Preparation D1, Step 1: 2-Amino-5-chlorobenzoic acid (1.00 g, 5.86 mmol, 1 eq.) and formic acid (3.94 mL, 104 mmol, 17.8 eq.) were mixed at room temperature and then refluxed for 2.5 hours. Cooled to room temperature then added 15 mL of water. Solids precipitated. Stirred the solids for 10 minutes. The solids were filtered, rerinsed 2 times with of water (5 mL). The solids were filtered then stirred in of ethyl acetate (10 mL) for 5 minutes. Filtered the solids to give 6-chloroquinazolin-4-ol (800 mg) as tan solids. Yield=75%. Mass Spec (ESI) detects $(M+H)^+=180.8$.

Preparation D1, Step 2: 6-Chloroquinazolin-4-ol (400 mg, 2.21 mmol, 1 eq.), phosphorus oxychloride (1.99 mL, 21.4 mmol, 9.64 eq.) and triethylamine (0.99 mL, 7.11 mmol, 3.21 eq.) were mixed at room temperature under nitrogen and then refluxed for 2.5 hours. Worked up by stripping the reaction, then re-rotovapping the residue 2 times from toluene to obtain brown solids. Methylene chloride (25 mL) was added to dissolve the solids. The organic mixture was then rinsed 2 times with saturated ammonium chloride (25 mL). The organic layer was dried (sodium sulfate) and stripped to give brown solids. The solids were purified over silica gel in 9:1 to 3:1 hexanes/ethyl acetate. Obtained 4,6-dichloroquinazoline (300 mg) as an off-white solid. Yield=68%. $^1$H NMR (400 MHz) (DMSO-D6) δ 9.16 (s, 1H): 8.33 (s, 1H), 8.17 (apparent t, 2H, J=7 Hz).

Preparation D2: Synthesis of
4-chloro-6-fluoroquinazoline

Preparation D2, Step1: 2-Amino-5-fluorobenzoic acid (2.00 g, 13.0 mmol, 1 eq.) and formic acid (8.72 mL, 231 mmol, 17.8 eq.) were mixed at room temperature and then refluxed for 2.5 hours. Cooled to room temperature then added 25 mL of water. Solids precipitated. Stirred the solids for 1 hour. The solids were filtered then stirred with hexanes (20 mL). The solids were filtered and dried at 110° C. under vacuum for 4 hours to give 6-fluoroquinazolin-4-ol (1.66 g) as a white solid. $^1$H NMR (400 MHz) (CD$_3$OD) δ 8.07(s, 1H); 7.85 (D, 1h); 7.74 (T, 1h); 7.62 (M, 1h).

Preparation D2, Step 2: 6-fluoroquinazolin-4-ol (1.00 g, 6.09 mmol, 1 eq.), phosphorus oxychloride (3.41 mL, 36.6 mmol, 6 eq.) and triethylamine (5.09 mL, 36.6 mmol, 6 eq.) were mixed at room temperature and then refluxed for 2 hours. Worked up by stripping 3 times from methylene chloride. The residue was dissolved in methylene chloride (25 mL) and rinsed 3 times with saturated sodium bicarbonate (25 mL) and 1× with brine (25 mL). The organic layer was dried (sodium sulfate) and stripped to give a crude oil. Purified over silica gel in 9:1 to 3:1 hexanes/ethyl acetate. Obtained 4-chloro-6-fluoroquinazoline (0.96 g) as a tan solid. Yield=86%. LCMS detects (M+H)$^+$=183.16.

Preparation D3: Synthesis of
4-chloro-6-(trifluoromethyl)quinazoline

Preparation D3, Step 1: A suspension of 2-(tert-butoxycarbonylamino)-5-(trifluoromethyl)benzoic acid (56.34 g, 185 mmol, see: S. Takagishi, et al., *Synlett* 1992) in dioxane (100 mL) was treated with the dropwise addition of 4 N hydrochloric acid solution in dioxane (250 mL, 1.0 mol), and the mixture was stirred for 4 h. Analysis by LC/MS indicated that the reaction was not complete, so additional 4 N hydrochloric acid solution in dioxane (250 mL, 1.0 mol) was added, and the mixture was stirred overnight. Analysis by LC/MS indicated that the reaction still contained c. 5% of the starting material, so additional 4 N hydrochloric acid solution in dioxane (100 mL, 0.4 mol) was added, and the mixture was stirred for 4 h. Analysis by LC/MS indicated that the reaction was now complete. The mixture was concentrated in-vacuo, and the residue was stripped 2× from methylene chloride to remove any remaining HCl. The 2-amino-5-(trifluoromethyl)benzoic acid, hydrochloride thus obtained was used immediately in the next step. MS (ES+)=206 (M+H+).

Preparation D3, Step 2: A suspension of 2-amino-5-(trifluoromethyl)benzoic acid, hydrochloride (44.7 g, 185 mmol) and formamidine acetate (38.52 g, 370 mmol) in 2-ethoxyethanol (200 mL) was heated at reflux overnight, during which time a clear solution was observed. The mixture was cooled to room temperature, and the resulting solids were collected by filtration, rinsed with a small amount of 2-ethoxyethanol followed by diethyl ether, and dried under vacuum to yield 9.7 g of an off-white solid, which was not desired product by NMR. The combined filtrates were concentrated in-vacuo, and the residue was crystallized from methanol to yield 31.07 g of 6-(trifluoromethyl)quinazolin-4-ol as off-white plates in two crops. $^1$H NMR (400 MHz, DMSO) δ ppm 12.60 (s, 1 H), 8.35 (s, 1 H), 8.24 (d, J=4.83 Hz, 1 H), 8.13-8.09 (m, 1 H), 7.85 (dd, J=8.35, 4.39 Hz, 1 H). MS (ES+)=215 (M+H+).

Preparation D3, Step 3: A suspension of 6-(trifluoromethyl)quinazolin-4-ol (10.41 g, 48.4 mmol) in phosphorous oxychloride (100 mL) was heated at reflux for 3 h, during which time a clear, amber solution was observed. The solution was cooled to room temperature, concentrated in-vacuo, and stripped 3× from 150 mL methylene chloride to remove any remaining phosphorous oxychloride. The residue was partitioned between EtOAc and saturated sodium bicarbonate (1:1, 300 mL), and the mixture was stirred until gas evolution ceased. The layers were separated, the organic phase was washed successively with saturated sodium bicarbonate and brine, the combined aqueous phases were extracted with EtOAc (50 mL), and the combined organic phases were dried over sodium sulfate then concentrated in-vacuo. The residue was purified over silica gel, eluting with 25% EtOAc/Heptane, to yield 8.14 g of 4-chloro-6-(trifluoromethyl)quinazoline as a white solid. MS (ES+)=233, 235 (M+H+).

Preparation D4: Synthesis of
4-chloro-6-trifluoromethoxyquinazoline

Preparation D4, Step 1 (Synthesis of
(4-Trifluoromethoxy-phenyl)-carbamic Acid
tert-butyl ester):

A solution of 4-(trifluoromethoxy)phenyl isocyanate (9.75 g, 48.0 mMol) in THF (100 mL) was cooled to 0° C., and a 1.0 M THF solution of potassium tert-butoxide (53 mL, 53 mMol) was added dropwise. The mixture was allowed to warm to room temperature, and stirred for 7 hours. The solution was poured into a mixture of saturated ammonium chloride solution (200 mL), and diethyl ether (200 mL). Enough water was added to redissolve the ammonium chloride that had crashed out, the mixture was shaken in a separatory funnel, and the layers were separated. The organic phase was washed with saturated ammonium chloride (100 mL), water (100 mL), brine (100 mL), dried over sodium sulfate, and concentrated in-vacuo. The residue was purified over silica gel, eluting with 10%-20% ethyl acetate/heptane to yield 11.7 g of white solids as product. NMR (500 MHz, DMSO) δ 9.54 (s, 1 H), 7.54 (d, 2H, J=7 Hz), 7.23 (d, 2H, J=8 Hz), 1.45 (s, 9H). Yield=88%.

Preparation D4, Step 2 (Synthesis of 2-tert-Butoxycarbonylamino-5-trifluoromethoxy-benzoic acid): A solution of (4-trifluoromethoxy-phenyl)-carbamic acid tert-butyl ester (2.31 g, 8.33 mMol) in anhydrous THF (50 mL) at −78° C. was treated with a 1.4 M solution of sec-butyllithium in cyclohexane (13 mL, 18.33 mMol), at a rate which did not allow the internal temperature to exceed −60° C. The solution was stirred at −78° C. for 15 minutes, then allowed to warm to −40° C. and stirred for 2.5 hours. The reaction was treated with gaseous CO$_2$, stirred 30 minutes while warming to −20° C., then quenched with saturated ammonium chloride. The mixture was warmed to room temperature, and extracted with ethyl acetate (3×50 mL). The combined organic phases were washed with water (50 mL), brine (50 mL), dried over sodium sulfate, and concentrated in-vacuo. The residue was triturated with hot heptane to yield 1.9 g of white powder as product. NMR (500 MHz, DMSO) δ 12.89 (s, 1H), 8.24 (d, 1 H, J=9 Hz), 7.84 (s, 1H), 7.21 (d, 1H, J=7 Hz), 1.51 (S, 9 Hz). Yield=72%.

Preparation D4, Step 3 (Synthesis of 2-Amino-5-trifluoromethoxy-benzoic acid, HCl salt): 2-tert-Butoxycarbonylamino-5-trifluoromethoxy-benzoic acid (1.9 g, 5.91 mMol) was dissolved in a 4 N HCl solution in dioxane (15 mL), and the resulting suspension was stirred at room temperature for 6 hours. Analysis by LC/MS showed that the reaction was incomplete, so concentrated HCl (1 mL) was added, followed by methylene chloride (20 mL) to dissolve the solids, and the reaction was stirred overnight at room temperature. The mixture was concentrated in-vacuo, then stripped from methanol (3×50 mL) to remove any excess HCl. The resulting solids were used as-is in the next step. MS (ES+)=222 (M+H)$^+$.

Preparation D4, Step 4 (Synthesis of 6-Trifluoromethoxy-quinazolin-4-ol): A mixture of 2-amino-5-trifluoromethoxy-benzoic acid, HCl salt (1.52 g, 5.91 mMol), and formamidine acetate (1.84 g, 17.73 mMol) in 2-ethoxyethanol (20 mL) was heated at reflux for 2 hours. Analysis by LC/MS showed that the reaction was complete, so the mixture was concentrated in-vacuo, and the residue was purified over silica gel, eluting with 50% ethyl acetate/heptane—100% ethyl acetate, to yield 1.1 g of white solids as product. MS (ES+)=231 (M+H)$^+$. Yield=82%.

Preparation D4, Step 5: A suspension of 6-(trifluoromethoxy)quinazolin-4-ol (515 mg, 2.23 mmol) in phosphorous oxychloride (1.9 mL) was treated with triethylamine (3 mL, 21.1 mmol), and the mixture was heated at reflux for 2 h. The resulting solution was cooled to room temperature, and stripped 3× from methylene chloride to remove residual phosphorous oxychloride. The residue was dissolved in 100 mL methylene chloride, 100 mL saturated sodium bicarbonate was carefully added, causing vigorous gas evolution, and the mixture was stirred for 10 min, until gas evolution had ceased. The layers were separated, and the organic phase was washed with saturated sodium bicarbonate (2×30 mL), followed by brine, dried over sodium sulfate, and concentrated in-vacuo. The residue was purified over silica gel, eluting with 40% EtOAc/heptane, to yield 377 mg of 4-chloro-6-(trifluoromethoxy)quinazoline as a colorless oil. $^1$H NMR (400 MHz, CDCl$_3$) δ ppm 9.10 (s, 1 H), 8.16 (d, J=9.23 Hz, 1 H), 8.10 (s, 1 H), 7.83 (dd, J=9.23, 2.20 Hz, 1 H). MS (ES+)=249 (M+H)$^+$.

Preparation D5: Synthesis of
2-tert-Butyl-8-chloro-pyrimido[5,4-d]pyrimidine

Preparation D5, Step 1 (Synthesis of 5-Bromo-2-tert-butyl-pyrimidine-4-carboxylic acid methyl ester): A 2.0 M hexanes solution of trimethylsilyldiazomethane (11.8 mL, 23.62 mMol) was added dropwise to a stirring solution of 5-bromo-2-tert-butyl-pyrimidine-4-carboxylic acid (6.12 g, 23.62 mMol) in 9:1 benzene/methanol (100 mL), and the reaction was stirred for 2 days. TLC analysis showed that the reaction was complete, so the mixture was concentrated in-vacuo. The residue was dissolved in ethyl acetate (100 mL), washed with water (3×20 mL), dried over sodium sulfate, then concentrated in-vacuo. Purified over silica gel, eluting with 10% ethyl acetate/hexanes, to yield 5.2 g of a colorless oil as product. MS (ES+)=273,275 (M+H)$^+$. Yield=81%.

Preparation D5, Step 2 (Synthesis of 5-tert-Butoxycarbonylamino-2-tert-butyl-pyrimidine-4-carboxylic acid methyl ester): A flame dried reaction tube charged with tert-butyl-carbamate (140 mg, 1.2 mMol), cesium carbonate (456 mg, 1.4 mMol), 4,5-bis(diphenylphosphino)-9,9-dimethylxanthane (18 mg, 0.03 mMol), and tris(dibenzylidineacetone) dipalladium(0) (19 mg, 0.02 mMol) was evacuated under vacuum, then backfilled with argon. Dioxane (2 mL) and 5-bromo-2-tert-butyl-pyrimidine-4-carboxylic acid methyl ester (273 mg, 1.0 mMol) were added, and the mixture was degassed under vacuum. The tube was then backfilled with argon, sealed, and heated at 100° C. for 2 hours. Analysis by LC/MS showed complete consumption of starting bromide. The mixture was diluted with methylene chloride (20 mL), filtered to remove solids, and concentrated in-vacuo. The residue was purified over silica gel, eluting with 10% ethyl acetate/heptane, to yield 152 mg of white solids as product. MS (ES+)=310 (M+H)$^+$. Yield=50%.

Preparation D5, Step 3 (Synthesis of 5-Amino-2-tert-butyl-pyrimidine-4-carboxylic acid methyl ester, HCl salt): 5-tert-Butoxycarbonylamino-2-tert-butyl-pyrimidine-4-carboxylic acid methyl ester (2.4 g, 7.75 mMol) was dissolved in a 4 M solution of HCl in dioxane (30 mL). After 10 minutes of stirring, a thick white solid precipitated. The reaction was allowed to stir overnight, during which time the mixture became a homogenous, amber solution. Concentrated in-vacuo, and the residue was stripped from toluene (2×50 mL) followed by methylene chloride (3×50 mL) to remove excess HCl. The resulting 1.85 g of yellow solids was used without further purification in the next step. MS (ES+)=210 (M+H)$^+$.

Preparation D5, Step 4 (Synthesis of 6-tert-Butyl-pyrimido[5,4-d]pyrimidin-4-ol): A mixture of 5-amino-2-tert-butyl-pyrimidine-4-carboxylic acid methyl ester, HCl salt (1.1 g, 4.48 mMol) and formamidine acetate (1.86 g, 17.90 mMol) in 2-ethoxyethanol (20 mL) was heated at reflux for 5 hours. LC/MS analysis showed the reaction to be essentially complete, so the mixture was cooled to room temperature, then concentrated in-vacuo. The residue was purified over silica gel, eluting with ethyl acetate, 1% methanol/ethyl acetate, then 2% methanol/ethyl acetate to yield 1.06 g of a beige solid as product. MS (ES+)=205 (M+H)$^+$. Yield=94%.

Preparation D5, Step 5 (Synthesis of 2-tert-Butyl-8-chloro-pyrimido[5,4-d]pyrimidine): 6-tert-Butyl-pyrimido[5,4-d]pyrimidin-4-ol (210 mg, 1.03 mMol) was dissolved in phosphorous oxychloride (10 mL), and the mixture was heated at reflux for 4 hours. The solution was concentrated in-vacuo, then stripped from methylene chloride (3×50 mL) to remove excess phosphorous oxychloride. The residue was stirred for 10 minutes in saturated sodium bicarbonate (50 mL), then extracted with ethyl acetate (3×30 mL). The combined organic phases were washed with water (30 mL), followed by brine (30 mL), dried over sodium sulfate, then concentrated in-vacuo. The residue was purified over silica gel, eluting with 50% ethyl acetate/heptane, to yield 150 mg of a white solid as product. NMR (500 MHz, CDCl3) δ 9.61 (s, 1H), 9.15 (S, 1H), 1.52 (s, 9H).

Preparation D6: Synthesis of
4-chloro-6-(2-methoxyphenyl)quinazoline

Preparation D6, Step 1: A suspension of 2-amino-5-bromobenzoic acid (2.00 g, 9.26 mmol) and formamidine acetate (3.86 g, 37.0 mmol) in 2-ethoxyethanol (20 mL) was heated at reflux for 2 hours, during which time, a clear solution was observed. The reaction was allowed to cool to room temperature, during which time solids precipitated. The precipitate was collected by filtration and rinsed with diethyl ether, to yield material which contained desired product, but was not pure by NMR analysis. The solids were partitioned between ethyl acetate and water, a small amount of material which did not dissolve was removed by filtration, and the layers were separated. The organic phase was washed twice with water, dried over sodium sulfate, and concentrated in-vacuo to yield 690 mg of 6-bromoquinazolin-4-ol as a tan solid. The initial organic filtrate was concentrated to give solids which were stirred in diethyl ether, collected by filtration, and air dried to yield 430 mg of 6-bromoquinazolin-4-ol as a tan solid. MS (ES+)=225/227 (M+H+).

Preparation D6, Step 2: A mixture of 6-bromoquinazolin-4-ol (227 mg, 1.01 mmol), 2-methoxyphenylboronic acid (307 mg, 2.02 mmol), 2.0 M potassium phosphate (aq) (1.5 mL, 3.0 mmol), and DMF (3 mL) in a 5 mL microwave tube was degassed under vacuum/Ar. A catalytic amount of tetrakis(triphenylphosphine)palladium(0) was added to the tube, the mixture was degassed again, the tube was sealed, and the reaction was heated at 150° C. in the microwave for 30 min. The resulting black mixture was filtered, then concentrated in-vacuo. The residue was taken up in 9:1 ethyl acetate/heptane (50 mL), washed with water (3×20 mL), then brine, then dried over sodium sulfate and concentrated in-vacuo. The residue was purified over silica gel, eluting with 1:1 ethyl acetate/heptane, 100% ethyl acetate, then 9:1 ethyl acetate/methanol, to yield 250 mg of 6-(2-methoxyphenyl)quinazolin-4-ol as a white powder. MS (ES+)=253 (M+H+).

Preparation D6, Step 3. A suspension of 6-(2-methoxyphenyl)quinazolin-4-ol (250 mg, 0.99 mmol) in $POCl_3$ (10 mL) was heated at reflux for 1 h, during which time a clear solution was observed. The mixture was cooled to room temperature, concentrated in-vacuo, then concentrated from methylene chloride (3×100 mL) to remove any remaining $POCl_3$. The residue was partitioned between ethyl acetate (25 mL) and saturated $NaHCO_3$ (30 mL), and the mixture was stirred until gas evolution ceased (10 min). The layers were separated, the organic phase was washed with saturated $NaHCO_3$, water, and brine, dried over sodium sulfate, and concentrated in-vacuo. The residue was purified over silica gel, eluting with 1:3 ethyl acetate/heptane, to yield 217 mg of 4-chloro-6-(2-methoxyphenyl)quinazoline as a white solid. $^1$H NMR (500 MHz, $CDCl_3$) δ ppm 9.03 (s, 1 H), 8.36 (s, 1 H), 8.19 (d, J=7.15 Hz, 1 H), 8.10 (d, J=8.80 Hz, 1 H), 7.42 (m, 2 H), 7.10 (t, J=7.42 Hz, 1 H), 7.04 (d, J=8.25 Hz, 1 H), 3.86 (m, 3 H).

Preparation D7: Synthesis of
3-(4-chloroquinazolin-6-yl)benzonitrile

The procedure described in Preparation D6 was followed, substituting 3-cyanobenzeneboronic acid for 2-methoxyphenylboronic acid in Preparation D6, step 2. MS (ES+)=266/268 (M+H+).

Preparation D8: Synthesis of
4,6-dichloro-2-(3-phenyl-propyl)-quinazoline

Preparation D8, Step 1: 2-Amino-5-chlorobenzamide (Avocado) (0.50 g, 2.93 mmol, 1 eq.), methyl 4-phenylbutyrate (3.14 g, 17.6 mmol, 6 eq.), NaOEt in ethanol (3.09 M, 5.69 mL, 17.6 mmol, 6 eq.) and ethanol (20 mL) were refluxed overnight. Cooled to 25° C. Added 10 mL of 10% HOAc/H2O. Solids formed which were filtered, the solids rinsed with 5 mL $H_2O$, then dissolved in 20 mL of EtOAc/THF. Dried and stripped in vacuo followed by purification over silica gel in 3:1 to 1:1 Hexanes/EtOAc to give 6-chloro-2-(3-phenyl-propyl)-quinazolin-4-ol as a tan solid (200 mg). MS found: (M+H)$^+$=299.

Preparation D8, Step 2: A sample of 6-chloro-2-(3-phenyl-propyl)-quinazolin-4-ol was converted to 4,6-dichloro-2-(3-phenyl-propyl)-quinazoline by the procedure detailed in Preparation D1, Step 2. The material was used immediately after synthesis.

Preparation D9: Synthesis of
2,4,6-Trichloro-quinazoline

Preparation D9, Step 1: 2-Amino-5-chlorobenzamide (Avocado) (3.00 g, 17.5 mmol, 1.0 eq.) was suspended in 105 mL of $H_2O$ and 1.75 mL of HOAc at 25° C. A 12 mL solution of $H_2O$ and sodium cyanate (2.80 g, 43.0 mmol, 2.46 eq.) was then added slowly. Stirred at 35° C. for 1 hour. Added 31.26 mL of 1.0 N NaOH slowly. Solids precipitated. Cooled to 0° C. Carefully added conc. HCl to pH=3. Filtered solids. Solids were then stirred in $Et_2O$ then refiltered and pumped under high vacuum to give 3.36 grams of 6-chloro-quinazoline-2,4-diol as a tan solid. MS found: (M+H)$^+$=197.

Preparation D9, Step 2: 6-Chloro-quinazoline-2,4-diol (0.50 g, 2.54 mmol, 1 eq.), phosphorous oxychloride (2.14 mL, 22.9 mmol, 9 eq.) and 2,6-lutidine (0.44 mL, 3.82 mmol, 1.5 eq.) were mixed and refluxed for 2 hours. The mixture was stripped and then restripped 3× from methylene chloride. The residue was dissolved in methylene chloride and washed with saturated sodium bicarbonate (3×) and once with water. The organic layer was dried, stripped, and purified over silica gel in 9:1 hexane/ethyl acetate to yield 220 mg of 2,4,6-Trichloro-quinazoline as a light colored solid. The compound was used as is in the next step.

Preparation D10: Synthesis of
4,6-dichloro-2-propylquinazoline

Preparation D10, Step 1: Butyryl chloride (0.68 mL, 6.5 mmol, 1 eq) was slowly dripped into a mixture of 2-amino-5-chlorobenzamide (1.10 g, 6.5 mmol, 1 eq), 1.000N NaOH (6.50 mL, 6.5 mmol, 1 eq) and THF (enough to dissolve) at 0° C. More acid chloride and base were added to drive the reaction to completion. After 4 days ethyl acetate was added followed by 1N HCl. The layers were separated and the organic layer washed with 1N HCl (2×), saturated sodium bicarbonate (1×), and brine (1×). The organic layer was dried (MgSO4) and stripped to yield 2-butyramido-5-chlorobenzamide (1.44 g) as a white powder. Mass Spec (ESI) (M+H)$^+$=241.0.

Preparation D10, Step 2: 2-butyramido-5-chlorobenzamide (1.08 g, 4.49 mmol, 1 eq) was dissolved in ethanol (10 mL) at room temperature then 1N NaOH (13.46 mL, 13.5 mmol, 3 eq) added. Worked up after 15 minutes by adding 1N HCl to pH=2. Solids precipitated and were filtered and pumped under high vacuum to give 6-chloro-2-propylquinazolin-4-ol (810 mg) as a white solid. Yield=81%. Mass Spec (ESI) (M+H)$^+$=223.0.

Preparation D10, Step 3: 6-Chloro-2-propylquinazolin-4-ol (810 mg, 3.64 mmol, 1 eq), phosphorus oxychloride (3.30 mL, 35.1 mmol, 9.64 eq) and triethylamine (1.63 mL, 11.7 mmol, 3.21 eq) were mixed at room temperature then refluxed for 2.5 hours. The reaction was stripped 3 times from methylene chloride. The residue was dissolved in methylene chloride (25 mL) and rinsed 3 times with saturated sodium bicarbonate (25 mL), 1× with water (25 mL). The organic layer was dried (sodium sulfate) and stripped to an amber oil. Purified over silica gel in 9:1 hexanes/ethyl acetate to give 4,6-dichloro-2-propylquinazoline (510 mg) as a light-amber solid. Yield=58%. $^1$H NMR (400 MHz) (CD3OD) □ 7.98 (s, 1H); 7.98 (d, 1H, J=7 Hz); 7.93 (d, 1H, J=7 Hz); 3.00 (t, 2H, J=7 Hz); 1.90 (t of q, 2 H, J=7 Hz); 1.00 (t, 3H, J=7 Hz).

Preparation D11: Synthesis of 2-butyl-4-chloro-6-(trifluoromethyl)quinazoline

Preparation D11, Step 1: 2-amino-5-(trifluoromethyl)-benzamide (100 mg, 0.49 mmol, 1 eq) was suspended in THF (5 mL) at 0° C. then 1.000N NaOH (0.73 mL, 0.735 mmol, 1.5 eq) was added. Valeryl chloride (87 µL, 0.735 mmol, 1.5 eq) was slowly dripped into the mixture. After 4 hours, little reaction. Added more 1.000N NaOH (5.84 mL, 5.88 mmol, 12 eq) followed by more valeryl chloride (0.70 mL, 5.88 mmol, 12 eq). After the reaction was complete, added conc. HCl until pH=3. Stripped off the THF. Extracted the aqueous 3 times with ethyl acetate. The organic layers were combined, dried (sodium sulfate) and stripped to give an oil. Purified over silica gel in 9:1 to 1:1 hexanes/ethyl acetate to give 2-butyl-6-(trifluoromethyl)quinazolin-4-ol (110 mg) as a white solid. Yield=78%. LCMS detects $(M+H)^+=271.21$.

Preparation D11, Step 2: 2-butyl-6-(trifluoromethyl)-quinazolin-4-ol (100 mg, 0.37 mmol, 1 eq) and phosphorus oxychloride (3.00 mL, 3.22 mmol, 87 eq) were mixed at room temperature under nitrogen then refluxed for 3 hours. The reaction was stripped 3 times from methylene chloride. The residue was dissolved in methylene chloride (25 mL) and rinsed 3 times with saturated sodium bicarbonate (25 mL), 1× with water (25 mL). The organic layer was dried (sodium sulfate) and stripped to give 2-butyl-4-chloro-6-(trifluoromethyl)quinazoline (130 mg) as a tan solid. LCMS of a an analytical sample prepared in MeOH detects $(M-Cl+OMe)^+=285.24$.

Preparation D12: Synthesis of 4-chloro-6-(pyridin-2-yl)quinazoline

Preparation D12, Step 1: A mixture of 2-amino-5-bromobenzoic acid (5.7 g, 24.78 mmol) and formamidine acetate (5.2 g, 49.5 mmol) in 2-ethoxyethanol (50 mL) was heated at reflux for 4 h. The reaction was cooled to room temperature, allowed to stand overnight, then diluted with diethyl ether (20 mL) to further precipitate the product. The solids were collected by filtration, rinsed with 2-ethoxyethanol (10 mL), diethyl ether (2×50 mL), and air dried to yield 4.4 g of 6-bromoquinazolin-4-ol as a tan solid. MS (ES+)=225/227 (M+H+).

Preparation D12, Step 2: A mixture of 6-bromoquinazolin-4-ol (173 mg, 0.77 mmol) and 2-tributylstannylpyridine (850 mg, 2.30 mmol) in toluene (10 mL), plus a few drops of DMF to improve solubility, was degassed under vacuum/argon, then a catalytic amount of tetrakis(triphenylphosphine)palladium(0) was added, the mixture was degassed again, and then heated at reflux for 4 h. The reaction was cooled to room temperature, and some solids were removed by filtration. Analysis by LC/MS indicated that the desired product was present in both the solids and the filtrate. The solids were slurried in 8:2 methylene chloride/methanol, the mixture was filtered, the filtrate was combined with the original filtrate, and this mixture was concentrated in-vacuo. The residue was purified over silica gel, eluting with 50% EtOAc/hexanes, 75% EtOAc/hexanes, 100% EtOAc, 5% MeOH/EtOAc, to yield 106 mg of 6-(pyridin-2-yl)quinazolin-4-ol as a colorless solid. MS (ES+)=224 (M+H+).

Preparation D12, Step 3: A suspension of 6-(pyridin-2-yl)quinazolin-4-ol (106 mg, 0.47 mmol) in phosphorous oxychloride (15 mL) was heated at reflux for 1.5 h, during which time a clear, amber solution was observed. The solution was cooled to room temperature, concentrated in-vacuo, and stripped 2× from 30 mL methylene chloride to remove any remaining phosphorous oxychloride. The residue was partitioned between EtOAc and saturated sodium bicarbonate, and the mixture was stirred for 10 min. The layers were separated, and the organic phase was washed successively with saturated sodium bicarbonate, water, and brine, dried over sodium sulfate, then concentrated in-vacuo. The residue was purified over silica gel, eluting with methylene chloride followed by 1:1 methylene chloride/EtOAc, to yield 105 mg of 4-chloro-6-(pyridin-2-yl)quinazoline as a white solid. MS (ES+)=242 (M+H+).

Preparation E1: 4-tert-butylthiazole-2-carboxylic acid

A solution of ethyl thiooxamate (0.75 g, 5.6 mol) and 1-bromopinacolone (1.0 g, 5.6 mol) in ethanol was heated to reflux for 2 h. The solvent was removed in vacuo and the residue dissolved in $CH_2Cl_2$ and washed with water and brine, concentrated and the residue chromatographed on silica gel (10% Ethyl acetate/hexane) to give 0.8 g of ethyl 4-tert-butylthiazole-2-carboxylate as an oil. The ester was dissolved in methanol (5 ml) and treated with 1N NaOH (30 ml) and stirred overnight at room temperature. The solution was acidified with 1N HCl and extracted into $CH_2Cl_2$ and washed with water. The solvent was removed under vacuum to give 0.55 g of 4-tert-butylthiazole-2-carboxylic acid as a off-white solid. MS found: $(M+H)^+=186.24$ Preparation E2: 4-(perfluoroethyl)thiazole-2-carboxylic acid This was synthesized using the procedure described for Preparation E1. MS found: $(M+H)^+=248$ Preparation E3: 4-(3-(trifluoromethyl)phenyl)thiazole-2-carboxylic acid This was synthesized using the procedure described for Preparation E1. MS found: $(M+H)^+=274.3$ Preparation E4: 4-phenylthiazole-2-carboxylic acid This was synthesized using the procedure described for Preparation E1. MS found: $(M+H)^+=206.17$ Preparation E5: 4-(4-chlorophenyl)thiazole-2-carboxylic acid This was synthesized using the procedure described for Preparation E1. MS found: $(M+H)^+=240.14$ Preparation E6: 4-(benzo[d]thiazol-2-yl)thiazole-2-carboxylic acid This was synthesized using the procedure described for Preparation E1. MS found: $(M+H)^+=263.13$ Preparation E7: 4-(1-adamantyl)thiazole-2-carboxylic acid This was synthesized using the procedure described for Preparation E1. MS found: $(M-H)^-=262.25$

Preparation E8:
4-(pyridin-2-yl)thiazole-2-carboxylic acid

This was synthesized using the procedure described for Preparation E1. MS found: $(M+H)^+=207.22$

Preparation E9:
4-(thiophen-2-yl)thiazole-2-carboxylic acid

This was synthesized using the procedure described for Preparation E1. MS found: $(M+H)^+=212.05$

Preparation E10:
4-(thiophen-3-yl)thiazole-2-carboxylic acid

This was synthesized using the procedure described for Preparation E1. MS found: $(M+H)^+=212.05$ Preparation F1: 4-phenylfuran-2-carboxylic acid Preparation F1, Step 1: Synthesis of 4-bromofuran-2-carboxylic acid: Commercially available 4,5-dibromofuran-2-carboxylic acid (6.1 g, 22.6 mol) was suspended in 100 ml of ammonium hydroxide and treated portion-wise with zinc dust (1.48 g, 22.6 mol) and stirred at room temperature for a few minutes. The reaction was filtered and the filtrate acidified with 5N HCl and extracted several times with methylene chloride. The extract was washed with brine and concentrated to give 2.93 g of a white solid consisting mainly of 4-bromofuran-2-carboxylic acid. MS (ES⁻)found: (M−H)⁻=190.95 and 188.95. NMR (500 MHz, DMSO-D6) δ 13.3 (bs, 1 H), 8.14 (s, 1 H), 7.36 (s, 1 H). Product was contaminated with 25% furan-2-carboxylic acid by-product. NMR (500 MHz, DMSO-D6) δ 13.3 (bs, 1 H), 7.90 (m, 1 H), 7.19 (m, 1 H), 6.64 (m, 1 H).

Preparation F1, Step 2: Synthesis of 4-phenylfuran-2-carboxylic acid: A solution of 4-bromofuran-2-carboxylic acid (380 mg, 2 mmol), phenylboronic acid (488 mg, 4 mmol) in DMF (3 ml) was place in a microwave reaction tube and treated with a 2 M K₃PO₄ (aq) (2 ml, 4 mmol). The solution was purged with nitrogen for 10 minutes before adding Pd(PPh3)4 (1.5 mg) catalyst. The mixture was again purged with nitrogen for 5 minutes before the reaction tube was sealed. The mixture was heated in a microwave oven at 150° C. for 30 minutes. The reaction mixture was filtered and the filtrate poured into 1N HCl (100 ml) with stirring. The precipitate was filtered and air-dried to give 190 mg of 4-phenylfuran-2-carboxylic acid. MS (ES⁻)found: (M−H)⁻=187.07.

Preparation F2:
4-(4-methoxyphenyl)furan-2-carboxylic acid

This was synthesized using the procedure described for Preparation F1. MS (ES⁻)found: (M−H)⁻=217.12

Preparation F3:
4-(4-(trifluoromethyl)phenyl)furan-2-carboxylic acid

This was synthesized using the procedure described for Preparation F1. MS (ES⁻)found: (M−H)⁻=255.14

Preparation G1: Synthesis of
5-phenylfuran-2-carboxylic acid

A solution of 5-bromofuran-2-carboxylic acid (381 mg, 2 mmol), phenylboronic acid (488 mg, 4 mmol) in DMF (3 ml) was place in a microwave reaction tube and treated with a 2 M K₃PO₄(aq) (2 ml, 4 mmol). The solution was purged with nitrogen for 10 minutes before adding Pd(PPh₃)₄ (1.5 mg) catalyst. The mixture was again purged with nitrogen for 5 minutes before the reaction tube was sealed. The mixture was heated in a microwave oven at 150° C. for 30 minutes. The reaction mixture was filtered and the filtrate poured into 1N HCl (100 ml) with stirring. The precipitate was filtered and air-dried to give 209 mg of 5-phenylfuran-2-carboxylic acid. MS (ES⁻)found: (M−H)⁻=187.13.

Preparation G2: Synthesis of
5-(4-(trifluoromethyl)-phenyl)furan-2-carboxylic acid This was synthesized using the procedure described for Preparation G1. MS (ES⁻)found: (M−H)⁻=255.11

Preparation G3: Synthesis of
5-(4-fluorophenyl)furan-2-carboxylic acid

This was synthesized using the procedure described for Preparation G1. MS (ES⁻)found: (M−H)⁻=205.10

Preparation G4: Synthesis of
5-(3-fluorophenyl)furan-2-carboxylic acid

This was synthesized using the procedure described for Preparation G1. MS (ES⁻)found: (M−H)⁻=205.10

Preparation G5: Synthesis of
5-(3,4-difluorophenyl)furan-2-carboxylic acid This was synthesized using the procedure described for Preparation G1. MS (ES⁻) found: (M−H)⁻=223.09

Preparation G6: Synthesis of
5-(4-isopropylphenyl)furan-2-carboxylic acid This was synthesized using the procedure described for Preparation G1. MS (ES⁻)found: (M−H)⁻=229.15

Preparation G7: Synthesis of
5-(3-methoxyphenyl)furan-2-carboxylic acid

This was synthesized using the procedure described for Preparation G1. MS (ES⁻)found: (M−H)⁻=217.13

Preparation G8: Synthesis of
5-(3-cyanophenyl)furan-2-carboxylic acid

This was synthesized using the procedure described for Preparation G1. MS (ES⁻)found: (M−H)⁻=212.12

Preparation G9: Synthesis of
5-(4-cyanophenyl)furan-2-carboxylic acid

This was synthesized using the procedure described for Preparation G1. MS (ES⁻)found: (M−H)⁻=212.12

Preparation H1: Synthesis of lithium
2-phenylisonicotinate, N-oxide

Preparation H1, Step 1: A mixture of 2-bromo-4-pyridinecarboxylic acid (1.1 g, 5.45 mmol), phenylboronic acid (1.3 g, 10.9 mmol), 2.0 M potassium phosphate (aq) (8.2 mL, 16.34 mmol), and DMF (10 mL) in a 20 mL microwave tube was degassed under vacuum/Ar. A catalytic amount of tetrakis(triphenylphosphine)palladium(0) was added to the tube, the mixture was degassed again, the tube was sealed, and the reaction was heated at 150° C. in the microwave for 30 min. The reaction mixture was filtered, the filtrate was concentrated in-vacuo, and the residue was dissolved in water (10 mL). The mixture was acidified to pH=6 with the addition of 1.0 N HCl, and the resulting precipitate was collected by filtration, rinsed with two portions of ice-cold water, and air dried to yield 575 mg of 2-phenylisonicotinic acid as an off-white solid. MS (ES+)=200 (M+H+).

Preparation H1, Step 2: A solution of 2-phenylisonicotinic acid (459 mg, 2.30 mmol) in 9:1 benzene/methanol (20 mL) was cooled to 0° C., and treated with the dropwise addition of a 2.0 M hexane solution of (trimethylsilyl)diazomethane (1.15 mL, 2.30 mmol). The mixture was allowed to come to room temperature and stirred for 6 h. Analysis by TLC indicated incomplete reaction, so the mixture was treated with additional (trimethylsilyl)diazomethane solution (230 µL, 0.23 mmol), and the reaction was stirred for an additional 2 h. TLC of the mixture remained unchanged. The solvent was stripped, and the residue was partitioned between ethyl acetate and saturated sodium bicarbonate. The layers were separated, the organic phase was washed 2× with saturated sodium bicarbonate, the combined aqueous phases were extracted with ethyl acetate, and the combined organic phases were washed with brine, dried over sodium sulfate, and concentrated in vacuo. The residue was purified over silica gel, eluting with 20% ethyl acetate/heptane, to yield 372 mg of methyl 2-phenylisonicotinate as a colorless oil. $^1$H NMR (400 MHz, CDCl$_3$) δ ppm 8.83 (d, J=5.27 Hz, 1 H), 8.29 (s, 1 H), 8.04 (d, J=7.03 Hz, 2 H), 7.77 (d, J=3.52 Hz, 1 H), 7.51-7.42 (m, 3 H), 3.98 (s, 3 H).

Preparation H1, Step 3: Methyl 2-phenylisonicotinate, N-oxide was prepared via the method of Sharpless, et. al., (J. Org. Chem. 1998, 63, 1740). A solution of methyl 2-phenylisonicotinate (370 mg, 1.73 mmol) and methyltrioxorhenium(VII) (3 mg, 0.01 mmol) in methylene chloride (2 mL) was treated with 30% aqueous hydrogen peroxide (347 µL, 3.47 mmol), causing the colorless solution to turn yellow, and the mixture was stirred overnight. Analysis by LCMS indicated a 8:2 mixture of desired product to starting material, so additional methyltrioxorhenium(VII) (30 mg, 0.1 mmol) was added, and the mixture was allowed to stir for 6 h. A catalytic amount of manganese dioxide was added, and the mixture was stirred until gas evolution ceased (30 min). The mixture was diluted with methylene chloride (20 mL), the layers were separated, the aqueous was extracted with methylene chloride (5 mL), and the combined organic phases were dried over sodium sulfate, then concentrated in vacuo to 397 mg of a colorless glass. Analysis by LCMS indicates a ratio of 95:5 methyl 2-phenylisonicotinate, N-oxide/methyl 2-phenylisonicotinate. This material was used as-is in the next step. MS (ES+)=230 (M+H+).

Preparation H1, Step 4: A solution of methyl 2-phenyl-isonicotinate, N-oxide (397 mg, 1.73 mmol) in THF (6 mL) was treated with 0.5 N aqueous lithium hydroxide (3.65 mL, 1.81 mmol), and the mixture was stirred overnight. The THF was stripped, and the aqueous solution was freeze dried to yield lithium 2-phenylisonicotinate, N-oxide a colorless glass, which was used as-is in the next step.

Preparation H2: Synthesis of 5-phenylnicotinic acid

Preparation H2, Step 1: 5-bromonicotinic acid (500 mg, 2.48 mmol, 1 eq.), phenylboronic acid (454 mg, 3.71 mmol, 1.5 eq.), tetrakis(triphenylphosphine)palladium(0) (143 mg, 0.124 mmol, 0.05 eq.), and sodium carbonate (787 mg, 7.43 mmol, 3 eq.) were mixed in ethanol (5 mL), toluene (25 mL), and water (5 mL) at room temperature under nitrogen. The reaction was then refluxed for 20 hours. Worked up by adding water then stripping off the ethanol. Rinsed the aqueous layer 2 times with diethyl ether. Adjusted the aqueous layer pH=3 with conc. HCl. The acidic aqueous layer was extracted 3 times with ethyl acetate and a little THF. The ethyl acetate/THF layers were combined, dried over sodium sulfate and stripped to give 5-phenylnicotinic acid (332 mg) as a white solid. Yield=67%. LCMS detects (M+H)$^+$=198.1.

Preparation H3: Synthesis of 3'-trifluoromethylsulfonamido-[1,1'-biphenyl]-3-carboxylic acid Preparation H3, Step 1: Ethyl 3-iodobenzoate (0.92 g, 3.34 mmol, 1 eq.), phenylboronic acid (0.87 g, 5.02 mmol, 1.5 eq.), palladium(II)acetate (37 mg, 0.167 mmol, 0.05 eq.) and sodium carbonate (706 mg, 6.66 mmol, 2 eq.) were dissolved in DMF (20 mL) at room temperature under nitrogen. The reaction was then heated at 80° C. for 1.5 hours. Worked up by adding ethyl acetate and rinsing 4 times with water. The organic layer was dried over sodium sulfate and stripped to give a dark oil. Purified over silica gel in 9:1 to 1:1 hexanes/ethyl acetate to obtain 3'-Amino-[1,1'-biphenyl]-3-carboxylic acid, ethyl ester (420 mg) as an oil. Yield=55%. LCMS detects (M+H)$^+$=242.41.

Preparation H3, Step 2: Ethyl-3-(3-aminophenyl)benzoate (100 mg, 0.44 mmol, 1 eq.) was dissolved in methylene chloride (10 mL) at room temperature and potassium carbonate (91 mg, 0.66 mmol, 1.5 eq.) was added. Cooled to −70° C. then added triflic anhydride (74 uL, 0.44 mmol, 1 eq.) dropwise via an addition funnel. After 1 hour, added 0.2 eq more of each of the above reagents. After 1 hour, the reaction was stripped to give 3'-trifluoromethylsulfonamido-[1,1'-biphenyl]-3-carboxylic acid, ethyl ester (150 mg) as an oil. Yield=91%. Mass Spec (ESI) detects (M+H)$^+$=372.1.

Preparation H3, Step 3: 3'-Trifluoromethylsulfonamido-[1,1'-biphenyl]-3-carboxylic acid, ethyl ester (150 mg, 0.40 mmol, 1 eq.) and 1.000 N NaOH (0.80 mL, 0.80 mmol, 2 eq.) were dissolved in THF (5 mL) at room temperature and stirred for 20 hours. Little reaction. Added 100 mg of NaOH and heated at 50° C. for 20 hours. Worked up by adding water then rinsing 2 times with diethyl ether. The aqueous layer's pH was adjusted to 3 with 1N HCl. The acidic aqueous layer was extracted 3 times with ethyl acetate. The ethyl acetate layers were combined, dried over sodium sulfate and stripped to give 3'-trifluoromethylsulfonamido-[1,1'-biphenyl]-3-carboxylic acid (90 mg) of an amber solid. Yield=65%. Mass Spec (ESI) detects (M+H)$^+$=344.0.

Preparation H4: Synthesis of 3-phenyl-4-hydroxybenzoic acid

Preparation H4, Step 1: 3-bromo-4-hydroxybenzoic acid (500 mg, 2.30 mmol, 1 eq.), phenylboronic acid (281 mg, 2.30 mmol, 1 eq.), palladium(II)acetate (16 mg, 0.069 mmol, 0.03 eq.) and 1.5M cesium carbonate (aqueous) (4.61 mL) were dissolved in DMF (10 mL) at room temperature under nitrogen then heated at 45° C. for 20 hours. Worked up by adding water (10 mL) then adjusting to pH=3 with 1N HCl. Extracted the acidic aqueous 3 times with ethyl acetate. The ethyl acetate layers were combined and rinsed 3 times with water (10 mL). The ethyl acetate layer was then dried over sodium sulfate and stripped to an oil. The oil was purified over silica gel in 1:1 hexanes/ethyl acetate.

Obtained 3-phenyl-4-hydroxybenzoic acid (330 mg) as an oil which eventually solidified. Yield=67%. LCMS detects $(M+H)^+=257.23$.

Preparation H5: Synthesis of
2-Phenylpyrazine-6-carboxylic acid

Preparation H5, Step 1: 2-Phenylpyrazine-6-carboxylic acid was synthesized by the method of E. Felder, D. Pitre, S. Boveri and E. B. Grabitz, Chem. Ber. 100 (1967) 555-559.
LCMS detects $(M+H)^+=201.29$.

Preparation H6: Synthesis of
3-tert-butyl-5-(2H-tetrazol-5-yl)benzoic acid

Preparation H6, Step 1: To a solution of dimethyl 5-tert-butylisophthalate (2.5 g, 10 mmol) in 20 mL of THF cooled to 0° C. was added dropwise a solution of lithium hydroxide monohydrate (168 mg, 7 mmol) in 5.0 mL of water. The reaction mixture was stirred at RT for 3 h. THF was removed under reduced pressure to give a yellow oil which was diluted with 10 mL of 1 N HCl. The aqueous phase was extracted with EtOAc (2×25 mL), and the extracts were combined, dried over Na$_2$SO$_4$, and concentrated to afford 700 mg of 3-tert-butyl-5-(methoxycarbonyl)benzoic acid. MS found: $(M+H)^+=237$.

Preparation H6, Step 2: To a soultion of 3-tert-butyl-5-(methoxycarbonyl)benzoic acid (700 mg) in DMF (15 mL) at rt was added HATU (1.2 eq), 3-aminopropanenitrile (1.2 eq), and iPr$_2$NEt (1.2 eq). The mixture was stirred at rt for 16 h before water and EtOAc were added. The organic layer was separated and re-washed twice before it was collected, dried over Na$_2$SO$_4$, and concentrated to provide methyl 3-tert-butyl-5-((2-cyanoethyl)carbamoyl)benzoate as a glassy solid (520 mg). MS found: $(M+H)^+=289$.

Preparation H6, Step 3: To a soultion of 3-tert-butyl-5-((2-cyanoethyl)carbamoyl)benzoat (520 mg, 1.8 mmol) in MeCN (15 mL) at 0° C. was added NaN$_3$ (117 mg, 1.8 mmol), and Tf$_2$0 (0.3 mL, 1.8 mm0l). The mixture was stirred at rt for 16 h before aq NaHCO$_3$ and EtOAc were added. The organic layer was separated and re-washed twice before it was collected, dried over Na$_2$SO$_4$, and concentrated to methyl 3-tert-butyl-5-(2-(2-cyanoethyl)-2H-tetrazol-5-yl)benzoate as an oil (450 mg, 80% yield). MS found: $(M+H)^+=314$.

Preparation H6, Step 4: To a solution of methyl 3-tert-butyl-5-(2-(2-cyanoethyl)-2H-tetrazol-5-yl)benzoate (500 mg) in 20 mL of THF cooled to 0° C. was added dropwise a solution of lithium hydroxide monohydrate (76 mg) in 5.0 mL of water. The reaction mixture was stirred at RT for 16 h. THF was removed under reduced pressure to give a yellow oil which was diluted with 10 mL of 1 N HCl. The aqueous phase was extracted with EtOAc (2×25 mL), and the extracts were combined, dried over Na$_2$SO$_4$, and concentrated to afford 3-tert-butyl-5-(2H-tetrazol-5-yl)benzoic acid. MS found: $(M+H)^+=247$.

Preparation H7: Synthesis of
3-(1H-tetrazol-5-yl)benzoic acid

Preparation H7, Step 1: To a soultion of 3-(methoxycarbonyl)benzoic acid (800 mg, 4.4 mmol) in DMF (15 mL) at rt was added HATU (2 g, 5.3 mmol), 3-aminopropanenitrile (0.33 mL, 4.4 mmol), and iPr$_2$NEt (0.92 mL, 5.3 mmol). The mixture was stirred at rt for 16 h before water and EtOAc were added. The organic layer was separated and re-washed twice before it was collected, dried over Na$_2$SO$_4$, and concentrated to provide methyl 3-((2-cyanoethyl)carbamoyl)benzoate as a glassy solid (900 mg). MS found: $(M+H)^+=233$.

Preparation H7, Step 2: To a soultion of methyl 3-((2-cyanoethyl)carbamoyl)benzoate (400 mg, 1.7 mmol) in MeCN (15 mL) at 0° C. was added NaN$_3$ (111 mg, 1.7 mmol), and Tf$_2$0 (0.3 mL, 1.7 mmol). The mixture was stirred at rt for 16 h before aq NaHCO$_3$ and EtOAc were added. The organic layer was separated and re-washed twice before it was collected, dried over Na$_2$SO$_4$, and concentrated to methyl 3-(1-(2-cyanoethyl)-1H-tetrazol-5-yl)benzoate as an oil (180 mg, 41% yield). MS found: $(M+H)^+=258$.

Preparation H7, Step 3: To a solution of methyl 3-(1-(2-cyanoethyl)-1H-tetrazol-5-yl)benzoate (180 mg, 0.7 mmol) in 20 mL of THF cooled to 0° C. was added dropwise a solution of lithium hydroxide monohydrate (50 mg, 2.1 mmol) in 5.0 mL of water. The reaction mixture was stirred at RT for 16 h. THF was removed under reduced pressure to give a yellow oil which was diluted with 10 mL of 1 N HCl. The aqueous phase was extracted with EtOAc (2×25 mL), and the extracts were combined, dried over Na$_2$SO$_4$, and concentrated to afford 100 mg (58% yield) of 3-(1H-tetrazol-5-yl)benzoic acid. MS found: $(M+H)^+=191$.

Preparation H8: Synthesis of
3-(4-methylthiazol-2-yl)benzoic acid

The title compound was synthesized followd by the literature procedures described in *Bioorg. Med. Chem.* 1999, 8, 7, 1559-1566. MS found: $(M+H)^+=220$.

Preparation H9: Synthesis of 6-phenylpicolinic acid

Preparation H9, Step 1: 6-Bromopicolinic acid (1.0 g) was dissolved in 1,2-dimethoxyethane (15 mL) prior to the addition of palladium tetrakistriphenylphoshine (572 mg), 2M Na$_2$CO$_3$ (5 mL), and phenyl boronic acid (905 mg). The resulting solution was heated at reflux for 48 h. After cooling, 1N HCL was added to adjust the pH<4. A white precipitate was formed and was removed by filtration. A small portion of the filtrate was purified by reverse phase HPLC (gradient elution, water/acetonitrile/TFA) to afford 6-phenylpicolinic acid (25 mg). MS found: $(M+H)^+=200.1$.

Preparation H10: Synthesis of 5-phenylnicotinic
acid N-oxide

Preparation H10, Step 1: 5-Phenylnicotinic acid (50 mg) was dissolved in dichloroethane (2 ml) prior to the addition of 77% mCPBA (250 mg). The reaction was stirred for 15 h and then it was concentrated, filtered, and purified by reverse phase HPLC (gradient elution, water/acetonitrile/TFA) to afford 5-phenylnicotinic acid N-oxide (20 mg). MS found: $(M+H)^+=216.1$.

Preparation H11: Synthesis of
3-(thiazol-2-yl)benzoic acid

Preparation H11, Step 1: 10 g (0.068 mol) of 3-cyano benzoic acid was taken in 150 ml of dry dichloromethane and cooled to 0° C. Added 50 ml of oxalyl chloride drop wise followed by 5 drops of dry DMF. The reaction mixture was stirred at RT overnight. Dichloromethane was removed and dry methanol (50 ml) was added and stirred at rt for 2 h. Excess methanol was removed and the residue was dissolved in ethyl acetate. The ethyl acetate layer was washed with 10% of sodium bicarbonate, brine and concentrated to give methyl 3-cyanobenzoate (7 g) as a white solid.

Preparation H11, Step 2: A solution of 2 g (0.01 mol) of methyl-3-cyanobenzoate in 32 ml of THF and 8 ml of water was charged with 2.3 g (0.012 mol) of diethyl dithiophosphate and heated at 80° C. for 24 h. THF was removed and the residue was taken in ethyl acetate. The extract was washed with water and concentrated to afford methyl 3-carbamothioylbenzoate (2.0 g) as a pale yellow solid.

Preparation H11, Step 3: A solution of 0.6 g (0.003 mol) of methyl 3-carbamothioylbenzoate in 6 ml of acetic acid was charged with 1.15 g (0.009 mol) of chloroacetaldehyde dimethyl acetal and a catalytic amount of PTSA. The RM was heated to 100° C. over night. Acetic acid was removed under vacuum and the crude product was purified by 60-120 silica gel column using 5% of ethyl acetate in pet ether as eluent to provide methyl 3-(thiazol-2-yl)benzoate (0.5 g) as a white solid.

Preparation H11, Step 4: A solution of 0.6 g (0.0027 mol) of methyl 3-(thiazol-2-yl)benzoate in 6 ml of THF and 1.2 ml of water was charged with 0.11 g (0.0046 mol) of lithium hydroxide. The reaction mixture was stirred at RT overnight. THF was removed and the aqueous layer was washed with ether and acidified with 1.5 N HCl. The solid product was extracted with ethyl acetate. The organic layer was washed with brine and concentrated to afford 3-(thiazol-2-yl)benzoic acid (0.4 g) as an off white solid obtained. $^1$H NMR (400 MHz, CDCl$_3$): 7.45 (d, 1H), 7.63 (m, 1H), 8.0 (d, 1H), 8.22 (d, 1H), 8.30 (d, 1H), 8.79 (s, 1H). MS found: (M–H)$^-$=204.

Preparation I1: Synthesis of 2-(3-(trifluoromethyl)benzamido)acetic acid and its analogs The synthesis of the benzamidoacetic acid derivatives from various substituted benzoic acids has been described in detail in WO 02/50019 (Carter and Cherney).

Preparation I2: Synthesis of N-(3-trifluoromethoxy)-malonamic acid

Preparation I2, Step 1: A solution of mono-benzyl malonate (1.1 g, 5.6 mmol) in 3:1 CH$_2$Cl$_2$/DMF (28 mL) was treated sequentially with N,N-diisopropylethylamine (2.5 mL, 14.0 mmol), meta-trifluoromethoxy-phenylamine (0.75 mL, 5.6 mmol), and HATU (2.6 g, 6.7 mmol). The mixture was stirred for 12 h at RT, concentrated in vacuo, and partitioned between EtOAc and sat. NH$_4$Cl. The aqueous phase was extracted with EtOAc (1×). The combined organic extracts were washed with sat. NaHCO$_3$ and brine, dried (Na$_2$SO$_4$), filtered, and concentrated in vacuo. The residue was purified by flash chromatography to provide N-(3-trifluoromethoxy-phenyl)-malonamic acid benzyl ester as an oil (1.65 g).

Preparation I2, Step 2: A sample of N-(3-trifluoromethoxy-phenyl)-malonamic acid benzyl ester (1.39 g) was dissolved in MeOH (39 mL). The resultant solution was charged with 10% Pd/C (278 mg), stirred under H$_2$ (1 atm) for 12 h at RT, filtered, and concentrated in vacuo to provide N-(3-trifluoromethoxy)-malonamic acid (quantitiative). MS found: (M+H)$^+$=264.06.

Preparation I3: Synthesis of N-(3-methoxy-5-trifluoromethyl-phenyl)-malonamic acid Preparation I2 was repeated, substituting 3-methoxy-5-trifluoromethyl-phenylamine for 3-trifluoromethoxy-phenylamine in Step 1. This yielded N-(3-methoxy-5-trifluoromethyl-phenyl)-malonamic acid. MS found: (M+H)$^+$=332.01.

Preparation I4: Synthesis of N-(2-trifluoromethyl-phenyl)-malonamic acid

Procedure I2 was followed, substituting 2-trifluoromethyl-phenylamine for 3-trifluoromethoxy-phenylamine. This yielded N-(2-trifluoromethyl-phenyl)-malonamic acid. MS found=(M+H)$^+$=248.02.

Preparation PHC Z4: Synthesis of (4-trifluoromethyl-1H-benzoimidazol-2-yl)-acetic acid lithium salt Preparation I5, Step 1: N-(2-Nitro-3-trifluoromethyl-phenyl)-acetamide (Helvetica 1947, p. 107) (3.6 g) was dissolved in EtOH and heated to 105° C. prior to the addition of 1N NaOH (60 ml) and 50% NaOH (10 ml). After 2.5 h, the reaction was cooled to rt and EtOAc was added. The organic layer was washed with water and brine. Then it was dried and concentrated to give a crude 2-nitro-3-trifluoromethyl-phenylamine (2.79 g): $^1$H NMR (CDCl$_3$, δ ppm, 300 mHz) 5.0 (s, 2H), 7.02 (d, 1H), 7.10 (d, 1H), 7.38 (t, 1H).

Preparation I5, Step 2: A portion (1.42 g) of this material was dissolved in MeOH (20 mL) prior to the addition of 10% Pd/C (260 mg). The reaction was placed on a Parr apparatus under hydrogen at 60 psi for 3 h. The Pd/C was filtered off and solvent was concentrated to give 3-trifluoromethyl-benzene-1,2-diamine (1.16 g): $^1$H NMR (CDCl$_3$, δ ppm, 300 mHz) 3.40 (s, 2H), 3.94 (s, 2H), 6.70 (t, 1H), 6.85 (d, 1H), 7.02 (d, 1H).

Preparation I5, Step 3: A portion (1.15 g) of this material was dissolved in diethyl malonate. The reaction was heated at 160° C. (oil bath temperature) for 1.5 h. After cooling to rt, flash chromatography of the crude reaction gave (4-trifluoromethyl-1H-benzoimidazol-2-yl)-acetic acid ethyl ester (1.14 g). MS found: (M+H)$^+$=273.0.

Preparation I5, Step 4: A portion (200 mg) of this material was dissolved in THF (2 mL) prior to the addition of a solution of LiOH.H$_2$O (37 mg) in water (0.1 ml). A couple drops of MeOH were added until the solution became clear. After 2 h at rt, the reaction was concentrated and freeze-dried to provide (4-trifluoromethyl-1H-benzoimidazol-2-yl)-acetic acid lithium salt (175 mg). MS found: (M+H)$^+$=245.0.

Preparation I6: Synthesis of 2-(5-(trifluoromethyl)-1H-indazol-3-ylamino)acetic acid Preparation I6, Step 1: A solution of 2-fluoro-5-(trifluoromethyl)benzonitrile (2.66 g, 14.1 mmol) in n-butanol (51 mL) was charged with hydrazine hydrate (1.02 mL, 21.1 mmol) and refluxed for 30 min. After cooling, the solution was concentrated to half volume and diluted with water. The mixture was extracted twice with methylene chloride, and the organic extracts were combined, dried (sodium sulfate), filtered, and concentrated in vacuo. The resulting yellow oil was placed under high vacuum in order to remove residual n-butanol; this provided 5-(trifluoromethyl)-1H-indazol-3-amine as a yellow solid (2.25 g).

Preparation I6, Step 2: A solution of 5-(trifluoromethyl)-1H-indazol-3-amine (2.08 g, 10.3 mmol) in 50 mL of 1% AcOH/MeOH was charged with ethyl glyoxylate (2.05 mL of a 50% solution in toluene, 10.3 mmol; note: the commercially available material is polymeric and was heated at 100° C. for 90 min before being used immediately in this reaction) and sodium cyanoborohydride (777 mg, 12.4 mmol). The mixture was stirred for 2.5 h, quenched with sat.

NaHCO$_3$, and extracted with EtOAc (2×). The organic extracts were combined, washed with brine, dried (sodium sulfate), filtered, and concentrated in vacuo. Purification by flash chromatography provided ethyl 2-(5-(trifluoromethyl)-1H-indazol-3-ylamino)acetate (819 mg).

Preparation I6, Step 3: A sample of ethyl 2-(5-(trifluoromethyl)-1H-indazol-3-ylamino)acetate (75 mg) was dissolved in THF (6 mL). The resulting solution was charged successively with an aqueous solution of LiOH (12.5 mg in 2 mL water) and methanol (2 mL). The reaction mixture was stirred for 2 h before being acidified with 1N HCl and extracted with EtOAc. The organic extracts were combined, washed with water and brine, dried (sodium sulfate), filtered, and concentrated under reduced pressure to afford 2-(5-(trifluoromethyl)-1H-indazol-3-ylamino)acetic acid. MS found: (M+H)+=260.22.

Preparation I7: Synthesis of 2-(5-(trifluoromethyl)benzo[d]isoxazol-3-ylamino)acetic acid Preparation I7, Step 1: A solution of 2-fluoro-5-trifluoromethylbenzoic acid (5.80 g) in N,N-dimethylformamide (190 mL) was treated sequentially with glycine t-butyl ester (5.50 g), BOP reagent (18.50 g), and N-methylmorpholine (9.20 mL). The mixture was stirred at rt for 12 h, then was diluted with ethyl acetate. The organic layer was washed with 1 M HCl, saturated aqueous NaHCO$_3$, 5% aqueous LiCl, and brine, then was dried over Na$_2$SO$_4$ and concentrated under vacuum to provide tert-butyl 2-(2-fluoro-5-(trifluoromethyl)benzamido)acetate (16 g) as a white solid. MS found: (M+H)$^+$=322.

Preparation I7, Step 2: A solution of tert-butyl 2-(2-fluoro-5-(trifluoromethyl)benzamido)acetate (1.00 g) in dioxane (18 mL) was treated with Lawesson's reagent (1.26 g) and the mixture was heated at 100° C. for 16 h. The mixture was cooled to rt and diluted with ethyl acetate, washed with water and brine, dried over Na$_2$SO$_4$ and concentrated under vacuum. The residue was purified by column chromatography on silica gel, eluting with 10% to 50% (v/v) ethyl acetate-hexane, to provide tert-butyl 2-(2-fluoro-5-(trifluoromethyl)phenylthioamido)acetate (560 mg) as a white solid. MS found: (M–H)$^-$=336.

Preparation I7, Step 3: A solution of tert-butyl 2-(2-fluoro-5-(trifluoromethyl)phenylthioamido)acetate (500 mg) in methanol (50 mL) was treated with NaHCO$_3$ (3.74 g) and hydroxylamine hydrochloride (3.09 g). The mixture was heated at 80° C. for 13 h and cooled to rt. The mixture was diluted with ethyl acetate and washed with water and brine, dried over Na$_2$SO$_4$, and concentrated under vacuum. The residue was purified by column chromatography on silica gel, eluting with 10% to 50% (v/v) ethyl acetate-hexane, to provide tert-butyl 2-(2-fluoro-N'-hydroxy-5-(trifluoromethyl)benzamidino)acetate (208 mg) as a white solid. MS found: (M+H)$^+$=337.

Preparation I7, Step 4: A solution of tert-butyl 2-(2-fluoro-N'-hydroxy-5-(trifluoromethyl)benzamidino)acetate (190 mg) in N,N-dimethylformamide (2 mL) was treated with K$_2$CO$_3$ (156 mg) and heated at 100° C. for 5 h. The mixture was cooled to rt and diluted with ethyl acetate, then was washed with water, 5% LiCl, and brine, dried over Na$_2$SO$_4$, and concentrated under vacuum. The residue was purified by column chromatography on silica gel, eluting with 1:9 v/v ethyl acetate-hexane, to provide tert-butyl 2-(5-(trifluoromethyl)benzo[d]isoxazol-3-ylamino)acetate (58 mg) as a white solid. MS found: (M+H)$^+$=317.

Preparation I7, Step 5: A solution of tert-butyl 2-(5-(trifluoromethyl)benzo[d]isoxazol-3-ylamino)acetate (367 mg) in dichloromethane (20 mL) at 0° C. was treated with trifluoroacetic acid (2 mL) and stirred at rt for 5 h. The mixture was concentrated under vacuum, and the residue was purified by column chromatography on silica gel, eluting with 10% to 50% (v/v) ethyl acetate-hexane, to provide 2-(5-(trifluoromethyl)benzo[d]isoxazol-3-ylamino)acetic acid (270 mg) as an off-white solid. MS found: (M+H)$^+$=261.

Examples 1a-1bq

Example 1a

Synthesis of N-(2-((1s,4s)-4-aminocyclohexylamino)-2-oxoethyl)-3-(trifluoromethyl)benzamide Example 1a, Step 1: Trans-4-aminocyclohexanol hydrochloride (500 mg) was dissolved DMF (11 mL) prior to the addition of (3-trifluoromethyl-benzoylamino)-acetic acid (815.0 mg) and 4-methylmorpholine (1.0 mL). After 5 min, BOP reagent (1.4 g) was added and the reaction was stirred overnight. Ethyl acetate was added, and the solution was washed with brine, 1N HCl, and saturated NaHCO$_3$. The desired (trans)-N-[(4-hydroxy-cyclohexylcarbamoyl)-methyl]-3-trifluoromethyl-benzamide (480.5 mg) was then collected as a solid. MS found: (M+H)$^+$=345.1.

Example 1a, Step 2: A portion of this material (300 g) was dissolved in CH$_2$Cl$_2$ (5 mL)/DMF (5 mL) and cooled to 0° C. prior to the addition of Et$_3$N (0.18 mL) and methanesulfonyl chloride (0.15 mL). After 3 h, the CH$_2$Cl$_2$ was removed and EtOAc was added. This was washed with brine. The organic layer was dried, filtered, and concentrated. The resulting solid was dissolved in DMF (10 mL) prior to the addition of NaN$_3$ (169.9 mg). This solution was heated at 80° C. for 18 h. After cooling to 0° C., water was added along with EtOAc. The organic layer was washed with brine, dried, filtered, and concentrated. Flash chromatography of the resulting residue gave (cis)-N-[(4-azido-cyclohexylcarbamoyl)-methyl]-3-trifluoromethyl-benzamide (180 mg). MS found: (M+H)=370.1.

Example 1a, Step 3: A portion (100 mg) of the above derivative was dissolved in MeOH (8 ml) prior to the addition of 10% Pd/C (20 mg). A hydrogen balloon was added, and the solution was stirred for 3 h. The palladium was filtered off, and the solution was concentrated to the title compound (93 mg). MS found: (M+H)$^+$=344.1.

Example 1b

Synthesis of N-(2-((1s,4s)-4-(isopropylamino)cyclohexylamino)-2-oxoethyl)-3-(trifluoromethyl)benzamide Example 1b, Step 1: N-(2-((1s,4s)-4-aminocyclohexylamino)-2-oxoethyl)-3-(trifluoromethyl)benzamide (50 mg) was dissolved in dichloroethane (5 mL) prior to the adddition of glacial acetic acid (17 mg), acetone (42 mg), and NaBH(OAc)$_3$ (154 mg). After 6 h, the solution was concentrated. The resulting residue was dissolved in EtOAc and was washed with saturated NaHCO$_3$, water, and brine. The organic layer was dried, filtered, and concentrated to give the title compound (52 mg). MS found: (M+H)$^+$=386.2.

Example 1c

Synthesis of N-(2-((1s,4s)-4-(isopropyl(methyl)amino)cyclohexylamino)-2-oxoethyl)-3-(trifluoromethyl)benzamide Example 1c, Step 1: N-(2-((1s,4s)-4-(isopropylamino)cyclohexylamino)-2-oxoethyl)-3-(trifluoromethyl)benzamide (10 mg) was dissolved in MeOH (1 mL) prior to the addition of 37% formaldehyde in water (50 mg). After 15 min, NaBH$_3$CN (10 mg) was added. After 1 h, saturated NaHCO$_3$ was added and some of the MeOH was removed. EtOAc was added and the organic layer was dried, filtered, and concentrated to give the title compound (10 mg). MS found: (M+H)$^+$=400.2.

Example 1d

Synthesis of 1-(2-((2-(((1s,4s)-4-(isopropyl(methyl)amino)cyclohexylamino)-2-oxoethyl)carbamoyl)-4-(trifluoromethyl)phenyl)-3-isopropylurea Example 1d, Step 1: Trans-4-aminocyclohexanol hydrochloride (5.0 g, 33 mmol) was dissolved in 1,4-dioxane (100 mL), and the resulting solution was cooled to 0° C., charged with NaOH (40 mL of a 1 N aq. Solution), stirred for 15 min, and then charged with Boc$_2$O (7.9 g, 36 mmol, pre-dissolved in 65 mL of 1,4-dioxane) before being stirred at RT for 14 h. The reaction was neutralized with 1 N HCl and extracted with EtOAc. The organic phase was washed successively with 1 N HCl, H$_2$O, and brine before being dried (Na$_2$SO$_4$), filtered, and concentrated in vacuo to afford (trans-4-hydroxy-cyclohexyl)-carbamic acid tert-butyl ester (7.0 g, 100% yield). MS found: (M+H)$^+$=216.15.

Example 1d, Step 2: A solution of (trans-4-hydroxy-cyclohexyl)-carbamic acid tert-butyl ester (7.0 g, 33 mmol) in CH$_2$Cl$_2$ (165 mL) was charged with pyridine (13 mL, 79 mmol) and methanesulfonylchloride (6.4 mL, 82 mmol). The reaction was stirred at RT for 14 h and concentrated in vacuo. The residue was dissolved in EtOAc and the resulting solution was washed successively with water (2×) and brine (1×) before being dried (MgSO$_4$), filtered, and concentrated in vacuo to afford methanesulfonic acid trans-4-tert-butoxycarbonylamino-cyclohexyl ester (9.3 g, 96% yield). MS found: (M+H)$^+$=294.2.

Example 1d, Step 3: A solution of methanesulfonic acid trans-4-tert-butoxycarbonylamino-cyclohexyl ester (21 g, 72 mmol) in DMSO (350 mL) was charged with sodium azide (14 g, 216 mmol) and heated at 65° C. for 14 h. After cooling to RT, the solution was diluted with EtOAc and washed successively with water, 5% aq. NaHCO$_3$, water, and brine. The solution was dried (Na$_2$SO$_4$), filtered, and concentrated in vacuo, and the resulting residue was purified via flash chromatography to afford (cis-4-azido-cyclohexyl)-carbamic acid tert-butyl ester (16 g, 92% yield). MS found: (M+H)$^+$=241.7.

Example 1d, Step 4: A solution of (cis-4-azido-cyclohexyl)-carbamic acid tert-butyl ester (6.3 g, 26 mmol) in MeOH (100 mL) was charged with 5% Pd/C, Degussa style (0.63 g). The sealed flask was evacuated and back-filled with hydrogen; this was repeated three times. The reaction was stirred under 1 atm of H$_2$ for 2 h before being filtered and concentrated in vacuo. The residue was partitioned between Et$_2$O and 1 N HCl. The aqueous phase was basified and extracted with EtOAc (2×). The organic phase was washed with brine, dried (Na$_2$SO$_4$), filtered, and concentrated in vacuo to afford (cis-4-amino-cyclohexyl)-carbamic acid tert-butyl ester (3.6 g, 64% yield). MS found: (M+H)$^+$=215.6.

Example 1d, Step 5: A solution of (cis-4-amino-cyclohexyl)-carbamic acid tert-butyl ester (1.8 g, 8.3 mmol) in MeOH (20 mL) was charged with acetone (2 mL), stirred for 10 minutes, charged with NaCNBH$_3$ (1.6 g, 24.9 mmol), stirred for 3 h, charged with formaldehyde (1 mL of a 37% aq. Solution), stirred for 1.5 h, and then concentrated in vacuo. The residue was dissolved in EtOAc and the solution was washed successively with water and brine before being dried (Na$_2$SO$_4$), filtered, and concentrated in vacuo. The residue was purified via flash chromatography to afford [cis-4-(isopropyl-methyl-amino)-cyclohexyl]-carbamic acid tert-butyl ester (1.4 g, 62% yield). MS found: (M+H)$^+$=271.3.

Example 1d, Step 6: A solution of [cis-4-(isopropyl-methyl-amino)-cyclohexyl]-carbamic acid tert-butyl ester (0.16 g, 0.6 mmol) in CH$_2$Cl$_2$ (3 mL) was cooled to 0° C., charged with trifluoroacetic acid (1 mL), and stirred at RT for 1 h before being concentrated in vacuo. The residue was dissolved in CH$_2$Cl$_2$ and concentrated in vacuo; this was repeated to afford N-isopropyl-N-methyl-cis-cyclohexane-1,4-diamine. A portion (25 mg, 0.15 mmol) of this material was dissolved in DMF (1 mL). The resulting solution was charged with N,N-diethylisopropylamine (0.13 mL, 0.7 mmol), {2-[2-(3-isopropyl-ureido)-5-trifluoromethyl-benzoylamino]-acetic acid (56 mg, 0.16 mmol), and BOP (97 mg, 0.22 mmol) and stirred for 14 h at RT. The reaction was partitioned between water and EtOAc, and organic phase was washed successively with sat. NH$_4$Cl, water, and brine before being dried (Na$_2$SO$_4$), filtered, and concentrated in vacuo. Purification of the residue by reverse phase HPLC afforded the TFA salt of the title compound as a white powder after lyopholization. MS found: (M+H)$^+$=500.3.

Example 1 h

Synthesis of 2-(6-chloroquinazolin-4-ylamino)-N-((1s,4s)-4-(isopropyl(methyl)amino)cyclohexyl)acetamide Example 1 h, Step 1: A sample of (4-Amino-cyclohexyl)-carbamic acid tert-butyl ester (available from Albany Molecular Research; 2.00 g, 10.7 mmol, 1 eq.), acetone (1.18 mL, 16.1 mmol, 1.5 eq.), sodium triacetoxyborohydride (3.41 g, 16.1 mmol, 1.5 eq.) and 50 mL of methylene chloride were stirred at RT for 20 hours. Added 20 mL of 1 N NaOH and stirred 10 minutes then extracted 3× with methylene chloride. The organic layers were combined, dried and stripped in vacuo to obtain an oil. Added sodium triacetoxyborohydride (3.41 g, 16.1 mmol, 1.5 eq.) and 37% formaldehyde (aqueous) (2.62 mL, 32.2 mmol, 3 eq). Stirred 4 hours. Added 20 mL of 1 N NaOH and stirred 10 minutes then extracted the aqueous 3× with methylene chloride. The organic layers were combined, dried and stripped in vacuo to give cis-[4-(Isopropyl-methyl-amino)-cyclohexyl]-carbamic acid tert-butyl ester (3.20 g) as a colorless oil. MS found: (M+H)$^+$=271.

Example 1 h, Step 2: cis-[4-(Isopropyl-methyl-amino)-cyclohexyl]-carbamic acid tert-butyl ester (3.20 g) was dissolved in 10 mL of methylene chloride at RT then TFA (3 mL) added. Stirred under nitrogen until reaction was complete by LCMS. Stripped in vacuo 3× from methylene chloride to give 5.00 g of cis-N-isopropyl-N-methyl-cyclohexane-1,4-diamine, TFA salt as an oil. MS found: (M+H)$^+$=170.

Example 1 h, Step 3: CBZ-Glycine (1.96 g, 9.35 mmol, 1 eq.) was dissoved in THF at RT under nitrogen then triethylamine (3.91 mL, 28.0 mmol, 3 eq.) added. Cooled to −20° C. then added isobutyl chloroformate dropwise via an addition funnel. Stirred 20 minutes at −20° C. then added cis-N-isopropyl-N-methyl-cyclohexane-1,4-diamine, TFA salt (3.72 g, 9.35 mmol, 1 eq.) in 10 mL of THF. Allowed to warm to RT. After 2 hours filtered off resultant solids then added 25 mL of ethyl acetate. Rinsed the ethyl acetate 2× with saturated sodium bicarbonate, 1× with brine. The organic layer was dried and stripped in vacuo to give cis-{[4-(Isopropyl-methyl-amino)-cyclohexylcarbamoyl]-methyl}-carbamic acid benzyl ester (1.86 g). MS found: (M+H)$^+$=362.

Example 1h, Step 4: cis-{[4-(Isopropyl-methyl-amino)-cyclohexylcarbamoyl]-methyl}-carbamic acid benzyl ester (1.86 g), methanol (20 mL), and 20% Pd(OH)$_2$ (400 mg) were hydrogenated until completion by TLC on a Parr shaker at 50 psi. Filtration through fiberglass filter paper under nitrogen and removal of solvent in vacuo yielded 870 mg of cis-2-amino-N-[4-(isopropyl-methyl-amino)-cyclohexyl]-acetamide. MS found: (M+H)$^+$=227.

Example 1h, Step 5: cis-2-Amino-N-[4-(isopropyl-methyl-amino)-cyclohexyl]-acetamide (40 mg, 0.105 mmol, 1 eq.), 4,6-dichloro-quinazoline (21 mg, 0.105 mmol, 1 eq.) triethylamine (58 ul, 0.419, 4 eq.), and ethanol (2 mL) were refluxed for 1 hour. Purified by RP-HPLC to provide the TFA salt of the title compound (60 mg) as a white powder after lyopholization. MS found: (M+H)$^+$=390.

Example 1i

Synthesis of 2-(6-chloro-2-(3-phenylpropyl) quinazolin-4-ylamino)-N-((1s,4s)-4-(isopropyl(methyl)amino)cyclohexyl)acetamide Example 1i, Step 1: cis-2-Amino-N-[4-(isopropyl-methyl-amino)-cyclohexyl]-acetamide (24 mg, 0.106 mmol), 4,6-dichloro-2-(3-phenyl-propyl)-quinazoline (50 mg, 0.159 mmol, 1 eq.) and triethylamine (59 µl, 0.423, 4 eq.) were dissolved in 2 mL of DMF then microwaved at 150° C. until reaction was complete by LCMS. Purification by RP-HPLC provided the TFA salt of the title compound (4.2 mg) as a white powder after lyopholization. MS found: (M+H)$^+$=508.

Example 1j

Synthesis of 5-bromo-2-tert-butyl-N-(2-(4-(tert-butylamino)cyclohexylamino)-2-oxoethyl)pyrimidine-4-carboxamide as a mixture of cis and trans diastereomers Example 1j, Step 1: N-4-BOC-aminocyclohexanone (5.00 g, 23 mmol, 1 eq.), tert-butylamine (2.46 mL, 23 mmol, 1 eq.), and titanium (IV) isoproproxide (6.87 mL, 23 mmol, 1 eq.), were mixed and stirred at RT under nitrogen overnight. MeOH (50 mL) was added followed by NaBH$_4$ pellets (0.89 g, 23 mmol, 1 eq.). After 30 minutes added 50 mL of 1 N NaOH. Methylene chloride was added, the insoluble matter filtered, and the layers separated. The aqueous layer was extracted twice more with methylene chloride. The organic layers were combined, dried and stripped to yield (4-tert-Butylamino-cyclohexyl)-carbamic acid tert-butyl ester (6.26 g) as an amber oil, which solidified upon standing. MS found: (M+H)$^+$=271.

Example 1j, Step 2: (4-tert-Butylamino-cyclohexyl)-carbamic acid tert-butyl ester (1.00 g, 3.7 mmol, 1 eq.), 4 N HCl in dioxane (9.24 mL, 3.7 mmol, 1 eq.), and dioxane (10 mL) were mixed and stirred at RT for 2 hours. MeOH was added to aid in dissolution. After 4 more hours, the reaction was stripped 3× from methylene chloride to remove traces of dioxane. Obtained 0.99 g of the HCl salt of N-tert-Butyl-cyclohexane-1,4-diamine as an off-white solid. MS found: (M+H)$^+$=171.

Example 1j, Step 3: Following the procedures described in Example 1h, Steps 3 and 4, N-tert-Butyl-cyclohexane-1,4-diamine was converted into 2-amino-N-(4-tert-butylamino-cyclohexyl)-acetamide (mixture of cis and trans diastereomers). MS found: (M+H)$^+$=228.

Example 1j, Step 4: 2-Amino-N-(4-tert-butylamino-cyclohexyl)-acetamide, (85 mg, 0.37 mmol, mixture of cis and trans diastereomers), 5-bromo-2-tert-butyl-pyrimidine-4-carboxylic acid, (97 mg, 0.37 mmol), HOBT (111 mg, 0.82 mmol), triethylamine (208 µL, 1.49 mmol), and 1-[3-(dimethylamino)-propyl]-3-ethylcarbodiimide HCl (EDCI, 157 mg, 0.82 mmol) were combined in CH$_2$Cl$_2$ (2 mL), and the mixture was stirred for 16 h at RT. The mixture was diluted with ethyl acetate (15 mL), and washed with saturated NaHCO$_3$ (3×5 mL), water (5 mL), and brine (5 mL). The organic layer was then dried over sodium sulfate, and concentrated in-vacuo. The residue was purified by RP-HPLC to afford the TFA salt of the title compound (47 mg) as a white powder after lyopholization. MS found: (M+H)$^+$=469, 471.

Example 1k

Synthesis of 2-tert-butyl-N-(2-(4-(tert-butylamino) cyclohexylamino)-2-oxoethyl)pyrimidine-4-carboxamide as a mixture of cis and trans diastereomers Example 1k, Step 1: A solution of 5-bromo-2-tert-butyl-N-(2-(4-(tert-butylamino)cyclohexylamino)-2-oxoethyl)pyrimidine-4-carboxamide, TFA salt (30 mg, 0.05 mmol) in methanol (10 mL) was hydrogenated at 50 psi in the presence of 10% palladium on activated carbon (20 mg) and 1 N aqueous sodium hydroxide solution (110 µL, 0.11 mmol) for 2 hours. The catalyst was removed by filtration and rinsed with a small amount of methanol, and the combined filtrates were concentrated in vacuo. The residue was purified by RP-HPLC to provide the TFA salt of the title compound (7.2 mg) as a white powder after lyopholization. MS found: (M+H)$^+$=390.

Example 1l

Synthesis of 3-tert-butyl-4-hydroxy-N-(2-((1s,4s)-4-(isopropyl(methyl)amino)cyclohexylamino)-2-oxoethyl)benzamide as a mixture of cis and trans diastereomers Example 1l, Step 1: cis-2-Amino-N-[4-(isopropyl-methyl-amino)-cyclohexyl]-acetamide was carried through the procedure of Example 1j, Step 4—substituting 3-tert-butyl-4-hydroxybenzoic acid instead for 5-bromo-2-tert-butyl-pyrimidine-4-carboxylic acid—to afford the TFA salt of the title compound as a white powder after lyopholization. MS found: (M+H)$^+$=404.

Example 1t

Synthesis of N-(4-(tert-butylamino)cyclohexyl)-2-(2,6-dichloro-quinazolin-4-ylamino)-acetamide as a Mixture of cis and trans diastereomers Example 1t, Step 1: 2-Amino-N-(4-tert-butylamino-cyclohexyl)-acetamide (100 mg, 0.44 mmol, 1 eq.), 2,4,6-trichloro-quinazoline (103 mg, 0.44 mmol, 1 eq.) and N,N-diisopropylethylamine (0.153 mL, 0.88 mmol, 2 eq.) were stirred in THF at RT for 20 hours. Purified by RP-HPLC to provide the TFA salt of the title compound (128 mg) as a white solid after lyopholization. MS found: (M+H)+=424.

Example 1u

Synthesis of N-(4-tert-butylamino-cyclohexyl)-2-(6-chloro-2-methylamino-quinazolin-4-ylamino)-acetamide as a Mixture of cis and trans diastereomers Example 1u, Step 1: N-(4-tert-Butylamino-cyclohexyl)-2-(2,6-dichloro-quinazolin-4-ylamino)-acetamide (40 mg, 0.074 mmol, 1 eq.) was microwaved in 2.0 M monomethylamine in THF (Aldrich) (1.86 mL, 3.71 mmol, 50 eq.) and 1 mL of THF until reaction was complete by LCMS. Purified by RP-HPLC to provide the TFA salt of the title compound (37 mg) as a white solid after lyopholization. MS found: $(M+H)^+=419$.

Example 1w

Synthesis of N-(4-(tert-butylamino)cyclohexyl)-2-(6-iodoquinazolin-4-ylamino)acetamide as a Mixture of cis and trans diastereomers Example 1w, Step 1: 2-amino-N-(4-(tert-butylamino)cyclohexyl)acetamide (487 mg, 2.13 mmol), 6-iodo-4-chloroquinazoline (obtained commercially; 805 mg, 2.77 mmol), and triethylamine (1.2 mL, 8.52 mmol) were combined with 5 mL of ethanol in a microwave reaction tube, the vessel was sealed, and the mixture was heated via microwave at 100° C. for 30 min. The resulting blood-red suspension was filtered, the solids were rinsed with ethanol, and the combined filtrates were concentrated in-vacuo. The residue was purified via flash chromatography to afford the title product (580 mg) as a colorless glass. MS found: $(M+H)^+=482$.

Example 1y

Synthesis of N-(4-tert-butyl(methyl)amino-cyclohexyl)-2-(6-trifluoromethyl-quinazolin-4-ylamino)-acetamide Example 1y, Step 1: N-(4-tert-Butylamino-cyclohexyl)-2-(6-trifluoromethyl-quinazolin-4-ylamino)-acetamide, TFA salt (25 mg, 0.465 mmol, 1 eq.), 37% formaldehyde(aqueous) (11 mL, 0.14 mmol, 3 eq.), sodium triacetoxyborohydride (15 mg, 0.0697 mmol, 1.5 eq.) and methylene chloride (5 mL) were mixed and stirred at RT overnight. Worked up by adding 1.0 N NaOH (10 mL). Stirred 10 minutes then extracted 3 times with methylene chloride. The organic layer was dried and stripped to give the title compound (11 mg) as an amorphous solid. MS found: $(M+H)^+=438$.

Example 1z

Synthesis of N-(4-(tert-Butylamino)cyclohexyl)-2-(6-phenylquinazolin-4-ylamino)acetamide as a mixture of cis and trans diastereomers Example 1z, Step 1: N-(4-(tert-butylamino)cyclohexyl)-2-(6-iodoquinazolin-4-ylamino)acetamide (34 mg, 0.07 mmol), phenyl boronic acid (18 mg, 0.14 mg), and 2.0 M aqueous $K_3PO_4$ solution (106 uL, 0.21 mmol) were combined in 2 mL of DMF in a microwave reaction tube, and the resulting solution was degassed under vacuum, then backfilled with argon. Tetrakis(triphenylphosphine)palladium(0) (10 mg, 0.01 mmol) was then added, and the mixture was again degassed as described above. The tube was sealed, and the reaction mixture was heated via microwave at 150° C. for 30 minutes. The reaction was cooled, some solids were removed by filtration and rinsed with ethyl acetate, and the combined filtrates were concentrated in-vacuo. The residue was purified by RP-HPLC to afford the TFA salt of the title compound (27 mg) as a white powder after lyopholization. MS found: $(M+H)^+=432$.

Example 1au

Synthesis of 3-bromo-5-tert-butyl-N-(2-(4-(tert-butylamino)cyclohexylamino)-2-oxoethyl)benzamide as a mixture of cis and trans diastereomers Example 1au, Step 1: 2-Amino-N-(4-(tert-butylamino)cyclohexyl)acetamide (35 mg, 0.13 mmol), lithium 3-bromo-5-tert-butylbenzoate (33 mg, 0.13 mmol), diisoproplyethylamine (110 µL, 0.62 mmol), and HATU (50 mg, 0.12 mmol) were combined in $CH_2Cl_2$ (2 mL), and the mixture was stirred overnight at room temperature. The mixture was diluted with ethyl acetate (15 mL), and washed with saturated $NaHCO_3$ (3×5 mL), water (5 mL), and brine (5 mL). The organic layer was then dried over sodium sulfate, and concentrated in-vacuo. The residue was purified by RP-HPLC to afford the TFA salt of the title compound (19 mg) as a white powder after lyopholization. MS found: $(M+H)^+=466, 468$.

Examples 1az and 1ba

Synthesis of N-(2-((1s,4s)-4-(tert-butylamino)cyclohexylamino)-2-oxoethyl)-6-(2-methoxyphenyl)picolinamide and its diastereomer, N-(2-((1r,4r)-4-(tert-butylamino)cyclohexylamino)-2-oxoethyl)-6-(2-methoxyphenyl)picolinamide Examples 1az and 1ba, Step 1: cis- and trans-6-bromo-N-(2-(4-(tert-butylamino)-cyclohexylamino)-2-oxoethyl)picolinamide (50 mg 0.122 mmol, 1 eq.), 2-methoxyphenylboronic acid (37 mg, 0.243 mmol, 2 eq.), tetrakis (triphenylphosphine)-palladium(0) 14 mg, 0.0121 mmol, 0.1 eq.), 2.0M potassium phosphate (aq) (0.18 mL, 0.365 mmol, 3 eq.) and DMF were mixed at room temperature under nitrogen then placed in a microwave at 150° C. for 30 minutes. The residue was purified by RP-HPLC to provide both N-(2-((1s,4s)-4-(tert-butylamino)cyclohexylamino)-2-oxoethyl)-6-(2-methoxyphenyl)picolinamide and its diastereomer, N-(2-((1r,4r)-4-(tert-butylamino)cyclohexylamino)-2-oxoethyl)-6-(2-methoxyphenyl)picolinamide (ca. 20 mg each). For both compounds, MS found: $(M+H)^+=439.3$.

Example 1bj

Synthesis of N-(4-(tert-butylamino)cyclohexyl)-2-(6-(2-methoxyphenyl)-2-propylquinazolin-4-ylamino)acetamide as a mixture of cis and trans diastereomers Example DSG1a: A mixture of cis- and trans-N-(4-(tert-butylamino)cyclohexyl)-2-(6-chloro-2-propylquinazolin-4-ylamino)acetamide, bis TFA salt (41 mg, 0.07 mmol), 2-methoxyphenylboronic acid (20 mg, 0.13 mmol), 2.0 M potassium phosphate (aq) (0.17 mL, 0.34 mmol), and DMF (2 mL) in a 5 mL microwave tube was degassed under vacuum/Ar. A catalytic amount of tetrakis(triphenylphosphine)palladium(0) was added to the tube, the mixture was degassed again, the tube was sealed, and the reaction was heated at 150° C. in the microwave for 30 min. The reaction mixture was filtered, the filtrate was concentrated in-vacuo, and the residue was taken up in 9:1 EtOAc/heptane (10 mL). This suspension was washed 3× with water, once with brine, then the organic phase was dried over sodium sulfate, and concentrated in-vacuo. The residue was purified via RP-

Example 1bl

Synthesis of N-(2-oxo-2-(cis-4-(cis- and trans-4-phenylcyclohexylamino)cyclohexylamino)ethyl)-3-(trifluoromethyl)benzamide Example 1bl, Step 1: 2-(3-(trifluoromethyl)-benzamido) acetic acid (277 mg, 1.12 mmol, 1.2 eq) and triethylamine (0.15 mL, 1.12 mmol, 1.2 eq) were dissolved in THF (15 mL) at room temperature under nitrogen. Cooled to 0° C. Added isobutyl chloroformate (0.16 µL, 1.12 mmol, 1.2 eq) dropwise. Stirred for 10 mintues followed by the dropwise addition of tert-butyl cis-4-amino-cyclo-hexylcarbamate (200 mg, 0.93 mmol, 1 eq) in THF ((5 mL). Warmed to room temperature. Worked up after 3 hours by adding methylene chloride (25 mL) and rinsing 3 times with saturated sodium bicarbonate (25 mL). The organic layer was dried (sodium sulfate) and stripped to give an oil. Purified over silica gel in 1:1 hexanes/ethyl acetate to give tert-butyl cis-4-(2-(3-(trifluoromethyl)-benzamido)acetamido)cyclohexylcarbamate (350 mg) as an oil. MS found: $(M+Na)^+$=466.20.

Example 1bl, Step 2: tert-Butyl cis-4-(2-(3-(trifluoromethyl)benzamido)acetamido)cyclohexylcarbamate hydrochloride salt (350 mg, 0.79 mmol, 1 eq) was dissolved in dioxane (5 mL) at room temperature then 4N HCl (1.97 mL, 7.9 mmol, 10 eq) was added. Stirred for 20 hours. The reaction was stripped 4 times from 1:1 THF/methylene chloride (20 mL) to give N-(2-(cis-4-amino-cyclohexylamino)-2-oxoethyl)-3-(trifluoromethyl)benzamide hydrochloride (300 mg) as a white amorphous solid. MS found: $(M+H)^+$=344.32.

Example 1bl, Step 3: N-(2-(cis-4-amino-cyclohexylamino)-2-oxoethyl)-3-(trifluoromethyl)benzamide hydrochloride (60 mg, 0.158 mmol, 1 eq), 4-phenylcyclohexanone (28 mg, 0.158 mmol, 1 eq) and sodium triacetoxyborohydride (67 mg, 0.316 mmol, 2 eq) were stirred in 2% acetic acid/methylene chloride (10 mL) at room temperature for 20 hours. Worked up by adding saturated sodium bicarbonate (10 mL). Stirred 10 minutes then extracted 3 times with methylene chloride (10 mL). The organic layers were combined, dried (sodium sulfate) and stripped to give an oil. Purified over silica gel in 100% ethyl acetate to 4:1 methylene chloride/methanol to give N-(2-oxo-2-(cis-4-(cis- and trans-4-phenylcyclohexylamino)cyclohexylamino)ethyl)-3-(trifluoromethyl)benzamide (42 mg) as an off-white amorphous solid. MS found: $(M+H)^+$=502.33.

Example 1bm

Synthesis of N-(2-oxo-2-(cis-4-(cis- and trans-4-phenylcyclohexyl-(N-methyl)-amino)cyclohexylamino)ethyl)-3-(trifluoromethyl)benzamide Example 1bm, Step 1: N-(2-oxo-2-(cis-4-(cis- and trans-4-phenylcyclohexylamino)cyclohexylamino)ethyl) -3-(trifluoromethyl)benzamide (32 mg, 0.064 mmol, 1 eq) and sodium triacetoxyborohydride ((20 mg, 0.096 mmol, 1.5 eq) were dissolved in methylene chloride (5 mL) at room temperature and then formaldehyde (16 µL, 0.19 mmol, 3 eq) was added. Worked up after 2 hours by adding 1N NaOH (10 mL). Stirred 10 minutes then extracted 3 times with methylene chloride. The organic layers were combined, dried (sodium sulfate) and stripped to give an oil. Purified by RP-HPLC to give the TFA salt of the title compound (24 mg) as a white solid after lyopholization. MS found: $(M+H)^+$=516.28.

Example 1bn

Synthesis of N-(2-oxo-2-(cis-4-(4-phenylcyclohex-3-enylamino)cyclohexylamino)ethyl)-3-(trifluoromethyl)benzamide Example 1bn, Step 1: N-(2-(cis-4-Amino-cyclohexylamino)-2-oxoethyl)-3-(trifluoromethyl)benzamide hydrochloride (120 mg, 0.315 mmol, 1 eq), 4-hydroxy-4-phenylcyclohexanone (60 mg, 0.315 mmol, 1 eq) and sodium triacetoxyborohydride (134 mg, 0.631 mmol, 2 eq) were stirred in 2% acetic acid/methylene chloride (10 mL) at room temperature for 20 hours. Worked up by adding saturated sodium bicarbonate (10 mL). Stirred 10 minutes then extracted 3 times with methylene chloride (10 mL). The organic layers were combined, dried (sodium sulfate) and stripped to give an oil. Purified over silica gel in 100% ethyl acetate to 4:1 methylene chloride/methanol to give N-(2-oxo-2-(cis-4-(4-phenylcyclohex-3-enylamino)cyclohexylamino)ethyl)-3-(trifluoromethyl)benzamide (10 mg) as a tan solid. MS found: $(M+H)^+$=500.33.

Example 1bo

Synthesis of N-(2-(cis-4-(cis- and trans-4-hydroxy-4-(pyridin-2-yl)cyclohexylamino)cyclohexylamino)-2-oxoethyl)-3-(trifluoromethyl)benzamide Example 1bo, Step 1: 2-Bromopyridine (1.40 g, 8.86 mmol, 1 eq) was dissolved in diethyl ether (30 mL) at room temperature under nitrogen then cooled to –70° C. Added 1.6M n-butyllithium (5.54 mL, 8.86 mmol, 1 eq) dropwise via an addition funnel. Stirred at –70° C. for 1 hour then added 1,4-cyclohexanedione-mono-ethylene ketal (1.52 g, 9.57 mmol, 1.1 eq) as a diethyl ether (30 mL) solution, dropwise via an addition funnel. Stirred at 0° C. for 1 hour. Quenched with saturated ammonium chloride (25 mL). Separated the 2 layers. The aqueous layer was extracted 2 times more with methylene chloride. The organic layers were combined, dried (sodium sulfate) and stripped to give an oil. Purified over silica gel in 9:1 to 1:1 hexanes/ethyl acetate to give 8-(2-pyridinyl)-1,4-dioxaspiro[4.5]decan-8-ol (2.70 g) of an amber oil. MS found: $(M+H)^+$=236.1

Example 1bo, Step 2: 8-(2-Pyridinyl)-1,4-dioxaspiro[4.5] decan-8-ol (2.70 g) was dissolved in 1:1 THF/H$_2$O (20 mL) then 3N HCl (10 mL) added. Refluxed for 2 hours then stirred overnight at room temperature. Worked up by slowly adding neat sodium bicarbonate until foaming ceased then extracted the mixture 3 times with ethyl acetate. The organic layers were combined, dried (sodium sulfate) and stripped to give an amber oil which solidified. The solids were dissolved in diethyl ether (10 mL). Hexanes (10 mL) were added which precipitated the solids which were then filtered to give 4-hydroxy-4-(pyridin-2-yl)cyclohexanone (680 mg) as a tan solid. MS found: $(M+H)^+$=192.1.

Example 1bo, Step 3: N-(2-(cis-4-Amino-cyclohexylamino)-2-oxoethyl)-3-(trifluoromethyl)benzamide hydrochloride (50 mg, 0.132 mmol, 1 eq), 4-hydroxy-4-(pyridin-2-yl)cyclohexanone (25 mg, 0.132 mmol, 1 eq) and sodium triacetoxyborohydride (56 mg, 0.263 mmol, 2 eq) were stirred in 2% acetic acid/methylene chloride (10 mL) at room temperature for 20 hours. Worked up by adding saturated sodium bicarbonate (10 mL). Stirred 10 minutes then extracted 3 times with methylene chloride (10 mL). The organic layers were combined, dried (sodium sulfate) and stripped to give an oil. Purified over silica gel in 100% ethyl acetate to 4:1 methylene chloride/methanol to give N-(2-(cis-4-(cis- and trans-4-hydroxy-4-(pyridin-2-yl)cyclohexylamino)cyclohexylamino)-2-oxoethyl)-3-(trifluoromethyl) benzamide (35 mg) as a white solid. MS found: (M+H)⁺ =519.27.

Example 1bp

Synthesis of N-(2-((1s,4s)-4-(benzyl(tert-butyl) amino)cyclohexylamino)-2-oxoethyl)-5-tert-butyl-2-methylfuran-3-carboxamide A sample of 5-tert-butyl-N-(2-(4-(tert-butylamino)cyclohexylamino)-2-oxoethyl)-2-methylfuran-3-carboxamide (40 mg, 0.1 mmol, see Example 1p) was free-based and then dissolved in methylene chloride (2 mL). The resultant solution was charged with potassium carbonate and benzyl bromide (1 eq. each) and stirred overnight. Since no reaction was observed, more potassium carbonate and benzyl bromide (10 equivalents) were added and the reaction was held at reflux for 6 h. The reaction mixture was cooled and purified directly by RP-HPLC to afford the title compound (18 mg) as a white powder after lyopholization. MS found: (M+H)⁺=482.

Example 1bq

Synthesis of N-(2-((1s,4s)-4-((isopropyl(methyl) amino)methyl)cyclohexylamino)-2-oxoethyl)-3-(trifluoromethyl)benzamide Example 1bq, Step 1: A sample of cis-4-aminocyclohexane carboxylic acid (1.0 g, 7.0 mmol) was benzylated using excess benzyl bromide and potassium carbonate (RT, several days, EtOH as solvent). The mixture was filtered, washed with water, dried (sodium sulfate), filtered, and concentrated in vacuo to afford (1s,4s)-benzyl 4-(dibenzylamino)cyclohexanecarboxylate. MS found: (M+H)⁺=414.

Example 1bq, Step 2: A sample of (1s,4s)-benzyl 4-(dibenzylamino)cyclohexanecarboxylate (2.5 g, 6 mmol) was dissolved in THF and the resultant solution was treated dropwise with lithium aluminum hydride (6.0 mL of a 1.0 M solution in THF). The mixture was stirred overnight and treated with 6 mL water and 6 mL 1N NaOH. The suspension was stirred for 1 h and filtered. The filtrate was concentrated in vacuo to afford ((1s,4s)-4-(dibenzylamino) cyclohexyl)methanol. MS found: (M+H)⁺=310.

Example 1bq, Step 3: A sample of ((1s,4s)-4-(dibenzylamino)cyclohexyl)methanol (1.86 g, 6.0 mmol) was converted to its mesylate (1 eq methanesulfonyl chloride, 1.5 eq triethylamine, methylene chloride, RT, overnight). After standard aqueous workup, the crude mesylate was dissolved in DMF (15 mL) and the resulting solution was charged with sodium azide (1 eq) and stirred at RT overnight. The mixture was diluted with EtOAc and washed with water. The organic phase was dried and stripped to give (1s,4s)-4-(azidomethyl)-N,N-dibenzylcyclohexanamine. This material was dissolved in MeOH and added to a pre-wet suspension of 20% Pd(OH)$_2$ (15 wt %) in MeOH. The suspension was hydrogenated at 30 psi for one hour before being filtered. The filtrate was concentrated to give 0.95 g of (1s,4s)-4-(aminomethyl)-N,N-dibenzylcyclohexanamine. MS found: (M+H)⁺=309.

Example 1bq, Step 4: A sample of (1s,4s)-4-(aminomethyl)-N,N-dibenzylcyclohexanamine (0.475 g) was taken through the procedure of Example 1 h, Step 1 to give (1s,4s)-N,N-dibenzyl-4-((isopropyl(methyl)amino)methyl) cyclohexanamine (280 mg). This material was hydrogenated according to the procedure of Example 1 h, Step 4 to give (1s,4s)-4-((isopropyl(methyl)amino)methyl)cyclohexanamine. The entirety of this sample (95 mg) was dissolved in methylene chloride (5 mL) and DMF (2 mL). The resultant solution was charged successively with (3-trifluoromethylbenzoylamino)-acetic acid (127 mg), PyBOP (268 mg), and triethylamine (0.14 mL). The mixture was stirred overnight and diluted with methylene chloride before being washed with water thrice. The organic phase was then washed with sat. sodium bicarbonate, dried (sodium sulfate), filtered, and concentrated in vacuo. The residue was purified by RP-HPLC to afford the title compound as an oil (5 mg). MS found: (M+H)⁺=414.

TABLE 1-A

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the (M + H)⁺ ions in electrospray mass spectroscopy experiments.

| Ex | R⁵ | Z | R² | Step Altered | MS |
|---|---|---|---|---|---|
| 1a | H₂N, cis | NHC(O) | 3-CF₃-phenyl | n/a | 344 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

| Ex | R⁵ | Z | R² | Step Altered | MS |
|---|---|---|---|---|---|
| 1b | i-PrHN, cis | NHC(O) | 3-CF₃-phenyl | n/a | 386 |
| 1c | i-Pr(Me)N cis | NHC(O) | 3-CF₃-phenyl | n/a | 400 |
| 1d | i-Pr(Me)N cis | NHC(O) | 2-(i-PrNHC(O)NH)-4-CF₃-phenyl | n/a | 500 |
| 1e | i-Pr(Me)N cis | NHC(O) | 2-(azetidin-1-yl-C(O)NH)-4-CF₃-phenyl | 1d, Step 6 | 498 |
| 1f | i-Pr(Me)N cis | C(O)NH | 3-OCF₃-phenyl | 1d, Step 6 | 416 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

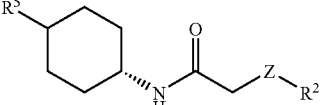

| Ex | $R^5$ | Z | $R^2$ | Step Altered | MS |
|---|---|---|---|---|---|
| 1g | i-Pr(Me)N cis | C(O)NH | 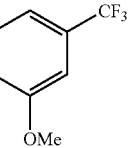 | 1d, Step 6 | 430 |
| 1h | i-Pr(Me)N cis | NH | 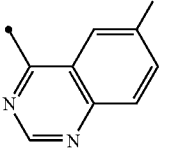 | n/a | 390 |
| 1i | i-Pr(Me)N cis | NH | 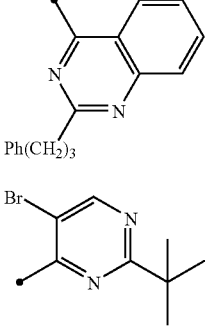 | n/a | 508 |
| 1j | t-Bu(H)N, cis/trans | NHC(O) | 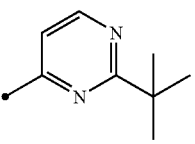 | n/a | 469 |
| 1k | t-Bu(H)N, cis/trans | NHC(O) | 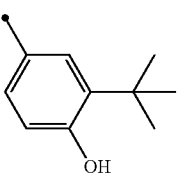 | n/a | 390 |
| 1l | i-Pr(Me)N cis | NHC(O) |  | n/a | 404 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

| Ex | $R^5$ | Z | $R^2$ | Step Altered | MS |
|---|---|---|---|---|---|
| 1m | i-Pr(Me)N cis | NHC(O) | (4-methoxy-3-trifluoromethylphenyl) | 1l, Step 1 | 430 |
| 1n | I-Pr(Me)N cis | NHC(O) | (3-tert-butoxyphenyl) | 1l, Step 1 | 404 |
| 1o | t-Bu(H)N, cis/trans | NHC(O) | (3-tert-butyl-4-hydroxyphenyl) | 1j, Step 4 | 404 |
| 1p | t-Bu(H)N, cis/trans | NHC(O) | (5-tert-butyl-2-methylfuran-3-yl) | 1j, Step 4 | 392 |
| 1q | t-Bu(H)N, cis/trans | NHC(O) | (4-adamantyl-1-methylpyrrol-2-yl) | 1j, Step 4 | 469 |
| 1r | t-Bu(H)N, cis/trans | NHC(O) | (4-adamantyl-1H-pyrrol-2-yl) | 1j, Step 4 | 455 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

| Ex | $R^5$ | Z | $R^2$ | Step Altered | MS |
|---|---|---|---|---|---|
| 1s | t-Bu(H)N, cis/trans | NHC(O) | (aryl urea with i-Pr, CF$_3$-phenyl) | 1j, Step 4 | 500 |
| 1t | t-Bu(H)N, cis/trans | NH | 2,4-dichloroquinazolinyl | n/a | 424 |
| 1u | t-Bu(H)N, cis/trans | NH | 4-chloro-2-(methylamino)quinazolinyl | n/a | 419 |
| 1v | t-Bu(H)N, cis/trans | NH | 4-chloro-2-(dimethylamino)quinazolinyl | 1u, Step 1 | 434 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

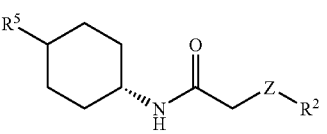

| Ex | $R^5$ | Z | $R^2$ | Step Altered | MS |
|---|---|---|---|---|---|
| 1w | t-Bu(H)N, cis/trans | NH | 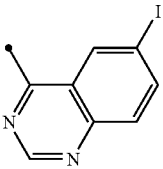 | n/a | 482 |
| 1x | t-Bu(H)N, cis/trans | NH | 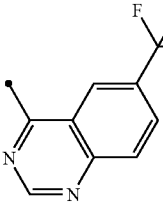 | 1w, Step 1 | 424 |
| 1y | t-Bu(Me)N cis/trans | NH | 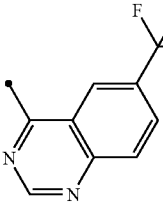 | n/a | 438 |
| 1z | t-Bu(H)N, cis/trans | NH | 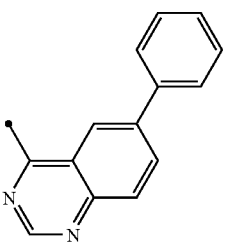 | n/a | 432 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the (M + H)⁺ ions in electrospray mass spectroscopy experiments.

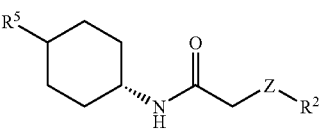

| Ex | R⁵ | Z | R² | Step Altered | MS |
|---|---|---|---|---|---|
| 1aa | t-Bu(H)N, cis/trans | NH | 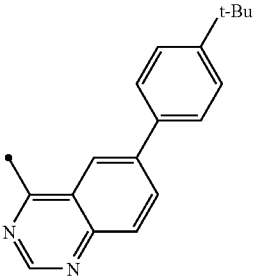 | 1z, Step 1 | 488 |
| 1ab | t-Bu(H)N, cis/trans | NH | 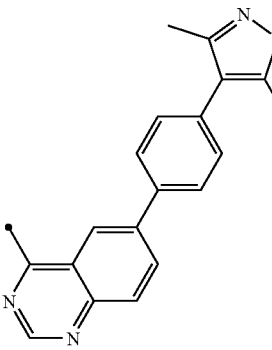 | 1z, Step 1 | 452 |
| 1ac | t-Bu(H)N, cis/trans | NH | | 1z, Step 1 | 474 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

| Ex | $R^5$ | Z | $R^2$ | Step Altered | MS |
|---|---|---|---|---|---|
| 1ad | t-Bu(H)N, cis/trans | NH | (4-i-Pr-phenyl)-quinazolin-6-yl | 1z, Step 1 | 474 |
| 1ae | t-Bu(H)N, cis/trans | NH | (2-OMe-phenyl)-quinazolin-6-yl | 1z, Step 1 | 462 |
| 1af | t-Bu(H)N, cis/trans | NH | (3-OMe-phenyl)-quinazolin-6-yl | 1z, Step 1 | 462 |
| 1ag | t-Bu(H)N, cis/trans | NH | (4-OMe-phenyl)-quinazolin-6-yl | 1z, Step 1 | 462 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the (M + H)+ ions in electrospray mass spectroscopy experiments.

| Ex | R⁵ | Z | R² | Step Altered | MS |
|---|---|---|---|---|---|
| 1ah | t-Bu(H)N, cis/trans | NH | 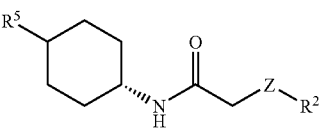 | 1z, Step 1 | 450 |
| 1ai | t-Bu(H)N, cis/trans | NH | 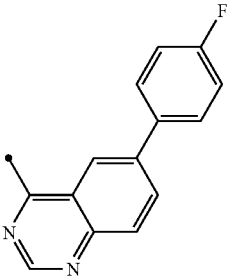 | 1z, Step 1 | 502 |
| 1aj | t-Bu(H)N, cis/trans | NH | 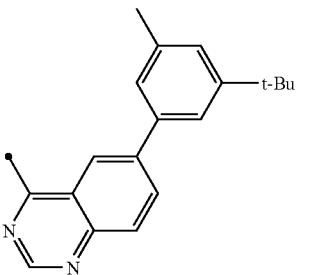 | 1z, Step 1 | 475 |
| 1ak | t-Bu(H)N, cis/trans | NH | 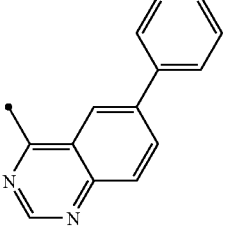 | 1z, Step 1 | 450 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

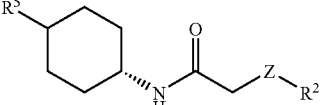

| Ex | $R^5$ | Z | $R^2$ | Step Altered | MS |
|---|---|---|---|---|---|
| 1al | t-Bu(H)N, cis/trans | NH | 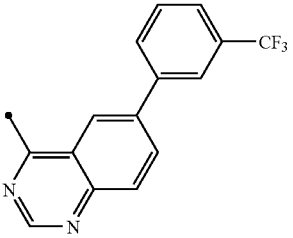 | 1z, Step 1 | 450 |
| 1am | t-Bu(H)N, cis/trans | NH | 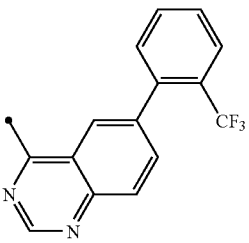 | 1z, Step 1 | 500 |
| 1an | t-Bu(H)N, cis/trans | NH | 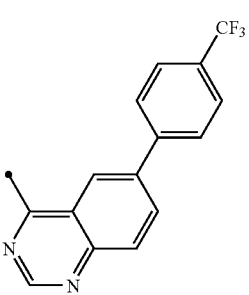 | 1z, Step 1 | 500 |
| 1ao | t-Bu(H)N, cis/trans | NH |  | 1z, Step 1 | 500 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

| Ex | $R^5$ | Z | $R^2$ | Step Altered | MS |
|---|---|---|---|---|---|
| 1ap | t-Bu(H)N, cis/trans | NH | 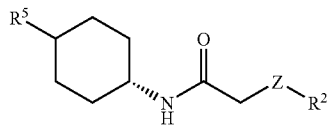 | 1z, Step 1 | 457 |
| 1aq | t-Bu(H)N, cis/trans | NH | 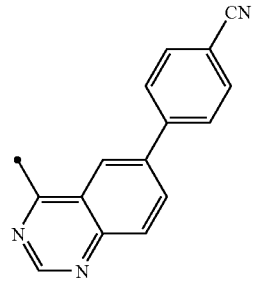 | 1z, Step 1 | 457 |
| 1ar | t-Bu(H)N, cis/trans | NH | 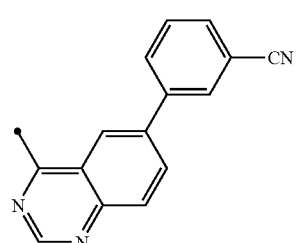 | 1z, Step 1 | 457 |
| 1as | t-Bu(H)N, cis/trans | NH | 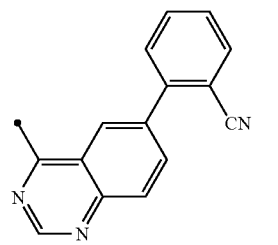 | 1w, Step 1 | 415 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

| Ex | R⁵ | Z | R² | Step Altered | MS |
|---|---|---|---|---|---|
| 1at | t-Bu(H)N, cis/trans | NHC(O) | 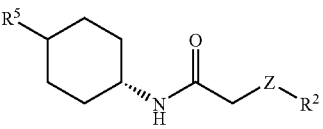 | 1j, Step 4 | 388 |
| 1au | t-Bu(H)N, cis/trans | NHC(O) | 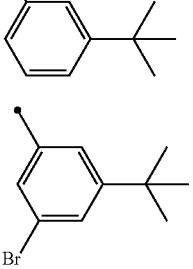 | n/a | 466 |
| 1av | t-Bu(H)N, cis/trans | NHC(O) | 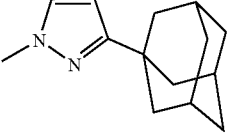 | 1j, Step 4 | 470 |
| 1aw | t-Bu(H)N, cis/trans | NHC(O) | 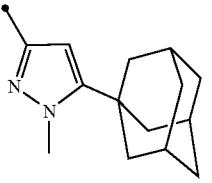 | 1j, Step 4 | 470 |
| 1ax | t-Bu(H)N, cis/trans | NHC(O) | 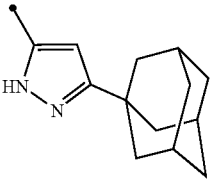 | 1j, Step 4 | 456 |
| 1ay | t-Bu(H)N, cis/trans | NHC(O) | 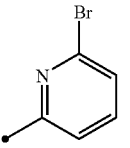 | 1j, Step 4 | 411 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

| Ex | $R^5$ | Z | $R^2$ | Step Altered | MS |
|---|---|---|---|---|---|
| 1az | t-Bu(H)N, cis | NHC(O) | (6-(2-methoxyphenyl)pyridin-2-yl) | n/a | 439 |
| 1ba | t-Bu(H)N, trans | NHC(O) | (6-(2-methoxyphenyl)pyridin-2-yl) | n/a | 439 |
| 1bb | t-Bu(H)N, cis | NHC(O) | (6-(3-cyanophenyl)pyridin-2-yl) | 1az, Step 1 | 434 |
| 1bc | t-Bu(H)N, trans | NHC(O) | (6-(3-cyanophenyl)pyridin-2-yl) | 1az, Step 1 | 434 |
| 1bd | t-Bu(H)N, cis/trans | NHC(O) | (6-(3-carboxyphenyl)pyridin-2-yl) | 1az, Step 1 | 453 |
| 1be | t-Bu(H)N, cis/trans | NHC(O) | (6-(4-carboxyphenyl)pyridin-2-yl) | 1az, Step 1 | 453 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

| Ex | R⁵ | Z | R² | Step Altered | MS |
|---|---|---|---|---|---|
| 1bf | t-Bu(H)N, cis/trans | NHC(O) | 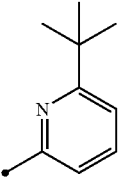 | 1j, Step 4 | 389 |
| 1bg | t-Bu(H)N, cis/trans | NHC(O) | 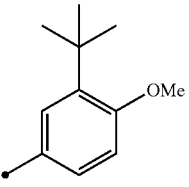 | 1j, Step 4 | 418 |
| 1bh | t-Bu(H)N, cis/trans | NHC(O) | 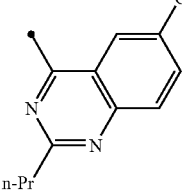 | 1w, Step 1 | 432 |
| 1bi | t-Bu(H)N, cis/trans | NHC(O) | 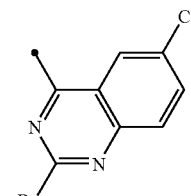 | 1w, Step 1 | 480 |
| 1bj | t-Bu(H)N, cis/trans | NhC(O) | 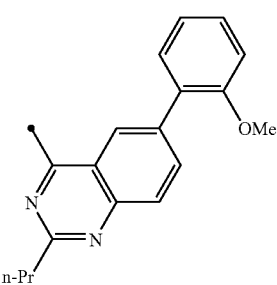 | n/a | 504 |

TABLE 1-A-continued

The compounds in the following table were made using the methods exemplified above. The substituents listed in each table are to be paired with the structure embedded in the table heading. In the synthesis of certain example compounds, substitutions for key reagents were made in order to provide a different compound, and the point(s) of variance is (are) indicated in the "Step Altered" column. Some of these alterations require reagents that are not commercially available, and the syntheses of such specialized reagents are described above in the section entitled "Preparation of non-standard reagents and synthetic intermediates utilized in the EXAMPLES." The nature of any given alteration will be obvious to one skilled in the art, given the large amount of teaching provided in the EXAMPLES that precede and follow this Table. The reference "n/a" in the Step Altered column indicates "not applicable," as the procedure has been carried out as written without alteration. The data in the "MS" columns represent the values observed for the $(M + H)^+$ ions in electrospray mass spectroscopy experiments.

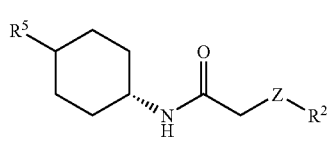

| Ex | $R^5$ | Z | $R^2$ | Step Altered | MS |
|---|---|---|---|---|---|
| 1bk | t-Bu(H)N, cis/trans | NHC(O) | 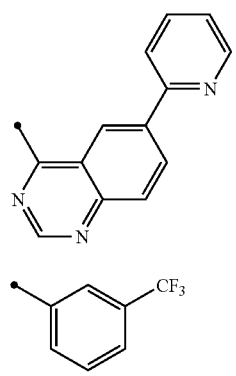 | 1w, Step 1 | 433 |
| 1bl | 4-Ph-c-Hex(H)N, cis | NHC(O) | 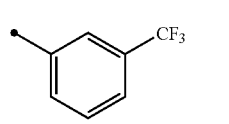 | n/a | 502 |
| 1bm | 4-Ph-c-Hex(Me)N, cis | NHC(O) | 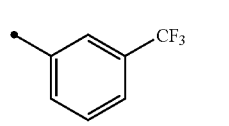 | n/a | 516 |
| 1bn | 4-Ph-c-Hex-3-enyl(H)N, cis | NHC(O) | 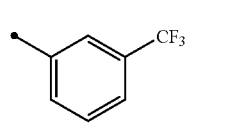 | n/a | 500 |
| 1bo | 4-(2-Pyr)-4-(HO)-c-Hex(H)N, cis | NHC(O) | | n/a | 519 |
| 1bp | t-Bu(Bn)N, cis/trans | NHC(O) | 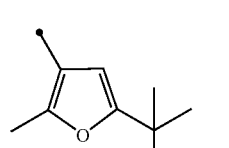 | n/a | 482 |
| 1bq | i-Pr(Me)N-CH₂ | NHC(O) | 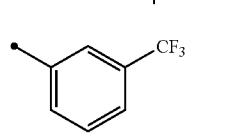 | n/a | 414 |

TABLE 1-B

The chemical names of the specific examples illustrated in Table 1-A are tabulated below.

| Example | Name |
| --- | --- |
| 1a | N-(2-((1s,4s)-4-aminocyclohexylamino)-2-oxoethyl)-3-(trifluoromethyl)benzamide |
| 1b | N-(2-((1s,4s)-4-(isopropylamino)cyclohexylamino)-2-oxoethyl)-3-(trifluoromethyl)benzamide |
| 1c | N-(2-((1s,4s)-4-(isopropyl(methyl)amino)cyclohexylamino)-2-oxoethyl)-3-(trifluoromethyl)benzamide |
| 1d | 1-(2-(2-((1s,4s)-4-(isopropyl(methyl)amino)cyclohexylamino)-2-oxoethyl)carbamoyl)-4-(trifluoromethyl)phenyl)-3-isopropylurea |
| 1e | N-(2-((2-((1s,4s)-4-(isopropyl(methyl)amino)cyclohexylamino)-2-oxoethyl)carbamoyl)-4-(trifluoromethyl)phenyl)azetidine-1-carboxamide |
| 1f | N1-((1s,4s)-4-(isopropyl(methyl)amino)cyclohexyl)-N3-(3-(trifluoromethoxy)phenyl)malonamide |
| 1g | N1-((1s,4s)-4-(isopropyl(methyl)amino)cyclohexyl)-N3-(3-methoxy-5-(trifluoromethyl)phenyl)malonamide |
| 1h | 2-(6-chloroquinazolin-4-ylamino)-N-((1s,4s)-4-(isopropyl(methyl)amino)cyclohexyl)acetamide |
| 1i | 2-(6-chloro-2-(3-phenylpropyl)quinazolin-4-ylamino)-N-((1s,4s)-4-(isopropyl(methyl)amino)cyclohexyl)acetamide |
| 1j | 5-bromo-2-tert-butyl-N-(2-(4-(tert-butylamino)cyclohexylamino)-2-oxoethyl)pyrimidine-4-carboxamide |
| 1k | 2-tert-butyl-N-(2-(4-(tert-butylamino)cyclohexylamino)-2-oxoethyl)pyrimidine-4-carboxamide |
| 1l | 3-tert-butyl-4-hydroxy-N-(2-((1s,4s)-4-(isopropyl(methyl)amino)cyclohexylamino)-2-oxoethyl)benzamide |
| 1m | N-(2-((1s,4s)-4-(isopropyl(methyl)amino)cyclohexylamino)-2-oxoethyl)-4-methoxy-3-(trifluoromethyl)benzamide |
| 1n | 3-tert-butoxy-N-(2-((1s,4s)-4-(isopropyl(methyl)amino)cyclohexylamino)-2-oxoethyl)benzamide |
| 1o | 3-tert-butyl-N-(2-(4-(tert-butylamino)cyclohexylamino)-2-oxoethyl)-4-hydroxybenzamide |
| 1p | 5-tert-butyl-N-(2-(4-(tert-butylamino)cyclohexylamino)-2-oxoethyl)-2-methylfuran-3-carboxamide |
| 1q | N-(2-(4-(tert-butylamino)cyclohexylamino)-2-oxoethyl)-4-adamantan-1-yl-1-methyl-1H-pyrrole-2-carboxamide |
| 1r | N-(2-(4-(tert-butylamino)cyclohexylamino)-2-oxoethyl)-4-adamantan-1-yl-1H-pyrrole-2-carboxamide |
| 1s | 1-(2-((2-(4-(tert-butylamino)cyclohexylamino)-2-oxoethyl)carbamoyl)-4-(trifluoromethyl)phenyl)-3-isopropylurea |
| 1t | N-(4-(tert-butylamino)cyclohexyl)-2-(2,6-dichloro-quinazolin-4-ylamino)-acetamide |
| 1u | N-(4-tert-butylamino-cyclohexyl)-2-(6-chloro-2-methylamino-quinazolin-4-ylamino)-acetamide |
| 1v | N-(4-tert-butylamino-cyclohexyl)-2-(6-chloro-2-dimethylamino-quinazolin-4-ylamino)-acetamide |
| 1w | N-(4-(tert-butylamino)cyclohexyl)-2-(6-iodoquinazolin-4-ylamino)acetamide |
| 1x | N-(4-tert-butylamino-cyclohexyl)-2-(6-trifluoromethyl-quinazolin-4-ylamino)-acetamide |
| 1y | N-(4-tert-butyl(methyl)amino-cyclohexyl)-2-(6-trifluoromethyl-quinazolin-4-ylamino)-acetamide |
| 1z | N-(4-(tert-Butylamino)cyclohexyl)-2-(6-phenylquinazolin-4-ylamino)acetamide |
| 1aa | N-(4-(tert-Butylamino)cyclohexyl)-2-(6-(4-tert-butylphenyl)quinazolin-4-ylamino)acetamide |
| 1ab | N-(4-(tert-butylamino)cyclohexyl)-2-(6-(3,5-dimethylisoxazol-4-yl)quinazolin-4-ylamino)acetamide |
| 1ac | N-(4-(tert-butylamino)cyclohexyl)-2-(6-(3-isopropylphenyl)quinazolin-4-ylamino)acetamide |
| 1ad | N-(4-(tert-butylamino)cyclohexyl)-2-(6-(4-isopropylphenyl)quinazolin-4-ylamino)acetamide |
| 1ae | N-(4-(tert-butylamino)cyclohexyl)-2-(6-(2-methoxyphenyl)quinazolin-4-ylamino)acetamide |
| 1af | N-(4-(tert-butylamino)cyclohexyl)-2-(6-(3-methoxyphenyl)quinazolin-4-ylamino)acetamide |
| 1ag | N-(4-(tert-butylamino)cyclohexyl)-2-(6-(4-methoxyphenyl)quinazolin-4-ylamino)acetamide |
| 1ah | N-(4-(tert-butylamino)cyclohexyl)-2-(6-(4-fluorophenyl)quinazolin-4-ylamino)acetamide |
| 1ai | 2-(6-(3-tert-butyl-5-methylphenyl)quinazoline-4-ylamino)-N-(4-(tert-butylamino)cyclohexyl)acetamide |
| 1aj | N-(4-(tert-butylamino)cyclohexyl)-2-(6-(4-(dimethylamino)phenyl)quinazolin-4-ylamino)acetamide |
| 1ak | N-4-tert-Butylamino-cyclohexyl)-2-[6-(2-fluoro-phenyl)-quinazolin-4-ylamino]-acetamide |
| 1al | N-(4-tert-Butylamino-cyclohexyl)-2-[6-(3-fluoro-phenyl)-quinazolin-4-ylamino]-acetamide |
| 1am | N-(4-(tert-butylamino)cyclohexyl)-2-(6-(3-(trifluoromethyl)phenyl)quinazolin-4-ylamino)acetamide |
| 1an | N-(4-(tert-butylamino)cyclohexyl)-2-(6-(2-(trifluoromethyl)phenyl)quinazolin-4-ylamino)acetamide |
| 1ao | N-(4-(tert-butylamino)cyclohexyl)-2-(6-(4-(trifluoromethyl)phenyl)quinazolin-4-ylamino)acetamide |
| 1ap | N-(4-(tert-butylamino)cyclohexyl)-2-(6-(4-cyanophenyl)quinazolin-4-ylamino)acetamide |
| 1aq | N-(4-(tert-butylamino)cyclohexyl)-2-(6-(3-cyanophenyl)quinazolin-4-ylamino)acetamide |
| 1ar | N-(4-(tert-butylamino)cyclohexyl)-2-(6-(2-cyanophenyl)quinazolin-4-ylamino)acetamide |
| 1as | N-(4-tert-butylamino-cyclohexyl)-2-(6-tert-butyl-pyrimido[5,4-d]pyrimidin-4-ylamino)-acetamide |
| 1at | 3-tert-butyl-N-(2-(4-(tert-butylamino)cyclohexylamino)-2-oxoethyl)benzamide |
| 1au | 3-bromo-5-tert-butyl-N-(2-(4-(tert-butylamino)cyclohexylamino)-2-oxoethyl)benzamide |
| 1av | 5-adamantan-1-yl-2-methyl-2H-pyrazole-3-carboxylic acid[(4-tert-butylamino-cyclohexylcarbamoyl)-methyl]-amide |
| 1aw | 5-adamantan-1-yl-1-methyl-1H-pyrazole-3-carboxylic acid[(4-tert-butylamino-cyclohexylcarbamoyl)-methyl]-amide |
| 1ax | 5-adamantan-1-yl-2H-pyrazole-3-carboxylic acid [(4-tert-butylamino-cyclohexylcarbamoyl)-methyl]-amide |
| 1ay | 6-bromo-N-(2-(4-(tert-butylamino)cyclohexylamino)-2-oxoethyl)picolinamide |
| 1az | N-(2-((1s,4s)-4-(tert-butylamino)cyclohexylamino)-2-oxoethyl)-6-(2-methoxyphenyl)picolinamide |
| 1ba | N-(2-((1r,4r)-4-(tert-butylamino)cyclohexylamino)-2-oxoethyl)-6-(2-methoxyphenyl)picolinamide |
| 1bb | N-(2-((1s,4s)-4-(tert-butylamino)cyclohexylamino)-2-oxoethyl)-6-(3-cyanophenyl)picolinamide |
| 1bc | N-(2-((1r,4r)-4-(tert-butylamino)cyclohexylamino)-2-oxoethyl)-6-(3-cyanophenyl)picolinamide |
| 1bd | 3-(6-((2-(4-(tert-butylamino)cyclohexylamino)-2-oxoethyl)carbamoyl)pyridin-2-yl)benzoic acid |
| 1be | 4-(6-((2-(4-(tert-butylamino)cyclohexylamino)-2-oxoethyl)carbamoyl)pyridin-2-yl)benzoic acid |

TABLE 1-B-continued

The chemical names of the specific examples illustrated in Table 1-A are tabulated below.

| Example | Name |
|---|---|
| 1bf | 6-tert-butyl-N-(2-((1s,4s)-4-(tert-butylamino)cyclohexylamino)-2-oxoethyl)picolinamide |
| 1bg | 3-tert-butyl-N-(2-((1s,4s)-4-(tert-butylamino)cyclohexylamino)-2-oxoethyl)-4-methoxybenzamide |
| 1bh | N-(4-(tert-butylamino)cyclohexyl)-2-(6-chloro-2-propylquinazolin-4-ylamino)acetamide |
| 1bi | 2-(2-butyl-6-(trifluoromethyl)quinazolin-4-ylamino)-N-(4-(tert-butylamino)cyclohexyl)acetamide |
| 1bj | N-(4-(tert-butylamino)cyclohexyl)-2-(6-(2-methoxyphenyl)-2-propylquinazolin-4-ylamino)acetamide |
| 1bk | N-(4-(tert-butylamino)cyclohexyl)-2-(6-(pyridin-2-yl)quinazolin-4-ylamino)acetamide |
| 1bl | N-(2-oxo-2-(cis-4-(cis- and trans-4-phenylcyclohexylamino)cyclohexylamino)ethyl)-3-(trifluoromethyl)benzamide |
| 1bm | N-(2-oxo-2-(cis-4-(methyl(cis- and trans-4-phenylcyclohexyl)amino)cyclohexylamino)ethyl)-3-(trifluoromethyl)benzamide |
| 1bn | N-(2-oxo-2-(cis-4-(4-phenylcyclohex-3-enylamino)cyclohexylamino)ethyl)-3-(trifluoromethyl)benzamide |
| 1bo | N-(2-(cis-4-(cis- and trans-4-hydroxy-4-(pyridin-2-yl)cyclohexylamino)cyclohexylamino)-2-oxoethyl)-3-(trifluoromethyl)benzamide |
| 1bp | N-(2-((1s,4s)-4-(benzyl(tert-butyl)amino)cyclohexylamino)-2-oxoethyl)-5-tert-butyl-2-methylfuran-3-carboxamide |
| 1bq | N-(2-((1s,4s)-4-((isopropyl(methyl)amino)methyl)cyclohexylamino)-2-oxoethyl)-3-(trifluoromethyl)benzamide |

Examples 2a-2am

Examples 2a and 2b

Synthesis of N-(2-((1S,2R,4R)-4-(isopropyl(methyl)amino)-2-propylcyclohexylamino)-2-oxoethyl)-3-(trifluoromethyl)benzamide and N-(2-((1S,2R,4S)-4-(isopropyl(methyl)amino)-2-propylcyclohexylamino)-2-oxoethyl)-3-(trifluoromethyl)benzamide Example 2a, Step 1: A solution of (7-Oxo-6-oxa-bicyclo[3.2.1]oct-2-yl)-carbamic acid benzyl ester (2.26 g, 8.2 mmol) in toluene (80 mL) was cooled to −78° C. and treated dropwise with DIBAL-H (11 mL of a 1.0 M toluene solution). The reaction mixture was stirred for 2 h at −78° C. and quenched with 50 mL of 1 N HCl. The mixture was allowed to warm to RT and then extracted with EtOAc (1×). The organic phase was washed with half-saturated brine. The combined aqueoues phases were back extracted with EtOAc (1×). The organic extracts were combined, washed with brine, dried (MgSO$_4$), filtered, and concentrated in vacuo to afford a colorless oil. This material was dissolved in THF (100 mL). The resultant solution was cooled to 0° C. and charged successively with ethyltriphenylphosphonium iodide (5.3 g, 12.3 mmol) and KHMDS (49 mL of a 0.5 M solution in toluene). The ice bath was removed and the reaction was stirred for 4 h at RT before being quenched with the addition of 1 N HCl (50 mL). The biphasic mixture was partitioned between 1 N HCl (50 mL) and EtOAc (50 mL). The aqueous phase was extracted with EtOAc (2×). The organic extracts were combined, washed with brine, dried (MgSO$_4$), filtered, and concentrated in vacuo. Purification of the residue via flash chromatography afforded the desired [(1S,2R,4R)-(4-hydroxy-2-propenyl-cyclohexyl)]-carbamic acid benzyl ester as a colorless oil (0.56 g). MS found: (M+H)$^+$=312.26.

Example 2a, Step 2: A solution of [(1S,2R,4R)-(4-hydroxy-2-propenyl-cyclohexyl)]-carbamic acid benzyl ester as a colorless oil (0.56 g, 1.9 mmol) in CH$_2$Cl$_2$ (20 mL) was charged with pyridine (0.8 mL, 9.5 mmol) and Dess-Martin Periodinane (0.9 g, 2.1 mmol). The reaction was stirred at RT for 12 h and concentrated in vacuo. Purification of the residue via flash chromatography afforded the desired [(1S,2R)-(4-oxo-2-propenyl-cyclohexyl)]-carbamic acid benzyl ester (0.37 g) as a 3:1 mixture of Z and E diastereomers. This material was dissolved in titanium tetraisopropoxide (2 mL) and N-methylisopropylamine (3 mL) with agitation. The resultant solution was stirred for 1 h at RT and then charged with MeOH (6 mL) and sodium borohydride (100 mg; added slowly—vigorous gas evolution was observed). The reaction was stirred for 1.5 h and then quenched with 0.2 N NaOH. The resultant mixture was diluted with CH$_2$Cl$_2$ and stirred vigorously before being filtered through Celite. The phases were separated and the organic phase was washed with brine, dried (MgSO$_4$), filtered, and concentrated in vacuo to give the desired [(1S,2R,4R)-4-(isopropyl-methyl-amino)-2-propenyl-cyclohexyl]-carbamic acid benzyl ester (295 mg, mixture of olefin diastereomers, some 4S diastereomer present) as a light yellow oil. MS found: (M+H)$^+$=345.31.

Example 2a, Step 3: The compound [(1S,2R,4R/S)-4-(isopropyl-methyl-amino)-2-propenyl-cyclohexyl]-carbamic acid benzyl ester (295 mg, 0.855 mmol) was dissolved in MeOH (10 mL). The resultant solution was charged with 5% Pd/C, Degussa style (300 mg), stirred under H$_2$ (1 atm) for 12 h at RT, filtered, and concentrated in vacuo. The residue was dissolved in CH$_2$Cl$_2$ (7 mL) and the resultant solution was charged with N,N-diethylisopropylamine (0.455 mL, 2.6 mmol) amd 4-dimethylaminopyridine (20 mg, 0.17 mmol). This solution was divided into equal portions (assumed 0.122 mmol) and used in the synthesis of Examples 2a-2n (See Table 2-A).

Example 2a, Step 4: A dry sample of (3-trifluoromethyl-benzoylamino)-acetic acid (37 mg, 0.15 mmol) was dissolved in 1.1 mL of the amine/DIEA/DMAP solution from Step 3 above. The resultant solution was charged with BOP (0.3 mL of a 0.5 M solution in DMF) and stirred for 12 h at RT. The reaction was partitioned between EtOAc and sat. NaHCO$_3$, and the aqueous phase was back extracted with EtOAc (1×). The organic phases were combined, washed with brine, dried (Na$_2$SO$_4$), filtered, and concentrated in vacuo. The residue was purified by reverse phase-HPLC to afford the TFA salt of N-(2-((1S,2R,4R)-4-(isopropyl(methyl)amino)-2-propylcyclohexylamino)-2-oxoethyl)-3-(trifluoromethyl)benzamide as a white powder (16 mg) after lyophilization. MS found: (M+H)$^+$=442. A sample of the diastereomer of this compound, N-(2-((1S,2R,4S)-4-(isopropyl(methyl)amino)-2-propylcyclohexylamino)-2-oxoethyl)-3-(trifluoromethyl)benzamide, was also isolated from this same purification. MS found: (M+H)$^+$=442.

Examples 2o and 2p

Synthesis of N-(2-((2-oxo-2-((1S,2R,4R)-2-propyl-4-(pyrrolidin-1-yl)cyclohexylamino)ethyl)carbamoyl)-4-(trifluoromethyl)phenyl)morpholine-4-carboxamide and N-(2-((2-((1S,2R,4R)-4-amino-2-propylcyclohexylamino)-2-oxoethyl)carbamoyl)-4-(trifluoromethyl)phenyl)morpholine-4-carboxamide Examples 2o and 2p, Step 1: To a cooled (0° C.) solution of (1R,2S,5R)-2-benzyloxycarbonylamino-7-oxo-6-aza-bicyclo[3.2.1]octane-6-carboxylic acid tert-butyl ester (4.6 g, 12.3 mmol) in $CH_2Cl_2$ (100 mL) was added DIBAL-H (37 mL of a 1.0 M solution in THF). The mixture was stirred for 105 min at 0° C. The reaction was quenched with 1N HCl and extracted with EtOAc (2×). The organic extracts were combined, washed with brine, dried ($Na_2SO_4$), filtered, and concentrated in vacuo to afford the hemi-aminal as a mixture of diastereomers. MS found: $(M-H_2O+H)^+=359.2$. This material was dissolved in THF (20 mL) and added by cannula (6 mL THF rinse) to a pre-mixed (15 min), pre-cooled (0° C.) solution of ethyltriphenylphosphonium iodide (6.4 g, 14.8 mmol) and KHMDS (31 mL of a 0.5 M solution in toluene). The reaction was stirred for 25 min at 0° C. before being quenched with the addition of sat. $NH_4Cl$. The biphasic mixture was extracted with EtOAc (2×). The organic extracts were combined, washed with brine, dried ($Na_2SO_4$), filtered, and concentrated in vacuo. Purification of the residue via flash chromatography afforded the desired [(1R,3R,4S)-(4-benzyloxycarbonyl-amino-3-propenyl-cyclohexyl)-carbamic acid tert-butyl ester as a colorless oil (3.44 g, 72% yield). MS found: $(M+H)^+=389.3$.

Examples 2o and 2p, Step 2: A solution of [(1R,3R,4S)-(4-benzyloxycarbonyl-amino-3-propenyl-cyclohexyl)-carbamic acid tert-butyl ester (3.44 g) in MeOH (50 mL) was charged with 5% Pd/C, Degussa (1 g). The reaction flask was evacuated and then back-filled with hydrogen; this was repeated three more times. The reaction was stirred under 1 atm of $H_2$ for 4 h and then filtered and concentrated in vacuo to afford (1R,3R,4S)-(4-amino-3-propyl-cyclohexyl)-carbamic acid tert-butyl ester (quantitative). MS found: $(M+H)^+=257.3$.

Examples 2o and 2p, Step 3: A sample of (1R,3R,4S)-(4-amino-3-propyl-cyclohexyl)-carbamic acid tert-butyl ester (212 mg, 0.83 mmol) was dissolved in DMF (10 mL) and the resultant solution was charged with {2-[(morpholine-1-carbonyl)-amino]-5-trifluoromethyl-benzoylamino}-acetic acid (341 mg, 0.91 mmol), N,N-diethylisopropylamine (0.73 mL, 4.2 mmol), and HATU (380 mg, 1.0 mmol). The reaction was stirred for 16 h at RT and then quenched with sat. $NH_4Cl$ and extracted with EtOAc. The organic extracts were combined, washed with brine, dried ($Na_2SO_4$), filtered, and concentrated in vacuo. Purification by flash chromatography afforded (1R,3R,4S)-[4-(2-{2-[(morpholine-4-carbonyl)-amino]-5-trifluoromethyl-benzoylamino}-acetylamino)-3-propyl-cyclohexyl]-carbamic acid tert-butyl ester (335 mg, 72% yield). MS found: $(M+H)^+=558.2$.

Examples 2o and 2p, Step 4: A sample of (1R,3R,4S)-[4-(2-{2-[(morpholine-4-carbonyl)-amino]-5-trifluoromethyl-benzoylamino}-acetylamino)-3-propyl-cyclohexyl]-carbamic acid tert-butyl ester (200 mg) was dissolved in 1:2 TFA:dichloromethane and stirred for 30 min at RT before being concentrated in vacuo. The residue was redissolved in 1:2 TFA:dichloromethane and stirred for 30 min at RT before being concentrated in vacuo. The residue was dissolved in 1 N HCl and washed with $Et_2O$; the aqueous phase was then basified (sat. $NaHCO_3$ & a small amount of 1 N NaOH) and extracted (EtOAc, 2×). The organic extracts were combined, washed with brine, dried ($Na_2SO_4$), filtered, and concentrated in vacuo to afford morpholine-4-carboxylic acid (2-{[(1S,2R,4R)-(4-amino-2-propyl-cyclohexylcarbamoyl)-methyl]-carbamoyl}-4-trifluoromethyl-phenyl)-amide as the free base (90 mg). MS found: $(M+H)^+=514.2$.

Examples 2o and 2p, Step 5: A sample of morpholine-4-carboxylic acid (2-{[(1S,2R,4R)-(4-amino-2-propyl-cyclohexylcarbamoyl)-methyl]-carbamoyl}-4-trifluoromethyl-phenyl)-amide as the free base (59 mg, 0.11 mmol) was dissolved in DMF (4 mL) and the resultant solution was charged with potassium carbonate (46 mg, 0.33 mmol) and 1,4-dibromobutane (0.017 mL, 0.14 mmol). The reaction was stirred for 16 h at RT, quenched with water, and extracted with EtOAc (2×). The organic extracts were combined, washed with brine, dried ($Na_2SO_4$), filtered, and concentrated in vacuo. The residue was purified by reverse phase HPLC to afford the TFA salt of N-(2-((2-oxo-2-((1S, 2R,4R)-2-propyl-4-(pyrrolidin-1-yl)cyclohexylamino)ethyl)carbamoyl)-4-(trifluoromethyl)phenyl)morpholine-4-carboxamide (9.9 mg) as a white powder after lyophilization. MS found: $(M+H)^+=568.3$. This purification also provided N-(2-((2-((1S,2R,4R)-4-amino-2-propylcyclohexylamino)-2-oxoethyl)carbamoyl)-4-(trifluoromethyl)phenyl)morpholine-4-carboxamide as a white powder (21.4 mg) after lyopholization. MS found: $(M+H)^+=514.2$.

Example 2q

Synthesis of N-(2-((2-((1S,2R,4R)-4-(ethyl(isopropyl)amino)-2-propylcyclohexylamino)-2-oxoethyl)carbamoyl)-4-(trifluoromethyl)phenyl)morpholine-4-carboxamide Example 2g, Step 1: A sample of morpholine-4-carboxylic acid (2-{[(1S,2R,4R)-(4-amino-2-propyl-cyclohexylcarbamoyl)-methyl]-carbamoyl}-4-trifluoromethyl-phenyl)-amide as the free base (31 mg, see Examples 2o and 2p), was dissolved in MeOH (4 mL) and the resultant solution was charged with acetone (0.5 mL). The reaction was stirred for 5 min at RT, charged with $NaCNBH_3$ (~50 mg), stirred for 12 h at RT, charged with acetaldehyde (0.05 mL), stirred for 4 h at RT, and then quenched with sat. $NaHCO_3$. The mixture was extracted with EtOAc (2×). The organic extracts were combined, washed with brine, dried ($Na_2SO_4$), filtered, and concentrated in vacuo. The residue was purified by reverse phase HPLC; lyopholization afforded the TFA salt of the title compound (17.8 mg) as a white powder. MS found: $(M+H)^+=584.29$.

Example 2r

Synthesis of N-(2-((1S,2R,4R)-2-isopentyl-4-(isopropyl(methyl)amino)cyclohexylamino)-2-oxoethyl)-3-(trifluoromethyl)benzamide Example 2r, Step 1: To a cooled (−55° C.) solution of (1R, 2S,5R)-2-benzyloxycarbonylamino-7-oxo-6-aza-bicyclo [3.2.1]octane-6-carboxylic acid tert-butyl ester (3.13 g, 8.4 mmol) in $CH_2Cl_2$ (84 mL) was added DIBAL-H (21 mL of a 1.0 M solution in THF). The mixture was stirred for 3 h, over which time the bath temperature warmed 0° C. The reaction was quenched with water and methanol. The suspension was treated with 1N HCl and extracted with EtOAc (2×). The organic extracts were combined, washed successively with 1N HCl, water, and brine, then dried ($Na_2SO_4$), filtered, and concentrated in vacuo to afford tert-butyl (1R, 2S,5R,7R/S)-2-(benzyloxycarbonyl)-7-hydroxy-6-aza-bicyclo[3.2.1]octane-6-carboxylate as a mixture of diastereomers at C7. MS found: $(M-H_2O+H)^+=359.2$. A portion of this material (1.3 g, 3.3 mmol) was dissolved in THF (8 mL). The resultant solution was cannulated into a pre-cooled (0° C.) solution of isobutylidene-triphenyl-λ5-phosphane (formed from 1.7 g of isobutyl triphenyl phosphonium iodide and 8 mL of 0.5 M KHMDS/THF in 8 mL of THF at 0° C.). The reaction was stirred for 3.5 h at RT before being quenched with the addition of sat. $NaHCO_3$. The biphasic mixture was extracted with EtOAc (2×). The organic extracts were combined, washed with brine, dried (Na$_2$SO$_4$), filtered, and concentrated in vacuo. Purification of the residue via flash chromatography afforded the desired [(1S,2R,4R)-[4-tert-butoxycarbonylamino-2-(3-methyl-but-1-enyl)-cyclohexyl]-carbamic acid benzyl ester as a colorless oil (0.88 g). MS found: (M+H)$^+$=417.3.

Example 2r, Step 2: A sample of [(1S,2R,4R)-[4-tert-butoxycarbonylamino-2-(3-methyl-but-1-enyl)-cyclohexyl]-carbamic acid benzyl ester (0.24 g, 0.57 mmol) was dissolved in methanol (8 mL) and the resultant solution was charged with 5% Pd/C, Degussa (47 mg). The flask was evacuated and back-filled with hydrogen; this was repeated three times. The reaction was stirred under 1 atm of hydrogen for 14 h before being filtered and concentrated in vacuo to afford (1R,3R,4S)-[4-amino-3-(3-methyl-butyl)-cyclohexyl]-carbamic acid tert-butyl ester. MS found: (M+H)$^+$=285.3.

Example 2r, Step 3: A sample of [(1R,3R,4S)-4-amino-3-(3-methyl-butyl)-cyclohexyl]-carbamic acid tert-butyl ester (50 mg, 0.18 mmol) was dissolved in 1:1 CH$_2$Cl$_2$/DMF (2 mL). The resultant solution was charged successively with N,N-diethylisopropylamine (0.16 mL, 0.9 mmol), (3-trifluoromethyl-benzoylamino)-acetic acid (47 mg, 0.19 mmol, prepared as described in WO PCT 0250019), and BOP (116 mg, 0.26 mmol). The reaction was stirred for 12 h at RT and then partitioned between EtOAc and sat. NaHCO$_3$; the aqueous phase was back extracted with EtOAc (1×). The organic phases were combined, washed with brine, dried (Na$_2$SO$_4$), filtered, and concentrated in vacuo. Purification by silica gel chromatography afforded {(1R, 3R,4S)-3-(3-methyl-butyl)-4-[2-(3-trifluoromethyl-benzoylamino)-acetylamino]-cyclohexyl}-carbamic acid tert-butyl ester (33 mg). MS found: (M+H)$^+$=514.3.

Example 2r, Step 4: A solution of {(1R,3R,4S)-3-(3-methyl-butyl)-4-[2-(3-trifluoromethyl-benzoylamino)-acetylamino]-cyclohexyl}-carbamic acid tert-butyl ester in CH$_2$Cl$_2$ (1.5 mL) was treated with trifluoroacetic acid (0.5 mL) and stirred for 2 h at RT. The reaction was concentrated in vacuo, and the resultant residue was partitioned between EtOAc and sat. NaHCO$_3$. The organic phase was washed with brine, dried (Na$_2$SO$_4$), filtered, and concentrated in vacuo to afford the amine. MS found: (M+H)$^+$=414.2. The amine was dissolved in MeOH (3 mL) and charged with acetone (~0.5 mL); the mixture was stirred for 5 min before being charged with NaCNBH$_3$ (~20 mg). The reaction was stirred for 4 h at RT and then charged with formaldehyde (~0.5 mL of a 30% aq. Solution). The mixture was stirred for 1.5 h, quenched with sat. NaHCO$_3$, and extracted with EtOAc (2×). The organic extracts were combined, washed with brine, dried (Na$_2$SO$_4$), filtered, and concentrated in vacuo. The residue was purified by reverse phase HPLC to afford the title compound as a white powder after lyopholization. MS found: (M+H)$^+$=470.3.

Examples 2y, 2z, & 2aa

General Note on Reductive Amination

As indicated in Table 2-A, the standard modifications were made to the procedures outlined in Example 2r. However, in each case, the final reductive amination (Step 4) failed to proceed as expected, and instead provided the dimethyl amine (Examples 2y and 2z) or the isopropylamine (Example 2aa).

Example 2ab

Synthesis of N-(2-((1S,2R,4R)-2-butyl-4-(tert-butylamino)cyclohexylamino)-2-oxoethyl)-3-(trifluoromethyl)benzamide Example 2ab, Step 1: A solution of DMSO (18.6 g, 0.22 mol) in 100 ml of methylene chloride was cooled to −78° C. (dry ice-acetone bath) and treated drop-wise with oxalyl chloride (16.2 g, 0.13 mol). After the addition was complete and solution was stirred for 30 minutes and then treated drop-wise with a solution of ((7S,8S)-7-Hydroxymethyl-1,4-dioxa-spiro[4.5]dec-8-yl)-carbamic acid benzyl ester (14.26g, 0.044 mol) in 20 ml of methylene chloride. After the addition was complete and solution was stirred for 40 minutes and then treated with triethylamine (26 g, 0.26 mol) and stirred for 30 minutes before removing the cooling bath and stirring at room temperature for 1 hour. The mixture was quench with 100 mL of saturated sodium bicarbonate and the organic layer was separated and washed successively with water and brine, and then dried over Na$_2$SO4. The drying agent is filtered and the solvent removed on a rotary evaporator to give 15 g of crude aldehyde which was used without further purification.

Example 2ab, Step 2: n-Propyltriphenylphosphonium bromide (20.42 g, 1.053 mol) was suspended in THF and cooled in an ice bath at 0° C. A 0.5 M solution of KHMDS in toluene (106 mL, 0.053 mol) was added drop wise via an addition funnel. The resulting red solution was stirred for an additional 10 min and then treated with a solution of the aldehyde intermediate (15 g, see Step 1) in THF. The mixture was stirred at room temperature for 3 hours. The solvents were removed on a rotary evaporator and the residue chromatograhed on silica gel to give 7.7 g of benzyl ((7S,8S)-7-(but-1-enyl)-1,4-dioxa-spiro[4.5]dec-8-yl)-carbamate.

Example 2ab, Step 3: A solution of ((7S,8S)-7-(but-1-enyl)-1,4-dioxa-spiro[4.5]dec-8-yl)-carbamate (7.7 g, 0.0221 mol) in 80 mL of MeOH was treated with 1.5 g of 10% Pd/C and hydrogenated overnight at 55 psi. The mixture was filtered through Celite and concentrated on a rotary evaporator to give 4.3 g of (7R,8S)-7-(butyl)-8-(amino)-1,4-dioxa-spiro[4.5]decane. This was used without further purification.

Example 2ab, Step 4: A solution of crude (7R,8S)-7-(butyl)-8-(amino)-1,4-dioxa-spiro[4.5]decane (4.2 g, 0.02 mol) in 100 mL of CH$_2$Cl$_2$ was treated with an aqueous solution of K$_2$CO$_3$ and cooled in a ice bath. The mixture is stirred vigorously while benzyl chloroformate (3.42 g, 0.02 mol) is added slowly. After the addition is complete the mixture is stirred an additional 30 min. The organic layer is separated and washed with water, brine and concentrated. The residue was chromatographed on silica gel to give 3 g of benzyl ((7S,8S)-7-(butyl)-1,4-dioxa-spiro[4.5]dec-8-yl)-carbamate.

Example 2ab, Step 5: A solution of benzyl ((7S,8S)-7-(butyl)-1,4-dioxa-spiro[4.5]dec-8-yl)-carbamate (3 g, 0.008 mol) in acetone (30 mL) is treated with 1 N HCl (30 mL) and heated to reflux for 2 hrs. The mixture is concentrated on a rotary evaporator and the residue neutralized with 1 N NaOH and extracted into CH$_2$Cl$_2$. The organic extracts were washed with water, brine, and the solvent remove under vacuum to give 2.8 g of the benzyl (1S,2R)-2-butyl-4-oxocyclohexylcarbamate. This is used without further purification.

Example 2ab, Step 6: Benzyl(1S,2R)-2-butyl-4-oxocyclohexylcarbamate (2.62 g, 8 mmol) was dissolved in titanium (IV) isopropoxide (7 g, 25 mmol) and treated with t-butylamine (1.7 g, 23 mmol). The resulting solution was stirred at room temperature for 12 hours. The solution was diluted with 20 ml of methanol and treated very slowly with NaBH₄ caplets (0.7 g, 18 mmol) over a period of 2 hours. [Caution: vigorous foaming occurs.] The solution was quenched with a 0.2 N NaOH and the resulting slurry was diluted with 1 L of CH₂Cl₂ and shaken thoroughly in a separatory funnel. The resulting emulsion is filtered through Celite and the solid cake washed two times with CH₂Cl₂. The combined filtrates were concentrated on a rotary evaporator to give 10 grams of yellow oil which was chromatographed on silica gel (elution with 0.8:7.2:92 NH₄OH/MeOH/CH₂Cl₂) to give 1.8 g of benzyl (1S,2R,4R/S)-2-butyl-4-(tert-butylamino) cyclohexylcarbamate as an oil. The ester was obtained as a mixture of diastereomers which was used as a mixture in the next step.

Example 2ab, Step 7: A solution of benzyl (1S,2R,4R/S)-2-butyl-4-(tert-butylamino)cyclohexylcarbamate (1.8 g, 0.005 mol), in 80 mL of MeOH was treated with 0.5 g of 10% Pd/C and hydrogenated overnight at 55 psi. The mixture was filtered through Celite and concentrated on a rotary evaporator to give 1.02 g of the amine. A mixture of this amine (1.02 g, 4.5 mmol), N-Cbz Glycine (1.13 g, 5.4 mmol), EDCI (1.04 g, 5.4 mmol), HOBT (0.75 g, 5.4 mmol), and triethylamine (0.55 g, 5.4 mmol) in CH₂Cl₂ was stirred at room temperature overnight. The mixture was washed with 1 N NaOH and the solvent removed on a rotary evaporator and the residue was chromatographed on silica gel (eluting with 2-6% NH₄OH/MeOH/CH₂Cl₂) to separate the diastereomers and provide 0.89 g of benzyl 2-((1S,2R,4R)-2-butyl-4-(tert-butylamino)cyclohexylamino)-2-oxoethylcarbamate as a white solid.

Example 2ab, Step 8: A solution of benzyl 2-((1S,2R,4R)-2-butyl-4-(tert-butylamino)cyclohexylamino)-2-oxoethylcarbamate (890 mg, 0.0021 mol), in 40 mL of MeOH was treated with 0.3 g of 10% Pd/C and hydrogenated overnight at 55 psi. The mixture was filtered through Celite and concentrated on a rotary evaporator to give 490 mg of 2-amino-N-((1S,2R,4R)-2-butyl-4-(tert-butylamino)cyclohexyl)acetamide. This was used without further purification.

Example 2ab, Step 9: A sample of 2-amino-N-((1S,2R,4R)-2-butyl-4-(tert-butylamino)cyclohexyl)acetamide was combined with 3-Trifluoromethylbenzoic acid (1 equivalent), EDCI (1 equivalent), HOBT (1.1 equivalents), and triethylamine (1 equivalent) in 2 mL of CH₂Cl₂ was stirred at room temperature overnight. The reaction mixture was directly chromatographed on silica gel (eluting with 2-8% NH₄OH/MeOH/CH₂Cl₂) to give N-(2-((1S,2R,4R)-2-butyl-4-(tert-butylamino)cyclohexylamino)-2-oxoethyl)-3-(trifluoromethyl)benzamide as a white solid. MS found: (M+H)⁺ =456.47; ¹H NMR (400 MHz, CDCl₃) δ(TMS): 0.83-1.98 (m, 25H), 2.67-2.79 (m, 1H) 4.12-4.28 (m, 3H), 6.80-6.90 (m, 1H), 7.49-7.63 (m, 2H), 7.78-7.84 (m, 1H), 8.00-8.06 (m, 1H), 8.15 (s, 1H).

Example 2ah

Synthesis of N-((1S,2R,4R)-2-butyl-4-(tert-butylamino)cyclohexyl)-2-(6-chloroquinazolin-4-ylamino)acetamide Example 2ah, Step 1: A sample of 2-amino-N-((1S,2R,4R)-2-butyl-4-(tert-butylamino)cyclohexyl)acetamide was combined with 4,6-dichloroquinazoline (1.2 equivalents) and triethylamine (1.2 equivalents) in ethanol. The resultant solution was heated at 100° C. in the microwvae for 1 hr. The reaction mixture was concentrated and the residue chromatographed on silica gel (eluting with 2-8% NH₄OH/MeOH/CH₂Cl₂) to give N-((1S,2R,4R)-2-butyl-4-(tert-butylamino)cyclohexyl)-2-(6-chloroquinazolin-4-ylamino) acetamide. MS found: (M+H)⁺=446.44; ¹H NMR (400 MHz, CDCl₃) δ(TMS): 0.52-1.77 (m, 25H), 2.36-2.48 (m, 1H), 3.92-4.06 (m, 3H), 6.52-6.63 (M, 1H), 7.37-7.55 (m, 3H), 7.70-7.73 (m, 1H), 7.36-7.41 (m, 1H).

Examples 2ak-2am

Synthesis of N-(2-((1S,2R,4R)-4-amino-2-phenethylcyclohexylamino)-2-oxoethyl)-3-(trifluoromethyl) benzamide and its isopropylamino and isopropyl (methyl)amino analogs A sample of tert-butyl (1R,3R,4S)-3-phenethyl-4-(2-(3-(trifluoromethyl)benzamido)acetamido)cyclohexylcarbamate was prepared according to Steps 1-3 of Example 2r, substituting benzyl triphenyl isobutyl triphenyl phosphonium iodide and n-BuLi in Step 1. This carbamate was then carried through the procedure of Example 2r, Step 4; small samples were saved after each of these three steps (TFA, acetone reductive amination, formaldehyde reductive amination) and purified by RP-HPLC to afford Examples 2ak-2am.

Table 2-A

The compounds in the following table were made using the methods exemplified above. See Table 1-A for a complete description of the table headings.

| Ex. | R⁵ | R⁶ | Z | R² | Step Alt. | MS |
|---|---|---|---|---|---|---|
| 2a | i-Pr(Me)N, (R) | Me | NHC=O | 3-CF₃-phenyl | n/a | 442 |

-continued
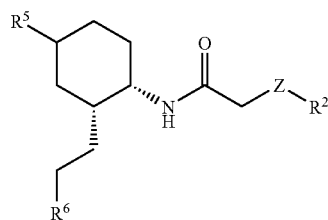
| Ex. | R⁵ | R⁶ | Z | R² | Step Alt. | MS |
|---|---|---|---|---|---|---|
| 2b | i-Pr(Me)N, (S) | Me | NHC=O | 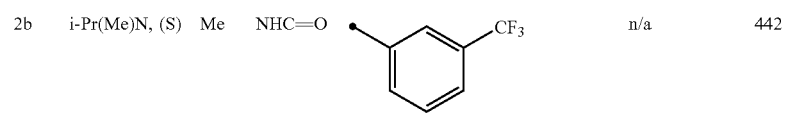 | n/a | 442 |
| 2c | i-Pr(Me)N, (R) | Me | NHC=O | 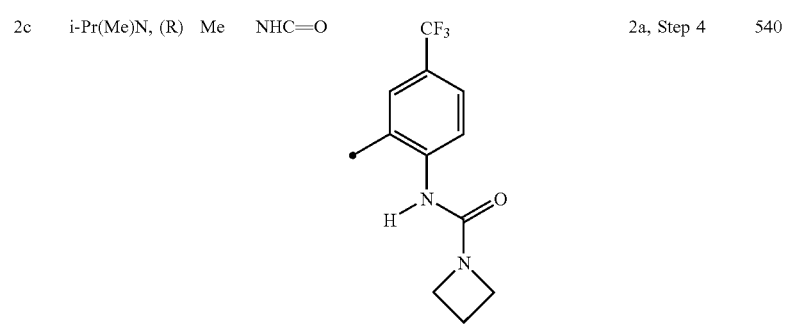 | 2a, Step 4 | 540 |
| 2d | i-Pr(Me)N, (S) | Me | NHC=O | 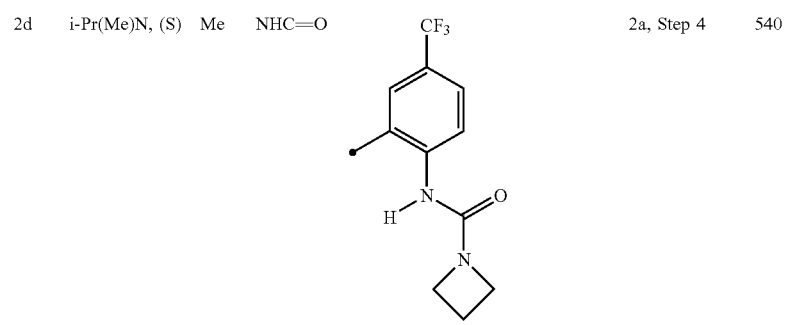 | 2a, Step 4 | 540 |
| 2e | i-Pr(Me)N, (R) | Me | NHC=O | 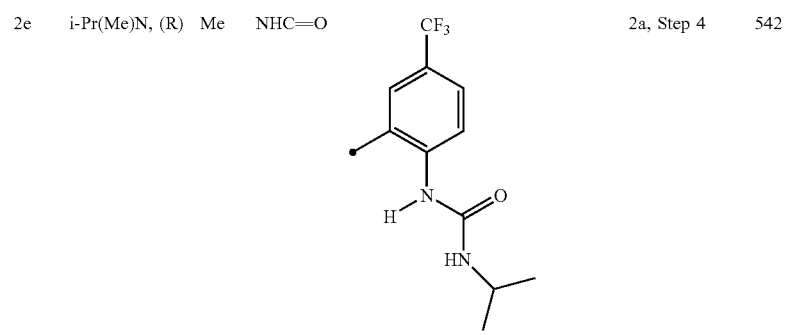 | 2a, Step 4 | 542 |

-continued
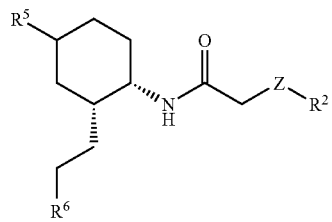
| Ex. | R⁵ | R⁶ | Z | R² | Step Alt. | MS |
|---|---|---|---|---|---|---|
| 2f | i-Pr(Me)N, (S) | Me | NHC=O | 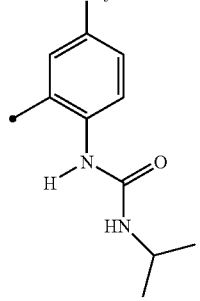 | 2a, Step 4 | 542 |
| 2g | i-Pr(Me)N, (R) | Me | NHC=O | 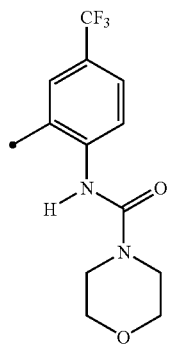 | 2a, Step 4 | 570 |
| 2h | i-Pr(Me)N, (S) | Me | NHC=O | 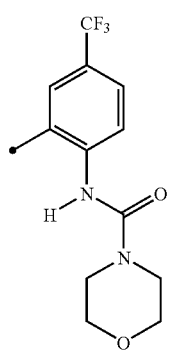 | 2a, Step 4 | 570 |
| 2i | i-Pr(Me)N, (R) | Me | O=CNH | 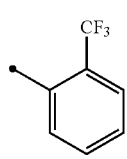 | 2a, Step 4 | 442 |
| 2j | i-Pr(Me)N, (S) | Me | O=CNH | 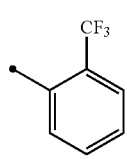 | 2a, Step 4 | 442 |

-continued

| Ex. | R⁵ | R⁶ | Z | R² | Step Alt. | MS |
|---|---|---|---|---|---|---|
| 2k | i-Pr(Me)N, (R) | Me | O=CNH | 3-OMe-5-CF₃-phenyl | 2a, Step 4 | 472 |
| 2l | i-Pr(Me)N, (S) | Me | O=CNH | 3-OMe-5-CF₃-phenyl | 2a, Step 4 | 472 |
| 2m | i-Pr(Me)N, (R) | Me | bond | 7-CF₃-1H-benzimidazol-2-yl | 2a, Step 4 | 439 |
| 2n | i-Pr(Me)N, (S) | Me | bond | 7-CF₃-1H-benzimidazol-2-yl | 2a, Step 4 | 439 |
| 2o | c-C₄H₈N, (R) | Me | NHC=O | 4-CF₃-2-(morpholine-4-carboxamido)phenyl | n/a | 568.3 |
| 2p | H₂N, (R) | Me | NHC=O | 4-CF₃-2-(morpholine-4-carboxamido)phenyl | n/a | 514.2 |

-continued
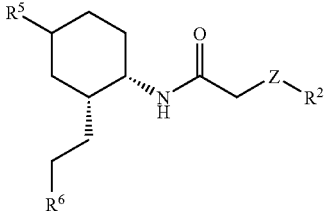
| Ex. | R⁵ | R⁶ | Z | R² | Step Alt. | MS |
|---|---|---|---|---|---|---|
| 2q | i-Pr(Et)N, (R) | Me | NHC=O | 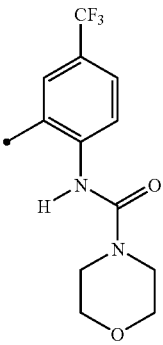 | n/a | 584.3 |
| 2r | i-Pr(Me)N, (R) | i-Pr | NHC=O | 3-CF₃-C₆H₄- | n/a | 470.3 |
| 2s | i-Pr(Me)N, (R) | i-Pr | NHC=O | 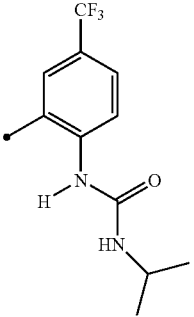 | 2r, Step 3 | 570.4 |
| 2t | i-Pr(Me)N, (R) | i-Pr | NHC=O | 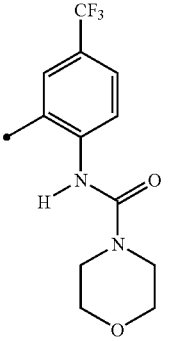 | 2r, Step 3 | 598.3 |
| 2u | i-Pr(Me)N, (R) | i-Bu | NHC=O | 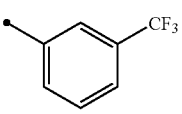 | 2r, Step 3 | 484 |

-continued
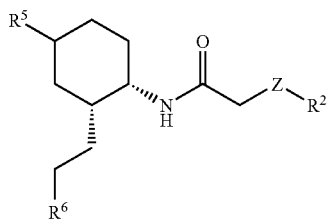
| Ex. | R⁵ | R⁶ | Z | R² | Step Alt. | MS |
|---|---|---|---|---|---|---|
| 2v | i-Pr(Me)N, (R) | i-Bu | NHC=O | 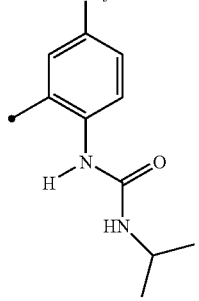 | 2r, Step 3 | 584 |
| 2w | i-Pr(Me)N, (R) | Et | NHC=O | 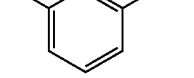 | 2r, Step 1 | 456 |
| 2x | i-Pr(Me)N, (R) | Et | NHC=O | 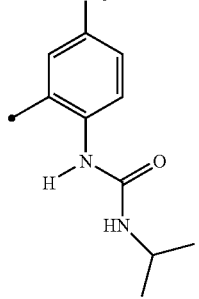 | 2r, Steps 1 & 3 | 556 |
| 2y | Me₂N, (R) See note | H | NHC=O | 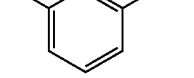 | 2r, Step 1 | 400 |
| 2z | Me₂N, (R) See note | H | NHC=O | 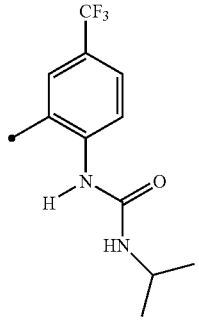 | 2r, Steps 1 & 3 | 500 |

-continued
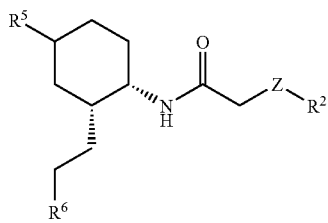
| Ex. | R⁵ | R⁶ | Z | R² | Step Alt. | MS |
|---|---|---|---|---|---|---|
| 2aa | i-Pr(H)N, (R) See note | H | O=CNH | 3-OMe, 5-CF₃-phenyl | 2r, Steps 1 & 3 | 444 |
| 2ab | t-Bu(H)N, (R) | Et | NHC=O | 3-CF₃-phenyl | n/a | 456 |
| 2ac | t-Bu(H)N, (R) | Et | NHC=O | 2-t-Bu-4-OH-phenyl | 2ab, Step 9 | 460 |
| 2ad | t-Bu(H)N, (R) | Et | NHC=O | 5-(4-Cl-phenyl)-furan-2-yl | 2ab, Step 9 | 488 |
| 2ae | t-Bu(H)N, (R) | Et | NHC=O | 5-t-Bu-3-methyl-furan-2-yl | 2ab, Step 9 | 448 |
| 2af | t-Bu(H)N, (R) | Et | NHC=O | 4-adamantyl-pyrrol-2-yl | 2ab, Step 9 | 511 |
| 2ag | t-Bu(H)N, (R) | Et | NHC=O | 3-t-Bu-phenyl | 2ab, Step 9 | 444 |
| 2ah | t-Bu(H)N, (R) | Et | NH | 6-Cl-quinazolin-4-yl | n/a | 446 |

-continued

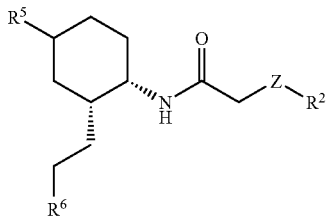

| Ex. | R⁵ | R⁶ | Z | R² | Step Alt. | MS |
|---|---|---|---|---|---|---|
| 2ai | t-Bu(H)N, (R) | Et | NH | 4-position of 6-(trifluoromethyl)quinazoline | 2ah, Step 1 | 480 |
| 2aj | t-Bu(H)N, (R) | Et | NH | 4-position of 2-tert-butylpyrimido[5,4-d]pyrimidine | 2ah, Step 1 | 470 |
| 2ak | H₂N, (R) | Ph | NHC=O | 3-(trifluoromethyl)phenyl | 2r, Steps 1 & 4 | 448 |
| 2al | i-PrHN, (R) | Ph | NHC=O | 3-(trifluoromethyl)phenyl | 2r, Steps 1 & 4 | 490 |
| 2am | i-Pr(Me)N, (R) | Ph | NHC=O | 3-(trifluoromethyl)phenyl | 2r, Steps 1 & 4 | 504 |

TABLE 2-B

The chemical names of the specific examples illustrated in Table 2-A are tabulated below.

| Example | Name |
|---|---|
| 2a | N-(2-((1S,2R,4R)-4-(isopropyl(methyl)amino)-2-propylcyclohexylamino)-2-oxoethyl)-3-(trifluoromethyl)benzamide |
| 2b | N-(2-((1S,2R,4S)-4-(isopropyl(methyl)amino)-2-propylcyclohexylamino)-2-oxoethyl)-3-(trifluoromethyl)benzamide |
| 2c | N-(2-((2-((1S,2R,4R)-4-(isopropyl(methyl)amino)-2-propylcyclohexylamino)-2-oxoethyl)carbamoyl)-4-(trifluoromethyl)phenyl)azetidine-1-carboxamide |
| 2d | N-(2-((2-((1S,2R,4S)-4-(isopropyl(methyl)amino)-2-propylcyclohexylamino)-2-oxoethyl)carbamoyl)-4-(trifluoromethyl)phenyl)azetidine-1-carboxamide |
| 2e | 1-(2-((2-((1S,2R,4R)-4-(isopropyl(methyl)amino)-2-propylcyclohexylamino)-2-oxoethyl)carbamoyl)-4-(trifluoromethyl)phenyl)-3-isopropylurea |
| 2f | 1-(2-((2-((1S,2R,4S)-4-(isopropyl(methyl)amino)-2-propylcyclohexylamino)-2-oxoethyl)carbamoyl)-4-(trifluoromethyl)phenyl)-3-isopropylurea |
| 2g | N-(2-((2-((1S,2R,4R)-4-(isopropyl(methyl)amino)-2-propylcyclohexylamino)-2-oxoethyl)carbamoyl)-4-(trifluoromethyl)phenyl)morpholine-4-carboxamide |
| 2h | N-(2-((2-((1S,2R,4S)-4-(isopropyl(methyl)amino)-2-propylcyclohexylamino)-2-oxoethyl)carbamoyl)-4-(trifluoromethyl)phenyl)morpholine-4-carboxamide |

TABLE 2-B-continued

The chemical names of the specific examples illustrated in Table 2-A are tabulated below.

| Example | Name |
|---|---|
| 2i | N1-((1S,2R,4R)-4-(isopropyl(methyl)amino)-2-propylcyclohexyl)-N3-(2-(trifluoromethyl)phenyl)malonamide |
| 2j | N1-((1S,2R,4S)-4-(isopropyl(methyl)amino)-2-propylcyclohexyl)-N3-(2-(trifluoromethyl)phenyl)malonamide |
| 2k | N1-((1S,2R,4R)-4-(isopropyl(methyl)amino)-2-propylcyclohexyl)-N3-(3-methoxy-5-(trifluoromethyl)phenyl)malonamide |
| 2l | N1-((1S,2R,4S)-4-(isopropyl(methyl)amino)-2-propylcyclohexyl)-N3-(3-methoxy-5-(trifluoromethyl)phenyl)malonamide |
| 2m | N-((1S,2R,4R)-4-(isopropyl(methyl)amino)-2-propylcyclohexyl)-2-(7-(trifluoromethyl)-1H-benzo[d]imidazol-2-yl)acetamide |
| 2n | N-((1S,2R,4S)-4-(isopropyl(methyl)amino)-2-propylcyclohexyl)-2-(7-(trifluoromethyl)-1H-benzo[d]imidazol-2-yl)acetamide |
| 2o | N-(2-((2-oxo-2-((1S,2R,4R)-2-propyl-4-(pyrrolidin-1-yl)cyclohexylamino)ethyl)carbamoyl)-4-(trifluoromethyl)phenyl)morpholine-4-carboxamide |
| 2p | N-(2-((2-(((1S,2R,4R)-4-amino-2-propylcyclohexylamino)-2-oxoethyl)carbamoyl)-4-(trifluoromethyl)phenyl)morpholine-4-carboxamide |
| 2q | N-(2-((2-((1S,2R,4R)-4-(ethyl(isopropyl)amino)-2-propylcyclohexylamino)-2-oxoethyl)carbamoyl)-4-(trifluoromethyl)phenyl)morpholine-4-carboxamide |
| 2r | N-(2-((1S,2R,4R)-2-isopentyl-4-(isopropyl(methyl)amino)cyclohexylamino)-2-oxoethyl)-3-(trifluoromethyl)benzamide |
| 2s | 1-(2-((2-((1S,2R,4R)-2-isopentyl-4-(isopropyl(methyl)amino)cyclohexylamino)-2-oxoethyl)carbamoyl)-4-(trifluoromethyl)phenyl)-3-isopropylurea |
| 2t | N-(2-((2-((1S,2R,4R)-2-isopentyl-4-(isopropyl(methyl)amino)cyclohexylamino)-2-oxoethyl)carbamoyl)-4-(trifluoromethyl)phenyl)morpholine-4-carboxamide |
| 2u | N-(2-((1S,2R,4R)-4-(isopropyl(methyl)amino)-2-(4-methylpentyl)cyclohexylamino)-2-oxoethyl)-3-(trifluoromethyl)benzamide |
| 2v | 1-(2-((2-((1S,2R,4R)-4-(isopropyl(methyl)amino)-2-(4-methylpentyl)cyclohexylamino)-2-oxoethyl)carbamoyl)-4-(trifluoromethyl)phenyl)-3-isopropylurea |
| 2w | N-(2-((1S,2R,4R)-2-butyl-4-(isopropyl(methyl)amino)cyclohexylamino)-2-oxoethyl)-3-(trifluoromethyl)benzamide |
| 2x | 1-(2-((2-((1S,2R,4R)-2-butyl-4-(isopropyl(methyl)amino)cyclohexylamino)-2-oxoethyl)carbamoyl)-4-(trifluoromethyl)phenyl)-3-isopropylurea |
| 2y | N-(2-((1S,2R,4R)-4-(dimethylamino)-2-ethylcyclohexylamino)-2-oxoethyl)-3-(trifluoromethyl)benzamide |
| 2z | 1-(2-((2-((1S,2R,4R)-4-(dimethylamino)-2-ethylcyclohexylamino)-2-oxoethyl)carbamoyl)-4-(trifluoromethyl)phenyl)-3-isopropylurea |
| 2aa | N1-((1S,2R,4R)-2-ethyl-4-(isopropylamino)cyclohexyl)-N3-(3-methoxy-5-(trifluoromethyl)phenyl)malonamide |
| 2ab | N-(2-((1S,2R,4R)-2-butyl-4-(tert-butylamino)cyclohexylamino)-2-oxoethyl)-3-(trifluoromethyl)benzamide |
| 2ac | 3-tert-butyl-N-(2-((1S,2R,4R)-2-butyl-4-(tert-butylamino)cyclohexylamino)-2-oxoethyl)-4-hydroxybenzamide |
| 2ad | N-(2-((1S,2R,4R)-2-butyl-4-(tert-butylamino)cyclohexylamino)-2-oxoethyl)-5-(4-chlorophenyl)furan-2-carboxamide |
| 2ae | 5-tert-butyl-N-(2-((1S,2R,4R)-2-butyl-4-(tert-butylamino)cyclohexylamino)-2-oxoethyl)-2-methylfuran-3-carboxamide |
| 2af | 4-(adamant-1-yl)-N-(2-((1S,2R,4R)-2-butyl-4-(tert-butylamino)cyclohexylamino)-2-oxoethyl)-1H-pyrrole-2-carboxamide |
| 2ag | 3-tert-butyl-N-(2-((1S,2R,4R)-2-butyl-4-(tert-butylamino)cyclohexylamino)-2-oxoethyl)benzamide |
| 2ah | N-((1S,2R,4R)-2-butyl-4-(tert-butylamino)cyclohexyl)-2-(6-chloroquinazolin-4-ylamino)acetamide |
| 2ai | N-((1S,2R,4R)-2-butyl-4-(tert-butylamino)cyclohexyl)-2-(6-(trifluoromethyl)quinazolin-4-ylamino)acetamide |
| 2aj | N-((1S,2R,4R)-2-butyl-4-(tert-butylamino)cyclohexyl)-2-(6-tert-butylpyrimido[5,4-d]pyrimidin-4-ylamino)acetamide |
| 2ak | N-(2-((1S,2R,4R)-4-amino-2-phenethylcyclohexylamino)-2-oxoethyl)-3-(trifluoromethyl)benzamide |
| 2al | N-(2-((1S,2R,4R)-4-(isopropylamino)-2-phenethylcyclohexylamino)-2-oxoethyl)-3-(trifluoromethyl)benzamide |
| 2am | N-(2-((1S,2R,4R)-4-(isopropyl(methyl)amino)-2-phenethylcyclohexylamino)-2-oxoethyl)-3-(trifluoromethyl)benzamide |

Examples 3a-3e

Example 3a

Synthesis of N-((1S,2R,4R)-2-butyl-4-(isopropyl(methyl)amino)cyclohexyl)-2-(5-(trifluoromethyl)-1H-indazol-3-ylamino)acetamide Example 3a, Step 1: To a cooled (−78° C.) solution of (1R,2S,5R)-2-benzyloxycarbonylamino-7-oxo-6-aza-bicyclo[3.2.1]octane-6-carboxylic acid tert-butyl ester (60 g, 160 mmol) in THF (320 mL) was added LiHBEt$_3$ (192 mL of a 1.0 M solution in THF). The reaction was stirred for 30 min at −78° C. before being quenched with the addition of sat. NaHCO$_3$ (0.6 mL/1 mL of LiHBEt$_3$). The reaction vessel was moved to a −15° C. bath, and the reaction mixture was rapidly stirred at this temperature during the dropwise addition of hydrogen peroxide (79 mL of a 30% solution). The resulting suspension was stirred at −15° C. for 30 min before being filtered and concentrated under reduced pressure. The residue was diluted with EtOAc and washed successively with sat. NaHCO$_3$, water, and brine before being dried (magnesium sulfate), filtered, and concentrated in vacuo to afford tert-butyl (1R,2S,5R,7R/S)-2-(benzyloxycarbonyl)-7-hydroxy-6-aza-bicyclo[3.2.1]octane-6-carboxylate as a mixture of diastereomers at C7. MS found: (M+Na)$^+$=399.4.

Example 3a, Step 2: A sample of tert-butyl (1R,2S,5R,7R/S)-2-(benzyloxycarbonyl)-7-hydroxy-6-aza-bicyclo[3.2.1]octane-6-carboxylate (16 mmol) was dissolved in THF (15 mL). The resultant solution was cannulated into a pre-cooled (0° C.) solution of n-propylidene-triphenyl-λ5- phosphane (formed from 6.7 g of n-propyl triphenyl phosphonium bromide and 34 mL of 0.5 M KHMDS/THF in 40 mL of THF at 0° C.). The reaction was stirred for 30 min at 0° C. before being quenched with the addition of sat. NaHCO$_3$. The biphasic mixture was extracted with EtOAc (2×). The organic extracts were combined, washed with brine, dried (Na$_2$SO$_4$), filtered, and concentrated in vacuo. Purification of the residue via flash chromatography afforded the desired [(1S,2R,4R)-[4-tert-butoxycarbonylamino-2-(but-1-enyl)-cyclohexyl]-carbamic acid benzyl ester as a colorless oil (4.87 g). MS found: (M+Na)$^+$=425.3.

Example 3a, Step 3: A solution of [(1S,2R,4R)-[4-tert-butoxycarbonylamino-2-(but-1-enyl)-cyclohexyl]-carbamic acid benzyl ester (4.87 g) in CH$_2$Cl$_2$ (100 mL) was treated with trifluoroacetic acid (25 mL) and stirred for 2 h at RT. The reaction was concentrated in vacuo, and the resultant residue was partitioned between EtOAc and sat. NaHCO$_3$. The organic phase was washed with brine, dried (Na$_2$SO$_4$), filtered, and concentrated in vacuo to afford the amine. MS found: (M+H)$^+$=303.3. The amine was dissolved in MeOH (60 mL) and charged with acetone (9.0 mL); the mixture was stirred for 5 min before being charged with NaCNBH$_3$ (2.3 g). The reaction was stirred for 4 h at RT and then charged with formaldehyde (~9 mL of a 30% aq. Solution). The mixture was stirred for 1.5 h, quenched with sat. NaHCO$_3$, and extracted with EtOAc (2×). The organic extracts were combined, washed with brine, dried (Na$_2$SO$_4$), filtered, and concentrated in vacuo to afford benzyl (1S,2S,4R)-2-((Z)-but-1-enyl)-4-(isopropyl(methyl)amino)cyclohexylcarbamate (4.14 g). MS found: (M+H)$^+$=359.4.

Example 3a, Step 4: A sample of benzyl (1S,2S,4R)-2-((Z)-but-1-enyl)-4-(isopropyl(methyl)amino)cyclohexylcarbamate (2.0 g, 5.6 mmol) was dissolved in MeOH (30 mL). The resulting solution was charged with Pearlman's catalyst (600 mg) and degassed under vacuum before being hydrogenated (50 psi H$_2$) for 12 h. The mixture was filtered and concentrated in vacuo. The residue was dissolved in 30% HBr/AcOH (15 mL) and stirred for 30 min before being partitioned between Et$_2$O and water. The aqueous phase was basified (NaOH) and extracted twice with EtOAc. The organic extracts were combined, dried (sodium sulfate), filtered, and concentrated to afford (1R,3R,4S)-3-butyl-N1-isopropyl-N1-methylcyclohexane-1,4-diamine (396 mg). MS found: (M+H)$^+$=227.3.

Example 3a, Step 5: A solution of (1R,3R,4S)-3-butyl-N1-isopropyl-N1-methylcyclohexane-1,4-diamine (58 mg, 0.25 mmol) in methylene chloride (5 mL) was charged successively with HATU (113 mg, 0.29 mmol), 2-(5-(trifluoromethyl)-1H-indazol-3-ylamino)acetic acid (58 mg, 0.22 mmol), and N,N-diisopropylethylamine (0.22 mL, 1.24 mmol). The reaction was stirred for 16 h at RT, concentrated in vacuo, and diluted with EtOAc. The organic phase was washed successively with sat. NaHCO$_3$, water, 1N HCl, water, and brine before being dried (sodium sulfate), filtered, and concentrated in vacuo. Purification of the residue by RP-HPLC afforded the TFA salt of the title compound, which was found to be unstable to long-term storage. Accordingly, this material was dissolved in EtOAc and the organic phase was washed with sat. NaHCO$_3$ and brine before being dried (sodium sulfate), filtered, and concentrated in vacuo to afford the free base of the title compound, N-((1S,2R,4R)-2-butyl-4-(isopropyl(methyl)amino)cyclohexyl)-2-(5-(trifluoromethyl)-1H-indazol-3-ylamino)acetamide. MS found: (M+H)$^+$=468.4.

Example 3b

Synthesis of N-((R)-1-((1S,2R,4R)-2-butyl-4-(isopropyl(methyl)amino)cyclohexylamino)-1-oxopropan-2-yl)-3-(trifluoromethyl)benzamide Example 3b, Step 1: A solution of (1R,3R,4S)-3-butyl-N1-isopropyl-N1-methylcyclohexane-1,4-diamine (81 mg, 0.35 mmol; see Example 3a, Step 4) in 1:1 DMF/methylene chloride (5 mL) was charged successively with HATU (162 mg, 0.43 mmol), N-Boc D-Alanine (67 mg, 0.35 mmol), and N,N-diisopropylethylamine (0.31 mL, 1.77 mmol). The reaction was stirred for 16 h at RT, concentrated in vacuo, and diluted with EtOAc. The organic phase was washed successively with sat. NaHCO$_3$, water, 1N HCl, water, and brine before being dried (sodium sulfate), filtered, and concentrated in vacuo to afford tert-butyl (R)-1-((1S,2R,4R)-2-butyl-4-(isopropyl(methyl)amino)cyclohexylamino)-1-oxopropan-2-ylcarbamate. MS found: (M+H)$^+$=398.4.

Example 3b, Step 2: Theentirety of tert-butyl (R)-1-((1S,2R,4R)-2-butyl-4-(isopropyl(methyl)amino)cyclohexylamino)-1-oxopropan-2-ylcarbamate from Step 1 was dissolved in methylene chloride (4 mL). The resulting solution was cooled to 0° C. before being treated with TFA (2 mL) and stirred for 1 h. The solution was concentrated in vacuo and then stripped from methylene chloride twice more to afford the TFA salt of (R)-2-amino-N-((1S,2R,4R)-2-butyl-4-(isopropyl(methyl)amino)cyclohexyl)propanamide. MS found: (M+H)$^+$=298.4.

Example 3b, Step 3: Theentirety of TFA salt of (R)-2-amino-N-((1S,2R,4R)-2-butyl-4-(isopropyl(methyl)amino)cyclohexyl)propanamide from Step 2 was dissolved in 1:1 DMF/methylene chloride (5 mL). The resultant solution was charged successively with HATU (202 mg, 0.53 mmol), 3-trifluoromethylbenzoic acid (67 mg, 0.35 mmol), and N,N-diisopropylethylamine (0.31 mL, 1.77 mmol). The reaction was stirred for 16 h at RT, concentrated in vacuo, and diluted with EtOAc. The organic phase was washed successively with sat. NaHCO$_3$, water, 1N HCl, water, and brine before being dried (sodium sulfate), filtered, and concentrated in vacuo. The residue was purified by RP-HPLC to afford the TFA salt of N-((R)-1-((1S,2R,4R)-2-butyl-4-(isopropyl(methyl)amino)cyclohexylamino)-1-oxopropan-2-yl)-3-(trifluoromethyl)benzamide as a white powder after lyopholization. MS found: (M+H)$^+$=470.3.

Example 3d

Synthesis of the bis-TFA salt of N-((1S,2S,4R)-2-isopropyl-4-(isopropyl(methyl)amino)cyclohexyl)-2-(6-(trifluoromethyl)quinazolin-4-ylamino)acetamide Example 3d, Step 1: Benzyloxycarbonylamino-7-oxo-6-aza-bicyclo[3.2.1]octane-6-carboxylic acid tert-butyl ester (1.0 g) was dissolved in THF (6 mL) at 0° C. prior to the addition of 3M MeMgI (4.4 mL) as a solution in Et$_2$O. After 2 h at 0° C., 1N HCl (aq) was added along with EtOAc. The organic layer was dried and concentrated to afford (1R,3R,4S)-(4-benzyloxycarbonylamino-3-acetylcyclohexyl)carbamic acid tert-butyl ester (1.0 g). MS found: (M+H)$^+$=391.2.

Example 3d, Step 2: Methyltriphenylphosphonium-bromide (729 mg) was dissolved in THF (4 mL) and cooled to 0° C. prior to the addition of 0.5M potassium bis(trimethylsilyl)amide (3.7 mL) in toluene. After 1 h, (1R,3R,4S)-(4-benzyloxycarbonylamino-3-acetylcyclohexyl)carbamic acid tert-butyl ester (400 mg) in THF (4 mL) was added dropwise. The reaction was warmed to rt over 2 h, before it was quenched with saturated NH₄Cl solution and extracted with EtOAc (3×) The organic extracts were combined, washed with brine, dried (Na₂SO₄), filtered, and concentrated. The resulting residue was purified by flash chromatography to provide tert-butyl (1R,3S,4S)-4-benzyloxycarbonylamino-3-(prop-1-en-2-yl)cyclohexylcarbamate (380 mg). MS (ES+)=389.2 (M+H)⁺.

Example 3d, Step 3: A solution of tert-butyl (1R,3S,4S)-4-benzyloxycarbonylamino-3-(prop-1-en-2-yl)cyclohexylcarbamate (1.1 g) in MeOH (10 mL) was charged with 10% Pd/C, Degussa (300 mg). The reaction flask was evacuated and then back-filled with hydrogen; this was repeated three more times. The reaction was stirred under 1 atm of H₂ for 12 h and then filtered and concentrated to provide tert-butyl (1R,3S,4S)-4-amino-3-isopropylcyclohexylcarbamate (780 mg). MS (ES+)=257.3 (M+H)⁺.

Example 3d, Step 4: Tert-butyl(1R,3S,4S)-4-amino-3-isopropylcyclohexylcarbamate (780 mg) dissolved in DMF (10 mL) and cooled to 0° C. prior to the addition of N-Cbz-Gly-OH (1.14 g), 4-methylmorpholine (1.2 mL), and BOP (2.42 g). The reaction was stirred for 12 h at rt and then partitioned between EtOAc and 1N HCl solution. The organic phases were combined, washed with saturated NaHCO₃ and brine, dried (MgSO₄), filtered, and concentrated in vacuo. The residue was purified by flash chromatography to afford tert-butyl (1R,3S,4S)-4-(2-benzyloxycarbonylaminoacetamido)-3-isopropylcyclohexylcarbamate (790 mg). MS found: (M+H)⁺=448.4.

Example 3d, Step 5: Tert-butyl(1R,3S,4S)-4-(2-benzyloxycarbonylaminoacetamido)-3-isopropylcyclohexylcarbamate (790 mg) was dissolved in CH₂Cl₂ (7 mL) at 0° C. prior to the addition of trifluoroacetic acid (10 mL). After 30 min at rt, the reaction was concentrated in vacuo. The resultant residue was dissolved in dichloromethane (11 ml) and acetone (3 mL) prior to the addition of NaBH(OAc)₃ (720.4 mg). After 1.5 h, formaldehyde (1.5 mL of a 37% aq. solution) was added along with NaBH(OAc)₃ (720 mg). The mixture was stirred for 12 h, quenched with sat. NaHCO₃, and extracted with EtOAc (2×). The organic extracts were combined, dried (Na₂SO₄), filtered, and concentrated. The resulting residue was purified by reverse phase HPLC (gradient elution, water/acetonitrile/TFA) to afford the TFA salt of benzyl 2-((1S,2S,4R)-2-isopropyl-4-(isopropyl(methyl)amino)cyclohexylamino)-2-oxoethylcarbamate (188 mg). MS found: (M+H)⁺=404.4.

Example 3d, Step 6: A solution of benzyl 2-((1S,2S,4R)-2-isopropyl-4-(isopropyl(methyl)amino)cyclohexylamino)-2-oxoethylcarbamate trifluoroacetate (188 mg) in MeOH (10 mL) was charged with 10% Pd/C, Degussa (30 mg). The reaction flask was evacuated and then back-filled with hydrogen; this was repeated three more times. The reaction was stirred under 1 atm of H₂ for 3 h and then filtered and concentrated to afford 2-amino-N-((1S,2S,4R)-2-isopropyl-4-(isopropyl(methyl)amino)cyclohexyl)acetamide (120 mg). MS found: (M+H)⁺=270.3.

Example 3d, Step 7: Toa solution of 2-amino-N-((1S,2S,4R)-2-isopropyl-4-(isopropyl(methyl)amino)cyclohexyl)acetamide (30 mg) in EtOH (2 mL) was added triethylamine (0.08 mL) and 4-chloro-6-(trifluoromethyl)quinazoline (30 mg). The mixture was heated at 80° C. for 14 h before it was filtered and concentrated in vacuo. The residue was purified by reverse phase HPLC (gradient elution, water/acetonitrile/TFA) to afford the bis-TFA salt of N-((1S,2S,4R)-2-isopropyl-4-(isopropyl(methyl)amino)cyclohexyl)-2-(6-(trifluoromethyl)quinazolin-4-ylamino)acetamide (32 mg). MS found: (M+H)⁺=466.4.

Table 3-A

The compounds in the following table were made using the methods exemplified above. See Table 1-A for a complete description of the table headings.

TABLE 3B

| Ex. | R¹ | R¹⁰ | Z | R² | Step Alt. | MS |
|-----|-----|------|-----|-----|-----------|-----|
| 3a | n-Bu | H | NH | 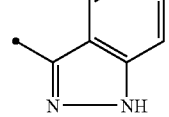 | n/a | 468 |
| 3b | n-Bu | (R)-Me | NHC=O | 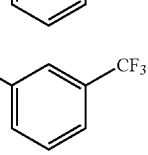 | n/a | 470 |
| 3c | n-Bu | (S)-Me | NHC=O | (same as 3b) | 3b, Step 1 | 470 |

TABLE 3B-continued

| Ex. | R¹ | R¹⁰ | Z | R² | Step Alt. | MS |
|---|---|---|---|---|---|---|
| 3d | i-Pr | H | NH | 6-chloroquinazolin-4-yl | n/a | 466 |
| 3e | i-Pr | H | NH | 6-(trifluoromethoxy)quinazolin-4-yl | 3d, Step 7 | 482 |

The chemical names of the specific examples illustrated in Table 3-A are tabulated below.

| Example | Name |
|---|---|
| 3a | N-((1S,2R,4R)-2-butyl-4-(isopropyl(methyl)amino)cyclohexyl)-2-(5-(trifluoromethyl)-1H-indazol-3-ylamino)acetamide |
| 3b | N-((R)-1-((1S,2R,4R)-2-butyl-4-(isopropyl(methyl)amino)cyclohexylamino)-1-oxopropan-2-yl)-3-(trifluoromethyl)benzamide |
| 3c | N-((S)-1-((1S,2R,4R)-2-butyl-4-(isopropyl(methyl)amino)cyclohexylamino)-1-oxopropan-2-yl)-3-(trifluoromethyl)benzamide |
| 3d | N-((1S,2S,4R)-2-isopropyl-4-(isopropyl(methyl)amino)cyclohexyl)-2-(6-(trifluoromethyl)quinazolin-4-ylamino)acetamide |
| 3e | N-((1S,2S,4R)-2-isopropyl-4-(isopropyl(methyl)amino)cyclohexyl)-2-(6-(trifluoromethoxy)quinazolin-4-ylamino)acetamide |

Examples 4a-4n

Example 4a

Synthesis of N-(2-((1S,2R,4R)-4-(isopropyl(methyl)amino)-2-(methoxymethyl)cyclohexylamino)-2-oxoethyl)-3-(trifluoromethyl)benzamide Example 4a, Step 1: A solution of tert-butyl (1R,3R,4S)-4-benzyloxycarbonylamino-3-(hydroxymethyl)cyclohexylcarbamate (1.8 g) in N,N-dimethylformamide (15 mL) was treated sequentially with iodomethane (50 mL) and Ag₂O (5.52 g), and the mixture was stirred at rt overnight. The mixture was filtered through Celite and the solids were washed with ethyl acetate. The combined filtrates were washed sequentially with water and brine, dried over Na₂SO₄ and concentrated. The residue was purified by flash chromatography on silica gel, eluting with 1:3 v/v ethyl acetate-hexane, to provide tert-butyl (1R,3R,4S)-4-benzyloxycarbonylamino-3-(methoxymethyl)cyclohexylcarbamate as a colorless gum (1.78 g). MS found: (M+H)⁺=393.

Example 4a, Step 2: A solution of tert-butyl (1R,3R,4S)-4-benzyloxycarbonylamino-3-(methoxymethyl)cyclohexylcarbamate (64 mg, 0.163 mmol) in methanol (3 mL) was stirred with Pearlman's catalyst (20% Pd(OH)₂ on charcoal, 65 mg) under hydrogen at atmospheric pressure and rt for 22 h. The mixture was filtered through Celite and the solids were washed with methanol. The filtrate was concentrated to provide tert-butyl (1R,3R,4S)-4-amino-3-(methoxymethyl)cyclohexylcarbamate as a pale yellow glassy foam (45 mg) which was used without further purification. MS found: (M+H)⁺=259.2.

Example 4a, Step 3: A solution of tert-butyl (1R,3R,4S)-4-amino-3-(methoxymethyl)cyclohexylcarbamate (45 mg, assumed 0.163 mmol) in acetonitrile (1.5 mL) was treated sequentially with 2-(3-(trifluoromethyl)benzamido)acetic acid (43 mg, 0.174 mmol, see PCT WO 0250019), diisopropylethylamine (61 µL, 0.348 mmol) and TBTU (62 mg, 0.192 mmol). The mixture was stirred at rt for 2.75 h, then was diluted with ethyl acetate, washed sequentially with 1.0 M aqueous HCl, saturated aqueous NaHCO₃, water and brine, dried over Na₂SO₄ and concentrated under vacuum. The residue was purified by flash column chromatography on silica gel, eluting with 1:3 v/v hexane-ethyl acetate, to provide tert-butyl (1R,3R,4S)-3-(methoxymethyl)-4-(2-(3-(trifluoromethyl)benzamido)acetamido)cyclohexylcarbamate as a white solid (48 mg). MS found: (M+H)⁺=488.3.

Example 4a, Step 4: A solution of tert-butyl (1R,3R,4S)-3-(methoxymethyl)-4-(2-(3-(trifluoromethyl)benzamido)acetamido)cyclohexylcarbamate (48 mg, 99 µmol) in dichloromethane (3 mL) was treated with trifluoroacetic acid (3 mL). After 2.25 h, the solution was concentrated under vacuum. Trituration of the residue in three changes of ether, followed by drying under vacuum, provided the trifluoroacetic acid salt of N-(2-((1S,2R,4R)-4-amino-2-(methoxymethyl)cyclohexylamino)-2-oxoethyl)-3-(trifluoromethyl)benzamide as a white solid (45 mg). MS found: (M+H)$^+$=388.2.

Example 4a, Step 5: The trifluoroacetic acid salt of N-(2-((1S,2R,4R)-4-amino-2-(methoxymethyl)cyclohexylamino)-2-oxoethyl)-3-(trifluoromethyl)benzamide (43 mg, 86 µmol) was converted to the free base by partitioning between 1.0 M aqueous NaOH and ethyl acetate, followed by drying of the organic phase over Na$_2$SO$_4$ and concentration under vacuum. The residue was dissolved in 1,2-dichloroethane (1 mL) and treated sequentially with acetic acid (25 µL, 0.429 mmol), acetone (19 µL, 0.257 mmol) and sodium triacetoxyborohydride (73 mg, 0.343 mmol). After 5.5 h, aqueous formaldehyde (37%, 32 µL, 0.429 mmol) was added and stirring was continued for 80 min. The mixture was concentrated under vacuum, and the residue was lyophilized from water containing a small amount of trifluoroacetic acid to provide the trifluoroacetic acid salt of title compound, N-(2-((1S,2R,4R)-4-(isopropyl(methyl)amino)-2-(methoxymethyl)cyclohexylamino)-2-oxoethyl)-3-(trifluoromethyl)benzamide, as a white powder (31 mg). MS found: (M+H)$^+$=444.3.

Example 4b

Synthesis of 1-(2-((2-((1S,2R,4R)-4-(isopropyl(methyl)amino)-2-(methoxymethyl)cyclohexylamino)-2-oxoethyl)carbamoyl)-4-(trifluoromethyl)phenyl)-3-isopropylurea Example 4b, Step 1: Following sequentially the procedures of Example 4a, Steps 4 and 5, tert-butyl (1R,3R,4S)-4-benzyloxycarbonylamino-3-(methoxymethyl)cyclohexylcarbamate (262 mg) was converted to benzyl (1S,2R,4R)-4-(isopropyl(methyl)amino)-2-(methoxymethyl)cyclohexylcarbamate (135 mg). MS found: (M+H)$^+$=349.3.

Example 4b, Step 2: Benzyl(1S,2R,4R)-4-(isopropyl(methyl)amino)-2-(methoxymethyl)cyclohexylcarbamate (135 mg) was dissolved in 30% HBr in acetic acid (3 ml) and stirred at rt for 45 min. Diethyl ether was added and the resulting gum was isolated, washed with additional ether, stripped four times from benzene and dried under vacuum to provide the dihydrobromide salt of (1R,3R,4S)-N1-isopropyl-3-(methoxymethyl)-N1-methylcyclohexane-1,4-diamine (280 mg) as a gum, used without further purification. MS found: (M+H)$^+$=215.2.

Example 4b, Step 3: A sample of the crude dihydrobromide salt of (1R,3R,4S)-N1-isopropyl-3-(methoxymethyl)-N1-methylcyclohexane-1,4-diamine prepared in Example 4b, Step 2 (48 mg, assume 0.128 mmol) was dissolved in acetonitrile (4 mL) and N,N-dimethylformamide (1 mL). This solution was treated sequentially with 2-(2-(3-isopropylureido)-5-(trifluoromethyl)benzamido)acetic acid (44 mg, 0.128 mmol; see PCT WO 0250019), diisopropylethylamine (0.13 mL, 0.768 mmol) and TBTU (49 mg, 0.153 mmol) and then was stirred at rt for 1.5 h. The mixture was concentrated under vacuum, and the residue was dissolved in ethyl acetate. This solution was washed with saturated aqueous NaHCO$_3$, and the aqueous phase extracted twice with ethyl acetate. The combined organic phases were dried over Na$_2$SO$_4$ and concentrated. Purification by reverse phase HPLC followed by lyophilization provided the trifluoroacetic acid salt of the title product, 1-(2-((2-((1S,2R,4R)-4-(isopropyl(methyl)amino)-2-(methoxymethyl)cyclohexylamino)-2-oxoethyl)carbamoyl)-4-(trifluoromethyl)phenyl)-3-isopropylurea, (47 mg) as a white powder. MS found: (M+H)$^+$=544.3.

Example 4c

Synthesis of N-(2-((2-((1S,2R,4R)-4-(isopropyl(methyl)amino)-2-(methoxymethyl)cyclohexylamino)-2-oxoethyl)carbamoyl)-4-(trifluoromethyl)phenyl)azetidine-1-carboxamide Following the procedure of Example 4b, Step 3, but substituting 2-(2-(azetidine-1-carboxamido)-5-(trifluoromethyl)benzamido)acetic acid (see PCT WO 0250019) for 2-(2-(3-isopropylureido)-5-(trifluoromethyl)benzamido)acetic acid, the crude dihydrobromide salt of (1R,3R,4S)-N1-isopropyl-3-(methoxymethyl)-N1-methylcyclohexane-1,4-diamine prepared in Example 4b, Step 2 (48 mg, assume 0.128 mmol) was converted, after purification by reverse phase HPLC and lyophilization, to the trifluoroacetic acid salt of the title compound as a white powder (40 mg). MS found: (M+H)$^+$=542.3.

Example 4d

Synthesis of 3-tert-butyl-4-hydroxy-N-(2-((1S,2R,4R)-4-(isopropyl(methyl)amino)-2-(methoxymethyl)cyclohexylamino)-2-oxoethyl)benzamide Example 4d, Step 1: A solution of crude dihydrobromide salt of (1R,3R,4S)-N1-isopropyl-3-(methoxymethyl)-N1-methylcyclohexane-1,4-diamine prepared according to the procedure of Example 4b, Step 2 (423 mg) in acetonitrile (5 mL) was treated with 2-(benzyloxycarbonylamino)acetic acid (259 mg), diisopropylethylamine (0.80 ml) and HATU (516 mg). The mixture was stirred overnight at rt, then was concentrated under vacuum. The residue was purified by reverse phase HPLC followed by lyopholization to provide benzyl 2-((1S,2R,4R)-4-(isopropyl(methyl)amino)-2-(methoxymethyl)cyclohexylamino)-2-oxoethylcarbamate (192 mg) as a white powder. MS found: (M+H)$^+$=406.3.

Example 4d, Step 2: Following the procedure of Example 4b, Step 2, benzyl 2-((1S,2R,4R)-4-(isopropyl(methyl)amino)-2-(methoxymethyl)cyclohexylamino)-2-oxoethylcarbamate (135 mg) was converted to the dihydrobromide salt of 2-amino-N-(1S,2R,4R)-[4-(isopropyl-methyl-amino)-2-methoxymethylcyclohexyl]acetamide as a white solid (120 mg), used without further purification. MS found: (M+H)$^+$=272.3.

Example 4d, Step 3: Following the procedure of Example 4b, Step 3, but substituting 3-tert-butyl-4-hydroxybenzoic acid for 2-(2-(3-isopropylureido)-5-(trifluoromethyl)benzamido)acetic acid, a sample of the crude dihydrobromide salt of 2-amino-N-(1S,2R,4R)-[4-(isopropyl-methyl-amino)-2-methoxymethylcyclohexyl]acetamide prepared according to Example 4d, Step 2 (45 mg) was converted, after purification by reverse phase HPLC and lyophilization, to the trifluoroacetic acid salt of the title product, 3-tert-butyl-4-hydroxy-N-(2-((1S,2R,4R)-4-(isopropyl(methyl)amino)-2-(methoxymethyl)cyclohexylamino)-2-oxoethyl)benzamide, as a white powder (17 mg). MS found: (M+H)$^+$=448.5.

Example 4e

Synthesis of 3-tert-butyl-N-(2-((1S,2R,4R)-4-(isopropyl(methyl)amino)-2-(methoxymethyl)cyclohexylamino)-2-oxoethyl)-1-methyl-1H-pyrazole-5-carboxamide Example 4e, Step 1: A solution of the crude dihydrobromide salt of (1R,3R,4S)-N1-isopropyl-3-(methoxymethyl)-N1-methylcyclohexane-1,4-diamine prepared according to the procedure of Example 4b, Step 2 (270 mg) in dichloromethane (5 mL) was treated with tert-butoxycarbonylaminoacetic acid (126 mg), diisopropylethylamine (0.80 ml) and HATU (516 mg). The mixture was stirred for 3 h at rt. Ethyl acetate and saturated aqueous $NaHCO_3$ were added and the layers were separated. The aqueous layer was extracted with additional ethyl acetate. The combined organic layers were washed with brine, dried over $Na_2SO_4$, and concentrated under vacuum to provide tert-butyl 2-((1S,2R,4R)-4-(isopropyl(methyl)amino)-2-(methoxymethyl)cyclohexylamino)-2-oxoethylcarbamate (185 mg) as a yellow gum, used without further purification. MS found: $(M+H)^+$=372.4.

Example 4e, Step 2: Following the procedure of Example 4a, Step 4, tert-butyl 2-((1S,2R,4R)-4-(isopropyl(methyl)amino)-2-(methoxymethyl)cyclohexylamino)-2-oxoethylcarbamate (185 mg) was converted to the bis-trifluoroacetic acid salt of 2-amino-N-((1S,2R,4R)-4-(isopropyl(methyl)amino)-2-(methoxymethyl)cyclohexyl)acetamide (145 mg) which was used without further purification. MS found: $(M+H)^+$=272.3.

Example 4e, Step 3: Following the procedure of Example 4d, Step 1, but substituting 3-tert-butyl-1-methyl-1H-pyrazole-5-carboxylic acid for 2-(benzyloxycarbonylamino)acetic acid, a portion of the crude bis-trifluoroacetic acid salt of 2-amino-N-((1S,2R,4R)-4-(isopropyl(methyl)amino)-2-(methoxymethyl)cyclohexyl)acetamide prepared according to Example 4e, Step 2 (50 mg) was converted, after purification by reverse phase HPLC and lyophilization, to the trifluoroacetic acid salt of the title compound, 3-tert-butyl-N-(2-((1S,2R,4R)-4-(isopropyl(methyl)amino)-2-(methoxymethyl)cyclohexylamino)-2-oxoethyl)-1-methyl-1H-pyrazole-5-carboxamide, as a white powder (35 mg). MS found: $(M+H)^+$=436.5.

Example 4f

Synthesis of N-(2-((1S,2R,4R)-4-(ethyl(isopropyl)amino)-2-(methoxymethyl)cyclohexylamino)-2-oxoethyl)-3-(trifluoromethyl)benzamide Example 4f, Step 1: Following the procedure of Example 4a, Step 4, tert-butyl (1R,3R,4S)-4-benzyloxycarbonylamino-3-(methoxymethyl)cyclohexylcarbamate (660 mg, 1.68 mmol) was converted to the trifluoroacetic acid salt of benzyl (1S,2R,4R)-4-amino-2-(methoxymethyl)cyclohexylcarbamate, which was used without further purification. MS found: $(M+H)^+$=259.2.

Example 4f, Step 2: Thetrifluoroacetic acid salt of benzyl (1S,2R,4R)-4-amino-2-(methoxymethyl)cyclohexylcarbamate (660 mg, assumed 1.68 mmol) was dissolved in methanol (5 mL) and treated with an excess of sodium cyanoborohydride (ca. 50-100 mg) and acetone (1 mL). The mixture was stirred overnight at rt, then treated with additional acetone and sodium cyanoborohydride. After 1 h, acetaldehyde (1 mL) was added, followed 4 h later by additional acetaldehyde and sodium cyanoborohydride. After stirring overnight at rt, additional acetaldehyde and sodium cyanoborohydride were added, followed by stirring for 3 days. The mixture was concentrated and the residue was dissolved in ethyl acetate and saturated aqueous $NaHCO_3$. The layers were separated and the aqueous phase was extracted four times with ethyl acetate. The combined organic phases were dried over $Na_2SO_4$ and concentrated under vacuum. Purification by rotary preparative layer chromatography, eluting with 95:4:1 (v/v) dichloromethane:methanol:aqueous ammonia, provided benzyl (1S,2R,4R)-4-(ethyl(isopropyl)amino)-2-(methoxymethyl)cyclohexylcarbamate (430 mg). MS found: $(M+H)^+$=363.4.

Example 4f, Step 3: Following the procedure of Example 4b, Step 2, benzyl (1S,2R,4R)-4-(ethyl(isopropyl)amino)-2-(methoxymethyl)cyclohexylcarbamate (430 mg) was converted to the dihydrobromide salt of (1R,3R,4S)-N1-ethyl-N1-isopropyl-3-(methoxymethyl)cyclohexane-1,4-diamine as a white solid (500 mg). This material was dissolved in 1.0 M aqueous HCl and the solution was washed with ethyl ether. The pH of the aqueous layer was adjusted to ca. 12 with 1.0 M aqueous NaOH. Solid NaCl was added until the solution was saturated, and the solution was then extracted five times with ethyl acetate. The combined organic layers were dried over $Na_2SO_4$ and concentrated to provide (1R,3R,4S)-N1-ethyl-N1-isopropyl-3-(methoxymethyl)cyclohexane-1,4-diamine (170 mg). MS found: $(M+H)^+$=229.3.

Example 4f, Step 4: Following the procedure of Example 4d, Step 1, but substituting 2-(3-(trifluoromethyl)benzamido)acetic acid for 2-(benzyloxycarbonylamino)acetic acid, (1R,3R,4S)-N1-ethyl-N1-isopropyl-3-(methoxymethyl)cyclohexane-1,4-diamine (40 mg) was converted to the trifluoroacetic acid salt of the title compound, N-(2-((1S,2R,4R)-4-(ethyl(isopropyl)amino)-2-(methoxymethyl)cyclohexylamino)-2-oxoethyl)-3-(trifluoromethyl)benzamide, as a white powder (75 mg) after purification by reverse phase HPLC and lyophilization. MS found: $(M+H)^+$=458.4.

Example 4g

Synthesis of N-((1S,2R,4R)-4-(isopropyl(methyl)amino)-2-(methoxymethyl)cyclohexyl)-2-(5-(trifluoromethyl)benzo[d]isoxazol-3-ylamino)acetamide Following the procedure of example 4b, Step 3, but substituting 2-(5-(trifluoromethyl)benzo[d]isoxazol-3-ylamino)acetic acid for 2-(2-(3-isopropylureido)-5-(trifluoromethyl)benzamido)acetic acid, substituting HATU for TBTU, and using N,N-dimethylformamide as the solvent, the crude dihydrobromide salt of (1R,3R,4S)-N1-isopropyl-3-(methoxymethyl)-N1-methylcyclohexane-1,4-diamine prepared according to Example 4b, Step 2 (35 mg) was converted to the trifluoroacetic acid salt of the title product, N-((1S,2R,4R)-4-(isopropyl(methyl)amino)-2-(methoxymethyl)cyclohexyl)-2-(5-(trifluoromethyl)benzo[d]isoxazol-3-ylamino)acetamide, as a white powder (43 mg) after purification by reverse phase HPLC and lyophilization. MS found: $(M+H)^+$=457.2

Example 4 h

Synthesis of N-((1S,2R,4R)-4-(isopropyl(ethyl)amino)-2-(methoxymethyl)cyclohexyl)-2-(5-(trifluoromethyl)benzo[d]isoxazol-3-ylamino)acetamide Following the procedure of Example 4d, Step 1, but substituting 2-(5-(trifluoromethyl)benzo[d]isoxazol-3-ylamino)acetic acid for 2-(benzyloxycarbonylamino)acetic acid, (1R,3R,4S)-N1-ethyl-N1-isopropyl-3-(methoxymethyl)cyclohexane-1,4-diamine (40 mg) was converted to the trifluoroacetic acid salt of the title compound as a white powder (40 mg) after purification by reverse phase HPLC and lyophilization. MS found: (M+H)$^+$=471.4.

Example 4i

Synthesis of N-((1S,2R,4R)-4-(isopropyl(methyl)amino)-2-(methoxymethyl)cyclohexyl)-2-(6-(trifluoromethyl)quinazolin-4-ylamino)acetamide A solution of the bis-trifluoroacetic acid salt of 2-amino-N-((1S,2R,4R)-4-(isopropyl(methyl)amino)-2-(methoxymethyl)cyclohexyl)acetamide (57 mg) in ethanol (4 mL) was treated with 4-chloro-6-(trifluoromethyl)quinazoline (40 mg) and triethylamine (0.08 mL). The mixture was heated at reflux overnight. The mixture was then cooled to rt and purified by reverse phase HPLC and lyopholization to provide the bis-trifluoroacetic acid salt of the title product as a white powder (42 mg). MS found: (M+H)$^+$=468.4.

Example 4j

Synthesis of N-((1S,2R,4R)-4-(ethyl(isopropyl)amino)-2-(methoxymethyl)cyclohexyl)-2-(6-(trifluoromethyl)quinazolin-4-ylamino)acetamide Example 4j, Step 1: Following the procedure of Example 4e, Step 1, but substituting (1R,3R,4S)-N1-ethyl-N1-isopropyl-3-(methoxymethyl)cyclohexane-1,4-diamine (90 mg) for the crude dihydrobromide salt of (1R,3R,4S)-N1-isopropyl-3-(methoxymethyl)-N1-methylcyclohexane-1,4-diamine and using acetonitrile as the solvent in place of dichloromethane, tert-butyl 2-((1S,2R,4R)-4-(ethyl(isopropyl)amino)-2-(methoxymethyl)cyclohexylamino)-2-oxoethylcarbamate (238 mg) was prepared and used without purification. MS found: (M+H)$^+$=386.7.

Example 4j, Step 2: Following the procedure of Example 4e, Step 2, crude tert-butyl 2-((1S,2R,4R)-4-(ethyl(isopropyl)amino)-2-(methoxymethyl)cyclohexylamino)-2-oxoethylcarbamate (238 mg) was converted to the bis-trifluoroacetic acid salt of 2-amino-N-((1S,2R,4R)-4-(ethyl(isopropyl)amino)-2-(methoxymethyl)cyclohexyl)acetamide (202 mg). MS found: (M+H)$^+$=286.3.

Example 4j, Step 3: Following the procedure of Example 4i, the bis-trifluoroacetic acid salt of 2-amino-N-((1S,2R,4R)-4-(ethyl(isopropyl)amino)-2-(methoxymethyl)cyclohexyl)acetamide (50.5 mg) was converted to the bis-trifluoroacetic acid salt of the title compound, N-((1S,2R,4R)-4-(ethyl(isopropyl)amino)-2-(methoxymethyl)cyclohexyl)-2-(6-(trifluoromethyl)quinazolin-4-ylamino)acetamide, as a white powder (40 mg) after purification by reverse phase HPLC and lyophilization. MS found: (M+H)$^+$=482.5.

Example 4k

Synthesis of 2-amino-N-(2-((1S,2R,4R)-4-(isopropyl(methyl)amino)-2-(methoxymethyl)cyclohexylamino)-2-oxoethyl)-5-(trifluoromethoxy)benzamide Example 4k, Step 1: Following the procedure of Example 4d, Step 1, but substituting 2-(tert-butoxycarbonylamino)-5-(trifluoromethoxy)benzoic acid (37 mg) for 2-(benzyloxycarbonylamino)acetic acid, the bis-trifluoroacetic acid salt of 2-amino-N-((1S,2R,4R)-4-(isopropyl(methyl)amino)-2-(methoxymethyl)cyclohexyl)acetamide (58 mg) was converted to the trifluoroacetic acid salt of tert-butyl 2-((2-((1S,2R,4R)-4-(isopropyl(methyl)amino)-2-(methoxymethyl)cyclohexylamino)-2-oxoethyl)carbamoyl)-4-(trifluoromethoxy)phenylcarbamate (20 mg) after purification by reverse phase HPLC and lyophilization. MS found: (M+H)$^+$=575.5.

Example 4k, Step 2: A solution of the trifluoroacetic acid salt of tert-butyl 2-((2-((1S,2R,4R)-4-(isopropyl(methyl)amino)-2-(methoxymethyl)cyclohexylamino)-2-oxoethyl)carbamoyl)-4-(trifluoromethoxy)phenylcarbamate (20 mg) in dichloromethane (2 mL) was treated with trifluoroacetic acid (2 mL). The mixture was stirred at rt for 2 h, then was concentrated under vacuum to provide the trifluoroacetic acid salt of the title compound, 2-amino-N-(2-((1S,2R,4R)-4-(isopropyl(methyl)amino)-2-(methoxymethyl)cyclohexylamino)-2-oxoethyl)-5-(trifluoromethoxy)benzamide, as a white powder (15 mg) after lyopholization. MS found: (M+H)$^+$=475.7.

Example 4m

Synthesis of 2-(2,6-dichloroquinazolin-4-ylamino)-N-((1S,2R,4R)-4-(ethyl(isopropyl)amino)-2-(methoxymethyl)cyclohexyl)acetamide A solution of 2,4,6-trichloroquinazoline (103 mg) and the bis-trifluoroacetic acid salt of 2-amino-N-((1S,2R,4R)-4-(ethyl(isopropyl)amino)-2-(methoxymethyl)cyclohexyl)acetamide (152 mg) in tetrahydrofuran (3 mL) was treated with diisopropylethylamine (0.31 mL) and the mixture was stirred overnight at rt. The mixture was concentrated and purified by reverse phase HPLC and lyophilization to provide the bis-trifluoroacetic acid salt of the title compound, 2-(2,6-dichloroquinazolin-4-ylamino)-N-((1S,2R,4R)-4-(ethyl(isopropyl)amino)-2-(methoxymethyl)cyclohexyl)acetamide, as a white powder (79 mg). MS found: (M+H)$^+$=482.2.

Example 4n

Synthesis of 2-(6-chloro-2-(dimethylamino)quinazolin-4-ylamino)-N-((1S,2R,4R)-4-(ethyl(isopropyl)amino)-2-(methoxymethyl)cyclohexyl)acetamide A solution of 2-(2,6-dichloroquinazolin-4-ylamino)-N-((1S,2R,4R)-4-(ethyl(isopropyl)amino)-2-(methoxymethyl)cyclohexyl)acetamide (61 mg) in tetrahydrofuran (2 mL) was treaded with dimethylamine (2 M in tetrahydrofuran, 80 µL) and the mixture was heated at reflux overnight. Additional dimethylamine solution (0.825 mL) was added and heating was continued for 3 more days. Concentration under vacuum and purification by reverse phase HPLC and lyophilization provided the bis-trifluoroacetic acid salt of the title product, 2-(6-chloro-2-(dimethylamino)quinazolin-4-ylamino)-N-((1S,2R,4R)-4-(ethyl(isopropyl)amino)-2-(methoxymethyl)cyclohexyl)acetamide, as a white powder (54 mg). MS found: (M+H)$^+$=491.7.

TABLE 4A

The compounds in the following table were made using the methods exemplified above.
See Table 1-A for a complete description of the table headings.

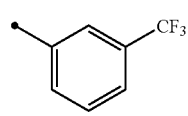

| Example | R⁵ | Z | R² | Step Altered | MS Data |
|---|---|---|---|---|---|
| 4a | i-Pr(Me)N | —NHC(=O)— | 3-CF₃-phenyl | n/a | 444.3 |
| 4b | i-Pr(Me)N | —NHC(=O)— | 4-CF₃-2-(iPrNHC(=O)NH)-phenyl | n/a | 544.3 |
| 4c | i-Pr(Me)N | —NHC(=O)— | 4-CF₃-2-(azetidine-1-carboxamido)-phenyl | 4b, | 542.3 |
| 4d | i-Pr(Me)N | —NHC(=O)— | 3-tBu-4-OH-phenyl | n/a | 448.5 |
| 4e | i-Pr(Ne)N | —NHC(=O)— | 3-tBu-1-Me-pyrazol-5-yl | n/a | 436.5 |
| 4f | i-Pr(Et)N | —NHC(=O)— | 3-CF₃-phenyl | n/a | 458.4 |

TABLE 4A-continued

The compounds in the following table were made using the methods exemplified above.
See Table 1-A for a complete description of the table headings.

| Example | R⁵ | Z | R² | Step Altered | MS Data |
|---|---|---|---|---|---|
| 4g | i-Pr(Me)N | —NH— | 5-CF₃-benzisoxazol-3-yl | 4b, Step 3 | 457.2 |
| 4h | i-Pr(Et)N | —NH— | 5-CF₃-benzisoxazol-3-yl | 4d, Step 1 | 471.4 |
| 4i | i-Pr(Me)N | —NH— | 6-CF₃-quinazolin-4-yl | n/a | 468.4 |
| 4j | i-Pr(Et)N | —NH— | 6-CF₃-quinazolin-4-yl | n/a | 482.5 |
| 4k | i-Pr(Me)N | —NHC(=O)— | 4-OCF₃-2-methyl-6-amino-phenyl | n/a | 475.7 |
| 4m | i-Pr(Et)N | —NH— | 2,6-dichloroquinazolin-4-yl | n/a | 482.2 |

TABLE 4A-continued

The compounds in the following table were made using the methods exemplified above.
See Table 1-A for a complete description of the table headings.

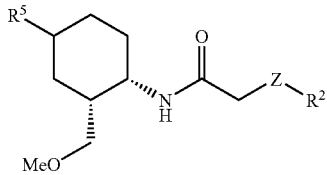

| Example | R⁵ | Z | R² | Step Altered | MS Data |
|---|---|---|---|---|---|
| 4n | i-Pr(Et)N | —NH— | (6-chloro-2-(methylamino)quinazolin-4-yl) | n/a | 491.7 |

TABLE 4-B

The chemical names of the specific examples illustrated in Table 4-A are tabulated below.

| Ex. | Name |
|---|---|
| 4a | N-(2-((1S,2R,4R)-4-(isopropyl(methyl)amino)-2-(methoxymethyl)cyclohexylamino)-2-oxoethyl)-3-(trifluoromethyl)benzamide |
| 4b | 1-(2-((2-((1S,2R,4R)-4-(isopropyl(methyl)amino)-2-(methoxymethyl)cyclohexylamino)-2-oxoethyl)carbamoyl)-4-(trifluoromethyl)phenyl)-3-isopropylurea |
| 4c | N-(2-((2-((1S,2R,4R)-4-(isopropyl(methyl)amino)-2-(methoxymethyl)cyclohexylamino)-2-oxoethyl)carbamoyl)-4-(trifluoromethyl)phenyl)azetidine-1-carboxamide |
| 4d | 3-tert-butyl-4-hydroxy-N-(2-((1S,2R,4R)-4-(isopropyl(methyl)amino)-2-(methoxymethyl)cyclohexylamino)-2-oxoethyl)benzamide |
| 4e | 3-tert-butyl-N-(2-((1S,2R,4R)-4-(isopropyl(methyl)amino)-2-(methoxymethyl)cyclohexylamino)-2-oxoethyl)-1-methyl-1H-pyrazole-5-carboxamide |
| 4f | N-(2-((1S,2R,4R)-4-(ethyl(isopropyl)amino)-2-(methoxymethyl)cyclohexylamino)-2-oxoethyl)-3-(trifluoromethyl)benzamide |
| 4g | N-((1S,2R,4R)-4-(isopropyl(methyl)amino)-2-(methoxymethyl)cyclohexyl)-2-(5-(trifluoromethyl)benzo[d]isoxazol-3-ylamino)acetamide |
| 4h | N-((1S,2R,4R)-4-(isopropyl(ethyl)amino)-2-(methoxymethyl)cyclohexyl)-2-(5-(trifluoromethyl)benzo[d]isoxazol-3-ylamino)acetamide |
| 4i | N-((1S,2R,4R)-4-(isopropyl(methyl)amino)-2-(methoxymethyl)cyclohexyl)-2-(6-(trifluoromethyl)quinazolin-4-ylamino)acetamide |
| 4j | N-((1S,2R,4R)-4-(ethyl(isopropyl)amino)-2-(methoxymethyl)cyclohexyl)-2-(6-(trifluoromethyl)quinazolin-4-ylamino)acetamide |
| 4k | 2-amino-N-(2-((1S,2R,4R)-4-(isopropyl(methyl)amino)-2-(methoxymethyl)cyclohexylamino)-2-oxoethyl)-5-(trifluoromethoxy)benzamide |
| 4m | 2-(2,6-dichloroquinazolin-4-ylamino)-N-((1S,2R,4R)-4-(ethyl(isopropyl)amino)-2-(methoxymethyl)cyclohexyl)acetamide |
| 4n | 2-(6-chloro-2-(dimethylamino)quinazolin-4-ylamino)-N-((1S,2R,4R)-4-(ethyl(isopropyl)amino)-2-(methoxymethyl)cyclohexyl)acetamide |

Examples 5a-5k

Example 5a

Synthesis of N-(2-((1S,2R,4R)-4-(isopropyl(methyl)amino)-2-(phenoxymethyl)cyclohexylamino)-2-oxoethyl)-3-(trifluoromethyl)benzamide Example 5a, Step 1: A solution of tert-butyl (1R,3R,4S)-4-benzyloxycarbonylamino-3-(hydroxymethyl)cyclohexylcarbamate (120 mg) in tetrahydrofuran (3 mL) was treated with phenol (45 mg) and triphenylphosphine (125 mg). The mixture was stirred at rt and treated dropwise over about 3 minutes with diethyl azodicarboxylate (74 µL). The mixture was stirred for 3.5 h, then was concentrated under vacuum. The residue was purified by flash chromatography on silica gel, eluting with 1:5 v/v ethyl acetate/hexane, to provide tert-butyl (1R,3R,4S)-4-benzyloxycarbonylamino-3-(phenoxymethyl)cyclohexylcarbamate as a white glassy foam (110 mg). MS found: (M+H)⁺=455.3.

Example 5a, Step 2: Following the procedure of Example 4a, Step 2, tert-butyl (1R,3R,4S)-4-benzyloxycarbonylamino-3-(phenoxymethyl)cyclohexylcarbamate (105 mg) was converted to tert-butyl (1R,3R,4S)-4-amino-3-(phenoxymethyl)cyclohexylcarbamate, which was used without further purification. MS found: (M+H)⁺=321.2.

Example 5a, Step 3: Following the procedure of Example 4a, Step 3, the crude tert-butyl (1R,3R,4S)-4-amino-3-(phenoxymethyl)cyclohexylcarbamate prepared in Example 5a, Step 2 was converted to tert-butyl (1R,3R,4S)-3-(phenoxymethyl)-4-(2-(3-(trifluoromethyl)benzamido)acetamido)cyclohexylcarbamate as an off-white glassy foam (105 mg). MS found: (M+H)⁺=550.3.

Example 5a, Step 4: Following the procedure of Example 4a, Step 4, tert-butyl (1R,3R,4S)-3-(phenoxymethyl)-4-(2-(3-(trifluoromethyl)benzamido)acetamido)cyclohexylcarbamate (92 mg) was converted to the trifluoroacetic acid salt of N-(2-((1S,2R,4R)-4-amino-2-(phenoxymethyl)cyclohexylamino)-2-oxoethyl)-3-(trifluoromethyl)benzamide (65 mg). MS found: (M+H)⁺=450.2.

Example 5a, Step 5: Following the procedure of Example 4a, Step 5, the trifluoroacetic acid salt of N-(2-((1S,2R,4R)-4-amino-2-(phenoxymethyl)cyclohexylamino)-2-oxoethyl)-3-(trifluoromethyl)benzamide (65 mg) was converted to the trifluoroacetic acid salt of the title product, N-(2-((1S,2R,4R)-4-(isopropyl(methyl)amino)-2-(phenoxymethyl)cyclohexylamino)-2-oxoethyl)-3-(trifluoromethyl)benzamide, as a white powder (52 mg) after lyophilization. MS found: (M+H)⁺=506.3.

Example 5b

Synthesis of N-(2-((2-((1S,2R,4R)-4-(isopropyl(methyl)amino)-2-(phenoxymethyl)cyclohexylamino)-2-oxoethyl)carbamoyl)-4-(trifluoromethyl)phenyl)azetidine-1-carboxamide The trifluoroacetic acid salt of the title compound was prepared following the procedures of Example 5a, but substituting 2-(2-(azetidine-1-carboxamido)-5-(trifluoromethyl)benzamido)acetic acid (see PCT WO 0250019) for 2-(3-(trifluoromethyl)benzamido)acetic acid in Step 3. MS found: (M+H)⁺=604.3.

Example 5c

Synthesis of N-(2-((1S,2R,4R)-4-(isopropyl(methyl)amino)-2-((pyridin-3-yloxy)methyl)cyclohexylamino)-2-oxoethyl)-3-(trifluoromethyl)benzamide Example 5c, Step 1: Following the procedure of Example 5a, Step 1, but substituting 3-hydroxypyridine for phenol, tert-butyl (1R,3R,4S)-4-benzyloxycarbonylamino-3-(hydroxymethyl)cyclohexylcarbamate (100 mg) was converted to tert-butyl (1R,3R,4S)-4-benzyloxycarbonylamino-3-((pyridin-3-yloxy)methyl)cyclohexylcarbamate (101 mg). MS found: (M+H)⁺=456.2.

Example 5c, Step 2: Following the procedures of Example 4a, Steps 2 through 4, tert-butyl (1R,3R,4S)-4-benzyloxycarbonylamino-3-((pyridin-3-yloxy)methyl)cyclohexylcarbamate (101 mg) was converted to the trifluoroacetic acid salt of N-(2-((1S,2R,4R)-4-amino-2-((pyridin-3-yloxy)methyl)cyclohexylamino)-2-oxoethyl)-3-(trifluoromethyl)benzamide, used without further purification. MS found: (M+H)⁺=451.

Example 5c, Step 3: The sample of the trifluoroacetic acid salt of N-(2-((1S,2R,4R)-4-amino-2-((pyridin-3-yloxy)methyl)cyclohexylamino)-2-oxoethyl)-3-(trifluoromethyl)benzamide prepared in Example 5c, Step 2 was dissolved in methanol (3 mL) and treated sequentially with acetone (ca. 1 mL) and sodium cyanoborohydride (28 mg). The mixture was stirred at rt for 3 h. Aqueous formaldehyde (ca. 1 mL) was added and the mixture was stirred at rt for 3 days. The mixture was concentrated under vacuum and the residue was taken up in ethyl acetate and saturated aqueous NaHCO₃. The phases were separated and the aqueous phase was extracted three times with ethyl acetate. The combined organic phases were dried over Na₂SO₄ and concentrated. Purification by reverse phase HPLC and lyophilization provided the bis-trifluoroacetic acid salt of the title product, N-(2-((1S,2R,4R)-4-(isopropyl(methyl)amino)-2-((pyridin-3-yloxy)methyl)cyclohexylamino)-2-oxoethyl)-3-(trifluoromethyl)benzamide, as a white powder (10 mg). MS found: (M+H)⁺=507.2.

Example 5d

Synthesis of methyl 2-(((1R,2S,5R)-5-(isopropyl(methyl)amino)-2-(2-(3-(trifluoromethyl)benzamido)acetamido)cyclohexyl)methoxy)benzoate Example 5d, Step 1: Following the procedure of Example 5a, Step 1, but substituting methyl 2-hydroxybenzoate for phenol, tert-butyl (1R,3R,4S)-4-benzyloxycarbonylamino-3-(hydroxymethyl)cyclohexylcarbamate (200 mg) was converted to methyl 2-(((1R,2S,5R)-2-(benzyloxycarbonylamino)-5-(tert-butoxycarbonylamino)cyclohexyl)methoxy)benzoate (213 mg) after radial preparative-layer chromatography. MS found: (M+H)⁺=513.4.

Example 5d, Step 2: Following the procedure of Example 4a, Step 2, methyl 2-(((1R,2S,5R)-2-(benzyloxycarbonylamino)-5-(tert-butoxycarbonylamino)cyclohexyl)methoxy)benzoate (200 mg) was converted to methyl 2-(((1R,2S,5R)-2-amino-5-(tert-butoxycarbonylamino)cyclohexyl)methoxy)benzoate (144 mg). MS found: (M+H)⁺=379.3.

Example 5d, Step 3: Following the procedure of Example 4d, Step 1, methyl 2-(((1R,2S,5R)-2-amino-5-(tert-butoxycarbonylamino)cyclohexyl)methoxy)benzoate (144 mg) was converted to methyl 2-(((1R,2S,5R)-5-(tert-butoxycarbonylamino)-2-(2-(3-trifluoromethyl)benzamido)acetamido)cyclohexyl)methoxy)benzoate (200 mg). MS found: (M+H)⁺=608.4.

Example 5d, Step 4: A solution of methyl 2-(((1R,2S,5R)-5-(tert-butoxycarbonylamino)-2-(2-(3-trifluoromethyl)benzamido)acetamido)cyclohexyl)methoxy)benzoate (200 mg) in dichloromethane (2 mL) was treated with trifluoroacetic acid (1 mL) and the mixture was stirred at rt for 1 h. The mixture was concentrated and the residue was dissolved in methanol (5 mL). The solution was treated sequentially with acetone (2 mL) and sodium cyanoborohydride (204 mg), and the mixture was stirred overnight at rt. The mixture was treated sequentially with additional sodium cyanoborohydride (102 mg) and aqueous formaldehyde (0.5 mL). The mixture was stirred for 1 h at rt, then was concentrated under vacuum. Purification by reverse phase HPLC and lyophilization provided the trifluoroacetic acid salt of the title product, methyl 2-(((1R,2S,5R)-5-(isopropyl(methyl)amino)-2-(2-(3-(trifluoromethyl)benzamido)acetamido)cyclohexyl)methoxy)benzoate, as a white powder (185 mg). MS found: (M+H)⁺=564.5.

Example 5e

Synthesis of 2-(((1R,2S,5R)-5-(isopropyl(methyl)amino)-2-(2-(3-trifluoromethyl)benzamido)acetamido)cyclohexyl)methoxy)benzoic acid A solution of the trifluoroacetic acid salt of methyl 2-(((1R,2S,5R)-5-(isopropyl(methyl)amino)-2-(2-(3-(trifluoromethyl)benzamido)acetamido)cyclohexyl)methoxy)benzoate (83 mg) in tetrahydrofuran (1 mL) was treated with 50% aqueous NaOH (1 mL) and the mixture was stirred overnight at rt. The mixture was concentrated and the residue was purified by reverse phase HPLC and lyophilization to provide the trifluoroacetic acid salt of the title compound, 2-(((1R,2S,5R)-5-(isopropyl(methyl)amino)-2-(2-(3-trifluoromethyl)benzamido)acetamido)cyclohexyl)methoxy)benzoic acid as a white powder (80 mg). MS found: $(M+H)^+$=550.4.

Example 5f

Synthesis of methyl 3-(((1R,2S,5R)-5-(isopropyl(methyl)amino)-2-(2-(3-(trifluoromethyl)benzamido)acetamido)cyclohexyl)methoxy)benzoate The trifluoroacetic acid salt of the title compound was prepared following the procedures of Example 5d, substituting methyl 3-hydroxybenzoate for methyl 2-hydroxybenzoate in Step 1. MS found: $(M+H)^+$=564.4.

Example 5g

Synthesis of 3-(((1R,2S,5R)-5-(isopropyl(methyl)amino)-2-(2-(3-trifluoromethyl)benzamido)acetamido)cyclohexyl)methoxy) benzoic acid The trifluoroacetic acid salt of the title compound was prepared following the procedure of Example 5e, substituting methyl 3-(((1R,2S,5R)-5-(isopropyl(methyl)amino)-2-(2-(3-(trifluoromethyl)benzamido)acetamido)cyclohexyl)methoxy)benzoate for methyl 2-(((1R,2S,5R)-5-(isopropyl(methyl)amino)-2-(2-(3-(trifluoromethyl)benzamido)acetamido)cyclohexyl)methoxy)benzoate. MS found: $(M+H)^+$=550.4.

Example 5 h

Synthesis of ethyl 4-(((1R,2S,5R)-5-(isopropyl(methyl)amino)-2-(2-(3-(trifluoromethyl)benzamido)acetamido)cyclohexyl)methoxy)benzoate The trifluoroacetic acid salt of the title compound was prepared following the procedures of Example 5d, substituting ethyl 4-hydroxybenzoate for methyl 2-hydroxybenzoate in Step 1. MS found: $(M+H)^+$=578.4.

Example 5i

Synthesis of 4-(((1R,2S,5R)-5-(isopropyl(methyl)amino)-2-(2-(3-trifluoromethyl)benzamido)acetamido)cyclohexyl)methoxy)benzoic acid The trifluoroacetic acid salt of the title compound was prepared following the procedure of Example 5e, substituting ethyl 4-(((1R,2S,5R)-5-(isopropyl(methyl)amino)-2-(2-(3-(trifluoromethyl)benzamido)acetamido)cyclohexyl)methoxy)benzoate for methyl 2-(((1R,2S,5R)-5-(isopropyl(methyl)amino)-2-(2-(3-(trifluoromethyl)benzamido)acetamido)cyclohexyl)methoxy)benzoate. MS found: $(M+H)^+$=550.4.

Example 5j

Synthesis of N-(2-((1S,2S,4R)-4-(isopropyl(methyl)amino)-2-((2-oxopyridin-1(2H)-yl)methyl)cyclohexylamino)-2-oxoethyl)-3-(trifluoromethyl)benzamide Example 5j, Step 1: A solution of tert-butyl(1R,3R,4S)-(4-benzyloxycarbonylamino-3-hydroxymethyl-cyclohexyl)carbamate (1.0 g), 2-hydroxypyridine (377 mg), and tributylphosphine (0.78 mL) in benzene (20 mL) was stirred at 0° C. and treated dropwise over 15 min with diisopropyl azodicarboxylate (0.8 g). The mixture was stirred overnight at rt and concentrated under vacuum. The residue was purified by radial preparative-layer chromatography to provide tert-butyl(1R,3S,4S)-(4-benzyloxycarbonylamino-3-((2-oxopyridin-1(2H)-yl)methyl)cyclohexyl)carbamic acid (1.06 g). MS found: $(M+H)^+$=456.4.

Example 5j, Step 2: Following the procedure of Example 4a, Step 2, but substituting ethanol in place of methanol as the solvent, tert-butyl(1R,3S,4S)-(4-benzyloxycarbonylamino-3-((2-oxopyridin-1(2H)-yl)methyl)cyclohexyl)carbamate (54 mg) was converted to tert-butyl(1R,3S,4S)-4-amino-3-((2-oxopyridin-1.(2H)-yl)methyl)cyclohexylcarbamate (36 mg). MS found: $(M+H)^+$=322.2.

Example 5j, Step 3: Following the procedure of Example 4d, Step 1, but substituting 2-(3-trifluoromethyl)benzamido)acetic acid for 2-(benzyloxycarbonylamino)acetic acid, tert-butyl(1R,3S,4S)-4-amino-3-((2-oxopyridin-1(2H)yl)methyl)cyclohexylcarbamate (36 mg) was converted to tert-butyl(1R,3S,4S)-3-((2-oxopyridin-1(2H)yl)methyl)-4-(2-(3-(trifluoroethyl)benzamido)acetamido)cyclohexylcarbamate (42 mg). MS found: $(M+H)^+$=551.4.

Example 5j, Step 4: Following the procedure of Example 5d, Step 4, tert-butyl(1R,3S,4S)-3-((2-oxopyridin-1(2H)yl)methyl)-4-(2-(3-(trifluoroethyl)benzamido)acetamido)cyclohexylcarbamate (42 mg) was converted to the trifluoroacetic acid salt of the title product, N-(2-((1S,2S,4R)-4-(isopropyl(methyl)amino)-2-((2-oxopyridin-1(2H)-yl)methyl)cyclohexylamino)-2-oxoethyl)-3-(trifluoromethyl)benzamide, as a white powder (25 mg) after purification by reverse phase HPLC and lyophilization. MS found: $(M+H)^+$=507.3

Example 5k: Synthesis of N-(2-((1S,2S,4R)-4-(dimethylamino)-2-(pyrrolidin-1-ylmethyl)cyclohexylamino)-2-oxoethyl)-3-(trifluoromethyl)benzamide Example 5k, Step 1: To a solution of oxalyl chloride (0.04 mL, 0.48 mmol) in 20 mL of $CH_2Cl_2$ cooled to −78° C. was added DMSO (0.08 mL, 0.96 mmol). Ten minutes later, (1R,3R,4S)-(4-benzyloxycarbonylamino-3-hydroxymethyl-cyclohexyl)-carbamic acid tert-butyl ester (150 mg, 0.4 mmol, see procedure 21a) in 10 mL of $CH_2Cl_2$ was added followed by $iPr_2NEt$ (0.35 mL, 2 mmol). The reaction mixture was stirred at −20° C. for 3 h before water was added. The aqueous phase was extracted with EtOAc (2×25 mL), and the extracts were combined, dried over $Na_2SO_4$, and concentrated to afford 120 mg of crude aldehyde. This material was dissolved in 20 mL of $CH_2Cl_2$ and the resulting solutoin was charged with pyrrolidine (0.05 mL, 0.58 mmol), followed by $NaH(OAc)_3$ (124 mg, 0.58 mmol). The reaction mixture was stirred at RT for 3 h before water was added. The aqueous phase was extracted with EtOAc (2×25 mL), and the extracts were combined, dried over $Na_2SO_4$, and concentrated to afford (1R,3R,4S)-(4-benzyloxycarbonylamino-3-pyrrolidin-1-ylmethyl-cyclohexyl)-carbamic acid tert-butyl ester (90 mg, 72%). MS found: $(M+H)^+$=431.

Example 5k, Step 2: A sample of (1R,3R,4S)-(4-benzyloxycarbonylamino-3-pyrrolidin-1-ylmethyl-cyclohexyl)-carbamic acid tert-butyl ester was carried through the procedures described in Example 1r, Steps 2-3, to afford (1R,3R,4S)-{3-pyrrolidin-1-ylmethyl-4-[2-(3-trifluoromethyl-benzoylamino)-acetylamino]-cyclohexyl}-carbamic acid tert-butyl ester, which was then carried through the procedure described in Example 1r, Step 4 (with the omission of acetone; only formaledhyde was used in the reductive amination) to afford the TFA salt of the title compound after RP-HPLC. MS found: $(M+H)^+$=454.

TABLE 5A

The compounds in the following table were made using the methods exemplified above. See Table 1-A for a complete description of the table headings.

| Ex | R⁵ | R⁶ | R² | Step Alt. | MS Data |
|---|---|---|---|---|---|
| 5a | i-Pr(Me)N | phenoxy | 3-CF₃-phenyl | n/a | 506.3 |
| 5b | i-Pr(Me)N | phenoxy | 4-CF₃-2-(azetidine-1-carboxamido)phenyl | 5a, Step 3 | 604.3 |
| 5c | i-Pr(Me)N | pyridin-3-yloxy | 3-CF₃-phenyl | n/a | 507.2 |
| 5d | i-Pr(Me)N | 2-COOMe-phenoxy | 3-CF₃-phenyl | n/a | 564.5 |
| 5e | i-Pr(Me)N | 2-COOH-phenoxy | 3-CF₃-phenyl | n/a | 550.4 |
| 5f | i-Pr(Me)N | 3-COOMe-phenoxy | 3-CF₃-phenyl | 5d, Step 1 | 564.4 |
| 5g | i-Pr(Me)N | 3-COOH-phenoxy | 3-CF₃-phenyl | 5e | 550.4 |
| 5h | i-Pr(Me)N | 4-COOEt-phenoxy | 3-CF₃-phenyl | 5d, Step 1 | 578.4 |

TABLE 5A-continued

The compounds in the following table were made using the methods exemplified above. See Table 1-A for a complete description of the table headings.

| Ex | R⁵ | R⁶ | R² | Step Alt. | MS Data |
|----|-----|-----|-----|-----------|---------|
| 5i | i-Pr(Me)N | -O-C₆H₄-COOH (4-position) | 3-CF₃-phenyl | 5e | 550.4 |
| 5j | i-Pr(Me)N | 2-oxopyridin-1(2H)-yl-methyl | 3-CF₃-phenyl | | |
| 5k | Me₂N | pyrrolidin-1-yl-methyl | 3-CF₃-phenyl | n/a | 454 |

TABLE 5-B

The chemical names of the specific examples illustrated in Table 5-A are tabulated below.

| Ex. | Name |
|-----|------|
| 5a | N-(2-((1S,2R,4R)-4-(isopropyl(methyl)amino)-2-(phenoxymethyl)cyclohexylamino)-2-oxoethyl)-3-(trifluoromethyl)benzamide |
| 5b | N-(2-((2-((1S,2R,4R)-4-(isopropyl(methyl)amino)-2-(phenoxymethyl)cyclohexylamino)-2-oxoethyl)carbamoyl)-4-(trifluoromethyl)phenyl)azetidine-1-carboxamide |
| 5c | N-(2-((1S,2R,4R)-4-(isopropyl(methyl)amino)-2-((pyridin-3-yloxy)methyl)cyclohexylamino)-2-oxoethyl)-3-(trifluoromethyl)benzamide |
| 5d | methyl 2-(((1R,2S,5R)-5-(isopropyl(methyl)amino)-2-(2-(3-(trifluoromethyl)benzamido)acetamido)cyclohexyl)methoxy)benzoate |
| 5e | 2-(((1R,2S,5R)-5-(isopropyl(methyl)amino)-2-(2-(3-trifluoromethyl)benzamido)acetamido)cyclohexyl)methoxy)benzoic acid |
| 5f | methyl 3-(((1R,2S,5R)-5-(isopropyl(methyl)amino)-2-(2-(3-(trifluoromethyl)benzamido)acetamido)cyclohexyl)methoxy)benzoate |
| 5g | 3-(((1R,2S,5R)-5-(isopropyl(methyl)amino)-2-(2-(3-trifluoromethyl)benzamido)acetamido)cyclohexyl)methoxy)benzoic acid |
| 5h | ethyl 4-(((1R,2S,5R)-5-(isopropyl(methyl)amino)-2-(2-(3-(trifluoromethyl)benzamido)acetamido)cyclohexyl)methoxy)benzoate |
| 5i | 4-(((1R,2S,5R)-5-(isopropyl(methyl)amino)-2-(2-(3-trifluoromethyl)benzamido)acetamido)cyclohexyl)methoxy)benzoic acid |
| 5j | N-(2-((1S,2S,4R)-4-(isopropyl(methyl)amino)-2-((2-oxopyridin-1(2H)-yl)methyl)cyclohexylamino)-2-oxoethyl)-3-(trifluoromethyl)benzamide |
| 5k | N-(2-((1S,2S,4R)-4-(dimethylamino)-2-(pyrrolidin-1-ylmethyl)cyclohexylamino)-2-oxoethyl)-3-(trifluoromethyl)benzamide |

Example 6a -6g

Example 6a

Synthesis of N-(2-((1S,2R,4R)-2-(tert-butoxymethyl)-4-(isopropyl(methyl)amino)cyclohexylamino)-2-oxoethyl)-3-(trifluoromethyl)benzamide A solution of N-(2-((1S,2R,4R)-2-(hydroxymethyl)-4-(isopropyl(methyl)amino)cyclohexylamino)-2-oxoethyl)-3-(trifluoromethyl)benzamide (70 mg) in dichloromethane (5 mL) in a pressure tube was treated with p-toluenesulfonic acid hydrate (122 mg), and the mixture was cooled to −78° C. Isobutylene (condensed at −78° C., approximately 2 mL) was added, and the tube was sealed. The mixture was stirred at rt for 90 h. The tube was cooled to −10° C., unsealed, and the mixture was stirred at rt until the excess isobutylene had evaporated. The residue was diluted with dichloromethane, washed with saturated aqueous NaHCO₃, dried over Na₂SO₄ and concentrated under vacuum. The residue was purified by reverse-phase HPLC and lyophilized to provide the trifluoroacetic acid salt of the title compound as a white powder (24 mg). MS found: (M+H)⁺=486.3.

Example 6b

Synthesis of ((1R,2S,5R)-5-(isopropyl(methyl)amino)-2-(2-(3-(trifluoromethyl)benzamido)acetamido)cyclohexyl)methylphenylcarbamate Example 6b, Step 1: A solution of tert-butyl(1R,3R,4S)-4-benzyloxycarbonylamino-3-(hydroxymethyl)cyclohexylcarbamate (75 mg) in dichloromethane (1 mL) and N,N-dimethylformamide (0.1 mL) was-treated with triethylamine (3 µL) and phenyl isocyanate (33 µL), and the mixture was and stirred at rt for 18 h. Additional phenyl isocyanate (22 µL) was added and stirring was continued for 96 h. The mixture was concentrated, and the residue was purified by flash column chromatography on silica gel, eluting with 4:6 v/v ethyl acetate/hexane, to provide tert-butyl(1R,3R,4S)-(4-benzyloxycarbonylamino-3-phenylcarbamoyloxymethylcyclohexyl)carbamate as a white glassy foam (85 mg). MS found: (M+H)⁺=498.3.

Example 6b, Step 2: Following the procedure of Example 4a, Step 2, tert-butyl(1R,3R,4S)-(4-benzyloxycarbonylamino-3-phenylcarbamoyloxymethylcyclohexyl)carbamate (80 mg) was converted to tert-butyl(1R,3R,4S)-(4-amino-3-phenylcarbamoyloxymethylcyclohexyl)carbamate as an off-pale yellowish solid (63 mg). MS found: (M+H)⁺=364.3.

Example 6b, Step 3: Following the procedure of Example 4a, Step 3, tert-butyl(1R,3R,4S)-(4-amino-3-phenylcarbamoyloxymethylcyclohexyl)carbamate (58 mg) was converted to tert-butyl(1R,3R,4S)-3-(phenylcarbamoyloxymethyl)-4-(2-(3-(trifluoromethyl)benzamido)acetamido)cyclohexylcarbamate as a white solid (68 mg). MS found: (M+H)⁺=593.3.

Example 6b, Step 4: Following the procedure of Example 4a, Step 4, tert-butyl(1R,3R,4S)-3-(phenylcarbamoyloxymethyl)-4-(2-(3-(trifluoromethyl)benzamido)acetamido)cyclohexylcarbamate (68 mg) was converted to the trifluoroacetic acid salt of ((1R,2S,5R)-5-amino-2-(2-(3-(trifluoromethyl)benzamido)acetamido)cyclohexyl)methylphenylcarbamate as a white solid (58 mg). MS found: (M+H)⁺=493.3.

Example 6b, Step 5: Following the procedure of Example 4a, Step 5, the trifluoroacetic acid salt of ((1R,2S,5R)-5-amino-2-(2-(3-(trifluoromethyl)benzamido)acetamido)cyclohexyl)methylphenylcarbamate (45 mg) was converted to the trifluoroacetic acid salt of ((1R,2S,5R)-5-(isopropyl(methyl)amino)-2-(2-(3-(trifluoromethyl)benzamido)acetamido)cyclohexyl)methylphenylcarbamate as a white powder (46 mg) after purification by reverse phase HPLC and lyophilization. MS found: (M+H)⁺=549.3.

Example 6c

Synthesis of ((1R,2S,5R)-5-(isopropyl(methyl)amino)-2-(2-(3-(trifluoromethyl)benzamido)acetamido)cyclohexyl)methyldimethylcarbamate Example 6c, Step 1: Sodium hydride (60% in mineral oil, 22 mg) was washed twice with hexane and dried under nitrogen. N,N-dimethylformamide (0.5 mL) was added, and the stirred suspension was treated with a solution of tert-butyl(1R,3R,4S)-3-(hydroxymethyl)-4-(2-(3-(trifluoromethyl)benzamido)acetamido)cyclohexylcarbamate (56 mg) in N,N-dimethylformamide (0.5 mL). The mixture was stirred at rt for 10 min, then was treated with dimethylcarbamyl chloride (16 µL) and stirred for 18 h. 1.0 M aqueous HCl (1 mL) was added, followed by water. The mixture was extracted four times with ethyl acetate. The combined organic phases were washed twice with water, then with brine, and dried over Na₂SO₄ and concentrated under vacuum. The residue was purified by flash column chromatography on silica gel, eluting with 1:3 v/v hexane/ethyl acetate to provide tert-butyl(1R,3R,4S)-3-(dimethylcarbamyloxymethyl)-4-(2-(3-(trifluoromethyl)benzamido)acetamido)cyclohexylcarbamate as a glassy foam (26 mg). MS found: (M+H)⁺=545.3.

Example 6c, Step 2: Sequentially following the procedures of Example 4a, Steps 4 and 5, tert-butyl(1R,3R,4S)-3-(dimethylcarbamyloxymethyl)-4-(2-(3-(trifluoromethyl)benzamido)acetamido)cyclohexylcarbamate was converted to the trifluoroacetic acid salt of the title compound, ((1R,2S,5R)-5-(isopropyl(methyl)amino)-2-(2-(3-(trifluoromethyl)benzamido)acetamido)cyclohexyl)methyldimethylcarbamate, as a white powder (26 mg) after purification by reverse phase HPLC and lyophilization. MS found: (M+H)⁺=501.3.

Example 6d

Synthesis of ((1R,2S,5R)-5-(isopropyl(methyl)amino)-2-(2-(3-(trifluoromethyl)benzamido)acetamido)cyclohexyl)methylmorpholine-4-carboxylate The trifluoroacetic acid salt of the title compound was prepared following the procedures of Example 6c, substituting morpholine-4-carbonyl chloride for dimethylcarbamyl chloride in Step 1. MS found: (M+H)⁺=543.3.

Example 6e

Synthesis of N-(2-((1S,2R,4R)-4-(isopropyl(methyl)amino)-2-(ethoxymethyl)cyclohexylamino)-2-oxoethyl)-3-(trifluoromethyl)benzamide The trifluoroacetic acid salt of the title compound was prepared following the procedures of Example 4a, substituting iodoethane for iodomethane in Step 1. MS found: (M+H)⁺=458.4

Example 6f

Synthesis of N-(2-((1S,2S,4R)-4-(isopropyl(methyl)amino)-2-(2-methoxyethyl)cyclohexylamino)-2-oxoethyl)-3-(trifluoromethyl)benzamide Example 6f, Step 1: Following the protocol described above in Example 2o, Step 1, 1.3 g of tert-butyl(1R,2S,5R,7R/S)-2-(benzyloxycarbonylamino)-7-hydroxy-6-aza-bicyclo[3.2.1]octane-6-carboxylate was combined with a solution of ylide formed from 1.7 g of methyl triphenyl phosphonium iodide and 8.5 mL of 0.5 M KHMDS to afford [(1S,2R,4R)-[4-tert-butoxycarbonylamino-2-(vinyl)-cyclohexyl]-carbamic acid benzyl ester after silica gel chromatography (0.50 g). MS found: (M+H)⁺=375.2.

Example 6f, Step 2: The compound [(1S,2R,4R)-[4-tert-butoxycarbonylamino-2-(vinyl)-cyclohexyl]-carbamic acid benzyl ester (0.82 g, 2.2 mmol) was dissolved in THF (15 mL). The resultant solution was cooled to 0° C. and charged with 9-BBN (11 mL of a 0.5 M solution in THF). The mixture was stirred for 20 h at RT and then quenched sequentially with aqueous sodium acetate (0.6 g in 1.5 mL water) and 30% hydrogen peroxide (1.5 mL). This was stirred at RT for 14 h and partitioned between EtOAc and sat. NaHCO₃. The aqueous phase was extracted with EtOAc, and the combined organic extracts were washed with brine, dried (Na₂SO₄), filtered, and concentrated in vacuo. The residue was purified by silica gel chromatography to afford [(1S,2R,4R)-[4-tert-butoxycarbonylamino-2-(hydroxyethyl)-cyclohexyl]-carbamic acid benzyl ester (0.42 g) as a white foam. MS found: (M+H)⁺=393.

Example 6f, Step 3: A solution of [(1S,2R,4R)-[4-tert-butoxycarbonylamino-2-(hydroxyethyl)-cyclohexyl]-carbamic acid benzyl ester (0.42 g, 1.07 mmol) in DMF (4 mL) was charged with iodomethane (20 mL) and Ag₂O (1.24 g, 5.35 mmol) and stirred at RT for 14 h. The mixture was filtered and the filtrate was diluted with sat. NaHCO₃ and minimum EtOAc. The mixture was separated (organic on bottom). The aqueous was extracted with EtOAc, and the combined organic extracts were washed with brine, dried (Na₂SO₄), filtered, and concentrated in vacuo. The residue was purified by silica gel chromatography to afford [(1S, 2R,4R)-[4-tert-butoxycarbonylamino-2-(methoxyethyl)-cyclohexyl]-carbamic acid benzyl ester (0.255 g). MS found: (M+H)⁺=429.2.

Example 6f, Step 4: A sample of [(1S,2R,4R)-[4-tert-butoxycarbonylamino-2-(methoxyethyl)-cyclohexyl]-carbamic acid benzyl ester was taken through the procedures described in Example 2r, Steps 2-4, to afford the TFA of the title compound as a white powder after lyopholization. MS found: (M+H)⁺=458.

TABLE 6-A

The compounds in the following table were made using the methods exemplified above. See Table 1-A for a complete description of the table headings.

| Ex. | R⁶ | R⁵ | Step Altered | MS Data |
|---|---|---|---|---|
| 6a | O-tBu | i-Pr(Me)N | n/a | 486.3 |
| 6b | HN-phenyl carbamate | i-Pr(Me)N | 4a Step 1 | 549.3 |
| 6c | N,N-dimethyl carbamate | i-Pr(Me)N | n/a | 501.3 |
| 6d | morpholine carbamate | i-Pr(Me)N | 6c Step 1 | 543.3 |
| 6e | OEt | i-Pr(Me)N | 4a Step 1 | 458.4 |
| 6f | CH₂OMe | i-Pr(Me)N | n/a | 458 |
| 6g | CH₂OMe | i-Pr(Me)N | 6f Step 4 | 472 |

TABLE 6-B

The chemical names of the specific examples illustrated in Table 6-A are tabulated below.

| Ex. | Name |
|---|---|
| 6a | N-(2-((1S,2R,4R)-2-(tert-butoxymethyl)-4-(isopropyl(methyl)amino)cyclohexylamino)-2-oxoethyl)-3-(trifluoromethyl)benzamide |
| 6b | ((1R,2S,5R)-5-(isopropyl(methyl)amino)-2-(2-(3-(trifluoromethyl)benzamido)acetamido)cyclohexyl)-methyl phenylcarbamate |
| 6c | ((1R,2S,5R)-5-(isopropyl(methyl)amino)-2-(2-(3-(trifluoromethyl)benzamido)acetamido)cyclohexyl)-methyl dimethylcarbamate |
| 6d | ((1R,2S,5R)-5-(isopropyl(methyl)amino)-2-(2-(3-(trifluoromethyl)benzamido)acetamido)cyclohexyl)-methyl morpholine-4-carboxylate |
| 6e | N-(2-((1S,2R,4R)-4-(isopropyl(methyl)amino)-2-(ethoxymethyl)cyclohexylamino)-2-oxoethyl)-3-(trifluoromethyl)benzamide |
| 6f | N-(2-((1S,2S,4R)-4-(isopropyl(methyl)amino)-2-(2-methoxyethyl)cyclohexylamino)-2-oxoethyl)-3-(trifluoromethyl)benzamide |
| 6g | N-(2-((1S,2S,4R)-4-(ethyl(isopropyl)amino)-2-(2-methoxyethyl)cyclohexylamino)-2-oxoethyl)-3-(trifluoromethyl)benzamide |

Examples 7a-7i

Example 7a

Synthesis of tert-butyl 3-((1R,2S,5R)-5-(isopropyl (methyl)amino)-2-(2-(3-(trifluoromethyl)benzamido) acetamido)cyclohexyl)propanoate Example 7a, Step 1: A stirred suspension of NaH (60% in mineral oil, 160 mg) in tetrahydrofuran (3 mL) on an ice bath was treated dropwise over 10 min with tert-butyl dimethylphosphonoacetate (0.796 mL). The mixture was stirred at rt for 15 min, then was cooled again on an ice bath and treated with a solution of (1R,2S,5R)-tert-butyl 2-(benzyloxycarbonylamino)-7-hydroxy-6-aza-bicyclo[3.2.1]octane-6-carboxylate (432 mg) in tetrahydrofuran (3 mL). The mixture was stirred at rt for 3 h. The mixture was treated with saturated aqueous NH₄Cl and diluted with ethyl acetate. The phases were separated and the aqueous phase was extracted three times with ethyl acetate. The combined organic phases were dried over Na₂SO₄ and concentrated under vacuum. The residue was purified by flash column chromatography on silica gel, eluting with hexane/ethyl acetate to provide tert-butyl 3-((1S,2S,5R)-2-(benzyloxycarbonylamino)-5-(tert-butoxycarbonylamino)cyclohexyl) acrylate as a white glassy foam (308 mg). MS found: (M+H)⁺=475.5.

Example 7a, Step 2: Following the procedure of Example 4a, Step 2, tert-butyl 3-((1S,2S,5R)-2-(benzyloxycarbonylamino)-5-(tert-butoxycarbonylamino)cyclohexyl)acrylate (300 mg) was converted to tert-butyl 3-((1R,2S,5R)-2-amino-5-(tert-butoxycarbonylamino)cyclohexyl)propanoate as an off-white glassy foam (192 mg). MS found: (M+H)⁺=343.4.

Example 7a, Step 3: A solution of tert-butyl 3-((1R,2S,5R)-2-amino-5-(tert-butoxycarbonylamino)cyclohexyl)propanoate (90 mg) and 2-(benzyloxycarbonylamino)acetic acid (55 mg) in dichloromethane (2 mL) was treated sequentially with diisopropylethylamine (92 μL), 1-hydroxybenzotriazole hydrate (45 mg) and 1-ethyl-3-(3-dimethylaminopropyl)carbodiimide hydrochloride (61 mg). The mixture was stirred at rt for 20 h, then was diluted with dichloromethane, washed sequentially with 1 M aqueous HCl, saturated aqueous NaHCO$_3$ and water, dried over Na$_2$SO$_4$ and concentrated under vacuum to provide tert-butyl 3-((1R,2S,5R)-2-(2-(benzyloxycarbonylamino)acetamido)-5-(tert-butoxycarbonylamino)cyclohexyl)propanoate as a pale yellow gum (125 mg). MS found: (M+H)$^+$=534.5.

Example 7a, Step 4: Following the procedure of Example 4a, Step 2, tert-butyl 3-((1R,2S,5R)-2-(2-(benzyloxycarbonylamino)acetamido)-5-(tert-butoxycarbonylamino)cyclohexyl)propanoate (125 mg) was converted to tert-butyl 3-((1R,2S,5R)-2-(2-aminoacetamido)-5-(tert-butoxycarbonylamino)cyclohexyl)propanoate as a white glassy solid (103 mg). MS found: (M+H)$^+$=400.4.

Example 7a, Step 5: Following the procedure of Example 7a, Step 3, but substituting 3-(trifluoromethyl)benzoic acid (25 mg) for 2-(benzyloxycarbonylamino)acetic acid and using acetonitrile in place of dichloromethane as solvent, tert-butyl 3-((1R,2S,5R)-2-(2-aminoacetamido)-5-(tert-butoxycarbonylamino)cyclohexyl)propanoate (46 mg) was converted to tert-butyl 3-((1R,2S,5R)-5-(tert-butoxycarbonylamino)-2-(2-(3-(trifluoromethyl)benzamido)acetamido)cyclohexyl)propanoate as a glassy solid (67 mg). MS found: (M+H)$^+$=572.4.

Example 7a, Step 6: tert-butyl 3-((1R,2S,5R)-5-(tert-butoxycarbonylamino)-2-(2-(3-(trifluoromethyl)benzamido)acetamido)cyclohexyl)propanoate (66 mg) was dissolved in a 1.0 M solution of HCl in ethyl acetate. After the mixture was allowed to stand at rt for 1.5 h, it was concentrated under vacuum to provide a mixture of tert-butyl 3-((1R,2S,5R)-5-amino-2-(2-(3-(trifluoromethyl)benzamido)acetamido)cyclohexyl)propanoate and 3-((1R,2S,5R)-5-amino-2-(2-(3-(trifluoromethyl)benzamido)acetamido)cyclohexyl)propanoic acid, in a weight/weight ratio of about 7:3, as an off-white glassy solid (58 mg). This was used without further purification. MS found: (M+H)$^+$=472.4, 416.2.

Example 7a, Step 7: The crude mixture of tert-butyl 3-((1R,2S,5R)-5-amino-2-(2-(3-(trifluoromethyl)benzamido)acetamido)cyclohexyl)propanoate and 3-((1R,2S,5R)-5-amino-2-(2-(3-(trifluoromethyl)benzamido)acetamido)cyclohexyl)propanoic acid prepared in Example 7a, Step 6 was dissolved in 1,2-dichloroethane (2 mL) and treated sequentially with acetone (32 μL), acetic acid (25 μL) and sodium triacetoxyborohydride (92 mg). The mixture was stirred at rt for 19.5 h, then was treated with aqueous formaldehyde (33 μL). After 1.5 h, additional aqueous formaldehyde (20 μL) and sodium triacetoxyborohydride (50 mg) were added and the mixture was stirred for an additional 2.5 h. The mixture was concentrated under vacuum and the residue was partitioned between saturated aqueous NaHCO$_3$ and ethyl acetate. The aqueous phase was extracted twice with ethyl acetate and the combined organic phases were dried over Na$_2$SO$_4$ and concentrated under vacuum to provide the title product, tert-butyl 3-((1R,2S,5R)-5-(isopropyl(methyl)amino)-2-(2-(3-(trifluoromethyl)benzamido)acetamido)cyclohexyl)propanoate, as a glassy foam (45 mg). MS found: (M+H)$^+$=528.4.

Example 7b

Synthesis of 3-((1R,2S,5R)-5-(isopropyl(methyl) amino)-2-(2-(3-(trifluoromethyl)benzamido)acetamido)cyclohexyl)propanoic acid A solution of tert-butyl 3-((1R,2S,5R)-5-(isopropyl(methyl)amino)-2-(2-(3-(trifluoromethyl)benzamido)acetamido)cyclohexyl)propanoate (45 mg) in dichloromethane (2 mL) was treated with trifluoroacetic acid (2 mL) and stirred at rt. After 30 min, the mixture was concentrated under vacuum. The residue was purified by reverse phase HPLC and lyphilized to provide the trifluoroacetic acid salt of the title product, 3-((1R,2S,5R)-5-(isopropyl(methyl)amino)-2-(2-(3-(trifluoromethyl)benzamido)acetamido)cyclohexyl) propanoic acid, as a white powder (26 mg). MS found: (M+H)$^+$=472.3.

Example 7c

Synthesis of methyl 3-(2-((1R,2S,5R)-5-(isopropyl (methyl)amino)-2-(2-(3-(trifluoromethyl)benzamido) acetamido)cyclohexyl)ethyl)benzoate Example 7c, Step 1: A suspension of 3-(methoxycarbonyl)benzyltriphenylphosphonium bromide (1.8 g, see J. Chem. Soc. 1961, 5015) in tetrahydrofuran (5 mL) was stirred on an ice bath and treated dropwise over 10 min with a solution of potassium bis(trimethylsilyl)amide (0.5 M in toluene, 7.3 mL). The resulting yellow suspension was stirred on ice for 15 min, then was treated with a solution of (1R,2S,5R)-tert-butyl 2-(benzyloxycarbonylamino)-7-hydroxy-6-aza-bicyclo[3.2.1]octane-6-carboxylate (460 mg) in tetrahydrofuran (3 mL). After allowing to stir on an ice bath for 75 min, the mixture was stirred at rt for 3 h. Saturated aqueous NH$_4$Cl was added, the mixture was stirred rapidly until colorless, then was extracted three times with ethyl acetate. The combined organic phases were washed with 1.0 M aqueous HCl, then with brine, dried over Na$_2$SO$_4$ and concentrated under vacuum. The residue was purified by flash column chromatography on silica gel, eluting with 2:1 v/v hexane-ethyl acetate, to provide methyl 3-((E)-2-((1S,2S,5R)-2-benzyloxycarbonylamino-5-(tert-butoxycarbonylamino)cyclohexyl)vinyl)benzoate as a glassy foam (365 mg). MS found: (M+H)$^+$=509.3.

Example 7c, Step 2: Following the procedure of Example 4a, Step 2, methyl 3-((E)-2-((1S,2S,5R)-2-benzyloxycarbonylamino-5-(tert-butoxycarbonylamino)cyclohexyl)vinyl) benzoate (361 mg) was converted to methyl 3-(2-((1R,2S,5R)-2-amino-5-(tert-butoxycarbonylamino)cyclohexyl) ethyl)benzoate as a white glassy foam (255 mg). MS found: (M+H)$^+$=377.3.

Example 7c, Step 3: Following the procedure of Example 7a, Step 3, but using 2-(3-(trifluoromethyl)benzamido)acetic acid in place of 2-(benzyloxycarbonylamino)acetic acid and acetonitrile in place of dichloromethane as the solvent, methyl 3-(2-((1R,2S,5R)-2-amino-5-(tert-butoxycarbonylamino)cyclohexyl)ethyl)benzoate (89 mg) was converted to methyl 3-(2-((1R,2S,5R)-5-(tert-butoxycarbonylamino)-2-(2-(3-(trifluoromethyl)benzamido)acetamido)cyclohexyl) ethyl)benzoate as a colorless glass (103 mg). MS found: (M+H)$^+$=606.4.

Example 7c, Step 4: A solution of methyl 3-(2-((1R,2S,5R)-5-(tert-butoxycarbonylamino)-2-(2-(3-(trifluoromethyl)benzamido)acetamido)cyclohexyl)ethyl)benzoate (94 mg) in dichloromethane (2 mL) was treated with trifluoroacetic acid (2 mL) for 3 h. The solution was concentrated under vacuum to provide the trifluoroacetic acid salts of methyl 3-(2-((1R,2S,5R)-5-amino-2-(2-(3-(trifluoromethyl) benzamido)acetamido)cyclohexyl)ethyl)benzoate, contaminated by excess trifluoroacetic acid, as a pale tan gum (150 mg), which was used without further purification. MS found: (M+H)$^+$=506.3.

Example 7c, Step 5: The trifluoroacetic acid salt of methyl 3-(2-((1R,2S,5R)-5-amino-2-(2-(3-(trifluoromethyl)benzamido)acetamido)cyclohexyl)ethyl)benzoate prepared in Example 7c, Step 4, was dissolved in 1,2-dichloroethane (2 mL) and treated sequentially with acetone (57 μL), acetic acid (44 μL) and sodium triacetoxyborohydride (164 mg). The mixture was stirred at rt for 7 h, then treated with additional acetone (50 μL) and sodium triacetoxyborohydride (164 mg) and stirred for 17 h more. Aqueous formaldehyde (58 μL) was added and stirring was continued for 1.5 h, then the mixture was treated with additional sodium triacetoxyborohydride (80 mg) and aqueous formaldehyde (30 μL). After 23.5 h, the mixture was concentrated and partitioned between saturated aqueous NaHCO$_3$ and ethyl acetate. The aqueous phase was extracted three times more with ethyl acetate and the combined organic phases were dried over Na$_2$SO$_4$ and concentrated. MS analysis of the residue indicated the presence of both the desired product ((M+H)$^+$=562.5) and a second compound ((M+H)$^+$=548.4). Further treatment of the mixture with formaldehyde, both with sodium cyanoborohydride in methanol or with sodium triacetoxyborohydride and acetic acid in 1,2-dichloroethane, did not lead to the disappearance of the lower molecular weight byproduct. Purification by reverse phase HPLC and lyophilization provided the trifluoroacetic acid salt of the title compound, methyl 3-(2-((1R,2S,5R)-5-(isopropyl(methyl)amino)-2-(2-(3-(trifluoromethyl)benzamido)acetamido)cyclohexyl)ethyl)benzoate, as a white powder (31 mg). MS found: (M+H)$^+$562.5.

Example 7d

Synthesis of methyl 3-(2-((1R,2S,5R)-5-(ethyl(methyl)amino)-2-(2-(3-(trifluoromethyl)benzamido) acetamido)cyclohexyl)ethyl)benzoate From the reverse phase HPLC purification of methyl 3-(2-((1R,2S,5R)-5-(isopropyl(methyl)amino)-2-(2-(3-(trifluoromethyl)benzamido)acetamido)cyclohexyl)ethyl)benzoate in Example 7c, Step 5, the trifluoroacetic acid salt of methyl 3-(2-((1R,2S,5R)-5-(ethyl(methyl)amino)-2-(2-(3-(trifluoromethyl)benzamido)acetamido)cyclohexyl)ethyl) benzoate was isolated as a white powder (19 mg) after lyophilization. This material was possibly formed from acetaldehyde contamination of one of the reagents or solvents used in the introduction of the N-isopropyl group in Example 7c, Step 5. MS found: (M+H)$^+$=548.4.

Example 7e

Synthesis of 3-(2-((1R,2S,5R)-5-(isopropyl(methyl) amino)-2-(2-(3-(trifluoromethyl)benzamido)acetamido)cyclohexyl)ethyl)benzoic acid Methyl 3-(2-((1R,2S,5R)-5-(isopropyl(methyl)amino)-2-(2-(3-(trifluoromethyl)benzamido)acetamido)cyclohexyl) ethyl)benzoate (25 mg) was dissolved in water (1 mL), tetrahydrofuran (1 mL) and 50% w/w aqueous NaOH. The 20 mixture was stirred at rt for 7.5 h. Additional 50% aqueous NaOH (0.5 mL) was added and the mixture was stirred overnight at rt. After 16 h the mixture was cooled on ice and acidified to pH <7 with trifluoroacetic acid. Purification by reverse phase HPLC 25 and lyophilization provided the trifluoroacetic acid of the title compound as a white powder (14 mg). MS found: (M+H)$^+$=548.4.

Example 7f

Synthesis of 3-(2-((1R,2S,5R)-5-(ethyl(methyl) amino)-2-(2-(3-(trifluoromethyl)benzamido)acetamido)cyclohexyl)ethyl)benzoic acid Following the procedure of Example 7e, methyl 3-(2-((1R,2S,5R)-5-(ethyl(methyl)amino)-2-(2-(3-(trifluoromethyl)benzamido)acetamido)cyclohexyl)ethyl)benzoate (13 mg) was converted to the trifluoroacetic acid salt of the title compound as a white powder (7 mg) after purification by reverse phase HPLC and lyophilization. MS found: (M+H)$^+$=534.4.

Example 7g

Synthesis of ethyl 2-(((1R,2S,5R)-5-(isopropyl(methyl)amino)-2-(2-(3-(trifluoromethyl)benzamido) acetamido)cyclohexyl)methyl)butanoate Example 7g, Step 1: Following the procedure of Example 7a, Step 1, but substituting triethyl 2-phosphonobutyrate for tert-butyl dimethylphosphonoacetate, (1R,2S,5R)-tert-butyl 2-(benzyloxycarbonylamino)-7-hydroxy-6-aza-bicyclo [3.2.1]octane-6-carboxylate (500 mg) was converted to ethyl 2-(((1S,2S,5R)-2-benzyloxycarbonylamino-5-(tert-butoxycarbonylamino)cyclohexyl)methylene)butanoate (316 mg). MS found: (M+H)$^+$=475.4.

Example 7g, Step 2: Following the procedure of Example 4a, Step 2, ethyl 2-(((1S,2S,5R)-2-benzyloxycarbonylamino-5-(tert-butoxycarbonylamino)cyclohexyl)methylene)butanoate (316 mg) was converted to ethyl 2-(((1R,2S,5R)-2-amino-5-(tert-butoxycarbonylamino)cyclohexyl) methyl)butanoate as a brown glass (210 mg), used without further purification. MS found: (M+H)$^+$=343.4.

Example 7g, Step 3: Following the procedure of Example 7a, Step 3, but using 2-(3-(trifluoromethyl)benzamido)acetic acid in place of 2-(benzyloxycarbonylamino)acetic acid and acetonitrile as solvent in place of dichloromethane, ethyl 2-(((1R,2S,5R)-2-amino-5-(tert-butoxycarbonylamino)cyclohexyl)methyl)butanoate (210 mg) was converted to ethyl 2-(((1R,2S,5R)-5-(tert-butoxycarbonylamino)-2-(2-(3-(trifluoromethyl)benzamido)acetamido)cyclohexyl)methyl)butanoate as a tan glassy foam (188 mg), used without further purification. MS found: (M+H)$^+$=572.5.

Example 7g, Step 4: A solution of ethyl 2-(((1R,2S,5R)-5-(tert-butoxycarbonylamino)-2-(2-(3-(trifluoromethyl)benzamido)acetamido)cyclohexyl)methyl)butanoate (188 mg) in dichloromethane (2 mL) was treated with trifluoroacetic acid (2 mL) for 2.5 h. The solution was concentrated under vacuum to provide the trifluoroacetic acid salt of ethyl 2-(((1R,2S,5R)-5-amino-2-(2-(3-(trifluoromethyl)benzamido)acetamido)cyclohexyl)methyl)butanoate as a gum (229 mg), used without further purification. MS found: (M+H)$^+$=472.4.

Example 7g, Step 5: The trifluoroacetic acid salt of ethyl 2-(((1R,2S,5R)-5-amino-2-(2-(3-(trifluoromethyl)benzamido)acetamido)cyclohexyl)methyl)butanoate prepared in Example 7g, Step 4, was dissolved in 1,2-dichloroethane (2 mL) and treated sequentially with acetone (121 μL), acetic acid (95 μL) and sodium triacetoxyborohydride (350 mg). The mixture was stirred at rt for 7 h, then treated with additional sodium triacetoxyborohydride (ca. 50 mg) and stirred for 16 h more. Aqueous formaldehyde (125 μL) was added and stirring was continued for 7.25 h, then the mixture was treated with additional 1,2-dichloroethane, sodium triacetoxyborohydride (200 mg), acetic acid (50 μL)

and aqueous formaldehyde (75 μL). After 118 h, the mixture was concentrated and partitioned between saturated aqueous NaHCO$_3$ and ethyl acetate. The aqueous phase was extracted twice more with ethyl acetate and the combined organic phases were dried over Na$_2$SO$_4$ and concentrated. The residue was purified by reverse phase HPLC and lyophilization to provide a white powder (68 mg) containing the trifluoroacetic acid salt of the title product, and a byproduct with MS (M+H)$^+$=526.4. NMR spectroscopy suggested the presence of the olefin, ethyl 2-(((1S,2S,5R)-5-(isopropyl (methyl)amino)-2-(2-(3-(trifluoromethyl)benzamido)acetamido)cyclohexyl)methylene)butanoate, presumably resulting from residual olefinic material in the product of Example 7g, Step 2, and carried through Example 7g, Steps 3 and 4. The powder was dissolved in ethanol (8 mL), treated with Pearlman's catalyst (20% Pd(OH)$_2$ on charcoal) and shaken under a hydrogen atmosphere at 50 psig for 2 h. The mixture was filtered through Celite, the solids were washed with ethanol and the combined filtrates were concentrated under vacuum to provide the trifluoroacetic acid salt of the title product, ethyl 2-(((1R,2S,5R)-5-(isopropyl(methyl)amino)-2-(2-(3-(trifluoromethyl)benzamido)acetamido)cyclohexyl) methyl)butanoate, as a glassy solid (64 mg). MS found: (M+H)$^+$=528.4.

Example 7 h

Synthesis of 2-(((1R,2S,5R)-5-(isopropyl(methyl) amino)-2-(2-(3-(trifluoromethyl)benzamido)acetamido)cyclohexyl)methyl)butanoic acid A solution of the trifluoroacetic acid salt of ethyl 2-(((1R, 2S,5R)-5-(isopropyl(methyl)amino)-2-(2-(3-(trifluoromethyl)benzamido)acetamido)cyclohexyl)methyl)butanoate (55 mg) in tetrahydrofuran (1 mL) was treated with a solution of lithium hydroxide hydrate (42 mg) in water (1 mL) and the mixture was stirred at rt for 5 h. Aqueous NaOH (50% w/w, 5 drops) was added, followed after 50 min by additional 50% aqueous NaOH (0.25 mL), and the mixture was stirred at rt for 22.5 h. The mixture was then warmed to 60° C., and additional 50% aqueous NaOH (0.5 mL) was added after 25 min. After 60 min, the tetrahydrofuran was removed, and water (1 mL) and ethanol (0.5 mL) were added. The mixture was heated to reflux for 1.75 h, then was cooled to rt. The ethanol was removed under vacuum, a small amount of water was added and the pH adjusted to less than 4 by the addition of trifluoroacetic acid. The solution was subjected to reverse phase HPLC to provide the trifluoroacetic acid of the title product as a white powder (9.9 mg) after lyophilization. MS found: (M+H)$^+$=500.3.

Example 7i

Synthesis of (1R,2S,5R)-2-(2-(3-tert-butyl-4-hydroxybenzamido)acetamido)-5-(isopropyl(methyl) amino)cyclohexanecarboxylic acid Example 7i, Step 1: A mixture of 3-t-butylhydroxybenzoic acid (2.00 g, 10.3 mmol), benzyl bromide (6.12 mL, 52.5 mmol), KOH (3.47 g, 61.8 mmol), EtOH (60 mL), and water (6 mL) was heated at 100° C. for 48 h under nitrogen atmosphere. The reaction mixture was concentrated in vacuo and the residue was diluted with EtOH (100 mL) and water (100 mL), then stirred with KOH (3.47 g, 61.8 mmol) at 100° C. for 2 h. The reaction mixture was cooled to room temperature and concentrated in vacuo. The residue was diluted with water (400 mL) and extracted with EtOAc (200 mL). The aqueous layer was acidified with 1 N HCl (10 mL) and extracted with EtOAc (2×200 mL). The combined organic layers were washed with brine (50 mL), dried (Na$_2$SO$_4$), and concentrated in vacuo to provide 4-(benzyloxy)-3-tert-butylbenzoic acid (2.36 g, 81%) as a white solid: $^1$H NMR (300 MHz, CDCl$_3$) δ 10.80 (br s, 1H), 8.08 (s, 1H), 8.07-7.94 (m, 1H), 7.45-7.34 (m, 5H), 6.99-6.96 (m, 1H), 5.20 (s, 2H), 1.42 (s, 9H); MS found: (M+H)$^+$=285.

Example 7i, Step 2: To a solution of 4-(benzyloxy)-3-tert-butylbenzoic acid (2.36 g, 8.31 mmol) in anhyd DMF (56 mL) was added glycine t-butyl ester (1.63 g, 12.5 mmol), BOP reagent (5.51 g, 12.5 mmol), and N-methylmorpholine (2.74 mL, 24.9 mmol). The mixture was stirred at room temperature for 12 h under nitrogen atmosphere and then diluted with EtOAc (200 mL). The organic layer was washed consecutively with 1 N HCl (250 mL), satd NaHCO$_3$ (100 mL), 5% LiCl (2×100 mL), and brine (50 mL), dried (Na$_2$SO$_4$), and concentrated in vacuo. tert-butyl 2-(4-(benzyloxy)-3-tert-butylbenzamido)acetate (3.37 g, quant.) was isolated as a white solid: $^1$H NMR (300 MHz, CDCl$_3$) δ 7.81 (s, 1H), 7.63-7.60 (m, 1H), 7.46-7.34 (m, 5H), 6.95-6.93 (m, 1H), 6.52 (s, 1H), 5.16 (s, 2H), 4.14-4.11 (m, 2H), 1.51 (s, 9H), 1.41 (s, 9H); MS found: (M+H)$^+$=398.

Example 7i, Step 3: To a solution of tert-butyl 2-(4-(benzyloxy)-3-tert-butylbenzamido)acetate (3.37 g, 8.48 mmol) in CH$_2$Cl$_2$ (100 mL) at 0° C. was added TFA (10 mL) and the mixture was stirred at room temperature under nitrogen atmosphere for 10 h. The reaction mixture was concentrated in vacuo to dryness to give 2-(4-(benzyloxy)-3-tert-butylbenzamido)acetic acid (2.50 g, 86%) as a white powder: mp 172-174° C.; $^1$H NMR (300 MHz, CD$_3$OD) δ 7.86 (s, 1H), 7.74-7.70 (m, 1H), 7.50-7.30 (m, 5H), 7.10-7.05 (m, 1H), 5.18 (s, 2H), 4.07 (s, 2H), 1.41 (s, 9H); IR (film) 3497, 3062, 3031, 2931, 2865, 1447, 1289, 1139, 1085, 1062 cm$^{-1}$; MS found: (M+H)$^+$=342.

Example 7i, Step 4: To a solution of 2-(4-(benzyloxy)-3-tert-butylbenzamido)acetic acid (418 mg, 1.22 mmol) in anhyd DMF (8 mL) was added (1R,2S,5R)-tert-butyl 2-amino-7-oxo-6-aza-bicyclo[3.2.1]octane-6-carboxylate (287 mg, 1.11 mmol), BOP reagent (738 mg, 1.67 mmol), and N-methylmorpholine (366 μL, 3.34 mmol). The mixture was stirred at room temperature for 12 h under nitrogen atmosphere and then diluted with EtOAc (250 mL). The organic layer was washed with water (100 mL), 0.1 N HCl (100 mL), satd NaHCO$_3$ (100 mL), and brine (50 mL), dried (Na$_2$SO$_4$), and concentrated in vacuo. 4-(benzyloxy)-3-tert-butyl-N-(2-oxo-2-((1R,2S,5R)-7-oxo-6-aza-bicyclo[3.2.1] octan-2-ylamino)ethyl)benzamide (713 mg, quant.) was isolated as a white solid: $^1$H NMR (300 MHz, CDCl$_3$) δ 7.81-6.93 (m, 8H), 6.69 (s, 1H), 5.15 (s. 1H); 5.16 (s, 1H), 4.13-4.06 (m, 4H), 3.20-2.80 (m, 2H), 2.40-1.30 (m, 6H), 1.52 (s, 9H), 1.42 (s, 9H); MS found: (M+H)$^+$=564.

Example 7i, Step 5: To a mixture of 4-(benzyloxy)-3-tert-butyl-N-(2-oxo-2-((1R,2S,5R)-7-oxo-6-aza-bicyclo[3.2.1] octan-2-ylamino)ethyl)benzamide (700 mg, 1.22 mmol), THF (12 mL), and water (3 mL) was added LiOH (257 mg, 6.12 mmol) and the reaction mixture was stirred at room temperature for 5 h. The mixture was concentrated in vacuo to dryness and the residue was dissolved in EtOAc (200 mL). The organic layer was washed with 1 N HCl (10 mL), water (3×50 mL), and brine (50 mL), dried (Na$_2$SO$_4$), and concentrated in vacuo. (1R,2S,5R)-2-(2-(4-(benzyloxy)-3-tert-butylbenzamido)acetamido)-5-(tert-butoxycarbonyl)cyclohexanecarboxylic acid (625 mg, quant.) was isolated as a white solid: mp 126-132° C.; $^1$H NMR (300 MHz, CDCl$_3$) δ 10.80 (br s, 1H), 8.40-6.82 (m, 8H), 5.15 (m, 2H), 4.80-2.92 (m, 8H), 2.70-1.10 (m, 6H), 1.45 (s, 9H), 1.41 (s, 9H); MS found: (M+H)+=582.

Example 7i, Step 6: A suspension of (1R,2S,5R)-2-(2-(4-(benzyloxy)-3-tert-butylbenzamido)acetamido)-5-(tert-butoxycarbonyl)cyclohexanecarboxylic acid (100 mg, 0.17 mmol) and 10% Pd/C (100 mg) in MeOH (10 mL) was exposed to an atmosphere of hydrogen for 14 h. The reaction mixture was filtered through diatomaceous earth, rinsed with MeOH (400 mL) and concentrated in vacuo to provide (1R,2S,5R)-5-(tert-butoxycarbonyl)-2-(2-(3-tert-butyl-4-hydroxybenzamido)acetamido)cyclohexanecarboxylic acid (87 mg, quant.) as a white solid: $^1$H NMR (300 MHz, CD$_3$OD) δ 7.79-7.78 (m, 1H), 7.61-7.58 (m, 1H), 6.80-6.75 (m, 1H), 4.59 (s, 1H), 3.99 (s, 2H), 3.45-2.89 (m, 4H), 2.54 (s, 1H), 2.18-1.25 (m, 6H), 1.42 (s, 9H), 1.41 (s, 9H); MS found: (M+H)+=492.

Example 7i, Step 7: To a solution of (1R,2S,5R)-5-(tert-butoxycarbonyl)-2-(2-(3-tert-butyl-4-hydroxybenzamido)acetamido)cyclohexanecarboxylic acid (87 mg, 0.17 mmol) in CH$_2$Cl$_2$ (10 mL) at 0° C. was added TFA (4 mL) and the mixture was stirred at room temperature under nitrogen atmosphere for 1.5 h. The reaction mixture was concentrated in vacuo to provide (1R,2S,5R)-5-amino-2-(2-(3-tert-butyl-4-hydroxybenzamido)acetamido)cyclohexanecarboxylic acid (67 mg) as a yellow oil: $^1$H NMR (300 MHz, CD$_3$OD) δ 7.83-7.77 (m, 2H), 7.57-7.54 (m, 1H), 7.33-7.30 (m, 1H), 6.79-6.75 (m, 2H), 4.50 (s, 1H), 3.98 (s, 2H), 3.34-2.82 (m, 3H), 2.20-1.25 (m, 6H), 1.41 (s, 9H); MS found: (M+H)+ =392.

Example 7i, Step 8: To a solution of (1R,2S,5R)-5-amino-2-(2-(3-tert-butyl-4-hydroxybenzamido)acetamido)cyclohexanecarboxylic acid (67 mg, 0.17 mmol) in anhyd CH$_2$Cl$_2$ (1 mL) and acetone (1 mL) was added acetic acid (0.5 mL) and NaBH(OAc)$_3$ (110 mg, 0.51 mmol) and the reaction mixture was stirred at room temperature for 12 h. The reaction mixture was concentrated in vacuo and the residue was dissolved in CH$_2$Cl$_2$ (1 mL) and CH$_3$CN (1 mL). To this solution was added formaldeyde (4 mL, 37% in water) and NaBH(OAc)$_3$ (200 mg, 0.84 mmol) in five portions over 10 h. The reaction mixture was stirred at room temperature for 12 h and then concentrated in vacuo to dryness. The residue was dissolved in water and purified by semi-preparative HPLC to give (1R,2S,5R)-2-(2-(3-tert-butyl-4-hydroxybenzamido)acetamido)-5-(isopropyl(methyl)amino)cyclohexanecarboxylic acid (22.4 mg, 29% over 3 steps) as a white powder: $^1$H NMR (300 MHz, CD$_3$OD) δ 7.95 (s, 1H), 7.78 (s, 1H), 7.58-7.54 (m, 1H), 6.80-6.77 (m, 1H), 4.55 (s, 1H), 4.08-3.91 (m, 3H), 3.90-3.71 (m, 1H), 3.69-3.45 (m, 1H), 2.92-2.85 (m, 1H), 2.79 (s, 3H), 2.15-1.55 (m, 7H), 1.41-1.33 (m, 15H); MS found: (M+H)+=448.

TABLE 7-A

The compounds in the following table were made using the methods exemplified above. See Table 1-A for a complete description of the table headings.

| Ex | R$^1$ | R$^2$ | R$^5$ | MS |
|---|---|---|---|---|
| 7a | CH$_2$CH$_2$CO$_2$-t-Bu | 3-CF$_3$-phenyl | i-Pr(Me)N | 528 |
| 7b | CH$_2$CH$_2$CO$_2$H | 3-CF$_3$-phenyl | i-Pr(Me)N | 472 |
| 7c | CH$_2$-(3-COOMe-phenyl) | 3-CF$_3$-phenyl | i-Pr(Me)N | 562 |
| 7d | CH$_2$-(3-COOMe-phenyl) | 3-CF$_3$-phenyl | Et(Me)N | 548 |
| 7e | CH$_2$-(3-COOH-phenyl) | 3-CF$_3$-phenyl | i-Pr(Me)N | 548 |

TABLE 7-A-continued

The compounds in the following table were made using the methods exemplified above. See Table 1-A for a complete description of the table headings.

| Ex | R¹ | R² | R⁵ | MS |
|---|---|---|---|---|
| 7f | (3-COOH-phenyl)ethyl | 3-CF₃-phenyl | Et(Me)N | 534 |
| 7g | CH₂CH(Et)CO₂Et | 3-CF₃-phenyl | i-Pr(Me)N | 528 |
| 7h | CH₂CH(Et)CO₂H | 3-CF₃-phenyl | i-Pr(Me)N | 500 |
| 7i | CO₂H | 3-tert-butyl-4-hydroxyphenyl | i-Pr(Me)N | 448 |

TABLE 7-B

The chemical names of the specific examples illustrated in Table 7-A are tabulated below.

| Ex | Name |
|---|---|
| 7a | tert-butyl 3-((1R,2S,5R)-5-(isopropyl(methyl)amino)-2-(2-(3-(trifluoromethyl)benzamido)acetamido)cyclohexyl)-propanoate |
| 7b | 3-((1R,2S,5R)-5-(isopropyl(methyl)amino)-2-(2-(3-(trifluoromethyl)benzamido)acetamido)cyclohexyl)-propanoic acid |
| 7c | methyl 3-(2-((1R,2S,5R)-5-(isopropyl(methyl)amino)-2-(2-(3-(trifluoromethyl)benzamido)acetamido)cyclohexyl)-ethyl)benzoate |
| 7d | methyl 3-(2-((1R,2S,5R)-5-(ethyl(methyl)amino)-2-(2-(3-(trifluoromethyl)benzamido)acetamido)cyclohexyl)-ethyl)benzoate |
| 7e | 3-(2-((1R,2S,5R)-5-(isopropyl(methyl)amino)-2-(2-(3-(trifluoromethyl)benzamido)acetamido)cyclohexyl)-ethyl)benzoic acid |
| 7f | 3-(2-((1R,2S,5R)-5-(ethyl(methyl)amino)-2-(2-(3-(trifluoromethyl)benzamido)acetamido)cyclohexyl)-ethyl)benzoic acid |
| 7g | ethyl 2-(((1R,2S,5R)-5-(isopropyl(methyl)amino)-2-(2-(3-(trifluoromethyl)benzamido)acetamido)cyclohexyl)-methyl)butanoate |
| 7h | 2-(((1R,2S,5R)-5-(isopropyl(methyl)amino)-2-(2-(3-(trifluoromethyl)benzamido)acetamido)cyclohexyl)-methyl)butanoic acid |
| 7i | (1R,2S,5R)-2-(2-(3-tert-butyl-4-hydroxybenzamido)acetamido)-5-(isopropyl(methyl)amino)cyclohexanecarboxylic acid |

Examples 8a -8l

Example 8a

Synthesis of N-(2-((1S,2R,4R)-2-(hydroxymethyl)-4-(isopropyl(methyl)amino)cyclohexylamino)-2-oxoethyl)-3-(trifluoromethyl)benzamide Example 8a, Step 1: A sample of (1R,2S)-ethyl 5-oxo-2-((S)-1-phenylethylamino)cyclohexanecarboxylate (10.7 g, 37 mmol) was dissolved in titanium(IV) isopropoxide (23 ml, 21.5 g, 75.6 mol) and treated with isopropylmethylamine (5.5 g, 74 mmol). The resulting solution was stirred at room temperature for 4 hours. The solution was diluted with 50 ml of methanol and treated very slowly with NaBH₄ caplets (2.85 g, 75 mmol) over a period of 2 hours. [Caution: vigorous foaming occurs.] The solution was stirred overnight at room temperature. The solution was quenched with a 0.2 N NaOH and the resulting slurry was diluted with 1 L of CH$_2$Cl$_2$ and shaken thoroughly in a separatory funnel. The resulting emulsion is filtered through Celite and the solid cake washed two times with CH$_2$Cl$_2$. The combined filtrates were concentrated on a rotary evaporator to give 12 grams of yellow oil which was chromatographed on silica gel (elution with 2-8% NH$_4$OH/MeOH/CH$_2$Cl$_2$) to give 6.6 g of (1R,2S,5R)-ethyl 5-(isopropyl(methyl)amino)-2-((S)-1-phenylethylamino)-cyclohexanecarboxylate as an oil.

Example 8a, Step 2: A solution of (1R,2S,5R)-ethyl 5-(isopropyl(methyl)amino)-2-((S)-1-phenylethylamino)-cyclohexanecarboxylate (4.0 g, 0.012 mol) in ether (100 ml) is cooled to 0° C. in an ice bath and treated slowly with LAH (0.66 g, 0.017 mol). After the addition is complete the mixture is stirred for an additional 45 min and then quenched by drop-wise addition of 1 ml of water followed by 4 ml of 1 N NaOH (caution: vigorous foaming). The resultant suspension is stirred in the ice bath for 1-2 hours to give a granular white suspension which is filtered on a buchner funnel. The solid is washed with ether and the combine ether filtrates are concentrated to give 3.5 g of the alcohol. A solution of crude amino alcohol (3.5 g, 0.011 mol) in 50 ml of MeOH was treated with 1 g of 20% Pd(OH)$_2$/C and hydrogenated overnight at 55 psi. The mixture was filtered through Celite and concentrated on a rotary evaporator to give 2.2 g of ((1R,2S,5R)-2-amino-5-(isopropyl(methyl) amino)cyclohexyl)methanol as a syrup. This was used without further purification.

Example 8a, Step 3: A solution of (3-Trifluoromethyl-benzoylamino)-acetic acid (1.76 g, 0.0071 mol) in THF was cooled in an ice bath and treated with N-methylmorpholine (0.80 g, 0.0080 mol) and then drop-wise with isobutyl chloroformate (1.0 g, 0.007 mol). The resulting mixture was stirred for 5 min and then treated with a solution of ((1R,2S,5R)-2-amino-5-(isopropyl(methyl)amino)cyclohexyl) methanol (1.3 g, 0.0065 mol) in THF. The resulting mixture was stirred for 30 minutes and then diluted with water and extracted into CH$_2$Cl$_2$. The extract was washed with dilute NaOH, water, and brine and then concentrated under vacuum. The residue was chromatographed on silica gel (elution 5-8% [NH$_4$OH/MeOH]/CH$_2$Cl$_2$) to give 1.2 g of the title compound as a white solid. $^1$H NMR (400 MHz, CDCl$_3$) δ(TMS): 8.15 (s, 1 H), 8.05 (d, J=7.8 Hz, 1 H), 7.76 (d, J=7.8 Hz, 1 H), 7.76 (bs, 1 H), 7.57 (t, J=7.8 Hz, 1 H), 7.17 (bs, 1 H), 4.26 (m, 1 H), 4.26 (dd, J=5 Hz, J=16 Hz, 1 H), 4.13 (dd, J=5 Hz, J=16 Hz, 1 H), 3.27 (m, 1 H), 3.17 (m, 1 H), 2.57 (m, 2 H), 2.24 (s, 3 H), 1.92-1.60 (m, 7 H), 1.05 (d, J=6.5 Hz, 6 H); MS found: (M+H)$^+$=430.48.

Example 8b

Synthesis of N-(2-((1S,2R,4R)-2-(hydroxymethyl)-4-(isopropylamino)cyclohexylamino)-2-oxoethyl)-3-(trifluoromethyl)benzamide Example 8b, Step 1: A sample of (1R,2S)-ethyl 5-oxo-2-((S)-1-phenylethylamino)cyclohexanecarboxylate (10.0 g, 35 mmol) was dissolved in titanium(IV) isopropoxide (23 ml, 21.5 g, 75.6 mol) and treated with isopropylamine (2.1 g, 35 mmol). The resulting solution was stirred at room temperature for 4 hours. The solution was diluted with 50 ml of methanol and treated very slowly with NaBH$_4$ caplets (2.85 g, 75 mmol) over a period of 2 hours. [Caution: vigorous foaming occurs.] The solution was stirred overnight at room temperature. The solution was quenched with a 0.2 N NaOH and the resulting slurry was diluted with 1 L of CH$_2$Cl$_2$ and shaken thoroughly in a separatory funnel. The resulting emulsion is filtered through Celite and the solid cake washed two times with CH$_2$Cl$_2$. The combined filtrates were concentrated on a rotary evaporator to give 10 grams of yellow oil which was chromatographed on silica gel (elution with 0.8:7.2:92 NH$_4$OH/MeOH/CH$_2$Cl$_2$) to give 5.0 g of the amine ester as oil. The ester was obtained as a mixture of methyl, ethyl, and isopropyl (1R,2S,5R)-5-(isopropylamino)-2-((S)-1-phenylethylamino)cyclohexane-carboxylate, with the ethyl ester predominating. This mixture was used "as is" in the next step.

Example 8b, Step 2: A solution of the Step 1 product in THF was treated with BOC$_2$O (3.6 g, 0.016 mol) and Et$_3$N (1.6 g, 0.015 mol) and heated at reflux for 24 hrs. The mixture is diluted with water and extracted into CH$_2$Cl$_2$. The extract is washed with water, aqueous NaHCO3, and brine. The solvent removed under vacuum and the residue chromatographed on silica gel (10% ethyl acetate/hexane) to give 4.5 g of N-BOC amino-ester. The ester was obtained as a mixture of methyl, ethyl, and isopropyl (1R,2S,5R)-5-(tert-butoxycarbonyl)-2-((S)-1-phenylethylamino)cyclohexane-carboxylate, with the ethyl ester predominating. This mixture was used "as is" in the next step.

Example 8b, Step 3: A solution of the Step 2 product (4.5 g, 0.01 mol) in ether (100 mL) is cooled to 0° C. in an ice bath and treated slowly with LAH (0.6 g, 0.015 mol). After the addition is complete the mixture is stirred for an additional 45 mins and then quenched by drop-wise addition of 1 ml of water followed by 4 ml of 1 N NaOH (caution: vigorous foaming). The resultant suspension is stirred in the ice bath for 1-2 hours to give a granular white suspension which is filtered on a buchner funnel. The solid is washed with ether and the combine ether filtrates are concentrated to give 4 g of the alcohol tert-butyl(1R,3R,4S)-3-(hydroxymethyl)-4-((S)-1-phenylethylamino)cyclohexyl-(isopropyl) carbamate as a colorless syrup (m/z ion 391.3 for M+H in the LC/MS). This syrup also contained significant amounts of unreacted isopropyl (1R,2S,5R)-5-(tert-butoxycarbonyl)-2-((S)-1-phenylethylamino)cyclohexane-carboxylate (m/z ion 447.3 for M+H in the LC/MS). The mixture was used without further purification in the next step.

Example 8b, Step 4: A solution of the Step 3 product (4 g, 0.01 mol) in 50 ml of MeOH was treated with 1 g of 20% Pd(OH)$_2$/C and hydrogenated overnight at 55 psi. The mixture was filtered through Celite and concentrated in vacuo to give a syrup, which was dissolved in THF. This solution was added to a pre-mixed, pre-cooled (ice bath) solution of Gly-CBZ (2.1 g, 0.01 mol), Et$_3$N (1.01 g, 0.01 mol), and isobutyl chloroformate (1.36 g, 0.01 mol). The reaction mixture was stirred for 30 minutes and then diluted with water and extracted into CH$_2$Cl$_2$. The extract was washed with dilute NaOH, water, and brine and then concentrated under vacuum. The residue was chromatographed on silica gel (elution 55% ethyl acetate/hexane, then 100% ethyl acetate) to give 0.7 g of isopropyl (1R,2S,5R)-2-(2-(benzyloxycarbonylamino)acetamido)-5-(tert-butoxycarbonyl-isopropylamino)cyclohexanecarboxylate as a white solid, MS found: (M+H)$^+$=534.4. The desired alcohol, tert-butyl(1R,3R,4S)-4-(2-Benzyloxycarbonylamino-acetylamino)-3-(hydroxymethyl)cyclohexyl(isopropyl)carbamate, eluted later and was dried to a white solid (2.4 g). MS found: (M+H)$^+$=478.3.

Example 8b, Step 5: A solution of tert-butyl(1R,3R,4S)-4-(2-Benzyloxycarbonylamino-acetylamino)-3-(hydroxymethyl)cyclohexyl(isopropyl)carbamate (2.2 g, 0.0046 mol), in 30 mL of MeOH was treated with 1 g of 10% Pd/C and hydrogenated overnight at 55 psi. The mixture was filtered through Celite and concentrated on a rotary evaporator to give tert-butyl(1R,3R,4S)-4-(2-aminoacetamido)-3-(hydroxymethyl)cyclohexyl-(isopropyl)carbamate as a white solid. This was used without further purification.

Example 8b, Step 6: A solution of 3-Trifluoromethyl-benzoic acid (0.55 g, 0.0029 mol) in THF was cooled in an ice bath and treated with N-methylmorpholine (0.3 g, 0.003 mol) and then drop-wise with isobutyl chloroformate (0.39 g, 0.0029 mol). The resulting mixture was stirred for 5 min and then treated with a solution of tert-butyl(1R,3R,4S)-4-(2-aminoacetamido)-3-(hydroxymethyl)cyclohexyl-(isopropyl)carbamate (2.8 g, 0.01 mol) in THF. The resulting mixture was stirred for 30 minutes and then diluted with water and extracted into $CH_2Cl_2$. The extract was washed with dilute NaOH, water, and brine and then concentrated under vacuum. The residue was chromatographed on silica gel (elution 55% ethyl acetate/hexane, then 100% ethyl acetate) to give 1.4 g of tert-butyl(1R,3R,4S)-3-(hydroxymethyl)-4-(2-(3-(trifluoromethyl)-benzamido)acetamido)cyclohexyl(isopropyl)carbamate as a white solid. MS found: $(M+H)^+=516.3$.

Example 8b, Step 7: A solution of tert-butyl(1R,3R,4S)-3-(hydroxymethyl)-4-(2-(3-(trifluoromethyl)-benzamido)acetamido)cyclohexyl(isopropyl)carbamate (130 mg) in $CH_2Cl_2$ is treated with $CF_3COOH$ (7 ml) and stirred at room temperature for 2 hours. The solution was evaporated and the residue neutralized with 1 N NaOH and extracted into $CH_2Cl_2$. The extract was washed with water, brine, dried over $Na_2SO_4$, filtered and the solvent evaporated to give 100 mg of the title compound as a white solid. $^1H$ NMR (400 MHz, $CDCl_3$) δ(TMS): 8.12 (s, 1 H), 8.03 (d, J=7.8 Hz, 1 H), 7.94 (bt, 1 H), 7.75 (d, J=7.8 Hz, 1 H), 7.57 (t, J=7.8 Hz,1 H), 7.39 (bd, 1 H), 4.31 (m, 1 H), 4.26 (dd, J=5 Hz, J=16 Hz, 1 H), 4.13 (dd, J=5 Hz, J=16 Hz, 1 H), 3.42 (m, 1 H), 3.27 (m, 1 H), 3.05 (m, 1 H), 2.84 (m, 1 H), 1.92-1.60 (m, 8 H), 1.12 (d, J=6.3 Hz, 6 H). MS found: $(M+H)^+=416.38$.

Example 8c

Synthesis of N-(2-((1S,2R,4R)-2-((R/S)-1-hydroxypropyl)-4-(isopropylamino)cyclohexylamino)-2-oxoethyl)-3-(trifluoromethyl)benzamide Example 8c, Step 1: A solution of DMSO (0.42 g, 5 mmol) in 30 ml of methylene chloride was cooled to −78° C. (dry ice-acetone bath) and treated drop-wise with oxalyl chloride (0.38 g, 3.0 mmol). After the addition was complete and solution was stirred for 30 minutes and then treated drop-wise with a solution of tert-butyl (1R,3R,4S)-3-(hydroxymethyl)-4-(2-(3-(trifluoromethyl)-benzamido)acetamido)cyclohexyl(isopropyl)carbamate (0.50 g, 0.97 mmol; see Example 8b, Step 6) in 20 ml of methylene chloride. After the addition was complete and solution was stirred for 40 minutes and then treated 1 ml of triethylamine (1 g, 10 mmol) and stirred for 30 minutes before removing the cooling bath and stirring at room temperature for 1 hour. The mixture was quench with 100 mL of saturated sodium bicarbonate and the organic layer was separated and washed successively with water and brine, and then dried over $Na_2SO4$. The drying agent is filtered and the solvent removed on a rotary evaporator to give 0.45 mg of tert-butyl(1R,3R,4S)-3-formyl-4-(2-(3-(trifluoromethyl)benzamido)acetamido)-cyclohexyl(isopropyl)carbamate as a white solid which was used without further purification. MS found: $(M+H)^+=514.29$.

Example 8c, Step 2: A solution of crude aldehyde Intermediate 20 (130 mg, 0.25 mmol) in THF was cooled in an ice bath and treated with a 3 M solution of ethyl magnesium bromide in THF (1 ml, 3 mmol). After 1 hour the mixture was quenched with 5 ml of 1N HCl, diluted with water and mixture extracted into $CH_2Cl_2$. The organic layer was separated and washed successively with water and brine, and then dried over $Na_2SO4$. The mixture is filtered and the solvent removed on a rotary evaporator to give 120 mg of crude alcohol as a white solid which was used without further purification. The crude alcohol was dissolved in 3 ml of $CH_2Cl_2$ and treated with 5 ml of TFA at room temperature for 1 hour. The solution was evaporated and the residue neutralized with 1 N NaOH and extracted into $CH_2Cl_2$. The extract was washed with water, brine, dried over $Na_2SO_4$, filtered and the solvent evaporated. The redidue obtained was chromatographed on silica gel (5% $NH_4OH$/MeOH/$CH_2Cl_2$) to give 50 mg of the title compound (mixture of diastereomers on the hydroxypropyl sidechain, with one predominating) as a white solid. $^1H$ NMR (400 MHz, $CDCl_3$) δ(TMS): 8.04 (s, 1 H), 7.94 (d, J=7.8 Hz, 1 H), 7.70 (d, J=7.8 Hz, 1 H), 7.66 (bt, 1 H), 7.50 (t, J=7.8 Hz, 1 H), 6.96 (bd, 1 H), 4.37-4.34 (m, 2 H), 4.10 (m, 2 H), 3.06 (m, 1 H), 2.91 (m, 1 H), 2.57 (m, 1 H), 1.84 (m, 2 H), 1.65 (m, 1 H), 1.58-1.00 (m, 7 H), 0.89 (d, J=6.2 Hz, 6 H), 0.86 (t, J=6.5 Hz, 3 H). MS found: $(M+H)^+=444.44$.

Example 8e

Example 8e, Step 1: A sample of ketone (1R,2S)-ethyl 5-oxo-2-((S)-1-phenylethylamino)cyclohexanecarboxylate (7.38 g, 25 mmol) was dissolved in titanium(IV) isopropoxide (15 g, 51 mol) and treated with t-butylamine (4.66 g, 64 mmol). The resulting solution was stirred at room temperature for 12 hours. The solution was diluted with 50 ml of methanol and treated very slowly with $NaBH_4$ caplets (1.0 g, 26 mmol) over a period of 2 hours. [Caution: vigorous foaming occurs.] The solution was quenched with a 0.2 N NaOH and the resulting slurry was diluted with 1 L of $CH_2Cl_2$ and shaken thoroughly in a separatory funnel. The resulting emulsion is filtered through Celite and the solid cake washed two times with $CH_2Cl_2$. The combined filtrates were concentrated on a rotary evaporator to give 10 grams of yellow oil which was chromatographed on silica gel (elution with 0.8:7.2:92 $NH_4OH$/MeOH/$CH_2Cl_2$) to give 6.8 g of the amine ester as an oil. The ester was obtained as a mixture of methyl, ethyl (main), and isopropyl esters which was used as a mixture in the next step.

Example 8e, Step 2: A solution of the Step 1 product (6.85 g, 0.020 mol) in ether (100 mL) is cooled to 0° C. in an ice bath and treated slowly with LAH (0.75 g, 0.020 mol). After the addition is complete the mixture is stirred for an additional 45 mins and then quenched by drop-wise addition of 1 ml of water followed by 4 ml of 1 N NaOH (caution: vigorous foaming). The resultant suspension is stirred in the ice bath for 1-2 hours to give a granular white suspension which is filtered on a buchner funnel. The solid is washed with ether and the combine ether filtrates are concentrated to give 6.4 g of the alcohol. This was chromatographed on silica gel (10% $NH_4OH$/MeOH/$CH_2Cl_2$) to give 4.66 g of alcohol. A solution of amino alcohol (4.66 g, 0.015 mol) in 50 ml of MeOH was treated with 1 g of 20% $Pd(OH)_2$/C and hydrogenated overnight at 55 psi. The mixture was filtered through Celite and concentrated on a rotary evaporator to give 3.9 g of ((1R,2S,5R)-2-amino-5-(tert-butylamino)cyclohexyl)methanol. This was used without further purification.

Example 8e, Step 3: A solution of the Step 2 product, (Gly-Cbz) (6.11 g, 29 mmol) EDCI (5.6 g, 29 mmol), HOBT (4.0 g, 29 mmol), and triethylamine (29 g, 29 mmol) in $CH_2Cl_2$ was stirred at room temperature overnight. The mixture was washed with 1 N NaOH and the solvent removed on a rotary evaporator and the residue was chromatographed on silica gel (eluting with 2-8% NH$_4$OH/MeOH/CH$_2$Cl$_2$) to give 4 g of benzyl 2-((1S,2R,4R)-4-(tert-butylamino)-2-(hydroxymethyl)cyclohexylamino)-2-oxoethylcarbamate as a white solid.

Example 8e, Step 4: A solution of benzyl 2-((1S,2R,4R)-4-(tert-butylamino)-2-(hydroxymethyl)cyclohexylamino)-2-oxoethylcarbamate (4.0 g, 0.01 mol), in 30 mL of MeOH was treated with 0.5 g of 10% Pd/C and hydrogenated overnight at 55 psi. The mixture was filtered through Celite and concentrated on a rotary evaporator to give 2-amino-N-((1S,2R,4R)-4-(tert-butylamino)-2-(hydroxymethyl)cyclohexyl)acetamide as a white solid. This was used without further purification.

Example 8e, Step 5: A solution of 2-amino-N-((1S,2R,4R)-4-(tert-butylamino)-2-(hydroxymethyl)cyclohexyl)acetamide (54 mg, 0.21 mmol), 3-Trifluoromethylbenzoic acid (52 mg, 0.25 mmol), EDCI (48 mg, 0.25 mmol), HOBT (35 mg, 0.28 mmol), and triethylamine (25 mg, 0.25 mmol) in 2 mL of CH$_2$Cl$_2$ was stirred at room temperature overnight. The reaction mixture was chromatographed on silica gel (eluting with 2-8% NH$_4$OH/MeOH/CH$_2$Cl$_2$) to give 21 mg of Example 10 as a white solid. $^1$H NMR (500 MHz, CDCl$_3$) δ(TMS): 0.84-1.97 (m, 17 H), 2.56-2.72 (m, 1 H), 3.11-3.42 (m, 2 H), 4.01-4.35 (m, 3 H), 6.95-7.13 (m, 1 H), 7.15-7.27 (m, 1 H), 7.45-7.60 (m, 1 H), 7.60-7.85 (m, 1 H), 7.92-8.16 (m, 2 H). MS found: (M+H)$^+$ 430.14.

Example 8i

Synthesis of N-((1S,2R,4R)-4-(tert-butylamino)-2-(hydroxymethyl)cyclohexyl)-2-(6-(trifluoromethyl)quinazolin-4-ylamino)acetamide A solution of 2-amino-N-((1S,2R,4R)-4-(tert-butylamino)-2-(hydroxymethyl)cyclohexyl)acetamide (54 mg, 0.21 mmol), 6-(trifluoromethyl)quinazolin-4-amine (52 mg, 0.25 mmol), and triethylamine (25 mg, 0.25 mmol) in 3 mL of ethanol was heated at 100° C. in the microwvae for 1 hr. The reaction mixture was concentrated and the residue chromatographed on silica gel (eluting with 2-8% NH$_4$OH/MeOH/CH$_2$Cl$_2$) to give 21 mg of the title compound as a white solid.

$^1$H NMR (500 MHz, CDCl$_3$) δ(TMS): 0.92-1.98 (m, 17H), 2.65-2.77 (m, 1H), 3.18-3.34 (m, 1H), 3.37-3.52 (m, 1H), 4.21-4.40 (m, 3H), 6.78-6.94(m, 1H), 7.35-7.66 (m, 1H), 7.78-7.94 (m, 2H), 8.13 (s, 1H), 0.59-8.73 (m, 1H). MS found: (M+H)$^+$=454.18.

Example 8k

Synthesis of N-(2-((1S,2R,4R)-2-((R/S)-1-hydroxyethyl)-4-(isopropyl(methyl)amino)cyclohexylamino)-2-oxoethyl)-3-(trifluoromethyl)benzamide Example 8k, Step 1: A portion of (1R,3R,4S)-(4-benzyloxycarbonylamino-3-acetylcyclohexyl)carbamic acid tert-butyl ester (600 mg, See Example 3d, Step 1) was dissolved in MeOH (5 ml) prior to the addition of 5% Pd/BaSO$_4$ (300 mg). A hydrogen balloon was added and the solution was stirred for 2 h. The palladium was filtered off and the solution was concentrated. This material was incorporated into Example 18c and flash chromatography afforded tert-butyl(1R,3R,4S)-3-acetyl-4-(2-(3-(trifluoromethyl)benzamido)acetamido)cyclohexylcarbamate (430 mg). MS found: (M+H)$^+$=486.2.

Example 8k, Step 2: A portion of the above material 73b (64 mg) was dissolved in MeOH (2 ml) at 0° C. prior to the addition of NaBH$_4$ (15 mg). After 3 h, a saturated brine solution was added and the mixture was extracted with EtOAc. The organic layer was dried, filtered, and concentrated to afford tert-butyl(1R,3R,4S)-3-(1-hydroxyethyl)-4-(2-(3-(trifluoromethyl)benzamido)acetamido)cyclohexylcarbamate (60 mg). MS found: (M+H)$^+$=488.2.

Example 8k, Step 3: The above material 73c (60 mg) was dissolved in CH$_2$Cl$_2$ (1 mL) and cooled to 0° C. prior to the addition of TFA (0.5 mL). After the reaction was warmed to rt over 1 h, it was concentrated and dried. The resulting material was dissolved in dichloroethane (1 mL) prior to the adddition of acetone (0.028 mL) and NaBH(OAc)$_3$ (83 mg). After 18 h, 37% formaldehyde in water (0.6 mL) was added along with additional MeOH (1 mL) and NaBH$_3$CN (44 mg). This mixture was stirred 2 h before saturated NaHCO$_3$ solution was added and some of the MeOH was removed. EtOAc was added and the organic layer was dried, filtered, and concentrated. Reverse phase HPLC purification (gradient elution, water/acetonitrile/TFA) of the resulting residue afforded the title compound (20 mg) as a mixture of alcohol diastereomers. MS found: (M+H)$^+$=444.2.

Example 8l

Synthesis of N-(2-((1S,2R,4R)-2-((S)-1-hydroxy-2-methylpropyl)-4-(isopropyl(methyl)amino)cyclohexylamino)-2-oxoethyl)-3-(trifluoromethyl)benzamide Example 8l, Step 1: To a solution of (1R,2S,5R)-tert-butyl 2-(benzyloxycarbonyl)-7-oxo-6-aza-bicyclo[3.2.1]octane-6-carboxylate (300 mg, 0.8 mmol) in THF (25 mL) was added iPrMgCl (1.6 mL, 3.2 mmol) at 0° C. The reaction was stirred at 0° C. for 3 h before the reaction mixture was partitioned between sat. NaH$_4$Cl (20 mL) and EtOAc (30 mL). The aqueous layer was extracted with EtOAc (2×30 mL) and the organic phases were combined, washed with brine (25 mL), dried (Na$_2$SO$_4$), filtered, and concentrated in vacuo to give benzyloxycarbonyl tert-butyl(1R,3R,4S)-4-amino-3-isobutyrylcyclohexylcarbamate. MS found: (M+H)$^+$=419.

Example 8l, Step 2: To a solution of benzyloxycarbonyl tert-butyl(1R,3R,4S)-4-amino-3-isobutyrylcyclohexylcarbamate (550 mg, 1.3 mmol) in MeOH (25 mL) was added NaBH$_4$ (74 mg, 1.95 mmol) at 0° C. The reaction was stirred at rt for 4 h before the reaction mixture was partitioned between sat. NaH$_4$Cl (20 mL) and EtOAc (30 mL). The aqueous layer was extracted with EtOAc (2×30 mL) and the organic phases were combined, washed with brine (25 mL), dried (Na$_2$SO$_4$), filtered, and concentrated in vacuo to give 450 mg of benzyloxycarbonyl tert-butyl(1R,3R,4S)-4-amino-3-((S)-1-hydroxy-2-methylpropyl)cyclohexylcarbamate. MS found: (M+H)$^+$=421.

Example 8l, Step 3: A solution of benzyloxycarbonyl tert-butyl(1R,3R,4S)-4-amino-3-((S)-1-hydroxy-2-methylpropyl)cyclohexylcarbamate (450 mg) in MeOH (30 mL) was charged with 10% Pd/C, Degussa (70 mg). The reaction flask was evacuated and then back-filled with hydrogen; this was repeated three more times. The reaction was stirred under 1 atm of H$_2$ for 4 h and then filtered and concentrated in vacuo to afford 300 mg of tert-butyl(1R,3R,4S)-4-amino-3-((S)-1-hydroxy-2-methylpropyl)cyclohexylcarbamate. MS found: (M+H)$^+$=287.

Example 8l, Step 4: To a solution of tert-butyl(1R,3R,4S)-4-amino-3-((S)-1-hydroxy-2-methylpropyl)cyclohexylcarbamate (300 mg, 1.05 mmol) in DMF (10 mL) was charged with 3-(trifluoromethyl)benzoic acid (330 mg, 1.26 mmol), N,N-diethylisopropylamine (0.2 mL, 1.26 mmol), and HATU (480 mg, 1.26 mmol). The reaction was stirred for 16 h at RT and then partitioned between EtOAc and sat. NaHCO$_3$; the aqueous phase was back extracted with EtOAc. The organic phases were combined, washed with brine, dried (Na$_2$SO$_4$), filtered, and concentrated in vacuo to afford tert-butyl(1R,3R,4S)-3-((S)-1-hydroxy-2-methylpropyl)-4-(2-(3-(trifluoromethyl)benzamido)acetamido)cyclohexylcarbamate. MS found: (M+H)$^+$=516.

Example 8l, Step 5: The entirety of tert-butyl(1R,3R,4S)-3-((S)-1-hydroxy-2-methylpropyl)-4-(2-(3-(trifluoromethyl)benzamido)acetamido)cyclohexylcarbamate prepared in previous Step (1 eq) in CH$_2$Cl$_2$ (20 mL) was added TFA (4 mL) at RT. The reaction was stirred for 5 h and concentrated in vacuo. The residue was partitioned between 1N NaOH (30 mL) and EtOAc (40 mL). The aqueous layer was extracted with EtOAc (2×50 mL) and the organic phases were combined, washed with brine (25 mL), dried (Na$_2$SO$_4$), filtered, and concentrated in vacuo to give N-(2-((1S,2R,4R)-4-amino-2-((S)-1-hydroxy-2-methylpropyl)cyclohexylamino)-2-oxoethyl)-3-(trifluoromethyl)benzamide. MS found: (M+H)$^+$=416.

Example 8l, Step 6: The entirety of N-(2-((1S,2R,4R)-4-amino-2-((S)-1-hydroxy-2-methylpropyl)cyclohexylamino)-2-oxoethyl)-3-(trifluoromethyl)benzamide te prepared in previous Step (1 eq) in CH$_2$Cl$_2$ (20 mL). The resultant solution was charged with acetone (10 eq) and stirred at RT for 10 min before sodium cyanoborohydride (2 eq) was added in one portion. The reaction was stirred at RT for 10 h and then charged successively with formaldehyde (10 eq in 37 wt % aq soln) and sodium cyanoborohydride (2 eq). The reaction was stirred for another 9 h at RT and then quenched with sat. NaHCO$_3$. The aqueous mixture was extracted with EtOAc (40 mL, then 2×40 mL). The organic extracts were combined, washed with brine (30 mL), dried (MgSO$_4$), filtered, and concentrated in vacuo. After the resulting oil stood, some paraformaldehyde-related products solidified; these were removed by dissolving the mixture in a minimal volume of EtOAc and filtering. Subsequent concentration provided N-(2-((1S,2R,4R)-2-((S)-1-hydroxy-2-methylpropyl)-4-(isopropyl(methyl)amino)cyclohexylamino)-2-oxoethyl)-3-(trifluoromethyl)benzamide. MS found: (M+H)$^+$=472.

TABLE 8-A

The compounds in the following table were made using the methods exemplified above. See Table 1-A for a complete description of the table headings.

| Ex. | R$^5$ | R$^6$ | Z | R$^2$ | Step Alt. | MS |
|---|---|---|---|---|---|---|
| 8a | i-Pr(Me)N | H | NHC=O | 3-CF$_3$-phenyl | n/a | 430 |
| 8b | i-Pr(Me)N | H | NHC=O | 3-CF$_3$-phenyl | n/a | 416 |
| 8c | i-Pr(Me)N | Et, R/S | NHC=O | 3-CF$_3$-phenyl | n/a | 444 |
| 8d | i-Pr(Me)N | n-Pr, R/S | NHC=O | 3-CF$_3$-phenyl | 8c, Step 2 | 458 |
| 8e | t-Bu(H)N | H | NHC=O | 3-CF$_3$-phenyl | n/a | 430 |

TABLE 8-A-continued

The compounds in the following table were made using the methods exemplified above. See Table 1-A for a complete description of the table headings.

| Ex. | R⁵ | R⁶ | Z | R² | Step Alt. | MS |
|---|---|---|---|---|---|---|
| 8f | t-Bu(H)N | H | NHC=O | 2-tert-butyl-4-substituted phenol | 8e, Step 5 | 434 |
| 8g | t-Bu(H)N | H | NHC=O | 5-(4-CF₃-phenyl)furan-2-yl | 8e, Step 5 | 462 |
| 8h | t-Bu(H)N | H | NHC=O | 5-tert-butyl-furan-3-yl | 8e, Step 5 | 422 |
| 8i | t-Bu(H)N | H | NHC=O | 6-CF₃-quinazolin-4-yl | n/a | 454 |
| 8j | t-Bu(H)N | H | NHC=O | 3-tert-butylphenyl | 8e, Step 5 | 418 |
| 8k | i-Pr(Me)N | Me, R/S | NHC=O | 3-CF₃-phenyl | n/a | 444 |
| 8l | i-Pr(Me)N | i-Pr, R/S | NHC=O | 3-CF₃-phenyl | n/a | 472 |

TABLE 8-B

The chemical names of the specific examples illustrated in Table 8-A are tabulated below.

| Example | Name |
|---|---|
| 8a | N-(2-((1S,2R,4R)-2-(hydroxymethyl)-4-(isopropyl(methyl)amino)cyclohexylamino)-2-oxoethyl)-3-(trifluoromethyl)benzamide |
| 8b | N-(2-((1S,2R,4R)-2-(hydroxymethyl)-4-(isopropylamino)cyclohexylamino)-2-oxoethyl)-3-(trifluoromethyl)benzamide |
| 8c | N-(2-((1S,2R,4R)-2-((R/S)-1-hydroxypropyl)-4-(isopropylamino)cyclohexylamino)-2-oxoethyl)-3-(trifluoromethyl)benzamide |
| 8d | N-(2-((1S,2R,4R)-2-((R/S)-1-hydroxybutyl)-4-(isopropylamino)cyclohexylamino)-2-oxoethyl)-3-(trifluoromethyl)benzamide |
| 8e | N-(2-((1S,2R,4R)-4-(tert-butylamino)-2-(hydroxymethyl)cyclohexylamino)-2-oxoethyl)-3-(trifluoromethyl)benzamide |
| 8f | 3-tert-butyl-N-(2-((1S,2R,4R)-4-(tert-butylamino)-2-(hydroxymethyl)cyclohexylamino)-2-oxoethyl)-4-hydroxybenzamide |
| 8g | N-(2-((1S,2R,4R)-4-(tert-butylamino)-2-(hydroxymethyl)cyclohexylamino)-2-oxoethyl)-5-(4-chlorophenyl)furan-2-carboxamide |
| 8h | 5-tert-butyl-N-(2-((1S,2R,4R)-4-(tert-butylamino)-2-(hydroxymethyl)cyclohexylamino)-2-oxoethyl)-2-methylfuran-carboxamide |
| 8i | N-((1S,2R,4R)-4-(tert-butylamino)-2-(hydroxymethyl)cyclohexyl)-2-(6-(trifluoromethyl)quinazolin-4-ylamino)acetamide |
| 8j | 3-tert-butyl-N-(2-((1S,2R,4R)-4-(tert-butylamino)-2-(hydroxymethyl)cyclohexylamino)-2-oxoethyl)benzamide |
| 8k | N-(2-((1S,2R,4R)-2-((R/S)-1-hydroxyethyl)-4-(isopropyl(methyl)amino)cyclohexylamino)-2-oxoethyl)-3-(trifluoromethyl)benzamide |
| 8l | N-(2-((1S,2R,4R)-2-((S)-1-hydroxy-2-methylpropyl)-4-(isopropyl(methyl)amino)cyclohexylamino)-2-oxoethyl)-3-(trifluoromethyl)benzamide |

Examples 9a -9b

Example 9a

Synthesis of N-(2-((1S,3S,4R)-3-(hydroxymethyl)-4-(isopropylamino)cyclohexylamino)-2-oxoethyl)-3-(trifluoromethyl)benzamide Example 9a, Step 1: To a solution of 8-(1-Phenyl-ethylamino)-1,4-dioxa-spiro[4.5]decane-7-carboxylic acid ethyl ester (2 g; see Preparations section; this material comes from the enantiomeric series) in Et$_2$O (30 mL) was slowly added LAH (273 mg) at 0° C. Two hours later, H$_2$O (5 mL) and 1N NaOH (10 mL) were added followed by filtration of the solid. The resulting filtrate was concentrated to [8-(1-Phenyl-ethylamino)-1,4-dioxa-spiro[4.5]dec-7-yl]-methanol. MS found: (M+H)$^+$=292.

Example 9a, Step 2: [8-(1-Phenyl-ethylamino)-1,4-dioxa-spiro[4.5]dec-7-yl]-methanol (1.5 g) was dissolved in MeOH (20 mL) prior to the addition of 10% Pd/C (200 mg). The solution was stirred under hydrogen at 50 psi for 16 h. The palladium was filtered and the solution was concentrated to the primary amine which was subsequently dissolved in CH$_2$Cl$_2$ (15 mL) and MeOH (15 mL) followed by NaHCO$_3$ (676 mg) and cbz$_2$O (1.5 g). After 16 h, the solution was diluted with H$_2$O and EtOAc. The organic layer was collected, dried over Na$_2$SO$_4$, and then concentrated to (7-Hydroxymethyl-1,4-dioxa-spiro[4.5]dec-8-yl)-carbamic acid benzyl ester. MS found: (M+H)$^+$=322.

Example 9a, Step 3: (7-Hydroxymethyl-1,4-dioxa-spiro[4.5]dec-8-yl)-carbamic acid benzyl ester (1.3 g) was dissolved in MeCN (20 mL) and 1N HCl (15 mL), and left with stirring at rt for 16 h. Upon the addition of EtOAc and 1N NaOH, the organic layer was collected, dried over Na$_2$SO$_4$, and then concentrated to a crude oil. The crude oil was re-dissolved in. EtOH (30 mL) followed by NH$_2$OH.HCl (1.8 g) and NaOAc (4.3 g). 16 h later, the reaction mixture was diluted With H$_2$O and EtOAc. The organic layer was collected, dried over Na$_2$SO$_4$, and then concentrated to (4-Hydroxyimino-2-hydroxymethyl-cyclohexyl)-carbamic acid benzyl ester. MS found: (M+H)$^+$=292.

Example 9a, Step 4: (4-Hydroxyimino-2-hydroxymethyl-cyclohexyl)-carbamic acid benzyl ester (1 g) was dissolved in AcOH (10 mL) and EtOH (10 mL) followed by Zinc powder (1.4 g). The reaction mixture was stirred at rt overnight. Saturated NaHCO$_3$ solution and EtOAc were added, and the organic layer was collected, dried over Na$_2$SO$_4$, and concentrated to (4-Amino-2-hydroxymethyl-cyclohexyl)-carbamic acid benzyl ester. MS found: (M+H)$^+$=279.

Example 9a, Step 5: (4-Amino-2-hydroxymethyl-cyclohexyl)-carbamic acid benzyl ester (450 mg) was dissolved in DMF prior to the addition of Hunig's base (0.42 mL) and 3-trifluoromethyl-benzoylamino)-acetic acid (460 mg). After cooling to 0° C., HATU Reagent (840 mg) was added. The resulting mixture was warmed to rt and was stirred overnight. EtOAc was added along with 1 N HCl solution (aq). The EtOAc layer was washed with 1 N HCl, NaHCO$_3$ solution (aq), and brine. The EtOAc was dried (MgSO$_4$), filtered, and concentrated. Flash chromatography of the resulting residue gave {2-Hydroxymethyl-4-[2-(3-trifluoromethyl-benzoylamino)-acetylamino]-cyclohexyl}-carbamic acid benzyl ester. MS found: (M+H)$^+$=508.

Example 9a, Step 6: {2-Hydroxymethyl-4-[2-(3-trifluoromethyl-benzoylamino)-acetylamino]-cyclohexyl}-carbamic acid benzyl ester (40 mg) was dissolved in MeOH (10 mL) prior to the addition of 10% Pd/C (10 mg). A hydrogen balloon was added and the solution was stirred for 4.0 h. The palladium was filtered and the filtrate was concentrated to the primary amine which was subsequently dissolved in dichloroethane (5 mL) prior to the adddition of glacial acetic acid (8 mg), acetone (0.5 mL), and NaBH(OAc)$_3$ (20 mg). After 20 h, the solution was concentrated. The resulting residue was dissolved in EtOAc and washed with saturated NaHCO$_3$, water, and brine. The organic layer was dried, filtered, and concentrated. Reverse phase HPLC purification (gradient elution, water/acetonitrile/TFA) of the crude product to give N-(2-((1S,3S,4R)-3-(hydroxymethyl)-4-(isopropylamino)cyclohexylamino)-2-oxoethyl)-3-(trifluoromethyl)benzamide. MS found: (M+H)$^+$=416.

TABLE 9-A

The compounds in the following table were made using the methods exemplified above. See Table 1-A for a complete description of the table headings.

| Ex. | $R^5$ | $R^6$ | Z | $R^2$ | Step Alt. | MS |
|---|---|---|---|---|---|---|
| 9a | i-Pr(H)N | H | NHC=O | 3-CF₃-phenyl | n/a | 416 |
| 9b | i-Pr(Me)N | H | NHC=O | 2-t-Bu-4-OH-phenyl | 9a, Steps 5 & 6 | 434 |

TABLE 9-B

The chemical names of the specific examples illustrated in Table 9-A are tabulated below.

| Example | Name |
|---|---|
| 9a | N-(2-((1S,3S,4R)-3-(hydroxymethyl)-4-(isopropylamino)cyclohexylamino)-2-oxoethyl)-3-(trifluoromethyl)benzamide |
| 9b | 3-tert-butyl-4-hydroxy-N-(2-((1S,3S,4R)-3-(hydroxymethyl)-4-(isopropyl(methyl)amino)cyclohexylamino)-2-oxoethyl)benzamide |

Examples 10a -10af

Example 10a

Synthesis of N-(2-((1S,2R,4R)-4-amino-2-(isopropylsulfonylmethyl)cyclohexylamino)-2-oxoethyl)-3-(trifluoromethyl)benzamide Example 10a, Step 1: To a solution of tert-butyl(1R,3R,4S)-4-benzyloxycarbonylamino-3-(hydroxymethyl)cyclohexylcarbamate (440 mg, 1.16 mmol) in 20 mL of $CH_2Cl_2$ cooled to 0° C. was added $Et_3N$ (0.3 mL, 2 mmol) and MsCl (0.1 mL, 1.39 mmol). The reaction mixture was stirred at rt for 2 h before water was added. The aqueous phase was extracted with EtOAc (2×25 mL) and concentrated to an oil for further use. In a separate flask, propane-2-thiol (0.22 mL, 2.3 mmol) was dissolved in 10 mL of DMF, cooled to 0° C., and charged with NaH (93 mg, 2.32 mmol). The reaction mixture was stirred at rt for 2 h before a solution of the just prepared oil in 10 mL of DMF was slowly added. The mixture was stirred at rt for 16 h before water and EtOAc were added. The organic layer was separated, dried over $Na_2SO_4$, and concentrated to afford an oil which was purified by column chromatography on silica gel with EtOAc: hexane (30:70) to give N-(1S,2R,4R)-4-Benzyloxycarbonylamino-3-isopropylsulfanylmethyl-cyclohexyl)-carbamic acid tert-butyl ester (160 mg, 33%). MS found: $(M+H)^+ =437$.

Example 10a, Step 2: To a solution of N-((1S,2R,4R)-4-Benzyloxycarbonylamino-3-isopropylsulfanylmethyl-cyclohexyl)-carbamic acid tert-butyl ester (1 g, 2.3 mmol) in iPrOH (20 mL) at rt was added Oxone (2.8 g, 4.6 mmol) in water (10 mL). The mixture was stirred at rt for 16 h before water and EtOAc were added. The organic layer was separated, dried over $Na_2SO_4$, and concentrated to afford to crude N-[(1S,2R,4R)-4-Benzyloxycarbonylamino-3-(propane-2-sulfonylmethyl)-cyclohexyl]-carbamic acid tert-butyl ester (900 mg, 90%). MS found: $(M+H)^+=469$.

Example 10a, Step 3: A solution of N-[(1S,2R,4R)-4-Benzyloxycarbonylamino-3-(propane-2-sulfonylmethyl)-cyclohexyl]-carbamic acid tert-butyl ester (2 g) in MeOH (50 mL) was charged with 10% Pd/C, Degussa (1.5 g). The reaction flask was evacuated and then back-filled with hydrogen; this was repeated three more times. The reaction was stirred under 1 atm of $H_2$ for 4 h and then filtered and concentrated in vacuo to afford tert-butyl(1R,3R,4S)-4-amino-3-(isopropylsulfonylmethyl)cyclohexylcarbamate (1 g). MS found: $(M+H)^+=335$.

Example 10a, Step 4: A sample of tert-butyl(1R,3R,4S)-4-amino-3-(isopropylsulfonylmethyl)cyclohexylcarbamate was carried through the procedure described in Example 2r, Step 3 to afford tert-butyl(1R,3R,4S)-3-(isopropylsulfonylmethyl)-4-(2-(3-(trifluoromethyl)benzamido)acetamido)cyclohexylcarbamate. A portion of this material (200 mg) was dissolved in dichloromethane (4 mL) and treated with trifluoroacetic acid (4 mL). After 4.5 h, the mixture was concentrated under vacuum, and the residue was partitioned between 1.0 M aqueous NaOH and ethyl acetate. The organic phase was dried over $Na_2SO_4$ and concentrated under vacuum to provide the title compound as a white solid (164 mg). MS found: $(M+H)^+=464.4$.

Example 10b

Synthesis of N-(2-((1S,2R,4R)-4-(isopropyl(methyl)amino)-2-(isopropylsulfonylmethyl)cyclohexylamino)-2-oxoethyl)-3-(trifluoromethyl)benzamide Following the procedure of Example 4a, Step 5, a sample of N-(2-((1S,2R,4R)-4-amino-2-(isopropylsulfonylmethyl)cyclohexylamino)-2-oxoethyl)-3-(trifluoromethyl)benzamide was converted to the title compound. MS found: $(M+H)^+=520$.

Example 10d

Synthesis of N-(2-((1S,2R,4R)-2-(isopropylsulfonylmethyl)-4-(5-(trifluoromethyl)-1H-tetrazol-1-yl)cyclohexylamino)-2-oxoethyl)-3-(trifluoromethyl)benzamide Example 10d, Step 1: A solution of tert-butyl(1R,3R,4S)-4-benzyloxycarbonylamino-3-(isopropylsulfonylmethyl)cyclohexylcarbamate (111 mg) in ethyl acetate (4 mL) was treated with a solution of HCl in dioxane (4.0 M, 4 mL). The mixture was stirred at rt for 50 min, then was concentrated to provide the hydrochloride salt of benzyl (1S,2R,4R)-4-amino-2-(isopropylsulfonylmethyl)cyclohexylcarbamate (100 mg) as a white glassy solid. MS found: $(M+H)^+=369.2$.

Example 10d, Step 2: The sample of benzyl (1S,2R,4R)-4-amino-2-(isopropylsulfonylmethyl)cyclohexylcarbamate prepared in Example 10d, Step 1, was converted to the free base by partitioning between aqueous NaOH (1.0 M) and ethyl acetate, with the organic phase being dried (Na₂SO₄) and concentrated under vacuum. A solution of triphenylphosphine (151 mg) and triethylamine (0.08 mL) in tetrachloromethane (1 mL) was stirred on an ice bath and treated with trifluoroacetic acid (0.018 mL). The mixture was stirred for 10 min, then was treated with a solution of the free base prepared above in tetrachloromethane (1 mL). The mixture was heated to reflux for 3.5 h, then was cooled to rt and concentrated. The residue was purified by flash column chromatography on silica gel, eluting with 4:6 v/v ethyl acetate/hexane, to provide benzyl (1S,2R,4R)-4-((Z)-1-chloro-2,2,2-trifluoroethylideneamino)-2-(isopropylsulfonylmethyl)cyclohexylcarbamate (50 mg) as a yellow oil. This material was dissolved in acetonitrile (1 mL) and treated with sodium azide (7 mg). The mixture was stirred at rt for 65 h, then was filtered and the filtrate was concentrated. The residue was purified by rotary thin layer chromatography to provide benzyl (1S,2R,4R)-2-(isopropylsulfonylmethyl)-4-(5-(trifluoromethyl)-1H-tetrazol-1-yl)cyclohexylcarbamate (45 mg). MS found: (M+H)⁺=490.2.

Example 10d, Step 3: Following the procedure of Example 4a Step 2, benzyl (1S,2R,4R)-2-(isopropylsulfonylmethyl)-4-(5-(trifluoromethyl)-1H-tetrazol-1-yl)cyclohexylcarbamate (45 mg) was converted to (1S,2R,4R)-2-(isopropylsulfonylmethyl)-4-(5-(trifluoromethyl)-1H-tetrazol-1-yl)cyclohexanamine as a gum (32 mg). MS found: (M+H)⁺=356.2.

Example 10d, Step 4: Following the procedure of Example 4a, Step 3, a sample of ((1S,2R,4R)-2-(isopropylsulfonylmethyl)-4-(5-(trifluoromethyl)-1H-tetrazol-1-yl)cyclohexanamine (16.5 mg) was converted to the title compound, N-(2-((1S,2R,4R)-2-(isopropylsulfonylmethyl)-4-(5-(trifluoromethyl)-1H-tetrazol-1-yl)cyclohexylamino)-2-oxoethyl)-3-(trifluoromethyl)benzamide, as an amorphous solid (12.9 mg) after purification by rotary thin layer chromatography, eluting with 3:1 v/v ethyl acetate/hexane. MS found: (M+H)⁺=585.2.

Example 10f

Synthesis of N-(2-((1S,2R,4R)-4-(1H-imidazol-1-yl)-2-(isopropylsulfonylmethyl)cyclohexylamino)-2-oxoethyl)-3-(trifluoromethyl)benzamide A solution of N-(2-((1S,2R,4R)-4-amino-2-(isopropylsulfonylmethyl)cyclohexylamino)-2-oxoethyl)-3-(trifluoromethyl)benzamide (54 mg) in methanol (1 mL) was treated with paraformaldehyde (4 mg), (NH₄)₂CO₃ (6 mg) and glyoxal trimer dihydrate (9 mg). The mixture was stirred at rt for 91 h, then was concentrated and purified by reverse phase HPLC and lyophilized. The resulting material contained significant starting material, and was resubjected to the same reaction conditions with the same amounts of reagents. After 20 h, the mixture was concentrated, purified by reverse phase HPLC and lyophilized to provide the trifluoroacetic acid salt of the title compound as a white powder (37 mg). MS found: (M+H)⁺=515.2.

Example 10i

Synthesis of (N-(2-((1S,2R,4R)-4-(Isopropylamino)-2-(methylsulfonylmethyl)cyclohexylamino)-2-oxoethyl)-3-(trifluoromethyl)benzamide Example 10i, Step 1: (1R,3R,4S)-(4-Benzyloxycarbonylamino-3-hydroxymethylcyclohexyl)carbamic acid tert-butyl ester (1.0 g) was dissolved in CH₂Cl₂ (120 ml) and cooled to 0° C. prior to the addition of Et₃N (0.5 mL) and methanesulfonyl chloride (0.55 mL). This mixture was warmed to RT and was stirred for 3 h. The CH₂Cl₂ was removed and EtOAc was added along with water. The organic layer was dried, filtered, and concentrated. This solid was dissolved in DMF (15 mL) and HMPA (2 mL) prior to the addition of NaSMe (1.1 g) and 18-crown-6 (500 mg). After 18 h, additional HMPA (0.5 mL) was added. After another 3 h, water was added and the solution was extracted with EtOAc. The organic layer was dried, filtered, and concentrated. Flash chromatography of the resulting residue gave (1R,3R,4S)-(4-benzyloxycarbonylamino-3-(methyl)thiomethylcyclohexyl)carbamic acid tert-butyl ester (1.1 g). MS found: (M+H)⁺=409.2.

Example 10i, Step 2: The above material was dissolved in MeOH (10 mL) prior to the addition of Oxone (3.0 g) in water (5 mL). After 2 h, the reaction was concentrated. Flash chromatography of the resulting residue gave (1R,3R,4S)-(4-benzyloxycarbonylamino-3-(methyl)sulfonylmethylcyclohexyl)carbamic acid tert-butyl ester (1.4 g). MS found: (M+H)⁺=441.2.

Example 10i, Step 3: A portion of (1R,3R,4S)-(4-benzyloxycarbonylamino-3-(methyl)sulfonylmethylcyclohexyl)carbamic acid tert-butyl ester (210 mg) was dissolved in CH₂Cl₂ (2 mL) and cooled to 0° C. prior to the addition of TFA (1 mL). After the reaction was warmed to rt over 1 h, it was concentrated. The resulting material was dissolved in dichloroethane (2 mL) prior to the adddition of glacial acetic acid (0.23 mL), acetone (0.15 mL), and NaBH(OAc)₃ (254 mg). After 20 h, the solution was concentrated (200 mg). A portion of this material (15 mg) was dissolved in MeOH (1 ml) prior to the addition of 10% Pd/C (10 mg). A hydrogen balloon was added and the solution was stirred for 2 h. The palladium was filtered off and the solution was concentrated. This material was incorporated into Example 2r, Step 3, and reverse phase HPLC purification (gradient elution, water/acetonitrile/TFA) provided the TFA salt of the title compound (10 mg). MS found: (M+H)⁺=478.2.

Example 10j

Synthesis of N-(2-((1S,2R,4R)-4-(Isopropyl(methyl)amino)-2-(methylsulfonylmethyl)cyclohexylamino)-2-oxoethyl)-3-(trifluoromethyl)benzamide Example 10j, Step 1: (1R,3R,4S)-(4-Benzyloxycarbonylamino-3-(methyl)sulfonylmethylcyclohexyl)carbamic acid tert-butyl ester (300 mg) was dissolved in MeOH (5 ml) prior to the addition of 10% Pd/C (200 mg). A hydrogen balloon was added and the solution was stirred for 3 h. The palladium was filtered off and the solution was concentrated to give tert-butyl(1R,3R,4S)-4-amino-3-(methylsulfonylmethyl)cyclohexylcarbamate (201 mg). MS found: (M+H)+ 307.2.

Example 10j, Step 2: The above compound (201 mg) was dissolved in DMF (5 mL) prior to the addition of 4-methylmorpholine (0.36 mL) and N-Cbz-Gly-OH (150 mg). After cooling to 0° C., BOP reagent (374 mg) was added. The resulting mixture was warmed to rt and was stirred overnight. EtOAc was added along with 1 N HCl solution. The organic layer was washed with 1 N HCl (aq), NaHCO₃ solution (aq), and brine. The organic layer was then dried (MgSO₄), filtered, and concentrated. Flash chromatography of the resulting residue gave tert-butyl(1R,3R,4S)-4-(2-

(benzyloxycarbonylamino)acetamido)-3-(methylsulfonylmethyl)cyclohexylcarbamate (260 mg). MS found: (M+Na)+ =498.2.

Example 10j, Step 3: The compound from Step 2 (260 mg) was dissolved in $CH_2Cl_2$ (2 mL) and cooled to 0° C. prior to the addition of TFA (1 mL). After the reaction was warmed to rt over 1 h, it was concentrated and dried. The resulting material was dissolved in MeOH (5 mL) prior to the adddition of acetone (0.4 mL) and $NaBH_3CN$ (176 mg) After 5 h, 37% formaldehyde in water (0.4 mL) was added along with additional MeOH (5 mL) and $NaBH_3CN$ (176 mg). This mixture was stirred 2 h before saturated $NaHCO_3$ solution was added and some of the MeOH was removed. EtOAc was added and the organic layer was dried, filtered, and concentrated. This material was dissolved in 30% HBr/ AcOH (2 mL). After 30 min, $Et_2O$ was added and the resulting solid was isolated to afford 2-amino-N-((1S,2R, 4R)-4-(isopropyl(methyl)amino)-2-(methylsulfonylmethyl) cyclohexyl)acetamide bis HBr salt (1.0 g). MS found: $(M+H)^+=320.5$.

Example 10j, Step 4: A portion of the above compound 66c (40 mg) was dissolved in DMF (1 mL) prior to the addition of 4-methylmorpholine (42.4 mg) and 3-(trifluoromethyl)benzoic acid (19 mg). After cooling to 0° C., BOP reagent (55 mg) was added. The resulting mixture was warmed to rt and was stirred overnight. EtOAc was added along with 1 N HCl solution. The organic layer was washed with 1 N HCl (aq), $NaHCO_3$ solution (aq), and brine. The organic layer was then dried ($MgSO_4$), filtered, and concentrated. Reverse phase HPLC purification (gradient elution, water/acetonitrile/TFA) of the resulting residue provided the TFA salt of the title compound (5.0 mg). MS found: $(M+H)^+$ =492.3.

Example 10l

Synthesis of 2-Amino-N-(2-((1S,2R,4R)-4-(isopropyl(methyl)amino)-2-(methylsulfonylmethyl)cyclohexylamino)-2-oxoethyl)-5-(trifluoromethoxy)benzamide Example 10l, Step 1: 2-(tert-Butoxycarbonylamino)-5-(trifluoromethoxy)benzoic acid was incorporated into Example 10j, Step 4, to give tert-butyl 2-((2-((1S,2R,4R)-4-(isopropyl(methyl)amino)-2-(methylsulfonylmethyl)cyclohexylamino)-2-oxoethyl)carbamoyl)-4-(trifluoromethoxy)phenylcarbamate. MS found: $(M+H)^+=623.3$.

Example 10l, Step 2: The above material was dissolved in $CH_2Cl_2$ (2 mL) and cooled to 0° C. prior to the addition of TFA (4 mL). After 30 min at rt, the reaction was concentrated and dried to provide the TFA salt of the title compound. MS found: $(M+H)^+=523.3$.

Example 10m

Synthesis of 2-(6-Chloroquinazolin-4-ylamino)-N-((1S,2R,4R)-4-(isopropyl(methyl)amino)-2-(methylsulfonylmethyl)cyclohexyl)acetamide A portion of the 2-amino-N-((1S,2R,4R)-4-(isopropyl (methyl)amino)-2-(methylsulfonylmethyl)cyclohexyl)acetamide bis HBr salt (20 mg, see Example 10j, Step 3), triethylamine (0.1 mL), and 4,6-dichloroquinazoline (33 mg) were dissolved in acetonitrile (2 mL) and placed in a microwave. The reaction was heated at 100° C. for 22 min. The solution was filtered and the filtrate was subjected to reverse phase HPLC purification (gradient elution, water/ acetonitrile/TFA) to provide the TFA salt of the title compound (5 mg). MS found: $(M+H)^+=482.3$.

Example 10n

Synthesis of N-(2-((1S,2R,4R)-4-Amino-2-(tertbutylsulfonylmethyl)cyclohexylamino)-2-oxoethyl)-3-(trifluoromethyl)benzamide Example 10n, Step 1: Sodium 2-methyl-2-propanethiolate (1.4 g) was incorporated into Example 10i, Steps 1 and 2, to give (1R,3R,4S)-(4-benzyloxycarbonylamino-3-(tert-butyl) sulfonylmethylcyclohexyl)carbamic acid tert-butyl ester (1.3 g). MS found: $(M+H)^+=483.6$.

Example 10n, Step 2: A portion of (1R,3R,4S)-(4-benzyloxycarbonylamino-3-(tert-butyl)sulfonylmethylcyclohexyl)carbamic acid tert-butyl ester (100 mg) was dissolved in MeOH (1.5 ml) prior to the addition of 10% Pd/C (50 mg). A hydrogen balloon was added and the solution was stirred for 2 h. The palladium was filtered off and the solution was concentrated. This material was incorporated into Example 2r, Step 3. Reverse phase HPLC purification (gradient elution, water/acetonitrile/TFA) afforded tert-butyl(1R,3R, 4S)-3-(tert-butylsulfonylmethyl)-4-(2-(3-(trifluoromethyl) benzamido)acetamido)cyclohexylcarbamate (67 mg). MS found: $(M+H)^+=578.4$.

Example 10n, Step 3: The above material (67 mg) was dissolved in $CH_2Cl_2$ (2 mL) and cooled to 0° C. prior to the addition of TFA (1 mL). After 30 min at rt, the reaction was concentrated and dried to provide the TFA salt of the title compound. MS found: $(M+H)^+=478.3$.

Example 10o

Synthesis of N-(2-((1S,2R,4R)-2-(tert-butylsulfonylmethyl)-4-(isopropylamino)cyclohexylamino)-2-oxoethyl)-3-(trifluoromethyl)benzamide A portion of N-(2-((1S,2R,4R)-4-amino-2-(tert-butylsulfonylmethyl)cyclohexylamino)-2-oxoethyl)-3-(trifluoromethyl)benzamide (71 mg) was dissolved in dichloroethane (3 mL) prior to the adddition of glacial acetic acid (36 mg), acetone (34 mg), and $NaBH(OAc)_3$ (76 mg). After 20 h, the solution was concentrated. Reverse phase HPLC purification (gradient elution, water/acetonitrile/TFA) of the resulting residue afforded the TFA salt of the title compound (5 mg). MS found: $(M+H)^+=520.3$.

Example 10p

Synthesis of N-(2-((1S,2R,4R)-2-(Tert-butylsulfonylmethyl)-4-(isopropyl(methyl)amino)cyclohexylamino)-2-oxoethyl)-3-(trifluoromethyl)benzamide A portion of N-(2-((1S,2R,4R)-2-(tert-butylsulfonylmethyl)-4-(isopropylamino)cyclohexylamino)-2-oxoethyl)-3-(trifluoromethyl)benzamide (31 mg) was dissolved in MeOH (2 mL) prior to the adddition of 37% formaldehyde in water (3.1 μL) along with $NaBH_3CN$ (102 mg). After 2 h, the solution was concentrated. Reverse phase HPLC purification (gradient elution, water/acetonitrile/TFA) of the resulting residue afforded the TFA salt of the title compound (5.8 mg). MS found: $(M+H)^+=534.4$.

Example 10q

Synthesis of N-(2-((1S,2R,4R)-4-(tert-butylamino)-2-(isopropylsulfonylmethyl)cyclohexylamino)-2-oxoethyl)-3-(trifluoromethyl)benzamide Example 10q, Step 1: A solution of ((7S,8S)-7-Hydroxymethyl-1,4-dioxa-spiro[4.5]dec-8-yl)-carbamic acid benzyl ester (4.45 g, 14 mmol), in $CH_2Cl_2$ (100 ml) was cooled at 0° C. and treated with $Et_3N$ (2.83 g, 28 mmol) and MsCl (1.92 g, 16.8 mmol) and stirred at room temperature for 2 hours. The mixture is washed with water and brine and concentrated to give the mesylate. To a solution of isopropylthiol (2.13 g, 28 mmol) in DMF was cooled at 0° C. and treated with NaH (60% oil dispersion 1.12 g, 28 mmol) portion wise. To the resulting solution was added a solution of the above mesylate in $CH_2Cl_2$ and stirred overnight at room temperature. The mixture is quenched with water and extracted into $CH_2Cl_2$ and washed with water, 1 N NaOH, brine and the solvent removed under vacuum. The residue is chromatographed on silica gel (10-50% Ethyl acetate/hexane) to give 2.72 g of benzyl ((7R,8S)-7-(isopropylthiomethyl)-1,4-dioxa-spiro[4.5]dec-8-yl)-carbamate.

Example 10q, Step 2: A solution of benzyl ((7R,8S)-7-(isopropylthiomethyl)-1,4-dioxa-spiro[4.5]dec-8-yl)-carbamate (2.72 g, 7.16 mmol) in i-PrOH (60 ml) was treated with a solution of Oxone® (8.8 g, 14 mmol) in water (30 ml) and stirred at room temperature for 1 hour. The mixture is diluted with water and extracted into $CH_2Cl_2$. The extracts were washed with water, brine and the solvent removed under vacuum. The residue is chromatographed on silica gel (10-50% Ethyl acetate/hexane) to give 2.3 g of benzyl ((7R,8S)-7-(isopropylsulfonylmethyl)-1,4-dioxa-spiro[4.5]dec-8-yl)-carbamate.

Example 10q, Step 3: A solution of benzyl ((7R,8S)-7-(isopropylsulfonylmethyl)-1,4-dioxa-spiro[4.5]dec-8-yl)-carbamate (2.3 g, 5.6 mmol) in acetone (30 ml) is treated with 5 N HCl (30 ml) and heated to reflux for 2 hrs. The The mixture is concentrated on a rotary evaporator and the residue neutralized with 1 N NaOH and extracted into $CH_2Cl_2$. The organic extracts were washed with water, brine, and the solvent remove under vacuum to give 2.0 g of benzyl (1S,2R)-2-(isopropylsulfonylmethyl)-4-oxocyclohexylcarbamate. This is used without further purification.

Example 10q, Step 4: The ketone from Step 3 (2.0 g, 5.6 mmol) was dissolved in titanium(IV) isopropoxide (3.5 g, 12 mmol) and treated with t-butylamine (1.1 g, 13 mmol). The resulting solution was stirred at room temperature for 12 hours. The solution was diluted with 20 ml of methanol and treated very slowly with $NaBH_4$ caplets (0.3 g, 8 mmol) over a period of 1 hours. [Caution: vigorous foaming occurs.] The solution was quenched with a 0.2 N NaOH and the resulting slurry was diluted with 1 L of $CH_2Cl_2$ and shaken thoroughly in a separatory funnel. The resulting emulsion is filtered through Celite and the solid cake washed two times with $CH_2Cl_2$. The combined filtrates were concentrated on a rotary evaporator to give a mixture of diasteromeric amines a yellow oil which was chromatographed on silica gel (elution with 4-5% ($NH_4OH$/MeOH)/$CH_2Cl_2$) to give 230 mg of benzyl, (1S,2R,4R)-4-(tert-butylamino)-2-(isopropylsulfonylmethyl)-cyclohexylcarbamate.

Example 10q, Step 5: A solution of benzyl (1S,2R,4R)-4-(tert-butylamino)-2-(isopropylsulfonylmethyl)-cyclohexylcarbamate (230 mg, 0.54 mmol), in 50 mL of MeOH was treated with 50 mg of 10% Pd/C and hydrogenated overnight at 55 psi. The mixture was filtered through Celite and concentrated on a rotary evaporator to give 150 mg of (1R,3R,4S)-N1-tert-butyl-3-(isopropylsulfonylmethyl)cyclohexane-1,4-diamine. This was used without further purification.

Example 10q, Step 6: A sample of (1R,3R,4S)-$N^1$-tert-butyl-3-(isopropylsulfonylmethyl)cyclohexane-1,4-diamine was taken through the procedure detailed in Example 2r, Step 3, to afford the title compound (free base) after purification by flash chromatography. $^1$H NMR (500 MHz, $CDCl_3$) δ(TMS): 0.99-1.83 (m, 19H), 2.10-2.16 (m, 1H), 2.47-2.55 (m, 1H), 2.63-2.77 (m, 2H), 2.93-3.12 (m, 2H), 3.99-4.18 (m, 2H), 4.28-4.34 (m, 1H), 6.57-6.63 (m, 1H), 7.19-7.30 (m, 1H), 7.51-7.65 (m, 1H), 7.71-7.83 (m, 1H), 7.94-8.02 (m, 1H), 8.08 (s, 1H); MS found: $(M+H)^+$ =520.53.

Example 10s

Synthesis of N-(2-((1S,2R)-4,4-difluoro-2-(isopropylsulfonylmethyl)cyclohexylamino)-2-oxoethyl)-3-(trifluoromethyl)benzamide Example 10s, Step 1: Lithium borohydride (2.0 N in THF, 35.6 mL, 71.2 mmol) was added dropwise to benzyl (1R, 2S,5R)-7-oxo-6-oxa-bicyclo[(3.2.1]octan-2-ylcarbamate (see 8a) (6.53 g) and methanol (2.28 g) in anhydrous THF (100 mL) at 0° C. After 3 h, the reaction was quenched by addition of water (50 mL) followed by 2N HCl (50 mL). The ice bath was removed and the reaction was warmed to room temperature over 0.5 h. This solution was extracted with ethyl acetate. The combined organic extracts were washed with water, brine, dried over $MgSO_4$ and then evaporated to give benzyl (1S,2R,4R)-4-hydroxy-2-(hydroxymethyl)cyclohexylcarbamate (5.94 g). MS found: $(M+H)^+$=280 (CI).

Example 10s, Step 2: tert-Butyldimethylsilylchloride (2.78 g, 18.5 mmol) in DMF (30 mL) was added dropwise over 3 h to the alcohol from Step 1 (5.43 g) and imidazole (1.33 g) in DMF (50 mL) at 0° C. After the addition was complete the ice bath was removed and the reaction warmed to room temperature overnight. The DMF solution was diluted with ether (400 mL) then washed with water (2×75 mL), sat'd $NaHCO_3$ (1×75 mL), and brine (1×075 mL). The organic layer was dried over $MgSO_4$, filtered, and then evaporated to dryness. The product was purified by flash chromatography (silica gel, 20-40% ethyl acetate/hexanes) to provide benzyl (1S,2R,4R)-2-((tert-butyldimethylsilyloxy)methyl)-4-hydroxycyclohexylcarbamate (4.15 g) as a color less oil. MS found: $(M+H)^+$=394.

Example 10s, Step 3: The compound benzyl (1S,2R,4R)-2-((tert-butyldimethylsilyloxy)methyl)-4-hydroxycyclohexylcarbamate (4.15 g) in $CH_2Cl_2$ (30 mL) was added to Dess-Martin periodane (13.4 g, 31.6 mmol) in $CH_2Cl_2$ (100 mL) at 0° C. After 1 h, the ice bath was removed and the reaction aws stirred overnight. This mixture was diluted with ether (425 mL) and washed with water (2×50 mL), sat'd $Na_2S_2O_3$ (2×50 mL), 1N sodium hydroxide (2×50 mL), and brine (1×50 mL). The organic layer was dried over $MgSO_4$, filtered, and then evaporated to dryness to give benzyl (1S,2R)-2-((tert-butyldimethylsilyloxy)methyl)-4-oxocyclohexylcarbamate (4.05 g) as a clear viscous oil after drying under vacuum overnight. MS found: $(M+H)^+$=392.

Example 10s, Step 4: A solution of acetic acid, water, and THF (30 mL, 3:1:1) was added to benzyl (1S,2R)-2-((tert-butyldimethylsilyloxy)methyl)-4-oxocyclohexylcarbamate (2.56 g) in one portion. After 48 h, the reaction solvent was removed in vacuo and replaced with ethyl acetate (100 mL). The mixture was washed with water (1×25 mL), sat'd $NaHCO_3$ (2×25 mL), and brine (1×25 mL). The resulting organic layer was dried over MgSO$_4$, filtered, and then evaporated to dryness in vacuo to give benzyl (1S,2R)-2-(hydroxymethyl)-4-oxocyclohexylcarbamate (1.80 g) as a clear viscous oil after drying under vacuum overnight: $^1$H NMR (300 MHz, CDCl$_3$) δ 7.37 (s, 5H), 5.57 (d, J=6.9 Hz, 1H), 5.13 (s, 2H), 4.25 (br s, 1H), 3.69 (m, H), 3.45 (m, 2H), 2.38-2.02 (m, 7H).

Example 10s, Step 5: Methanesulfonyl chloride (0.89 g, 7.79 mmol) was added dropwise to the benzyl (1S,2R)-2-(hydroxymethyl)-4-oxocyclohexylcarbamate (1.80 g, 6.49 mmol) and triethylamine (0.99 g, 9.74 mmol) in CH$_2$Cl$_2$ (25 mL) at 0° C. After 2 h at rt, the mixture was diluted with CH$_2$Cl$_2$ (75 mL). The reaction was washed with water (1×25 mL), sat'd NaCO$_3$ (1×25 mL), and brine (1×25 mL). The resulting organic layer was dried over MgSO$_4$, filtered, and then evaporated to dryness in vacuo. The residue was purified by flash chromatography (silica gel, 50-70% ethyl acetate/hexanes) to give ((1R,2S)-2-(benzyloxycarbonyl)-5-oxocyclohexyl)methyl methanesulfonate (1.80 g) as a clear viscous oil. MS found: (M+H)$^+$=356.

Example 10s, Step 6: 2-Propanethiol (0.48 g) was added dropwise to sodium hydride (60% in mineral oil, 0.24 g, 6.08 mmol) in DMF (10 mL) at 0° C. The reaction was stirred at 0° C. for 0.5 h, and then was warmed to room temperature for 0.5 h, before it was recooled to 0° C. The compound ((1R,2S)-2-(benzyloxycarbonyl)-5-oxocyclohexyl)methyl methanesulfonate (1.80 g) in DMF (10 mL) was added dropwise. After the addition was complete, the reaction was stirred at rt for 18 h. The DMF was removed and the residue was taken up in ethyl acetate (100 mL). The solution was washed with water (1×25 mL), sat'd NaCO$_3$ (2×25 mL), and brine (1×25 mL). The resulting organic layer was dried over MgSO$_4$, filtered, and then evaporated to dryness. This residue was purified by flash chromatography (silica gel, 40-65% ethyl acetate/hexanes) to give benzyl (1S,2R)-2-(isopropylthiomethyl)-4-oxocyclohexylcarbamate (95 mg) as a clear oil. MS found: (M+H)$^+$=336.

Example 10s, Step 7: Oxone (0.52 g, 0.85 mmol) in water (5 mL) was added in one portion to (1S,2R)-2-(isopropylthiomethyl)-4-oxocyclohexylcarbamate (95 mg) in methanol (5 mL) at 0° C. After 15 min at 0° C., the reaction was warmed to rt over 15 min. Water (20 mL) was added and this was extracted with chloroform (3×15 mL). The combined organic extracts were washed with water (1×10 mL), sat'd NaCO$_3$ (1×10 mL), and brine (1×10 mL). The resulting organic layer was dried over MgSO$_4$, filtered, and then evaporated to dryness. This residue was purified by flash chromatography (silica gel, 40-70% ethyl acetate/hexanes) to give benzyl (1S,2R)-2-(isopropylsulfonylmethyl)-4-oxocyclohexylcarbamate (91 mg) as a clear film. MS found: (M+H)$^+$=367.

Example 10s, Step 8: (Diethylamino)sulfur trifluoride (91 mg, 0.56 mmol) was added dropwise to benzyl (1S,2R)-2-(isopropylsulfonylmethyl)-4-oxocyclohexylcarbamate (69 mg) in CH$_2$Cl$_2$ (4 mL) at –10° C. After 0.5 h at –10° C., the ice bath was removed and the reaction was stirred at room temperature for 0.5 h. Methanol (0.2 mL) was added to quench the reaction and the solvent was removed in vacuo. This residue was purified by flash chromatography (silica gel, 30-60% ethyl acetate/hexanes) to give benzyl (1S,2R)-4,4-difluoro-2-(isopropylsulfonylmethyl)cyclohexylcarbamate (38 mg) as a clear film. MS found: (M+H)$^+$=608.

Example 10s, Step 9: Hydrobromic acid (30% in acetic acid, 0.3 mL) was added to benzyl (1S,2R)-4,4-difluoro-2-(isopropylsulfonylmethyl)cyclohexylcarbamate (50 mg). After 20 min, Et$_2$O (5 mL) was added and the reaction was stirred vigorously for 5 min. The resulting white solid was allowed to settle and the solvent was decanted off. This procedure was repeated two times before the solid was dried under vacuum. This material was incorporated in Example 2r, Step 3, and partially purified by flash chromatography (silica gel, 50% ethyl acetate/hexanes to 10% methanol/ethyl acetate). Final purification was effected by C18 HPLC (acetonitrile/water 0.05% TFA) to give the title compound (22 mg) contaminated with 25% of N-(2-((1S,2R)-4-fluoro-2-(isopropylsulfonylmethyl)cyclohex-3-enylamino)-2-oxoethyl)-3-(trifluoromethyl)benzamide. Title compound, MS found: (M+H)$^+$=485.

Example 10t: Synthesis of N-(2-((1S,2R,4R)-2-(ethylsulfonylmethyl)-4-(isopropyl(methyl)amino)cyclohexylamino)-2-oxoethyl)-3-(trifluoromethyl)benzamide Example 10t, Step 1: To a solution of (1S,2R,4R)-(4-tert-Butoxycarbonylamino-2-hydroxymethyl-cyclohexyl)-carbamic acid benzyl ester (5.60 g, 14.7 mmol) in CH$_2$Cl$_2$ (32 mL) at 0° C. was added NEt$_3$ (4.73 g, 44.2 mmol), and methanesulfonyl chloride (1.71 mL, 22.1 mmol). The reaction mixture was stirred at room temperature for 2 h under nitrogen atmosphere, then cooled to 0° C. and quenched with satd NH$_4$Cl (200 mL). The organic layer was washed with satd NaHCO$_3$ (250 mL) and brine (100 mL), dried (Na$_2$SO$_4$), and concentrated in vacuo. (1S,2R,4R)-Methanesulfonic acid 2-benzyloxycarbonylamino-5-tert-butoxycarbonylamino-cyclohexylmethyl ester (7.00 g) was isolated as a yellow foam and used without futher purification: $^1$H NMR (300 MHz, CDCl$_3$) δ 7.40-7.31 (m, 5H), 5.25 (s, 2H), 4.85-4.83 (m, 2H), 4.39 (s, 1H), 4.17-3.96 (m, 3H), 3.70-3.35 (m, 1H), 3.30-3.20 (m, 1H), 2.96 (s, 3H), 2.10-0.94 (m, 7H), 1.44 (s, 9H); MS found: (M+H)$^+$=457.

Example 10t, Step 2: A solution of ethanethiol (908 µL, 12.3 mmol) and anhydrous DMF (31 mL) was cooled to 0° C. under nitrogen atmosphere, then sodium hydride (60% dispersion in mineral oil; 491 mg, 12.3 mmol) was added. To this mixture, a solution of (1S,2R,4R)-Methanesulfonic acid 2-benzyloxycarbonylamino-5-tert-butoxycarbonylamino-cyclohexylmethyl ester (2.80 g, 6.1 mmol) in anhyd DMF (30 mL) was added at 0° C. The reaction mixture was warmed to room temperature, stirred for 12 h, cooled back to 0° C., and quenched with satd NH$_4$Cl (200 mL). The mixture was extracted with EtOAc (500 mL) and the organic layer was washed with 5% LiCl (2×250 mL), dried (Na$_2$SO$_4$), and concentrated. (1S,2R,4R)-(4-tert-Butoxycarbonylamino-2-ethylsulfanylmethyl-cyclohexyl)-carbamic acid benzyl ester (3.00 g) was isolated as a yellow foam and used without further purification: $^1$H NMR (300 MHz, CDCl$_3$) δ 7.61-7.20 (m, 5H), 5.10 (s, 2H), 4.45-4.30 (m, 1H), 4.12-4.02 (m, 2H), 3.52-3.35 (m, 1H) 2.78-2.41 (m, 4H), 2.40-2.25 (m, 1H), 2.20-0.72 (m, 9H), 1.44 (s, 9H); MS found: (M+H)$^+$=423.

Example 10t, Step 3: To a solution of (1S,2R,4R)-(4-tert-Butoxycarbonylamino-2-ethylsulfanylmethyl-cyclohexyl)-carbamic acid benzyl ester (3.00 g, 6.13 mmol) in 2-PrOH (16 mL) at 0° C. was added a suspension of Oxone® (23.0 g, 36.8 mmol) in water (30 mL). The reaction mixture was stirred at room temperature for 12 h, then diluted with water (200 mL) and extracted with EtOAc (3×250 mL). The organic layer was washed with brine (50 mL), dried (Na$_2$SO$_4$), and concentrated in vacuo. Purification of the residue by column chromatography (silica gel, 50 g, EtOAc) gave (1S,2R,4R)-(4-tert-Butoxycarbonylamino-2-ethanesulfonylmethyl-cyclohexyl)-carbamic acid benzyl ester (1.89 g, 68%) as a white solid: mp 54-58° C.; H NMR (300 MHz, CDCl$_3$) δ 7.60-7.32 (m, 5H), 5.10 (s, 2H), 4.90-4.87 (m, 1H), 4.41-4.30 (m, 1H), 4.07-3.98 (m, 1H), 3.58-3.35

(m, 1H), 3.28-3.10 (m, 1H), 3.08-2.88 (m, 2H), 2.72-2.65 (m, 1H), 2.50-2.18 (m, 2H), 2.08-0.80 (m, 8H), 1.43 (s, 9H); MS found: (M+H)$^+$=455.

Example 10t, Step 4: (1S,2R,4R)-(4-tert-Butoxycarbonylamino-2-ethanesulfonylmethyl-cyclohexyl)-carbamic acid benzyl ester (70 mg) was dissolved in MeOH (10 mL) prior to the addition of 10% Pd/C (20 mg). A hydrogen balloon was added and the solution was stirred at rt for 16 h. The palladium was filtered and the solvent was concentrated to (1S,2R,4R)-(4-Amino-3-ethanesulfonylmethyl-cyclohexyl)-carbamic acid tert-butyl ester. MS found: (M+H)$^+$=321.

Example 10t, Step 5: To a solution of (1S,2R,4R)-(4-Amino-3-ethanesulfonylmethyl-cyclohexyl)-carbamic acid tert-butyl ester (47 mg, 0.12 mmol) in DMF (15 mL) was added 2-(3-(trifluoromethyl)benzamido)acetic acid (28 mg, 0.15 mmol), HATU (57 mg, 0.15 mmol) and Hunig's base (0.03 mL, 0.15 mmol. The resulting mixture was stirred for 16 h before EtOAc was added. The EtOAc layer was washed with 1 N HCl, NaHCO$_3$ solution (aq), and brine. The EtOAc was dried (MgSO$_4$), filtered, and concentrated. Flash chromatography-of the resulting residue gave N-[1-(1S,2R,4R)-Ethanesulfonylmethyl-4-2-(3-trifluoromethyl-benzoylamino)-acetylamino]-cyclohexyl}-carbamic acid tert-butyl ester. MS found: (M+H)$^+$=550.

Example 10t, Step 6: To a solution of N-[1-(1S,2R,4R)-Ethanesulfonylmethyl-4-2-(3-trifluoromethyl-benzoylamino)-acetylamino]-cyclohexyl}-carbamic acid tert-butyl ester (50 mg) in CH$_2$Cl$_2$ (10 mL) was added TFA (3.3 mL). After 45 min, the solution was diluted with NaHCO$_3$ solution (aq) and EtOAc. The organic layer was collected, dried, and concentrated to afford to a crude oil N-[-(1S,2R,4R)-(4-Amino-2-ethanesulfonylmethyl-cyclohexylcarbamoyl)-methyl]-3-trifluoromethyl-benzamide. MS found: (M+H)$^+$=450.

Example 10t, Step 7: To a solution of N-[-(1S,2R,4R)-(4-Amino-2-ethanesulfonylmethyl-cyclohexylcarbamoyl)-methyl]-3-trifluoromethyl-benzamide (30 mg) in CH$_2$Cl$_2$ (15 mL) at rt was added NaBH(OAc)$_3$ (50 mg), acetone (2 mL), and three drops of AcOH. After 2 h, formaldehyde (2 mL) was added and the solution was stirred for another 2 h. The reaction mixture was diluted with EtOAc and washed with saturated NaHCO$_3$, water, and brine. The organic layer was dried, filtered, and concentrated to afford to a crude oil which was purified by semi-preparative HPLC to give the TFA salt of the title compound. MS found: (M+H)$^+$=506.

TABLE 10-A

The compounds in the following table were made using the methods exemplified above. See Table 1-A for a complete description of the table headings.

| Ex. | R$^5$ | R$^6$ | Z | R$^2$ | Step Altered | MS Data |
|---|---|---|---|---|---|---|
| 10a | H$_2$N | i-PrSO$_2$ | NHC=O | 3-CF$_3$-phenyl | n/a | 464 |
| 10b | i-Pr(Me)N | i-PrSO$_2$ | NHC=O | 3-CF$_3$-phenyl | n/a | 520 |
| 10c | i-Pr(Et)N | i-PrSO$_2$ | NHC=O | 3-CF$_3$-phenyl | 10b | 534 |
| 10d | (5-CF$_3$-tetrazolyl) | i-PrSO$_2$ | NHC=O | 3-CF$_3$-phenyl | n/a | 585.1 |

TABLE 10-A-continued

The compounds in the following table were made using the methods exemplified above. See Table 1-A for a complete description of the table headings.

| Ex. | R⁵ | R⁶ | Z | R² | Step Altered | MS Data |
|---|---|---|---|---|---|---|
| 10e | 5-CF₃-tetrazol-1-yl | i-PrSO₂ | NHC=O | 4-CF₃-2-(3-isopropylureido)phenyl | 10d, Step 4 | 685.2 |
| 10f | imidazol-1-yl | i-PrSO₂ | NHC=O | 3-CF₃-phenyl | n/a | 515.2 |
| 10g | 2-Me-imidazol-1-yl | i-PrSO₂ | NHC=O | 3-CF₃-phenyl | 10f | 529.6 |
| 10h | 2-iPr-imidazol-1-yl | i-PrSO₂ | NHC=O | 3-CF₃-phenyl | 10f | 557.3 |
| 10i | i-Pr(H)N | MeSO₂ | NHC=O | 3-CF₃-phenyl | n/a | 478.2 |
| 10j | i-Pr(Me)N | MeSO₂ | NHC=O | 3-CF₃-phenyl | n/a | 492.3 |
| 10k | i-Pr(Me)N | MeSO₂ | NHC=O | 3-t-Bu-1-methyl-pyrazol-5-yl | 10j, Step 4 | 484.2 |

TABLE 10-A-continued

The compounds in the following table were made using the
methods exemplified above. See Table 1-A for a complete description of the table headings.

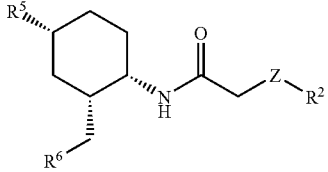

| Ex. | R⁵ | R⁶ | Z | R² | Step Altered | MS Data |
|---|---|---|---|---|---|---|
| 10l | i-Pr(Me)N | MeSO₂ | NHC=O | 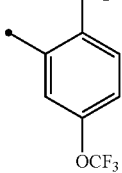 | n/a | 523.3 |
| 10m | i-Pr(Me)N | MeSO₂ | NH | 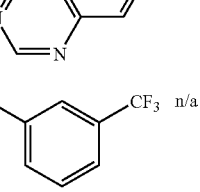 | n/a | |
| 10n | H₂N | t-BuSO₂ | NHC=O | 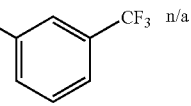 | n/a | 478.3 |
| 10o | i-Pr(H)N | t-BuSO₂ | NHC=O | 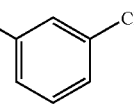 | n/a | 520.3 |
| 10p | i-Pr(Me)N | t-BuSO₂ | NHC=O | 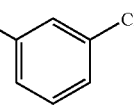 | n/a | 534.4 |
| 10q | i-Bu(H)N | i-PrSO₂ | NHC=O | 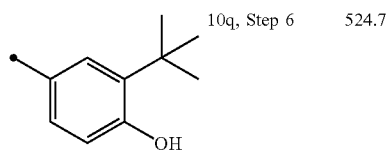 | n/a | 520 |
| 10r | t-Bu(H)N | i-PrSO₂ | NHC=O | 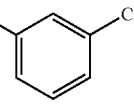 | 10q, Step 6 | 524.7 |
| 10s | F, F (two R⁵ on same C4) | i-PrSO₂ | NHC=O | 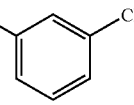 | n/a | 485 |
| 10t | i-Pr(Me)N | EtSO₂ | NHC=O | 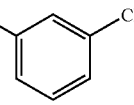 | n/a | 506 |

TABLE 10-A-continued

The compounds in the following table were made using the methods exemplified above. See Table 1-A for a complete description of the table headings.

| Ex. | R$^5$ | R$^6$ | Z | R$^2$ | Step Altered | MS Data |
|---|---|---|---|---|---|---|
| 10u | c-PrCH$_2$(Me)N | EtSO$_2$ | NHC=O | 3-CF$_3$-phenyl | 10t, Step 7 | 518 |
| 10v | c-PrCH$_2$(c-Pr)N | EtSO$_2$ | NHC=O | 3-CF$_3$-phenyl | 10t, Step 7 | 544 |
| 10w | i-Pr(Me)N | EtSO$_2$ | NHC=O | 3-t-Bu-1-Me-pyrazol-5-yl | 10t, Step 5 | 498 |
| 10x | i-Pr(H)N | i-PrSO$_2$ | NHC=O | 3-CF$_3$-phenyl | 10b | 506 |
| 10y | c-C$_4$H$_8$N | i-PrSO$_2$ | NHC=O | 3-CF$_3$-phenyl | 10b | 518 |
| 10z | HO(CH$_2$)$_2$(i-Pr)N | i-PrSO$_2$ | NHC=O | 3-CF$_3$-phenyl | 10b | 550 |
| 10aa | i-Pr(H)N | i-PrSO$_2$ | NH | 5-CF$_3$-benzisoxazol-3-yl | 10a, Step 4, then 10b | 519 |
| 10ab | i-Pr(Me)N | i-PrSO$_2$ | NH | 5-CF$_3$-benzisoxazol-3-yl | 10a, Step 4, then 10b | 533 |

TABLE 10-A-continued

The compounds in the following table were made using the methods exemplified above. See Table 1-A for a complete description of the table headings.

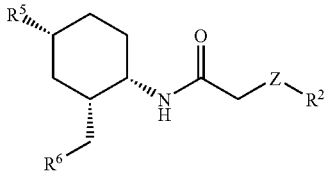

| Ex. | R⁵ | R⁶ | Z | R² | Step Altered | MS Data |
|---|---|---|---|---|---|---|
| 10ac | i-Pr(Me)N | i-PrSO₂ | NHC=O | 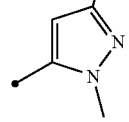 | 10a, Step 4, then 10b | 512 |
| 10ad | i-Pr(H)N | i-PrSO₂ | NH | 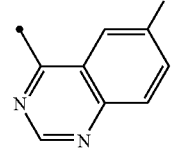 | 10a, Step 4, then 10b | 530 |
| 10ae | i-Pr(Me)N | i-PrSO₂ | NH | 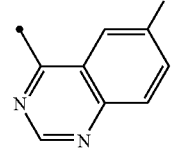 | 10a, Step 4, then 10b | 544 |
| 10af | 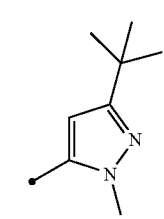 | i-PrSO₂ | NHC=O | 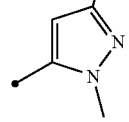 | 10a, Step 4, then 10b | 538 |

TABLE 10-B

The chemical names of the specific examples illustrated in Table 10-A are tabulated below.

| Ex. | Name |
|---|---|
| 10a | N-(2-((1S,2R,4R)-4-amino-2-(isopropylsulfonylmethyl)cyclohexylamino)-2-oxoethyl)-3-(trifluoromethyl)benzamide |
| 10b | N-(2-((1S,2R,4R)-4-(isopropyl(methyl)amino)-2-(isopropylsulfonylmethyl)cyclohexylamino)-2-oxoethyl)-3-(trifluoromethyl)benzamide |
| 10c | N-(2-((1S,2R,4R)-4-(ethyl(isopropyl)amino)-2-(isopropylsulfonylmethyl)cyclohexylamino)-2-oxoethyl)-3-(trifluoromethyl)benzamide |
| 10d | N-(2-((1S,2R,4R)-2-(isopropylsulfonylmethyl)-4-(5-(trifluoromethyl)-1H-tetrazol-1-yl)cyclohexylamino)-2-oxoethyl)-3-(trifluoromethyl)benzamide |
| 10e | 1-(2-((2-(((1S,2R,4R)-2-(isopropylsulfonylmethyl)-4-(5-(trifluoromethyl)-1H-tetrazol-1-yl)cyclohexylamino)-2-oxoethyl)carbamoyl)-4-(trifluoromethyl)phenyl)-3-isopropylurea |
| 10f | N-(2-((1S,2R,4R)-4-(1H-imidazol-1-yl)-2-(isopropylsulfonylmethyl)cyclohexylamino)-2-oxoethyl)-3-(trifluoromethyl)benzamide |
| 10g | N-(2-((1S,2R,4R)-2-(isopropylsulfonylmethyl)-4-(2-methyl-1H-imidazol-1-yl)cyclohexylamino)-2-oxoethyl)-3-(trifluoromethyl)benzamide |
| 10h | N-(2-((1S,2R,4R)-4-(2-isopropyl-1H-imidazol-1-yl)-2-(isopropylsulfonylmethyl)cyclohexylamino)-2-oxoethyl)-3-(trifluoromethyl)benzamide |
| 10i | (N-(2-((1S,2R,4R)-4-(Isopropylamino)-2-(methylsulfonylmethyl)cyclohexylamino)-2-oxoethyl)-3-(trifluoromethyl)benzamide |

TABLE 10-B-continued

The chemical names of the specific examples illustrated in Table 10-A are tabulated below.

| Ex. | Name |
|---|---|
| 10j | N-(2-((1S,2R,4R)-4-(Isopropyl(methyl)amino)-2-(methylsulfonylmethyl)cyclohexylamino)-2-oxoethyl)-3-(trifluoromethyl)benzamide |
| 10k | 3-tert-Butyl-N-(2-((1S,2R,4R)-4-(isopropyl(methyl)amino)-2-(methylsulfonylmethyl)cyclohexylamino)-2-oxoethyl)-1-methyl-1H-pyrazole-5-carboxamide |
| 10l | 2-Amino-N-(2-((1S,2R,4R)-4-(isopropyl(methyl)amino)-2-(methylsulfonylmethyl)cyclohexylamino)-2-oxoethyl)-5-(trifluoromethoxy)benzamide |
| 10m | 2-(6-Chloroquinazolin-4-ylamino)-N-((1S,2R,4R)-4-(isopropyl(methyl)amino)-2-(methylsulfonylmethyl)cyclohexyl)acetamide |
| 10n | N-(2-((1S,2R,4R)-4-Amino-2-(tert-butylsulfonylmethyl)cyclohexylamino)-2-oxoethyl)-3-(trifluoromethyl)benzamide |
| 10o | N-(2-((1S,2R,4R)-2-(tert-butylsulfonylmethyl)-4-(isopropylamino)cyclohexylamino)-2-oxoethyl)-3-(trifluoromethyl)benzamide |
| 10p | N-(2-((1S,2R,4R)-2-(Tert-butylsulfonylmethyl)-4-(isopropyl(methyl)amino)cyclohexylamino)-2-oxoethyl)-3-(trifluoromethyl)benzamide |
| 10q | N-(2-((1S,2R,4R)-4-(tert-butylamino)-2-(isopropylsulfonylmethyl)cyclohexylamino)-2-oxoethyl)-3-(trifluoromethyl)benzamide |
| 10r | 3-tert-butyl-N-(2-((1S,2R,4R)-4-(tert-butylamino)-2-(isopropylsulfonylmethyl)cyclohexylamino)-2-oxoethyl)-4-hydroxybenzamide |
| 10s | N-(2-((1S,2R)-4,4-difluoro-2-(isopropylsulfonylmethyl)cyclohexylamino)-2-oxoethyl)-3-(trifluoromethyl)benzamide |
| 10t | N-(2-((1S,2R,4R)-2-(ethylsulfonylmethyl)-4-(isopropyl(methyl)amino)cyclohexylamino)-2-oxoethyl)-3-(trifluoromethyl)benzamide |
| 10u | N-(2-((1S,2R,4R)-4-((cyclopropylmethyl)(methyl)amino)-2-(ethylsulfonylmethyl)cyclohexylamino)-2-oxoethyl)-3-(trifluoromethyl)benzamide |
| 10v | N-(2-((1S,2R,4R)-4-(cyclopropyl(cyclopropylmethyl)amino)-2-(ethylsulfonylmethyl)cyclohexylamino)-2-oxoethyl)-3-(trifluoromethyl)benzamide |
| 10w | 3-tert-butyl-N-(2-((1S,2R,4R)-2-(ethylsulfonylmethyl)-4-(isopropyl(methyl)amino)cyclohexylamino)-2-oxoethyl)-1-methyl-1H-pyrazole-5-carboxamide |
| 10x | N-(2-((1S,2R,4R)-4-(isopropylamino)-2-(isopropylsulfonylmethyl)cyclohexylamino)-2-oxoethyl)-3-(trifluoromethyl)benzamide |
| 10y | N-(2-((1S,2R,4R)-2-(isopropylsulfonylmethyl)-4-(pyrrolidin-1-yl)cyclohexylamino)-2-oxoethyl)-3-(trifluoromethyl)benzamide |
| 10z | N-(2-((1S,2R,4R)-4-((2-hydroxyethyl)(isopropyl)amino)-2-(isopropylsulfonylmethyl)cyclohexylamino)-2-oxoethyl)-3-(trifluoromethyl)benzamide |
| 10aa | N-((1S,2R,4R)-4-(isopropylamino)-2-(isopropylsulfonylmethyl)cyclohexyl)-2-(5-(trifluoromethyl)benzo[d]isoxazol-3-ylamino)acetamide |
| 10ab | N-((1S,2R,4R)-4-(isopropyl(methyl)amino)-2-(isopropylsulfonylmethyl)cyclohexyl)-2-(5-(trifluoromethyl)benzo[d]isoxazol-3-ylamino)acetamide |
| 10ac | 3-tert-butyl-N-(2-((1S,2R,4R)-4-(isopropyl(methyl)amino)-2-(isopropylsulfonylmethyl)cyclohexylamino)-2-oxoethyl)-1-methyl-1H-pyrazole-5-carboxamide |
| 10ad | N-((1S,2R,4R)-4-(isopropylamino)-2-(isopropylsulfonylmethyl)cyclohexyl)-2-(6-(trifluoromethyl)quinazolin-4-ylamino)acetamide |

TABLE 10-B-continued

The chemical names of the specific examples illustrated in Table 10-A are tabulated below.

| Ex. | Name |
|---|---|
| 10ae | N-((1S,2R,4R)-4-(isopropyl(methyl)amino)-2-(isopropylsulfonylmethyl)cyclohexyl)-2-(6-(trifluoromethyl)quinazolin-4-ylamino)acetamide |
| 10af | 3-tert-butyl-N-(2-((1S,2R,4R)-4-(2,5-dimethylpyrrolidin-1-yl)-2-(isopropylsulfonylmethyl)cyclohexylamino)-2-oxoethyl)-1-methyl-1H-pyrazole-5-carboxamide |

Examples 11a-11w

Example 11a

Synthesis of N-(2-((1S,2R,4R)-4-(isopropyl(methyl) amino)-2-(pyrrolidine-1-carbonyl)cyclohexylamino)-2-oxoethyl)-3-(trifluoromethyl)benzamide Example 11a, Step 1: To a solution of (1R,2S,5R)-2-benzyloxycarbonylamino-5-tert-butoxycarbonylamino-cyclohexanecarboxylic acid (240 mg, 0.6 mmol) in DMF (15 mL) at rt was added HATU (278 mg, 0.73 mmol), pyrrolidine (0.06 mL, 0.73 mmol), and iPr$_2$NEt (0.13 mL, 0.73 mmol). The mixture was stirred at rt for 16 h before water and EtOAc were added. The organic layer was separated and re-washed twice before it was collected, dried over Na$_2$SO$_4$, and concentrated to provide (1S,2R,4R)-[4-tert-butoxycarbonylamino-2-(pyrrolidine-1-carbonyl)-cyclohexyl]-carbamic acid benzyl ester as a glassy solid (190 mg, 69%). MS found: (M+H)$^+$=446.

Example 11a, Step 2: A sample of (1S,2R,4R)-[4-tert-butoxycarbonylamino-2-(pyrrolidine-1-carbonyl)-cyclohexyl]-carbamic acid benzyl ester was carried through the procedures described in Example 10a, Steps 3 & 4, to afford N-(2-((1S,2R,4R)-4-amino-2-(pyrrolidine-1-carbonyl)cyclohexylamino)-2-oxoethyl)-3-(trifluoromethyl)benzamide. MS found: (M+H)$^+$=441.1

Example 11a, Step 3: A sample of N-(2-((1R,2S,4R)-4-amino-2-(pyrrolidine-1-carbonyl)cyclohexylamino)-2-oxoethyl)-3-(trifluoromethyl)benzamide (30 mg) was carried through the procedure of Example 4a, Step 5, substituting acetaldehyde for formaldehyde, to afford the TFA salt of the title compound (10 mg) after RP-HPLC. MS found: (M+H)$^+$=511.

Example 11l

Synthesis of (1R,2S,5R)-isopropyl 5-(isopropylamino)-2-(2-(3-trifluoromethyl-benzamido)acetamido)cyclohexanecarboxylate Example 11l, Step 1: A solution of 3-Trifluoromethyl-benzoic acid (0.23 g, 0.0012 mol) in THF was cooled in an ice bath and treated with N-methylmorpholine(0.13 g, 0.0013 mol) and then drop-wise with isobutyl chloroformate (0.16 g, 0.0012 mol). The resulting mixture was stirred for 5 min and then treated with a solution of isopropyl (1R,2S,5R)-2-(2-aminoacetamido)-5-(tert-butoxycarbonyl-isopropyl-amino)cyclohexanecarboxylate (0.45 g, 0.0011 mol; See Example 8b, Step 4) in THF. The resulting mixture was stirred for 30 minutes and then diluted with water and extracted into CH$_2$Cl$_2$. The extract was washed with dilute NaOH, water, and brine and then concentrated under vacuum. The residue was chromatographed on silica gel (elution 55% ethyl acetate/hexane) to give 0.4 g of isopropyl (1R,2S,5R)-5-(tert-butoxycarbonyl-isopropyl-amino)-2-(2-(3-trifluoromethyl-benzamido)acetamido)cyclohexanecarboxylate as a white solid, MS found: (M+H)$^+$=572.4.

Example 11l, Step 2: A solution of Step 1 product (120 mg) in $CH_2Cl_2$ is treated with $CF_3COOH$ (7 ml) and stirred at room temperature for 2 hours. The solution was evaporated and the residue neutralized with 1 N NaOH and extracted into $CH_2Cl_2$. The extract was washed with water, brine, dried over $Na_2SO_4$, filtered and the solvent evaporated to give 90 mg of the title compound as a white solid. $^1$H NMR (400 MHz, CDCl$_3$) δ(TMS): 8.12 (s, 1 H), 8.02 (d, J=7.8 Hz, 1 H), 7.76 (d, J=7.8 Hz, 1 H), 7.57 (t, J=7.8 Hz, 1 H), 7.35 (bt, 1 H), 6.96 (bd, 1 H), 4.93 (m, 1 H), 4.51 (m, 1 H), 4.12 (d, J=4.8 Hz, 2 H), 3.03 (m, 1 H), 2.77 (m, 1 H), 2.61 (m, 1 H), 2.31 (bs, 1 H), 2.04 (m, 2 H), 1.80-1.30 (m, 4 H), 1.17 (m, 6 H), 1.08 (d, J=6.2 Hz, 6 H). MS found: (M+H)$^+$=472.36.

Example 11m

Synthesis of (1R,2S,5R)-isopropyl 5-(isopropyl(methyl)amino)-2-(2-(3-trifluoromethyl-benzamido)acetamido)cyclohexanecarboxylate Example 11m, Step 1: A solution of (1R,2S,5R)-isopropyl 5-(isopropylamino)-2-(2-(3-trifluoromethyl-benzamido)acetamido)cyclohexanecarboxylate (210 mg, 0.45 mmol; Example 11l) in 10 ml of $CH_2Cl_2$ is treated with 37% aqueous formaldehyde (0.5 ml) and $NaBH(OAc)_3$ (0.3 g, 1.4 mmol) powder and stirred at room temperature for 2 hours. The mixture was treated with 1 N NaOH and stirred at room temperature for 1 hr and extracted into $CH_2Cl_2$. The extract was washed with water, brine, dried over $Na_2SO_4$, filtered and the solvent evaporated to give 200 mg of the title compound as a white solid. $^1$H NMR (400 MHz, CDCl$_3$) δ(TMS): 8.16 (s, 1 H), 8.06 (d, J=7.8 Hz, 1 H), 7.86 (bt, 1 H), 7.75 (d, J=7.8 Hz, 1 H), 7.55 (t, J=7.8 Hz, 1 H), 7.21 (bs, 1 H), 4.91 (m, 1 H), 4.51 (m, 1 H), 4.12 (d, J=5.2 Hz, 2 H), 3.01 (m, 1 H), 2.58 (m, 1 H), 2.57 (m, 2 H), 2.21 (s, 3 H), 2.02-1.40 (m, 7 H), 1.16 (m, 6 H), 1.02 (m, 6 H). MS found: (M+H)$^+$=486.46.

Example 11n

Synthesis of N-(2-((1R,2S,4R)-2-isobutyryl-4-(isopropyl(methyl)amino)cyclohexylamino)-2-oxoethyl)-3-(trifluoromethyl)benzamide Example 11n, Step 1: To a solution of N-(2-((1R,2S,4R)-2-((S)-1-hydroxy-2-methylpropyl)-4-(isopropyl(methyl)amino)cyclohexylamino)-2-oxoethyl)-3-(trifluoromethyl)benzamide (250 mg, 0.53 mmol; See Example 81, Step 6) in $CH_2Cl_2$ (15 mL) was added PDC (599 mg, 1.5 mmol), and 4A molecular sieves (excess). The reaction was stirred for 16 h at RT and then filtered, and concentrated in vacuo. The residue was purified by HPLC to N-(2-((1R,2S,4R)-2-isobutyryl-4-(isopropyl(methyl)amino)cyclohexylamino)-2-oxoethyl)-3-(trifluoromethyl)benzamide. MS found: (M+H)$^+$=470.

Example 11o

Synthesis of N-(2-((1R,2S,4R)-2-acetyl-4-aminocyclohexylamino)-2-oxoethyl)-3-(trifluoromethyl)benzamide Example 11o, Step 1: Tert-butyl (1R,3R,4S)-3-acetyl-4-benzyloxycarbonylaminocyclohexylcarbamate (600 mg) in MeOH (5 mL) was charged with 5% Pd/BaSO$_4$ (300 mg). The reaction flask was evacuated and then back-filled with hydrogen; this was repeated three more times. The reaction was stirred under 1 atm of H$_2$ for 2 h and then filtered and concentrated to provide tert-butyl (1R,3R,4S)-3-acetyl-4-aminocyclohexylcarbamate (430 mg). MS (ES+)=279.2 (M+H)$^+$.

Example 11o, Step 2: Tert-butyl (1R,3R,4S)-3-acetyl-4-aminocyclohexylcarbamate (500 mg) dissolved in DMF (2 mL) prior to the addition of 2-(3-(trifluoromethyl)benzamido)acetic acid (626 mg), 4-methylmorpholine (1.1 mL), and BOP (1.3 g). The reaction was stirred for 12 h at rt and then partitioned between EtOAc and 1N HCl solution. The organic phases were combined, washed with saturated NaHCO$_3$ and brine, dried (MgSO$_4$), filtered, and concentrated in vacuo. The residue was purified by flash chromatography to afford tert-butyl (1R,3R,4S)-3-acetyl-4-(2-(3-(trifluoromethyl)benzamido)acetamido)cyclohexylcarbamate (430 mg). MS found: (M+H)$^+$=486.2.

Example 11o, Step 3: Tert-butyl (1R,3R,4S)-3-acetyl-4-(2-(3-trifluoromethyl)benzamido)acetamido)cyclohexylcarbamate (30 mg) was dissolved in $CH_2Cl_2$ (1 mL) prior to the addition of trifluoroacetic acid (0.5 mL). After 30 min, the reaction was concentrated in vacuo to afford the TFA salt of N-(2-((1S,2R,4R)-2-acetyl-4-aminocyclohexylamino)-2-oxoethyl)-3-(trifluoromethyl)benzamide (30 mg). MS found: (M+H)$^+$=386.2.

Examples 11p and 11q

Synthesis of N-(2-((1S,2S,4R)-2-((2R)-2-hydroxy-3-methylbutyl)-4-(isopropyl(methyl)amino)cyclohexylamino)-2-oxoethyl)-3-(trifluoromethyl)benzamide and N-(2-((1S,2S,4R)-2-((2S)-2-hydroxy-3-methylbutyl)-4-(isopropyl(methyl)amino)cyclohexylamino)-2-oxoethyl)-3-(trifluoromethyl)benzamide Examples 11p and 11q, Step 1: To a solution of the (1R,2S,5R)-2-benzyloxycarbonylamino-7-oxo-6-aza-bicyclo[3.2.1]octane-6-carboxylic acid tert-butyl ester (8 g, 21.36 mmoles) in 160 ml of methanol was added 1.6 g of 10% Pd/C (50% wet), and it was treated with H$_2$ (52 psi)for 18 hrs. It was filtered through a plug of Celite to remove the catalyst, and the solvent was evaporated off to give (1R,2S,5R)-tert-butyl 2-amino-7-oxo-6-aza-bicyclo[3.2.1]octane-6-carboxylate as a foamy solid, which was used for the next step without purification.

Examples 11p and 11q, Step 2: To a solution of the crude product of the step a in 80 ml of anhydrous DMF and 20 ml of anhydrous DMSO was added potassium carbonate anhydrous (7.38 g, 52.5 mmoles) followed by benzylbromide (6.35 ml, 52.5 mmoles), and the mixture was stirred at 50° C. for 20 hours. After cooling it was poured into water and extracted with ethyl acetate twice. The combined extracts were washed with water and brine, dried over Na$_2$SO$_4$ and evaporated to give an oily residue. It was purified by column chromatography (silica gel, 3:7 followed by 6:4 EtOAc and hexane) to give 3.55 g of (1R,2S,5R)-tert-butyl 2-(dibenzylamino)-7-oxo-6-aza-bicyclo[3.2.1]octane-6-carboxylate.

Examples 11p and 11q, Step 3: To a solution of tert-butyl 2-(dibenzylamino)-7-oxo-6-aza-bicyclo[3.2.1]octane-6-carboxylate (3.12 g, 7.42 mmoles) in 50 ml of THF and 10 ml of water was added sodium borohydride (1.4 g, 37.1 mmoles), and the mixture was stirred for 6 hours at room temperature. The reaction was quenched with saturatedd sodium bicarbonate, and the product was extracted with EtOAc three times. The combined extracts were washed with brine, dried over Na$_2$SO$_4$ and evaporated to give an oily residue. It was purified by column chromatography (silica gel, 3:7 EtOAc and hexane) to give 2.28 g of tert-butyl (1R,3R,4S)-4-(dibenzylamino)-3-(hydroxymethyl)cyclohexylcarbamate as an oil.

Examples 11p and 11q, Step 4: To a solution of triphenylphosphine (4.47 g, 17.04 mmoles) in 50 ml of anhydrous THF at −20° C. was added 7.41 ml of 40% solution of diethyl azodicarboxylate in THF (17.04 mmoles) dropwise, and the mixture was stirred for 20 minutes at −20° C. Then to the mixture was added a solution of tert-butyl (1R,3R,4S)-4-(dibenzylamino)-3-(hydroxymethyl)cyclohexylcarbamate (1.81 g, 4.26 mmoles) in 20 ml of anhydrous THF, and it was stirred for 20 minutes at −20° C. At the end of the stirring was added 20 ml of anhydrous THF followed by acetone cyanohydrin (1.56 ml, 17.04 mmoles), and it was continued to stir for 1.5 hours while gradually raising the temperature to 8° C. The reaction was quenched by several drops of methanol, and the solvent was evaporated off. The residue was purified by column chromatography (silica gel, 25:75 EtOAc and hexane) to give 1.87 g of tert-butyl (1R,3S,4S)-3-(cyanomethyl)-4-(dibenzylamino)cyclohexylcarbamate.

Examples 11p and 11q, Step 5: To a solution of tert-butyl (1R,3S,4S)-3-(cyanomethyl)-4-(dibenzylamino)cyclohexylcarbamate (1.89 g, 4.35 mmoles) in 16 ml of anhydrous dichloromethane was added trifluoroacetic acid (3.35 ml, 43.5 mmoles), and the mixture was stirred for 55 minutes at room temperature. The acid and the solvent were evaporated off, and the residue was dissolved in toluene and evaporated (2×). The residue was dissolved in EtOAc and washed with saturated NaHCO₃. It was dried over Na₂SO₄ and evaporated to give 2-((1S,2S,5R)-5-amino-2-(dibenzylamino)cyclohexyl)acetonitrile as an oil, which was used for the next step without purification.

Examples 11p and 11q, Step 6: To a solution of 2-((1S,2S,5R)-5-amino-2-(dibenzylamino)cyclohexyl)acetonitrile (4.35 mmoles) in 40 ml of anhydrous dichloroethane was added acetone (3.5 ml), and the mixture was stirred for 30 minutes at room temperature. Then sodium triacetoxyborohydride (3 g) was added, and the mixture was stirred for 1.5 hours. To the mixture was added 37% aqueous formaldehyde (2.2 ml) and it was stirred for 15 minutes. Then additional 1.6 g of sodium triacetoxyborohydride was added, and the mixture was continued to stir for 2.5 hours. At the end of the stirring, was added saturated Na₂CO₃, and the product was extracted with EtOAc. The extract was washed with brine, dried over Na₂SO₄, and evaporated to give an oily residue. It was purified by column chromatography (silica gel, 0.5:4.5:95 cNH₄OH-MeOH—CH₂Cl₂) to give 1 g of ((1S,2S,5R)-2-(dibenzylamino)-5-(isopropyl(methyl)amino)cyclohexyl)acetonitrile as an oil.

Examples 11p and 11q, Step 7: To a solution of 2-((1S,2S,5R)-2-(dibenzylamino)-5-(isopropyl(methyl)amino)cyclohexyl)acetonitrile (0.996 g, 2.56 mmoles) in 10 ml of anhydrous THF at −78° C. was added 0.7M-isopropyl lithium in pentane (5.5 ml, 3.84 mmoles) dropwise, and the mixture was stirred for 2.5 hours while the temperature was raised to −7° C. gradually. The reaction was quenched with saturated NH₄Cl and then the solution was made basic with saturated NaHCO₃. It was extracted with EtOAc (2×), and the combined extracts were washed with brine, dried over Na₂SO₄, and evaporated to give an oily residue. It was purified by flash chromatography (silica gel, 0.5:4.5:95 cNH₄OH-MeOH—CH₂Cl₂) to give 0.73 g of 1-((1S,2S,5R)-2-(dibenzylamino)-5-(isopropyl(methyl)amino)cyclohexyl)-3-methylbutan-2-one.

Examples 11p and 11q, Step 8: To a solution of 1-((1S,2S,5R)-2-(dibenzylamino)-5-(isopropyl(methyl)amino)cyclohexyl)-3-methylbutan-2-one (168 mg, 0.39 mmoles) in 3 ml of methanol was added sodium borohydride (29.2 mg, 0.78 mmoles), the mixture was stirred for 2 hours at room temperature. At the end of the stirring was added saturated NH₄Cl, and then the mixture was made basic with saturated NaHCO₃. It was extracted with EtOAc, washed with brine, dried over Na₂SO₄, and evaporated to give 166 mg of 1-((1S,2S,5R)-2-(dibenzylamino)-5-(isopropyl(methyl)amino)cyclohexyl)-3-methylbutan-2-ol as a mixture of the two isomers (ratio ~2:1).

Examples 11p and 11q, Step 9: To a solution of the isomeric mixture of 1-((1S,2S,5R)-2-(dibenzylamino)-5-(isopropyl(methyl)amino)cyclohexyl)-3-methylbutan-2-ol (166 mg, 0.38 mmoles) in 5 ml of ethanol and 1 ml of acetic acid was added about 150 mg of Pd(OH)₂ on carbon (20%, wet, Aldrich), and the mixture was stirred under hydrogen (52 psi) for 24 hours. After removal of the catalyst by filtration. The solvents were evaporated off to give an oily residue. The residue was dissolved in methanol and 1 ml of 1N—HCl was added. It was evaporated and azeotroped with toluene twice to remove the excess acid and water, and dried under vacuum to give 1-((1S,2S,5R)-2-amino-5-(isopropyl(methyl)amino)cyclohexyl)-3-methylbutan-2-ol as a bis-HCl salt.

Examples 11p and 11q, Step 10: To a solution of 1-((1S,2S,5R)-2-amino-5-(isopropyl(methyl)amino)cyclohexyl)-3-methylbutan-2-ol (0.38 mmoles) in 3 ml of anhydrous acetonitrile were added diisopropylethylamine (0.27 ml, 1.52 mmoles), 2-(3-(trifluoromethyl)benzamido)acetic acid (141 mg, 0.57 mmoles) and 2-(1H-benzotriazol-1-yl)-1,1,3,3-tetramethyluronium tetrafluoroborate (183 mg, 0.57 mmoles, Bachem), and the mixture was stirred for 12.5 hours at room temperature. Then several drops of methanol was added, and it was stirred for additional two hours. The solvent was evaporated off and the residue was purified by chromatography (silica gel, 1:9:90 cNH₄OH-MeOH—CH₂Cl₂) to give N-(2-((1S,2S,4R)-2-((2R)-2-hydroxy-3-methylbutyl)-4-(isopropyl(methyl)amino)cyclohexylamino)-2-oxoethyl)-3-(trifluoromethyl)benzamide (Example 11p) and N-(2-((1S,2S,4R)-2-((2S)-2-hydroxy-3-methylbutyl)-4-(isopropyl(methyl)amino)cyclohexylamino)-2-oxoethyl)-3-(trifluoromethyl)benzamide (Example 11q). For both, MS found: (M+H)⁺=486.4.

Example 11r

Synthesis of N-(2-((1S,2S,4R)-4-(isopropyl(methyl)amino)-2-(3-methyl-2-oxobutyl)cyclohexylamino)-2-oxoethyl)-3-(trifluoromethyl)benzamide To a solution of the isomeric mixture of N-(2-((1S,2S,4R)-2-(2-hydroxy-3-methylbutyl)-4-(isopropyl(methyl)amino)cyclohexylamino)-2-oxoethyl)-3-(trifluoromethyl)benzamide (34 mg; see Examples 11p and 11q) in 3 ml of anhydrous CH₂Cl₂ were added excess amounts of powdered 4A molecular sieves and pyridinium dichromate, and the mixture was stirred for 2 hours at room temperature. After addition of about 15 ml of EtOAc it was filtered through a plug of Celite, and evaporated to give an oily residue, which was purified by chromatography (silica gel, CH₂Cl₂ then 1:9:90 cNH₄OH-MeOH—CH₂Cl₂) to give N-(2-((1S,2S,4R)-4-(isopropyl(methyl)amino)-2-(3-methyl-2-oxobutyl)cyclohexylamino)-2-oxoethyl)-3-(trifluoromethyl)benzamide as an amorphous solid. MS found: (M+H)⁺=484.3.

Example 11s

Synthesis of N-(2-((1S,2S,4R)-2-(cyanomethyl)-4-(isopropyl(methyl)amino)cyclohexylamino)-2-oxoethyl)-3-(trifluoromethyl)benzamide Example 11s, Step 1: Using the procedures detailed above in Example 11q, Steps 3-6, a sample of (1R,2S,5R)-2-benzyloxycarbonylamino-7-oxo-6-aza-bicyclo[3.2.1]octane-6-carboxylic acid tert-butyl ester (3.91 g, 10.45 mmoles) was converted to benzyl (1S,2S,4R)-2-(cyanomethyl)-4-(isopropyl(methyl)amino)cyclohexylcarbamate.

Example 11s, Step 2: To a solution of (1S,2S,4R)-2-(cyanomethyl)-4-(isopropyl(methyl)amino)cyclohexylcarbamate (479 mg) in 4 ml of acetic acid was added 4 ml of 30% HBr in acetic acid, and the mixture was stirred for 2.5 hours. The acid was evaporated off under reduced pressure and residue was dried by azeotroping with benzene several times. The residue was further dried under vacuum to give 2-((1S,2S,5R)-2-amino-5-(isopropyl(methyl)amino)cyclohexyl)acetonitrile as a bis-HBr salt as a solid (673 mg).

Example 11s, Step 3: To a solution of 2-((1S,2S,5R)-2-amino-5-(isopropyl(methyl)amino)cyclohexyl)acetonitrile (100 mg, 0.27 mmoles) in 2 ml of anhydrous acetonitrile were added diisopropylethylamine (0.24 ml, 1.35 mmoles), 2-(3-(trifluoromethyl)benzamido)acetic acid (66.6 mg, 0.27 mmoles) and 2-(1H-benzotriazol-1-yl)-1,1,3,3-tetramethyluronium tetrafluoroborate (95.2 mg, 0.3 mmoles, Bachem), and the mixture was stirred for 18 hours at room temperature. Then several drops of methanol was added, and it was stirred for additional two hours. The solvent was evaporated off and the residue was purified by chromatography (silica gel, 0.7:6.3:93 cNH$_4$H-MeOH—CH$_2$Cl$_2$) to give N-(2-((1S,2S,4R)-2-(cyanomethyl)-4-(isopropyl(methyl)amino)cyclohexylamino)-2-oxoethyl)-3-(trifluoromethyl)benzamide. MS found: (M+H)$^+$=439.3.

Example 11v

Synthesis of ((1R,2S,5R)-5-(isopropyl(methyl)amino)-2-(2-(3-(trifluoromethyl)benzamido)acetamido)cyclohexyl)methyl 2-(3-(trifluoromethyl)benzamido)acetate The titled compound was isolated during the purification of the reaction mixture obtained in Example 8a, Step 3. MS found: (M+H)$^+$=659.4.

Example 11w

Synthesis of ((1R,2S,5R)-5-(isopropylamino)-2-(2-(3-(trifluoromethyl)benzamido)acetamido)cyclohexyl)methyl 3-(trifluoromethyl)benzoate A sample of ((1R,2S,5R)-5-(tert-butoxycarbonyl)-2-(2-(3-(trifluoromethyl)benzamido)acetamido)cyclohexyl)methyl 3-(trifluoromethyl)benzoate was isolated during the purification of the reaction mixture obtained in Example 8b, Step 6. This product was then taken through the procedure detailed in Example 8b, Step 7, to afford the title compound. MS found: (M+H)$^+$=588.3.

TABLE 11-A

The compounds in the following table were made using the methods exemplified above. See Table 1-A for a complete description of the table headings.

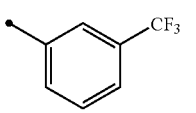

| Ex. | R$^5$ | R$^1$ | R$^2$ | Step Altered | MS Data |
|---|---|---|---|---|---|
| 11a | i-Pr(Et)N | C(O)c-NC$_4$H$_8$ | 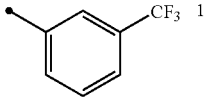 | n/a | 511 |
| 11b | Me$_2$N | C(O)c-NC$_4$H$_8$ | 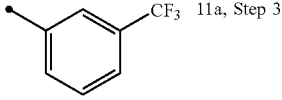 | 11a, Step 3 | 469 |
| 11c | i-Pr(Me)N | C(O)c-NC$_4$H$_8$ | 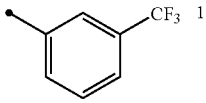 | 11a, Step 3 | 497 |
| 11d | i-Pr(Et)N | C(O)c-NC$_5$H$_{10}$ | CF$_3$ | 11a, Step 1 | 525 |

TABLE 11-A-continued

The compounds in the following table were made using the methods exemplified above. See Table 1-A for a complete description of the table headings.

| Ex. | R⁵ | R¹ | R² | Step Altered | MS Data |
|---|---|---|---|---|---|
| 11e | i-Pr(Me)N | C(O)c-NHEt | 3-CF₃-phenyl | 11a, Steps 1 and 3 | 471 |
| 11f | i-Pr(Et)N | C(O)c-NHi-Pr | 3-CF₃-phenyl | 11a, Step 1 | 499 |
| 11g | i-Pr(Et)N | C(O)c-NC₃H₆ | 3-CF₃-phenyl | 11a, Step 1 | 497 |
| 11h | i-Pr(Et)N | C(O)N(Me)Et | 3-CF₃-phenyl | 11a, Step 1 | 499 |
| 11i | i-Pr(Et)N | C(O)NHt-Bu | 3-CF₃-phenyl | 11a, Step 1 | 513 |
| 11j | i-Pr(Et)N | C(O)N(Me)i-Pr | 3-CF₃-phenyl | 11a, Step 1 | 513 |
| 11k | i-Pr(Et)N | C(O)N(Me)i-Pr | 2-t-Bu-4-OH-phenyl | 11a, Steps 1,2,3 | 503 |
| 11l | i-Pr(H)N | CO₂i-Pr | 3-CF₃-phenyl | n/a | 472 |
| 11m | i-Pr(Me)N | CO₂i-Pr | 3-CF₃-phenyl | n/a | 486 |
| 11n | i-Pr(Me)N | CO₂i-Pr | 3-CF₃-phenyl | n/a | 470 |
| 11o | H₂N | C(O)Me | 3-CF₃-phenyl | n/a | 386 |

TABLE 11-A-continued

The compounds in the following table were made using the methods exemplified above. See Table 1-A for a complete description of the table headings.

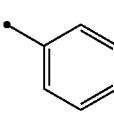

| Ex. | R⁵ | R¹ | R² | Step Altered | MS Data |
|---|---|---|---|---|---|
| 11p | i-Pr(Me)N | CH₂CH(OH)i-Pr,(R) | 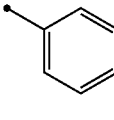 3-CF₃-Ph | n/a | 486 |
| 11q | i-Pr(Me)N | CH₂CH(OH)i-Pr,(S) | 3-CF₃-Ph | n/a | 486 |
| 11r | i-Pr(Me)N | CH₂C(O)i-Pr | 3-CF₃-Ph | n/a | 484 |
| 11s | i-Pr(Me)N | CH₂CN | 3-CF₃-Ph | n/a | 439 |
| 11t | i-Pr(Me)N | CH₂CN | 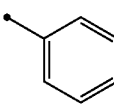 | 11s, Step 3 | 443 |
| 11u | i-Pr(Me)N | CH₂CN | 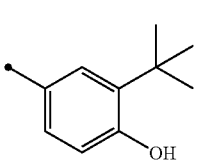 | 11s, Step 3 | 539 |
| 11v | i-Pr(Me)N | CH₂O₂CCH₂NHC(O)3-CF₃Ph | 3-CF₃-Ph | n/a | 659 |
| 11w | i-Pr(H)N | CH₂O₂C(3-CF₃)Ph | 3-CF₃-Ph | n/a | 588 |

TABLE 11-B

The chemical names of the specific examples illustrated in Table 11-A are tabulated below.

| Ex. | Name |
|---|---|
| 11a | N-(2-((1S,2R,4R)-4-(ethyl(isopropyl)amino)-2-(pyrrolidine-1-carbonyl)cyclohexylamino)-2-oxoethyl)-3-(trifluoromethyl)benzamide |
| 11b | N-(2-((1S,2R,4R)-4-(dimethylamino)-2-(pyrrolidine-1-carbonyl)cyclohexylamino)-2-oxoethyl)-3-(trifluoromethyl)benzamide |
| 11c | N-(2-((1S,2R,4R)-4-(isopropyl(methyl)amino)-2-(pyrrolidine-1-carbonyl)cyclohexylamino)-2-oxoethyl)-3-(trifluoromethyl)benzamide |
| 11d | N-(2-((1S,2R,4R)-4-(ethyl(isopropyl)amino)-2-(piperidine-1-carbonyl)cyclohexylamino)-2-oxoethyl)-3-(trifluoromethyl)benzamide |
| 11e | N-(2-((1S,2R,4R)-2-(ethylcarbamoyl)-4-(isopropyl(methyl)amino)cyclohexylamino)-2-oxoethyl)-3-(trifluoromethyl)benzamide |
| 11f | N-(2-((1S,2R,4R)-4-(ethyl(isopropyl)amino)-2-(isopropylcarbamoyl)cyclohexylamino)-2-oxoethyl)-3-(trifluoromethyl)benzamide |
| 11g | N-(2-((1S,2R,4R)-2-(azetidine-1-carbonyl)-4-(ethyl(isopropyl)amino)cyclohexylamino)-2-oxoethyl)-3-(trifluoromethyl)benzamide |
| 11h | N-(2-((1S,2R,4R)-4-(ethyl(isopropyl)amino)-2-(ethyl(methyl)carbamoyl)cyclohexylamino)-2-oxoethyl)-3-(trifluoromethyl)benzamide |
| 11i | N-(2-((1S,2R,4R)-2-(tert-butylcarbamoyl)-4-(ethyl(isopropyl)amino)cyclohexylamino)-2-oxoethyl)-3-(trifluoromethyl)benzamide |
| 11j | N-(2-((1S,2R,4R)-4-(ethyl(isopropyl)amino)-2-(isopropyl(methyl)carbamoyl)cyclohexylamino)-2-oxoethyl)-3-(trifluoromethyl)benzamide |
| 11k | 3-tert-butyl-4-hydroxy-N-(2-((1S,2R,4R)-4-(isopropyl(methyl)amino)-2-(isopropyl(methyl)carbamoyl)cyclohexylamino)-2-oxoethyl)benzamide |
| 11l | (1R,2S,5R)-isopropyl 5-(isopropylamino)-2-(2-(3-trifluoromethyl-benzamido)acetamido)cyclohexanecarboxylate |
| 11m | (1R,2S,5R)-isopropyl 5-(isopropyl(methyl)amino)-2-(2-(3-trifluoromethyl-benzamido)acetamido)cyclohexanecarboxylate |
| 11n | N-(2-((1S,2R,4R)-2-isobutyryl-4-(isopropyl(methyl)amino)cyclohexylamino)-2-oxoethyl)-3-(trifluoromethyl)benzamide |
| 11o | N-(2-((1S,2R,4R)-2-acetyl-4-aminocyclohexylamino)-2-oxoethyl)-3-(trifluoromethyl)benzamide |
| 11p | N-(2-((1S,2S,4R)-2-((2R)-2-hydroxy-3-methylbutyl)-4-(isopropyl(methyl)amino)cyclohexylamino)-2-oxoethyl)-3-(trifluoromethyl)benzamide |
| 11q | N-(2-((1S,2S,4R)-2-((2S)-2-hydroxy-3-methylbutyl)-4-(isopropyl(methyl)amino)cyclohexylamino)-2-oxoethyl)-3-(trifluoromethyl)benzamide |
| 11r | N-(2-((1S,2S,4R)-4-(isopropyl(methyl)amino)-2-(3-methyl-2-oxobutyl)cyclohexylamino)-2-oxoethyl)-3-(trifluoromethyl)benzamide |
| 11s | N-(2-((1S,2S,4R)-2-(cyanomethyl)-4-(isopropyl(methyl)amino)cyclohexylamino)-2-oxoethyl)-3-(trifluoromethyl)benzamide |
| 11t | 3-tert-butyl-N-(2-((1S,2S,4R)-2-(cyanomethyl)-4-(isopropyl(methyl)amino)cyclohexylamino)-2-oxoethyl)-4-hydroxybenzamide |
| 11u | 1-(2-((2-((1S,2S,4R)-2-(cyanomethyl)-4-(isopropyl(methyl)amino)cyclohexylamino)-2-oxoethyl)carbamoyl)-4-(trifluoromethyl)phenyl)-3-isopropylurea |
| 11v | ((1R,2S,5R)-5-(isopropyl(methyl)amino)-2-(2-(3-(trifluoromethyl)benzamido)acetamido)-cyclohexyl)methyl 2-(3-(trifluoromethyl)benzamido)acetate |
| 11w | ((1R,2S,5R)-5-(isopropylamino)-2-(2-(3-(trifluoromethyl)benzamido)acetamido)cyclohexyl)methyl 3-(trifluoromethyl)benzoate |

Examples 12a-12g

Example 12a

Synthesis of N-(2-((1S,2R,4R)-4-(isopropyl(methyl)amino)-2-(3-methyl-1,2,4-oxadiazol-5-yl)cyclohexylamino)-2-oxoethyl)-3-(trifluoromethyl)benzamide Example 12a, Step 1: A mixture of (1R,2S,5R)-2-(benzyloxycarbonylamino)-5-(tert-butoxycarbonylamino)cyclohexanecarboxylic acid (11.0 g, 0.0382 mol), pyridine (40 ml), methanesulfonlylchloride (0.5 g, 0.0012 mol) in dry dichloromethane (10 ml) at −15° C. was added triethylamine (0.3 g, 0.003 mol) followed by ethyl chloroformate (0.2 g, 0.0019 mol) slowly. The reaction mixture was stirred at −15° C. for 1 h. Acetamidoxime (0.4 g, 0.0019 mol) was added and the reaction mixture was allowed to warm to RT and stirred for 2 h. The reaction mixture was diluted with dichloromethane (50 ml), washed with water (15 ml), saturated potassium carbonate solution (15 ml) and concentrated. The crude material was taken for the next step without further purification.

Example 12a, Step 2: The crude material from the above step was dissolved in dioxane (10 ml) and stirred at 100° C. over night. The solvent was removed under vacuum and the residue obtained was purified by recrystallisation using diethylether to get 0.275 g (51%) of tert-butyl (1R,3R,4S)-4-((benzyloxycarbonyl)amino)-3-(3-methyl-1,2,4-oxadiazol-5-yl)cyclohexylcarbamate as a colorless solid. $^1$H NMR (400 MHz, DMSO-$d_6$) δ 0.9 to 1.3 (m, 2H), 1.35 (s, 9H), 1.35 to 1.95 (6H), 2.20 (s, 3H), 4.13 (bs, 1H), 4.90 (m, 2H), 6.65 (bs, 1H), 7.30 (m, 5H); $^{13}$C NMR (400 MHz, DMSO-$d_6$) δ 11.2, 25.8, 28.3, 29.2, 37.8, 47.3, 48.1, 65.1, 77.7, 127.6, 127.7, 128.3, 137.1, 154.8, 155.7, 166.3, 179.3; MS found: (M+H)$^+$=431.

Example 12a, Step 3: To absolution of tert-butyl (1R,3R,4S)-4-((benzyloxycarbonyl)amino)-3-(3-methyl-1,2,4-oxadiazol-5-yl)cyclohexylcarbamate (250 mg) in $CH_2Cl_2$ (10 mL) was added TFA (3 mL) at RT. The reaction was stirred for 5 h and concentrated in vacuo. The residue was partitioned between 1N NaOH (30 mL) and EtOAc (40 mL). The aqueous layer was extracted with EtOAc (2×50 mL) and the organic phases were combined, washed with brine (25 mL), dried ($Na_2SO_4$), filtered, and concentrated in vacuo to give benzyl (1S,2R,4R)-4-amino-2-(3-methyl-1,2,4-oxadiazol-5-yl)cyclohexylcarbamate. MS found: (M+H)$^+$=331.

Example 12a, Step 4: The entirety of (1S,2R,4R)-4-amino-2-(3-methyl-1,2,4-oxadiazol-5-yl)cyclohexylcarbamate prepared in Step 1 (1 eq) was dissolved in $CH_2Cl_2$ (20 mL) The resultant solution was charged with acetone (10 eq) and stirred at RT for 10 min before sodium cyanoborohydride (2 eq) was added in one portion. The reaction was stirred at RT for 10 h and then charged successively with formaldehyde (10 eq in 37 wt % aq soln) and sodium cyanoborohydride (2 eq). The reaction was stirred for another 9 h at RT and then quenched with sat. $NaHCO_3$. The aqueous mixture was extracted with EtOAc (40 mL, then 2×40 mL). The organic extracts were combined, washed with brine (30 mL), dried ($MgSO_4$), filtered, and concentrated in vacuo. After the resulting oil stood, some paraformaldehyde-related products solidified; these were removed by dissolving the mixture in a minimal volume of EtOAc and filtering. Subsequent concentration provided 270 mg of benzyl (1S,2R,4R)-4-(isopropyl(methyl)amino)-2-(3-methyl-1,2,4-oxadiazol-5-yl)cyclohexylcarbamate. MS found: (M+H)$^+$=387.

Example 12a, Step 5: The entirety of benzyl (1S,2R,4R)-4-(isopropyl(methyl)amino)-2-(3-methyl-1,2,4-oxadiazol-5-yl)cyclohexylcarbamate prepared in Step 2 (270 mg, 0.7 mmol) was charged with 30% HBr/AcOH (5 mL). The reaction vessel warms and a vigorous gas evolution occurs. The mixture was stirred for 25 min at RT and then the flask was placed in a cool water bath before the addition of 20 mL of $Et_2O$. The resulting solid was collected, washed with $Et_2O$ twice, and concentrated in vacuo to give (1R,3R,4S)-N1-isopropyl-N1-methyl-3-(3-methyl-1,2,4-oxadiazol-5-yl)cyclohexane-1,4-diamine (250 mg). MS found: $(M+H)^+$ =253.

Example 12a, Step 6: To a solution of ((1R,3R,4S)-N1-isopropyl-N1-methyl-3-(3-methyl-1,2,4-oxadiazol-5-yl)cyclohexane-1,4-diamine (30 mg, 0.07 mmol) in DMF (10 mL) was charged with 2-(3-(trifluoromethyl)benzamido)acetic acid (21 mg, 0.08 mmol), N,N-diethylisopropylamine (0.06 mL, 0.35 mmol), and HATU (31 mg, 0.08 mmol). The reaction was stirred for 16 h at RT and then partitioned between EtOAc and sat. $NaHCO_3$; the aqueous phase was back extracted with EtOAc (1×). The organic phases were combined, washed with brine, dried ($Na_2SO_4$), filtered, and concentrated in vacuo. The residue was purified by HPLC to afford the TFA salt of N-(2-((1S,2R,4R)-4-(isopropyl(methyl)amino)-2-(3-methyl-1,2,4-oxadiazol-5-yl)cyclohexylamino)-2-oxoethyl)-3-(trifluoromethyl)benzamide. MS found: $(M+H)^+$=482.

Example 12d

Synthesis of N-(2-((1S,2R,4R)-4-(isopropyl(methyl)amino)-2-(3-isopropyl-1,2,4-oxadiazol-5-yl)cyclohexylamino)-2-oxoethyl)-3-(trifluoromethyl)benzamide Example 12d, Step 1: To a solution of (1R,2S,5R)-2-(benzyloxycarbonylamino)-5-(tert-butoxycarbonylamino)cyclohexanecarboxylic acid (0.5 g, 0.0012 mol) in dry dichloromethane (10 ml) at −15° C. was added triethylamine (0.3 g, 0.003 mol) followed by ethyl chloroformate (0.2 g, 0.0019 mol) slowly. The reaction mixture was stirred at −15° C. for 1 h. Isobutyradoxime (0.19 g, 0.0018 mol) was added and the reaction mixture was allowed to warm to RT and stirred for 2 h. The reaction mixture was diluted with dichloromethane (50 ml), washed with water (15 ml), saturated potassium carbonate solution (15 ml) and concentrated. The crude material was taken to the next step without further purification.

Example 12d, Step 2: The crude material from the above step was dissolved in dioxane (10 ml) and stirred at 100° C. over night. The solvent was removed under vacuum and the residue obtained was purified by recrystallization using diethylether to get 0.275 g (51%) of tert-butyl (1R,3R,4S)-4-((benzyloxycarbonyl)amino)-3-(3-isopropyl-1,2,4-oxadiazol-5-yl)cyclohexylcarbamate as a colorless solid. $^1$H NMR (400 MHz, DMSO-$d_6$) δ 0.9 to 1.3 (m, 2H), 1.35 (s, 9H), 1.35 to 1.95 (6H), 2.20 (s, 3H), 4.13 (bs, 1H), 4.90 (m, 2H), 6.65 (bs, 1H), 7.30 (m, 5H); $^{13}$C NMR (400 MHz, DMSO-$d_6$) δ 11.2, 25.8, 28.3, 29.2, 37.8, 47.3, 48.1, 65.1, 77.7, 127.6, 127.7, 128.3, 137.1, 154.8, 155.7, 166.3, 179.3; MS found: $(M+H)^+$=431.

Example 12d, Step 3: A sample of tert-butyl (1R,3R,4S)-4-((benzyloxycarbonyl)amino)-3-(3-isopropyl-1,2,4-oxadiazol-5-yl)cyclohexylcarbamate was taken through the procedures detailed in Example 12a, Steps 3-6, to provide the TFA salt of the title compound. MS found: $(M+H)^+$=510.

Example 12e

Synthesis of N-(2-((1S,2R,4R)-2-(3-tert-butyl-1,2,4-oxadiazol-5-yl)-4-(isopropyl(methyl)amino)cyclohexylamino)-2-oxoethyl)-3-(trifluoromethyl)benzamide Example 12e, Step 1: To a solution of (1R,2S,5R)-2-(benzyloxycarbonylamino)-5-(tert-butoxycarbonylamino)cyclohexanecarboxylic acid (0.5 g, 0.0012 mol) in dry dichloromethane (10 ml) at −15° C. was added triethylamine (0.3 g, 0.003 mol) followed by ethyl chloroformate (0.2 g, 0.0019 mol) slowly. The reaction mixture was stirred at −15° C. for 1 h. N-Hydroxy-2,2-dimethylpropanimidoxime (0.22 g, 0.0019 mol) was added and the reaction mixture was allowed to warm to RT and stirred for 2 h. The reaction mixture was diluted with dichloromethane (50 ml), washed with water (15 ml), saturated potassium carbonate solution (15 ml) and concentrated. The crude material was taken to the next step with out further purification.

Example 12e, Step 2: The crude material from the above step was dissolved in dioxane (10 ml) and stirred at 100° C. over night. The solvent was removed under vacuum and the residue obtained was purified by recrystallization using diethylether to give 0.1 g (16%) of tert-butyl(1R,3R,4S)-4-((benzyloxycarbonyl)amino)-3-(3-tert-butyl-1,2,4-oxadiazol-5-yl)cyclohexylcarbamate as a colorless solid. $^1$H NMR (400 MHz, CDCl$_3$) δ 1.38 (s, 9H), 1.44 (s, 9H), 1.66 (m, 2H), 1.85 (bs, 1H), 2.03 (m, 2H), 2.19 (m, 1H), 3.52 (bs, 1H), 3.75 (bs, 1H), 4.14 (bs, 1H), 5.06 (s, 2H), 5.19 (bs, 1H), 5.35 (bs, 1H), 7.32 (m, 5H). MS found: $(M+H)^+$=473.

Example 12e, Step 3: A sample of tert-butyl (1R,3R,4S)-4-((benzyloxycarbonyl)amino)-3-(3-tert-butyl-1,2,4-oxadiazol-5-yl)cyclohexylcarbamate was taken through the procedures detailed in Example 12a, Steps 3-6, to provide the TFA salt of the title compound. MS found: $(M+H)^+$=524.

Example 12f

Synthesis of N-(2-((1S,2R,4R)-4-(isopropyl(methyl)amino)-2-(4-methylthiazol-2-yl)cyclohexylamino)-2-oxoethyl)-3-(trifluoromethyl)benzamide Example 12f, Step 1: To a solution of (1R,2S,5R)-2-(benzyloxycarbonylamino)-5-(tert-butoxycarbonylamino)cyclohexanecarboxylic acid (7 g, 0.01 mol) in dry THF was added 7.5 ml (0.05 mol) of triethyl amine under nitrogen. The reaction mixture was cooled to −30° C. and added 4.8 g (0.04 mol) of ethylchloroformate drop wise and stirred at −20° C. for 2 h. The reaction mixture was then purged with ammonia gas at −20° C. for 3 h and stirred at RT for over night. THF was removed completely and the crude compound was dissolved in ethyl acetate. The organic layer was washed with 10% sodium hydroxide, water, brine and concentrated to 5 g (72%) of tert-butyl (1R,3R,4S)-4-((benzyloxycarbonyl)amino)-3-carbamoylcyclohexylcarbamate as a white solid. MS found: $(M+H)^+$=392

Example 12f, Step 2: To a solution of tert-butyl (1R,3R,4S)-4-((benzyloxycarbonyl)amino)-3-carbamoylcyclohexylcarbamate (4.8 g, 0.01 mol) in 50 ml of dry THF was added Lawesson's reagent (2.97 g, 0.007 mol) portionwise under nitrogen. After the completion of addition the reaction mixture was stirred for 5 h at RT. THF was removed and the crude product was dissolved in ethyl acetate. The organic layer was washed with 10% sodium hydroxide, water, brine and concentrated. The crude product was purified by recrystallization from pet-ether and ether mixture to give 3.5 g crude of tert-butyl (1R,3R,4S)-4-((benzyloxycarbonyl)amino)-3-carbamothioylcyclohexylcarbamate as a white solid.

Example 12f, Step 3: To a solution of tert-butyl (1R,3R,4S)-4-((benzyloxycarbonyl)amino)-3-carbamothioylcyclohexylcarbamate (0.5 g, 0.0012 mol) in dry benzene (20 mL) under nitrogen was added chloroacetone (0.34 g, 0.0036 mol) and the reaction mixture was heated at 75° C. over night. Benzene was removed under vacuum and the crude was extracted with ethyl acetate. The organic layer was washed with brine, concentrated and purified by recrystallisation from ether to give 0.24 g (44%) of tert-butyl (1R,3R,4S)-4-((benzyloxycarbonyl)amino)-3-(4-methylthiazol-2-yl)cyclohexylcarbamate as a white solid. $^1$H NMR (400 MHz, CDCl$_3$) δ 1.44 (s, 9H), 1.65 (m, 3H), 1.78 (m, 2H), 2.19 (m, 2H), 2.42 (s, 3H), 3.49 (m, 1H), 3.70 (m, 1H), 4.05 (m, 1H), 5.04 (s, 2H), 5.29 (bs, 1H), 6.75 (s, 1H), 7.34 (m, 5H); $^{13}$H NMR (400 MHz, CDCl$_3$) δ 16.4, 27.4, 27.8, 32.7, 41.9, 46.5, 49.7, 66.0, 78.5, 112.3, 127.3, 127.4, 127.8, 135.9, 151.8, 154.6, 155.2, 169.2. MS found: (M+H)$^+$=446.

Example 12f, Step 4: A sample of tert-butyl (1R,3R,4S)-4-((benzyloxycarbonyl)amino)-3-(4-methylthiazol-2-yl)cyclohexylcarbamate was taken through the procedures detailed in Example 12a, Steps 3-6, to provide the TFA salt of the title compound. MS found: (M+H)$^+$=497.

Example 12g

Synthesis of N-(2-((1S,2R,4R)-2-(4-ethylthiazol-2-yl)-4-(isopropyl(methyl)amino)cyclohexylamino)-2-oxoethyl)-3-(trifluoromethyl)benzamide Example 12g, Step 1: To a solution of tert-butyl (1R,3R,4S)-4-((benzyloxycarbonyl)amino)-3-carbamothioylcyclohexylcarbamate (0.5 g, 0.0012 mol, see Example 12f, Step 2) in dry benzene (20 ml) under nitrogen was added 1-chloro-butan-2-one (0.42 g, 0.0039 mol) of and the reaction mixture was heated at 75° C. for over night. Benzene was removed under vaccum and the crude product was extracted with ethyl acetate. The organic layer was washed with brine, concentrated, and purified by recrystallization from ether to give 0.2 g (35%) of tert-butyl (1R,3R,4S)-4-((benzyloxycarbonyl)amino)-3-(4-ethylthiazol-2-yl)cyclohexylcarbamate as a white solid obtained. $^1$H NMR (400 MHz, CDCl$_3$) δ 1.27 (t, 3H), 1.44 (s, 9H), 1.62 (m, 2H), 1.81 (m, 3 H), 2.22 (m, 2H), 2.78 (q, 2H), 3.50 (bs, 1H), 3.72 (bs, 1H), 4.12 (bs, 1H), 5.04 (s, 2H), 5.40 (bs, 1H), 5.74 (s, 1H), 7.33 (m, 5H); $^{13}$H NMR (400 MHz, CDCl$_3$) 13.45, 24.7, 28.0, 28.24, 28.4, 33.3, 42.3, 47.0, 50.4, 61.0, 66.5, 79.0, 111.6, 127.9, 128.0, 128.4, 136.5, 155.2, 155.8, 158.8, 169.8. MS found: (M+H)$^+$=460.

Example 12g, Step 2: A sample of tert-butyl (1R,3R,4S)-4-((benzyloxycarbonyl)amino)-3-(4-ethylthiazol-2-yl)cyclohexylcarbamate was taken through the procedures detailed in Example 12a, Steps 3-6, to provide the TFA salt of the title compound. MS found: (M+H)$^+$=511.

TABLE 12-A

The compounds in the following table were made using the methods exemplified above. See Table 1-A for a complete description of the table headings.

| Example | R$^1$ | R$^2$ | Step Altered | MS Data |
|---|---|---|---|---|
| 12a | 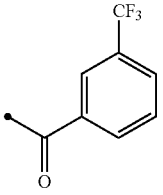 | 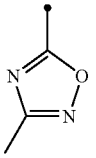 | n/a | 482 |
| 12b | 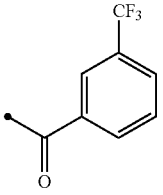 | 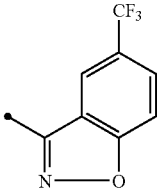 | 12a Step 6 | 495 |

TABLE 12-A-continued

The compounds in the following table were made using the methods exemplified above. See Table 1-A for a complete description of the table headings.

| Example | R¹ | R² | Step Altered | MS Data |
|---------|----|----|--------------|---------|
| 12c | 3-methyl-1,2,4-oxadiazol-5-yl | 2-(azetidine-1-carboxamido)-5-(trifluoromethyl)benzoyl | 12a Step 6 | 580 |
| 12d | 3-isopropyl-1,2,4-oxadiazol-5-yl | 3-(trifluoromethyl)benzoyl | n/a | 510 |
| 12e | 3-tert-butyl-1,2,4-oxadiazol-5-yl | 3-(trifluoromethyl)benzoyl | n/a | 524 |
| 12f | 4-methylthiazol-2-yl | 3-(trifluoromethyl)benzoyl | n/a | 497 |
| 12g | 4-ethylthiazol-2-yl | 3-(trifluoromethyl)benzoyl | n/a | 511 |

TABLE 12-B

The chemical names of the specific examples illustrated in Table 12-A are tabulated below.

| Example | Name |
|---|---|
| 12a | N-(2-(((1S,2R,4R)-4-(isopropyl(methyl)amino)-2-(3-methyl-1,2,4-oxadiazol-5-yl)cyclohexylamino)-2-oxoethyl)-3-(trifluoromethyl)benzamide |
| 12b | N-((1S,2R,4R)-4-(isopropyl(methyl)amino)-2-(3-methyl-1,2,4-oxadiazol-5-yl)cyclohexyl)-2-(5-(trifluoromethyl)benzo[d]isoxazol-3-ylamino)acetamide |
| 12c | N-(2-((2-(((1S,2R,4R)-4-(isopropyl(methyl)amino)-2-(3-methyl-1,2,4-oxadiazol-5-yl)cyclohexylamino)-2-oxoethyl)carbamoyl)-4-(trifluoromethyl)phenyl)azetidine-1-carboxamide |
| 12d | N-(2-(((1S,2R,4R)-4-(isopropyl(methyl)amino)-2-(3-isopropyl-1,2,4-oxadiazol-5-yl)cyclohexylamino)-2-oxoethyl)-3-(trifluoromethyl)benzamide |
| 12e | N-(2-((1S,2R,4R)-2-(3-tert-butyl-1,2,4-oxadiazol-5-yl)-4-(isopropyl(methyl)amino)cyclohexylamino)-2-oxoethyl)-3-(trifluoromethyl)benzamide |
| 12f | N-(2-(((1S,2R,4R)-4-(isopropyl(methyl)amino)-2-(4-methylthiazol-2-yl)cyclohexylamino)-2-oxoethyl)-3-(trifluoromethyl)benzamide |
| 12g | N-(2-(((1S,2R,4R)-2-(4-ethylthiazol-2-yl)-4-(isopropyl(methyl)amino)cyclohexylamino)-2-oxoethyl)-3-(trifluoromethyl)benzamide |

Compounds of formula I are shown to be modulators of chemokine receptor activity using assays know by those skilled in the art. In this section, we describe these assays and give their literature reference. By displaying activity in these assays of MCP-1 antagonism, compounds of formula I are expected to be useful in the treatment of human diseases associated with chemokines and their cognate receptors. The definition of activity in these assays is a compound demonstrating an $IC_{50}$ of 20 μM or lower in concentration when measured in a particular assay.

Antagonism of MCP-1 Binding to Human PBMC (Yoshimura et al., *J. Immunol.* 1990, 145, 292)

Compounds of the present invention have activity in the antagonism of MCP-1 binding to human PBMC (human peripheral blood mononuclear cells) described here.

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration compound, is combined with 50 μl of $^{125}$-I labeled human MCP-1 (to give a final concentration of 150 pM radioligand) and 50 μl of binding buffer containing $5\times10^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-induced Calcium Influx (Sullivan, et al. Methods Mol. Biol., 114, 125-133 (1999)

Compounds of the present invention have activity in the antagonism of MCP-1-induced calcium influx assay described here.

Calcium mobilization is measured using the fluorescent $Ca^{2+}$ indicator dye, Fluo-3. Cells are incubated at $8\times10^5$ cells/ml in phosphate-buffered saline containing 0.1% bovine serum albumin, 20 mM HEPES buffer, 5 mM glucose, 1% fetal bovine serum, 4 μM Fluo-3 AM and 2.5 mM probenecid for 60 minutes at 37° C. Cells used for such calcium assays can include human monocytes isolated as described by Weiner et al., J. Immunol. Methods, 36, 89-97 (1980) or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of $2-4\times10^6$ cells/ml. Cells are plated into 96-well, black-wall microplates (100 μl/well) and the plates centrifuged at 200×g for 5 minutes. Various concentrations of compound are added to the wells (50 μl/well) and after 5 minutes, 50 μl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-Induced Human PBMC Chemotaxis (Bacon et al., *Brit. J. Pharmacol.* 1988, 95, 966)

Compounds of the present invention have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1\times10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 μl to each well and there should be a positive meniscus after dispensing. The 8 micron filter is placed gently on top of the 96 well plate, a rubber gasket is attached to the bottom of the upper chamber, and the chamber is assembled. A 200 μl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the-methods above is a mammal, male or female, in whom modulation-of chemokine receptor activity is desired. "Modulation" as used herein is intended to encompass antagonism, agonism, partial antagonism and/or partial agonism.

CCR5 Binding and Functional Assays

Cell derivation and cell culture: A pool of HT1080 cells stably expressing endogenous CC chemokine receptor 5 (CCR5) were developed using the methods outlined by Harrington, Sherf, and Rundlet (see U.S. Pat. Nos. 6,361, 972 and 6,410,266). The highest-expressing clones were isolated using repetitive flow cytometry, followed by subcloning. These cells were then cultured in 6-well dishes at $3\times10^5$ cells/well and transfected with a DNA vector containing the chimeric HA-tagged G protein Gqi5 (Molecular Devices; 5 micrograms of linearized vector DNA in 15 microL of Ex-Gen from Fermentes was used for the transfection). Two days after transfection, the wells were combined and plated into P100 plates. Seven days after plating, colonies were picked, expanded, and analyzed for Gqi5 content by Western blot. A clone (designated as 3559.1.6) having high expression of Gqi5 (from transfection) and of CCR5 (endogenous) was selected and used for the experiments described below. The HT1080 cells (clone 3559.1.6) were cultured with alpha-MEM supplemented with 10% dialyzed fetal bovine serum, 2% penicillin/streptomycin/glutamine, and 500 microgram/mL hygromycin B (final concentration) at 37° C. with 5% $CO_2$ in a humidified atmosphere.

Membrane Preparation: A cell pellet containing $1\times10^8$ HT1080 cells (clone 3559.1.6) was resuspended in 5 mL of ice-cold Membrane Prep Buffer (50 mM HEPES, 5 mM $MgCl_2$, 1 mM $CaCl_2$) and homogenized at high-speed on a Polytron homogenizer for 20 sec on ice. The homogenate was diluted with another 25 mL of Membrane Prep Buffer and centrifuged for 12 min (48,000×g at 4° C.). The cell pellet was resuspended in 5 mL of Membrane Prep Buffer before being rehomogenized as described previously. The homogenate was diluted with 5 mL of Membrane Prep Buffer and assayed for CCR5 protein concentration.

Binding assay: The freshly-prepared homogenate from the Membrane Preparation described above was diluted in Binding buffer (50 mM HEPES, 5 mM $MgCl_2$, 1 mM $CaCl_2$, 0.1% BSA; one complete protease inhibitor tablet was added before assay) to achieve a final protein concentration of 10 micrograms/well (solid white 96-well plates from Corning, Inc.). This membrane preparation was mixed with WGA-SPA beads (Amerhsam; pre-soaked in Binding buffer) to give a concentration of 200 micrograms/well. The membrane/SPA bead mix (100 microliters/well) was then added to a plate that had been pre-dotted with 2 microliters DMSO containing various concentrations of test articles (pure DMSO for negative control; various concentrations of examples of this invention for test articles; 500 nM MIP-1 beta as a positive control). The binding assay was initiated through the addition of 50 microliters of $[^{125}I]$-MIP-1 beta (Perkin Elmer; material was diluted in Binding buffer such that the addition of 50 microliters/well gives a final concentration of 0.1 nM ($^{125}I$)-MIP-1 beta). The plate was sealed and allowed to stand at room temperature for 4-6 h before being counted on a Packard TopCount. The percentage bound for the test article was calculated, using negative and positive controls to define the window for each experiment.

Fluorometric Imaging Plate Reader (FLIPR)-based Functional assay: HT1080 cells (clone 3559.1.6) were plated at 10,000 cells/well (30 microliters) in 384-well plates (black/clear bottom Biocoat PDL, Beckton Dickinson) and charged with 30 microliters/well of Fluro-4 AM fluorescent dye (prepared by dissolving 1 mg Fluro-4 AM in 440 microliters DMSO and diluting with 100 microliters of pluronic solution before diluting further with 10 mL of Hanks buffer). The cells were incubated at 37° C. with 5% $CO_2$ for 30 min before being washed three times and suspended in Assay Buffer (20 mM HEPES, 1.2 mM $CaCl_2$, 5 MM $MgCl_2$, 2.5 mM Probenecid, 0.5% BSA, 1× Hanks). The test article was serially diluted in DMSO and then diluted 1:10 with Assay Buffer before being added to the cells (10 microliters/well). Using FLIPR, the plates were read (10-70 sec) for induction of flux (i.e. agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR for one minute. Antagonist activity of the test article was determined relative to 0.4% DMSO/Buffer negative control.

The compounds of the present invention are inhibitors of both CCR2 and CCR5 and may be used to treat diseases associated with either chemokine.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis*, Hookworm, *Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurism, fever, cardiovascular effects, haemodynamic shock, sepsis syndrom, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes melitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selecting, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternativley, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field. Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin. Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit. Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula (I):

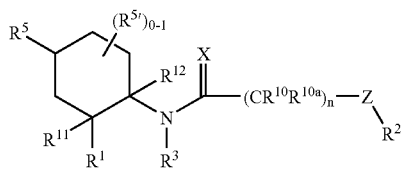

or a stereoisomer or a pharmaceutically acceptable salt thereof, wherein:

X is selected from O;

Z is —$NR^8C(O)$—;

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, and a 5-10 membered heterocyclic system containing 1-4 heteroatoms selected from N, O, and S, substituted with 0-3 $R^6$;

with the proviso that if $R^1$ is H, then $R^{5a}$ is selected from H, methyl substituted with 0-1 $R^{5g}$, $C_{2-6}$ alkyl substituted with 0-2 $R^{5e}$, and a $(CH_2)_r$—$C_{3-10}$ carbocyclic residue substituted with 0-5 $R^{5e}$;

$R^2$ is selected from a $C_{6-10}$ aryl group substituted with 0-5 $R^7$ and a 5-10 membered heteroaryl system containing 1-4 heteroatoms selected from N, O, and S, substituted with 0-3 $R^7$;

$R^3$ is selected from H, methyl, and ethyl;

$R^{5'}$, at each occurrence, is independently selected from H, =O, $C_{1-6}$ alkyl, $C_{2-8}$ alkenyl, $C_{2-8}$ alkynyl, F, Cl, Br, I, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rN(O)R^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(S)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5d}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}S(O)_2NR^{5a}R^{5a}$, $(CRR)_rNHC(=NR^{5f})NR^{5f}R^{5f}$, $C_{1-6}$ haloalkyl, a $(CRR)_r$-$C_{3-10}$ carbocyclic residue substituted with 0-3 $R^{5c}$, and a $(CRR)_r$-4-10 membered heterocyclic system containing 1-4 heteroatoms selected from N, O, and S, substituted with 0-2 $R^{5c}$;

$R^{5a}$, at each occurrence, is independently selected from H, methyl, $C_{1-6}$ alkyl substituted with 0-2 $R^{5e}$ wherein the alkyl is selected from ethyl, propyl, i-propyl, butyl, i-butyl, s-butyl, t-butyl, 2-methyl-butyl, pentyl, hexyl, $C_3$ alkenyl substituted with 0-1 $R^{5e}$ wherein the alkenyl is selected from allyl, $C_3$ alkynyl substituted with 0-1 $R^{5e}$ wherein the alkynyl is selected from propynyl, and a $(CH_2)_r$—$C_{3-4}$ carbocyclic residue substituted with 0-5 $R^{5e}$, wherein the carbocyclic residue is selected from cyclopropyl, cyclobutyl, cyclopentyl, and cyclohexyl;

$R^{5b}$, at each occurrence, is selected from $C_{1-6}$ alkyl substituted with 0-2 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0-2 $R^{5e}$, wherein the carbocyclic residue is selected from cyclopropyl, and cyclobutyl;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)_rOC(O)NR^{5f}R^{5f}$, $(CH_2)_rNR^{5f}C(O)R^{5b}$, $(CH_2)_rC(O)OC_{1-4}$ alkyl, $(CH_2)_rNR^{5f}C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, $(CH_2)_rC(O)NHR^{5h}$, $(CH_2)_rOC(O)NHR^{5h}$, $(CH_2)_rOH$, $(CH_2)_rC(O)OH$, $(CH_2)_rC(O)OR^{5h}$, $(CH_2)_rC(O)NHSO_2$—$R^{5h}$, $NHSO_2R^{5h}$, a $(CH_2)_r$-5-6 membered heterocyclic system containing 1-4 heteroatoms selected from N, O, and S, and $(CH_2)_r$ phenyl;

$R^{5f}$, at each occurrence, is selected from H, $C_{1-6}$ alkyl, and $C_{3-6}$ cycloalkyl;

$R^{5g}$ is independently selected from —CN, —$C(O)R^{5b}$, —$C(O)OR^{5d}$, —$C(O)NR^{5f}R^{5f}$, —C(O)OH, $(CH_2)_rC(O)NHSO_2$—$R^{5h}$, and $(CH_2)_r$phenyl;

$R^{5h}$, at each occurrence, is selected from $C_{1-5}$ alkyl, $C_{1-5}$ haloalkyl, and $C_{3-6}$ cycloalkyl, and phenyl;

R, at each occurrence, is selected from H, $C_{1-6}$ alkyl substituted with $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{6a'}R^{6a'}$, $(CR'R')_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rSC(O)$ $(CR'R')_rR^{6b}$, $(CR'R')_rC(O)OH$, $(CR'R')_rC(O)(CR'R')_rR^{6b}$, $(CR'R')_rC(O)NR^{6a}R^{6a}$, $(CR'R')_rNR^{6f}C(O)(CR'R')_rR^{6b'}$, $(CR'R')_rC(O)O(CR'R')_rR^{6d}$, $(CR'R')_rOC(O)(CR'R')_rR^{6b}$, $(CR'R')_rOC(O)NR^{6a}(CR'R')_rR^{6d}$, $(CR'R')_rNR^{6a}C(O)NR^{6a}R^{6d}$, $(CR'R')_rNR^{6a}C(S)NR^{6a}(CR'R')_rR^{6d}$, $(CR'R')_rNR^{6f}C(O)O(CR'R')_rR^{6b}$, $(CR'R')_rC(=NR^{6f})NR^{6a}R^{6a}$, $(CR'R')_rNHC(=NR^{6f})NR^{6f}R^{6f}$, $(CR'R')_rS(O)_pR^{6b'}$, $(CR'R')_rS(O)_2NR^{6a}R^{6a}$, $(CR'R')_rNR^{6f}S(O)_2NR^{6a'}R^{6a'}$, $(CR'R')_rNR^{6f}S(O)_2(CR'R')_rR^{6b}$, $C_{1-6}$ haloalkyl, $C_{2-8}$ alkenyl substituted with 0-3 R', $C_{2-8}$ alkynyl substituted with 0-3 R', $(CR'R')_r$phenyl substituted with 0-3 $R^{6e}$, and a $(CH_2)_r$-5-6 membered heterocyclic system containing 1-2 heteroatoms selected from N, O, and S, substituted with 0-2 $R^{6e}$;

alternatively, two $R^6$ on adjacent atoms on $R^1$ may join to form a cyclic acetal;

$R^{6a}$, at each occurrence, is selected from H, methyl substituted with 0-1 $R^{6g}$, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_r$—$C_{3-10}$ carbocyclic residue substituted with 0-5 $R^{6e}$, and a $(CH_2)_r$-5-10 membered heterocyclic system containing 1-4 heteroatoms selected from N, O, and S, substituted with 0-2 $R^{6e}$;

alternatively, two $R^{6a}$, together with the N to which they are attached, join to form a 3-8 membered heterocycle containing 0-1 additional heteroatoms selected from N, O, and S;

$R^{6a'}$, at each occurrence, is selected from H, $C_{1-6}$ alkyl, and $C_{3-6}$ cycloalkyl;

$R^{6b}$, at each occurrence, is selected from H, $C_{1-6}$ alkyl substituted with 0-3 $R^{6e}$, $C_{1-6}$ haloalkyl, $C_{3-8}$ alkenyl substituted with 0-2 $R^{6e}$, $C_{3-8}$ alkynyl substituted with 0-2 $R^{6e}$, a $(CH_2)_rC_{3-6}$ carbocyclic residue substituted with 0-3 $R^{6e}$, and a $(CH_2)_r$-5-6 membered heterocyclic system containing 1-4 heteroatoms selected from N, O, and S, substituted with 0-2 $R^{6e}$;

$R^{6b'}$, at each occurrence, is selected from H, $C_{1-6}$ alkyl, and $C_{3-6}$ cycloalkyl;

$R^{6d}$, at each occurrence, is selected from $C_{3-8}$ alkenyl substituted with 0-2 $R^{6e}$, $C_{3-8}$ alkynyl substituted with 0-2 $R^{6e}$, methyl, $CF_3$, $C_{2-6}$ alkyl substituted with 0-3 $R^{6e}$, $C_{2-4}$ haloalkyl, a $(CH_2)_r$-$C_{3-10}$ carbocyclic residue substituted with 0-3 $R^{6e}$, and a $(CH_2)_r$-5-6 membered heterocyclic system containing 1-4 heteroatoms selected from N, O, and S, substituted with 0-3 $R^{6e}$;

$R^{6d'}$, at each occurrence, is selected from H, $CF_3$ and $C_{1-6}$ alkyl and $C_{3-6}$ cycloalkyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, $C(O)NHR^{6h}$, $C(O)NHR^{6h}$, $(CH_2)_rOH$, C(O)OH, $C(O)OC_{1-5}$ alkyl, $(CH_2)_rC(O)NHSO_2$—$R^{6h}$, $NHSO_2R^{6h}$, $(CH_2)_r$tetrazolyl, and $(CH_2)_r$phenyl and a $(CH_2)_r$-5-6 membered heterocyclic system containing 1-4 heteroatoms selected from N, O, and S;

$R^{6f}$, at each occurrence, is selected from H, $C_{1-5}$ alkyl, and $C_{3-6}$ cycloalkyl, and phenyl;

$R^{6g}$ is independently selected from —$C(O)R^{6b}$, —$C(O)OR^{6d}$, —$C(O)NR^{6f}R^{6f}$, $(CH_2)_rOH$, C(O)OH, $(CH_2)_rC(O)NHSO_2$—$R^{6h}$, $NHSO_2R^{6h}$, $(CH_2)_r$tetrazolyl, and $(CH_2)_r$phenyl;

$R^{6h}$, at each occurrence, is selected from $C_{1-5}$ alkyl, $C_{1-5}$ haloalkyl, and $C_{3-6}$ cycloalkyl, and phenyl, and phenyl further substituted with 1-2 of $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rNR^{6f}R^{6f}$;

$R^7$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{7a}R^{7a}$, $(CR'R')_rOH$, $(CR'R')_rO(CR'R')_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O)(CR'R')_rR^{7b}$, $(CR'R')_rC(O)NR^{7a}R^{7a}$, $(CR'R')_rNR^{7f}C(O)'(CR'R')_rR^{7b}$, $(CR'R')_rC(O)O(CR'R')_rR^{7d}$, $(CR'R')_rOC(O)(CR'R')_rR^{7b}$, $(CR'R')_rOC(O)NR^{7a}(CR'R')_rR^{7a}$, $(CR'R')_rNR^{7a}C(O)NR^{7a}(CR'R')_rR^{7a}$, $(CR'R')_rNR^{7f}C(O)O(CR'R')_rR^{7d}$, $(CR'R')_rC(=NR^{7f})NR^{7a}R^{7a}$, $(CR'R')_rNHC(=NR^{7f})NR^{7f}R^{7f}$, $(CR'R')_rS(O)_p R^{7b}$, $(CR'R')_rS(O)_2NR^{7a}R^{7a}$, $(CR'R')_rNR^{7a}S(O)_2NR^{7a}R^{7a}$, $(CR'R')_rNR^{7f}S(O)_2(CR'R')_rR^{7b}$, $(CR'R')_rC(O)NHSO_2R^{7b}$, $C_{1-6}$ haloalkyl, $C_{2-8}$ alkenyl substituted with 0-3 R', $C_{2-8}$ alkynyl substituted with 0-3 R', and $(CR'R')_r$phenyl substituted with 0-3 $R^{7e}$, and a $(CH_2)_r$ -5-6 membered heterocyclic system containing 1-4 heteroatoms selected from N, O, and S, substituted with 0-3 $R^{7e}$;

alternatively, two $R^7$ on adjacent atoms on $R^2$ may join to form a cyclic acetal;

$R^{7a}$, at each occurrence, is independently selected from H, methyl substituted with 0-1 $R^{7g}$, $C_{2-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-2 $R^{7e}$;

$R^{7b}$, at each occurrence, is selected from $C_{1-6}$ alkyl substituted with 0-3 $R^{7e}$, $C_{1-6}$ haloalkyl, $C_{3-8}$ alkenyl substituted with 0-2 $R^{7e}$, $C_{3-8}$ alkynyl substituted with 0-2 $R^{7e}$, a $(CH_2)_rC_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{2-4}$ haloalkyl, $C_{2-6}$ alkyl substituted with 0-3 $R^{7e}$, a $(CH_2)_r$—$C_{3-10}$ carbocyclic residue substituted with 0-3 $R^{7e}$, and a $(CH_2)_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, $(CH_2)_rOH$, OH, SH, C(O)OH, $C(O)NHR^{7h}$, $C(O)OC_{1-5}$ alkyl, $(CH_2)_rSC_{1-5}$ alkyl, $(CH_2)_rNR^{7f}R^{7f}$, $(CH_2)_rC(O)NHSO_2$—$R^{7h}$, $NHSO_2R^{7h}$, and $(CH_2)_r$phenyl, $(CH_2)_r$tetrazolyl;

$R^{7f}$, at each occurrence, is selected from H, $C_{1-5}$ alkyl, and $C_{3-6}$ cycloalkyl, and phenyl;

$R^{7g}$ is independently selected from —$C(O)R^{7b}$, —$C(O)OR^{7d}$, —$C(O)NR^{7f}R^{7f}$, and $(CH_2)_r$phenyl;

$R^{7h}$, at each occurrence, is selected from $C_{1-5}$ alkyl, $C_{1-5}$ haloalkyl, and $C_{3-6}$ cycloalkyl, and phenyl;

R', at each occurrence, is independently, selected from H, $C_{1-6}$ alkyl substituted with $R^{6e}$, $C_{2-8}$ alkenyl, $C_{2-8}$ alkynyl, $(CH_2)_rC_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^{10}$ and $R^{10a}$ are independently selected from H, and $C_{1-4}$alkyl substituted with 0-1 $R^{10b}$, alternatively, $R^{10}$ and $R^{10a}$ can join to form a $C_{3-6}$ cycloalkyl;

$R^{10b}$, at each occurrence, is independently selected from —OH, —SH, —$NR^{10c}R^{10c}$, —$C(O)NR^{10c}R^{10c}$, and —$NHC(O)R^{10c}$;

$R^{10c}$ is selected from H, $C_{1-4}$ alkyl and $C_{3-6}$ cycloalkyl;

$R^{11}$ is;

$R^{12}$ is;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{15}$ is independently selected from H, $C_{1-4}$ alkyl, and $C_{3-4}$ cycloalkyl;

$R^{24}$, at each occurrence, is independently selected from H and $C_{1-4}$alkyl;

alternatively, two $R^{24}$s, along with the carbon atom to which they are attached, join to form a $C_{3-6}$ carbocyclic ring;

$R^{25}$, at each occurrence, is independently selected from H, $C_{1-4}$alkyl, OH, $NH_2$, —O—$C_{1-4}$ alkyl, $NR^{25a}R^{25a}$, $C(O)NR^{25a}R^{25a}$, $NR^{25a}C(O)R^{25b}$, $NR^{25a}C(O)OR^{25d}$, $OC(O)NR^{25a}R^{25a}$, and $(CHR)_rC(O)OR^{25d}$;

alternatively, two $R^{25}$s, along with the carbon atom or atoms to which they are attached, join to form a $C_{3-6}$ carbocyclic ring;

$R^{25a}$, at each occurrence, is independently seleced from H, and $C_{1-4}$ alkyl, $R^{25b}$, at each occurrence, is independently selected from H, $C_{1-4}$ alkyl, $C_{3-6}$ alkenyl, and $C_{3-6}$ alkynyl;

$R^{25d}$, at each occurrence, is independently selected from $C_{1-4}$ alkyl, $C_{3-6}$ alkenyl, and $C_{3-6}$ alkynyl;

$R^{26}$ is selected from $C_{1-4}$ alkyl;

n is selected from 1 and 2;

p, at each occurrence, is independently selected from 0, 1, and 2;

q, at each occurrence, is independently selected from 1, 2, 3, and 4;

r, at each occurrence, is independently selected from 0, 1, 2, 3, and 4; and t, at each occurrence, is independently selected from 2, 3, and 4, and u is selected from 1, 2 and 3.

2. The compound of claim 1, wherein:

R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$;

$R^{5a}$, at each occurrence, is independently selected from H, $C_{1-6}$ alkyl substituted with 0-2 $R^{5e}$ wherein the alkyl methyl, ethyl, propyl, i-propyl, butyl, i-butyl, pentyl, hexyl, cyclopropyl, cyclobutyl, and cyclohexyl; and r, at each occurrence, is selected from 0, 1, and 2.

3. The compound of claim 2, wherein:

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, wherein the aryl group is selected from phenyl and napthyl, and a 5-10 membered heterocyclic system containing 1-4 heteroatoms selected from N, O, and S, substituted with 0-3 $R^6$, wherein the heterocyclic system is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, oxadiazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isonicotinyl, isoquinolinyl isothiazolyl, isoxazolinyl, isoxazolyl, oxazolyl, phthalazinyl, picolinyl, pyrazinyl, pyrazolyl, pyridazinyl, pyridyl, pyridinyl, pyrimidinyl, pyrrolyl, pyrrolotriazinyl, quinazolinyl, quinolinyl, thiazolyl, thienyl, tetrazolyl, and triazinyl; and $R^8$ is selected from H, methyl, ethyl, propyl, i-propyl, and cyclopropyl.

4. The compound of claim 3, wherein:

$R^6$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{6a'}R^{6a'}$, $(CRR)_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rC(O)OH$, $(CR'R')_rC(O)(CR'R')_rR^{6b}$, $(CR'R')_rC(O)NR^{6a'}R^{6a}$, $(CR'R')_rNR^{6f}C(O)(CR'R')_rR^{6b'}$, $(CR'R')_rC(O)O(CR'R')_rR^{6d}$, $(CR'R')_rNR^{6a}C(O)NR^{6a'}R^{6a'}$, $(CR'R')_rNR^{6a}C(S)NR^{6a'}R^{6a}$, $(CR'R')_rOC(O)(CR'R')_rR^{6b}$, $(CR'R')_rOC(O)NR^{6a}(CR'R')_rR^{6d}$, $(CR'R')_r S(O)_pR^{6b'}$, $(CR'R')_rS(O)_2NR^{6a'}R^{6a}$, $(CR'R')_r NR^{6f}S(O)_2(CR'R')_rR^{6b}$, $(CR'R')_r NR^{6f}S(O)_2NR^{6a'}R^{6a'}$, $C_{1-6}$ haloalkyl, and $(CR'R')_r$phenyl substituted with 0-3 $R^{6e}$, and a $(CH_2)_r$-5-6 membered heterocyclic system containing 1-2 heteroatoms selected from N, O and S, substituted with 0-2 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

alternatively, two $R^{6a}$, together with the N to which they are attached, join to form a 3-8 membered heterocycle containing 0-1 additional heteroatoms selected from N, O, and S, wherein the heterocycle is selected from aziridinyl, azetidinyl, pyrrolyl, piperidinyl, and morpholinyl;

$R^{6b}$, at each occurrence, is selected from methyl, ethyl, propyl, i-propyl, butyl, i-butyl, t-butyl, pentyl, hexyl, cyclopropyl, and phenyl substituted with 0-1 $R^{6e}$;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, $C(O)NHR^{6h}$, $C(O)NHR^{6h}$, $(CH_2)_rOH$, $C(O)OH$, $C(O)OC_{1-5}$ alkyl, $(CH_2)_rC(O)NHSO_2-R^{6h}$, $NHSO_2R^{6h}$, $(CH_2)_r$tetrazolyl,and $(CH_2)_r$phenyl and a $(CH_2)_r$-5-6 membered heterocyclic system containing 1-4 heteroatoms selected from N, O, and S;

$R^{6f}$, at each occurrence, is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{7a}R^{7a}$, $(CR'R')_rOH$, $(CR'R')_rO(CH)_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O)(CR'R')_rR^{7b}$, $(CR'R')_rC(O)NR^{7a}R^{7a}$, $(CR'R')_rNR^{7f}C(O)(CR'R')_rR^{7b}$, $(CR'R')_rC(O)O(CR'R')_r R^{7d}$, $(CR'R')_rOC(O)(CR'R')_rR^{7b}$, $(CR'R')_rNR^{7a}C(O)NR^{7a}R^{7a}$, $(CR'R')_rNR^{7a}C(O)O(CR'R')_rR^{7d}$, $(CR'R')_rS(O)_p(CR'R')_rR^{7b}$, $(CR'R')_rS(O)_2NR^{7a}R^{7a}$, $(CR'R')_r NR^{7f}S(O)_2(CR'R')_rR^{7b}$, $C_{1-6}$ haloalkyl, adamantyl, and $(CR'R')_r$phenyl substituted with 0-3 $R^{7e}$, and pyridyl substituted with 0-3 $R^{7e}$;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl substituted with 0-1 $R^{6e}$;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, piperidinyl, morpholinyl, piperizenyl substituted with 0-1 $R^{7e}$, and azetidinyl;

$R^{7d}$, at each occurrence, is selected from methyl, $CF_3$, $CF_2CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, $(CH_2)_rOH$, OH, SH, $C(O)OH$, $C(O)NHR^{7h}$, $C(O)OC_{1-5}$ alkyl, $(CH_2)_rSC_{1-5}$ alkyl, $(CH_2)_rNR^{7f}R^{7f}$, $(CH_2)_rC(O)NHSO_2-R^{7h}$, $NHSO_2R^{7h}$, and $(CH_2)_r$phenyl, $(CH_2)_r$tetrazolyl;

$R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

5. The compound of claim 4, wherein:

$R^6$, at each occurrence, is selected from $C_{1-8}$ alkyl, $C_{2-8}$ alkenyl, $C_{2-8}$ alkynyl, $(CHR')_rC_{3-6}$ cycloalkyl, Cl, Br, I, F, $NO_2$, CN, $(CHR')_rNR^{6a'}R^{6a'}$, $(CHR')_rOH$, $(CHR')_rOR^{6d}$, $(CHR')_rSH$, $(CHR')_rC(O)H$, $(CHR')_rSR^{6d}$, $(CHR')_rC(O)OH$, $(CHR')_rC(O)R^{6b}$, $(CHR')_rC(O)NR^{6a'}R^{6a}$, $(CHR')_rNR^{6f}C(O)R^{6b'}$, $(CHR')_rC(O)OR^{6d}$, $(CHR')_rOC(O)NR^{6a}R^{6d}$, $(CHR')_rNR^{6a}C(O)NR^{6a}R^{6a}$, $(CHR')_rNR^{6a}C(S)NR^{6a}R^{6a}$, $(CHR')_rOC(O)R^{6b}$, $(CHR')_rS(O)_pR^{6b'}$, $(CHR')_rS(O)_2NR^{6a}R^{6a}$, $(CHR')_r NR^{6f}S(O)_2R^{6b}$, $(CHR')_rNR^{6f}S(O)_2NR^{6a'}R^{6a'}$, $C_{1-6}$ haloalkyl, and $(CHR')_r$phenyl substituted with 0-3 $R^{6e}$.

6. The compound of claim 5, wherein $R^2$ is a 5-10 membered heteroaryl system containing 1-4 heteroatoms selected from N, O, and S, substituted with 0-3 $R^7$ wherein the heteroaryl is selected from quinazolinyl, triazinyl, pyrimidinyl, picolinyl, isonicotinyl, furanyl, indolyl, pyridinyl, pyrazolyl, pyrazinyl, thiazolyl, thiophenyl, and isoxazolyl.

7. The compound of claim 6, wherein the compound is of formula (Ia)

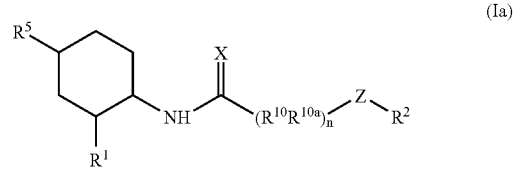

(Ia)

8. A pharmaceutical composition, comprising a pharmaceutically acceptable carrier and a therapeutically effective amount of a compound of claim 1.

9. A method for treating disorders, comprising administering to a patient in need thereof a therapeutically effective amount of a compound of claim 1, said disorders being selected from asthma, multiple sclerosis, artherosclerosis, and rheumatoid arthritis.

* * * * *

UNITED STATES PATENT AND TRADEMARK OFFICE
CERTIFICATE OF CORRECTION

PATENT NO.       : 7,378,409 B2
APPLICATION NO.  : 10/923538
DATED            : May 27, 2008
INVENTOR(S)      : Percy H. Carter et al.

It is certified that error appears in the above-identified patent and that said Letters Patent is hereby corrected as shown below:

Front Page, Column 2, Abstract
Lines 5-6, "artherosclerosis," should read -- atherosclerosis, --.

Column 252
Line 42, below "ethyl;" insert -- $R^5$ is $NR^{5a}R^{5a}$; --.

Column 254
Lines 56-57, "$(CR'R')_rNR^{7f}C(O)'(CR'R')_rR^{7b}$," should read -- $(CR'R')_rNR^{7f}C(O)(CR'R')_rR^{7b}$, --.

Column 255
Line 54, "$R^{11}$ is;" should read -- $R^{11}$ is H; --;
Line 55, "$R^{12}$ is;" should read -- $R^{12}$ is H; --.

Column 256
Line 8, "seleced" should read -- selected --;
Line 31, "alkyl" should read -- alkyl, --;
Line 47, "isoquinolinyl" should read -- isoquinolinyl, --;
Line 60, "isoquinolinyl" should read -- isoquinolinyl, --.

Column 257
Line 16, "O" should read -- O, --,

Column 258
Lines 45-50,

" 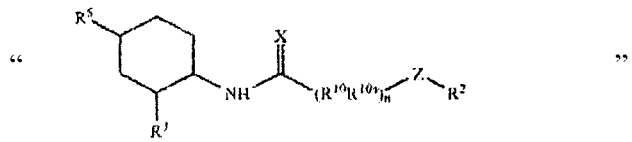 "

Signed and Sealed this

Ninth Day of November, 2010

David J. Kappos
*Director of the United States Patent and Trademark Office* should read
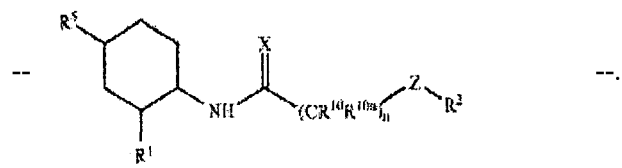
Line 58, "artherosclerosis," should read -- atherosclerosis, --.